(12) United States Patent
Takahashi et al.

(10) Patent No.: US 8,211,910 B2
(45) Date of Patent: Jul. 3, 2012

(54) TRI-, TETRA-SUBSTITUTED-3-AMINOPYRROLIDINE DERIVATIVE

(75) Inventors: Hisashi Takahashi, Edogawa-ku (JP);
Hiroaki Inagaki, Edogawa-ku (JP);
Satoshi Komoriya, Edogawa-ku (JP);
Makoto Takemura, Edogawa-ku (JP);
Rie Miyauchi, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 391 days.

(21) Appl. No.: 12/422,726

(22) Filed: Apr. 13, 2009

(65) Prior Publication Data
US 2009/0253726 A1    Oct. 8, 2009

Related U.S. Application Data

(62) Division of application No. 11/413,153, filed on Apr. 28, 2006, now Pat. No. 7,563,805.

(30) Foreign Application Priority Data

May 19, 2005    (JP) ................. 2005-146386
Nov. 29, 2005   (JP) ................. 2005-344514
Mar. 23, 2006   (JP) ................. 2006-080629

(51) Int. Cl.
*A01N 43/42*    (2006.01)
*A61K 31/47*    (2006.01)
*C07D 215/00*   (2006.01)

(52) U.S. Cl. ......... 514/312; 514/314; 546/153; 546/156
(58) Field of Classification Search ............ 514/312, 514/314; 546/154, 156, 153
See application file for complete search history.

(56) References Cited

U.S. PATENT DOCUMENTS

| | | | |
|---|---|---|---|
| 4,735,949 A | | 4/1988 | Domagala et al. |
| 4,753,953 A | | 6/1988 | Masuzawa et al. |
| 4,997,943 A | * | 3/1991 | Iwata et al. ............ 544/363 |
| 5,286,723 A | | 2/1994 | Hayakawa et al. |
| 5,324,735 A | | 6/1994 | Shibata et al. |
| 5,587,386 A | | 12/1996 | Hayakawa et al. |
| 5,696,132 A | | 12/1997 | Hayakawa et al. |
| 6,656,952 B2 | | 12/2003 | Takemura et al. |
| 6,900,225 B2 | | 5/2005 | Takemura et al. |
| 2007/0191356 A1 | | 8/2007 | Takemura et al. |
| 2008/0045520 A1 | | 2/2008 | Takahashi et al. |

FOREIGN PATENT DOCUMENTS

| | | |
|---|---|---|
| EP | 0 172 651 | 2/1986 |
| EP | 0 242 789 A2 | 10/1987 |
| EP | 0 259 804 A2 | 3/1988 |
| EP | 0 265 230 | 4/1988 |
| EP | 0 266 576 | 5/1988 |
| EP | 0 341 493 | 11/1989 |
| EP | 0 357 047 | 3/1990 |
| EP | 0 470 578 A1 | 2/1992 |
| EP | 0 523 512 A1 | 1/1993 |
| EP | 0 596 126 A1 | 5/1994 |
| EP | 0 700 912 | 3/1996 |
| EP | 0 787 720 A1 | 8/1997 |
| EP | 0 787 726 A1 | 8/1997 |
| JP | 58-72589 | 4/1983 |
| JP | 61-137885 | 6/1986 |
| JP | 61-282382 | 12/1986 |
| JP | 63-045261 | 2/1988 |
| JP | 63-130594 | 6/1988 |
| JP | 63-152318 | 6/1988 |
| JP | 63-188626 | 8/1988 |
| JP | 64-3181 | 1/1989 |
| JP | 2-231475 | 9/1990 |
| JP | 3-95176 | 4/1991 |
| JP | 4-74167 | 3/1992 |
| JP | 5-279364 | 10/1993 |
| JP | 6-228138 | 8/1994 |
| JP | 7-25873 | 1/1995 |
| JP | 9-221424 | 8/1997 |
| WO | 9325545 | * 12/1993 |
| WO | WO 96/23775 | 8/1996 |
| WO | 2005/073238 | 8/2005 |
| WO | 2005/111015 | 11/2005 |

OTHER PUBLICATIONS

West (Solid State Chemistry). West, Anthony R., Solid State Chemistry and its Applications, Wiley, New York, 1988, pp. 358 & 365.*
Remuzon et al., Journal of Medicinal Chemistry (1991), 34(1), 29-37.*
Takenouchi et al., Antimicrobial Agents and Chemotherapy (1996), 40(8), 1835-1842.*
Asahina et al., Journal of Medicinal Chemistry (2005), 48(9), 3443-3446.*
D. Bouzard, et al., "Fluoronaphthyridines and Quinolones as Antibacterial Agents. 2. Synthesis and Structure-Activity Relationships of New 1-tert-Butyl 7-Substituted Derivatives"; J. Med. Chem. 1990, 22, pp. 1344-1352.

(Continued)

*Primary Examiner* — Niloofar Rahmani
(74) *Attorney, Agent, or Firm* — Oblon, Spivak, McClelland, Maier & Neustadt, L.L.P.

(57) ABSTRACT

A quinolone synthetic antibacterial agent and a therapeutic agent for an infection which exhibit broad spectrum and strong antibacterial activity for both Gram positive and Gram negative bacteria, and which are also highly safe are provided. The compound provided is represented by formula (I):

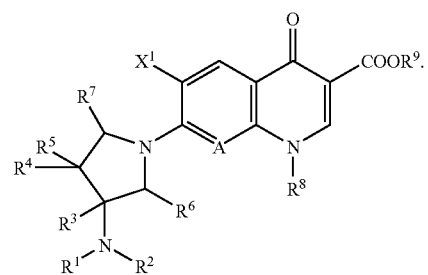

22 Claims, 4 Drawing Sheets

OTHER PUBLICATIONS

Clinical Applications of New-quinolone Agents, Iyaku-Journal-sha; 2001.
George G. Zhanel et al., "A Critical Review of the Fluoroquinolones"; Drugs, vol. 62, No. 1, pp. 13-59; 2002.
Ralf Stahlmann; "Clinical Toxicological Aspects of Fluoroquinolones", Toxicology Letters, vol. 127, pp. 269-277; 2002.
Scott G. Franzblau, et al., "Comparative in Vitro Activities of 20 Fluoroquinolones against Mycobacterium leprae", Antimicrobial Agents and Chemotherapy, Feb. 1990, vol. 34, No. 2, pp. 229-231.
Yasunori Tsuzuki, et al., "Synthesis and Structure-Activity Relationships of Novel 7-Substituted 1, 4-Dihydro-4-oxo-1-(2-thiazolyl)-1, 8-naphthyridine-3-carboxylic Acids as Antitumor Agents. Part 2", Journal of Medical Chemistry, vol. 47, No. 8, XP002475250, Apr. 8, 2004, pp. 2097-2109.

* cited by examiner

Comparative Compound 1

Compound of Example 9

TRI-, TETRA-SUBSTITUTED-3-AMINOPYRROLIDINE DERIVATIVE

BACKGROUND OF THE INVENTION

This invention relates to a quinolone synthetic antibacterial drug which is useful as a drug for human, animals, or fish, or as a antibacterial preservatives.

Since discovery of norfloxacin, antibacterial activity and pharmacokinetics of quinolone synthetic antibacterial drugs (including those containing pyridobenzoxazine skeleton) have been greatly improved, and, today, they are used in chemotherapy for infections including almost all systemic infections, and a large number of drugs are in clinical use.

However, a of bacteria exhibiting low sensitivity for quinolone synthetic antibacterial drugs have been recently increasing in its number in clinical field. For example, bacteria which are resistant to drugs other than quinolone synthetic antibacterial drugs, and which also exhibit low sensitivity to quinolone synthetic antibacterial drugs are increasing such as Gram positive coccus like *Staphylococcus aureus* (MRSA) and *pneumococcus* (PRSP) insensitive to β-Lactam antibiotics and *enterococcus* (VRE) insensitive to aminoglycoside antibacterial drugs. Accordingly, there is a strong clinical demand for a drug exhibiting an improved effectiveness to Gram positive coccus.

In the meanwhile, antibacterial activity of recently developed quinolone synthetic antibacterial compounds are by far stronger than former quinolone synthetic antibacterial compounds. However, many such quinolone compound having high antibacterial activity have been reported to produce side effects based on physiological or pharmacological action not observed in the former quinolone synthetic antibacterial compounds. For example, restrictions are imposed on the administration of some compounds due to side effects such as development of abnormal blood glucose level, cardiotoxicity, or delayed allergy, or development of convulsion, and development and use as a drug have been abandoned in some compounds. In other words, many compounds have been found to be insufficient in their suitability as a drug due to the strong side effects despite their high antibacterial activity. Accordingly, a drug design methodology which is different from former compounds is required to thereby prevent the situation that a highly antibacterial compound can not be developed as a drug due to production of side effects. In other words, a design methodology is required that is capable of producing a compound which has a considerably high antibacterial activity comparable or similar to those of the conventional compounds, and at the same time, which is provided with suitability for a drug that allows use of the compound as a drug, for example, high safety without side effects.

Exemplary side effects which have been reported for the quinolone synthetic antibacterial agents include induction of convulsion associated with concomitant, use of a nonsteroidal anti-inflammatory agent, central action (relatively light central nerve disorders such as reeling, headache, and insomnia as well as serious side effects such as development of lethal convulsion), phototoxicity (photosensitivity), hepatotoxicity, and cardiotoxicity (an abnormality observed as an abnormality of electrocardiogram which induces lethal arrhythmia), delayed allergy, and abnormal glucose blood level (see Non-patent documents 1 to 3).

Of the side effects as mentioned above, significant recently reported clinical cases involve cardiotoxicity (a heart abnormality inducing lethal arrhythmia which is observed as an abnormality of electrocardiogram with prolonged QT or QTc interval). Some commercially available quinolone antibacterial agents have been reported to produce clearly prolonged QT or QTc interval including some serious cases (abnormality of electrocardiogram inducing lethal arrhythmia) (Non-patent documents 1 to 3). Also reported are side effects such as induction of rash, which is a result of delayed allergy, and abnormal blood glucose level.

Accordingly, in order to enable use the quinolone antibacterial agent as a human or animal drug, there is a demand for a quinolone synthetic antibacterial agent which is provided with an improved safety with weaker side effects such as induction of convulsion associated with concomitant use of a nonsteroidal anti-inflammatory agent, central action, phototoxicity (photosensitivity), and hepatotoxicity, as well as side effects such as cardiotoxicity, delayed allergy, and abnormal glucose blood level. In other words, there is a strong demand for a quinolone compound simultaneously provided with a strong antibacterial activity and selective toxicity.

[Patent Document 1] Japanese Patent Application Laid-Open No. (JP-A) 61-282382
[Patent Document 2] JP-A 63-4526-1
[Patent Document 3] JP-A 2-231475
[Patent Document 4] JP-A 3-95176
[Non-patent Document 1] Hiroyuka Kobayashi Ed., "Clinical Applications of New-quinolone Agents", Iyaku-Journal-Sha (2001)
[Non-patent Document 2] Drugs, Vol. 62, No. 1, page 13 (2002)
[Non-patent Document 3] Toxicology Letters, Vol. 127, page 269 (2002)

SUMMARY OF THE INVENTION

In view of the situation as described above, an object of the present invention is to provide a quinolone synthetic antibacterial agent and a therapeutic agent for an infection which exhibit broad spectrum and strong antibacterial activity for both Gram positive and Gram negative bacteria, and which are also highly safe.

The inventors of the present invention have conducted investigation by focusing on a compound which has 3-aminopyrrolidinyl group at position 7 or equivalent position of a quinolone compound. In the course of the investigation, the inventors found that a quinolone compound having an 3-aminopyrrolidinyl group which is tri- or tetra-substituted at positions 3 and 4 represented by the following formula:

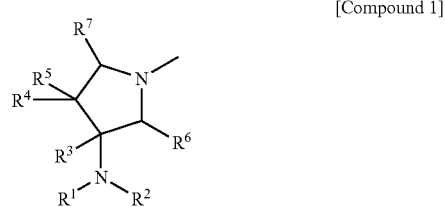

[Compound 1]

which has substituent which is typically an aliphatic substituent on the carbon atom at position 3, and one or two substituents which are also typically an aliphatic substituent on the carbon atom at position 4 has a broad spectrum of strong antibacterial activity for Gram-positive and Gram-negative bacteria including drug resistant Gram positive cocci such as multiple drug resistant pneumococcus having the resistance for quinolone. The inventors also found that such quinolone compound has not only such high antibacterial activity but also lower cardiotoxicity compared to the quinolone antibacterial drugs whose cardiotoxicity has recently been reported in clinical practice as a side effect of the quinolone antibacterial drugs. It was also found that this compound has reduced risk of producing side effects such as delayed allergy and abnormal blood glucose level. It was also found that this compound has excellent oral absorptivity, organ permeability, and excretion rate in urine. Accordingly, the inventors of the present invention have found that the quinolone compound represented by formula (I) is a quinolone synthetic antibacterial drug which has excellent drug properties including excellent antibacterial activity and high safety, and also excellent pharmacokinetics. The present invention has been completed on the bases of such findings.

Accordingly, the present invention provides a compound represented by following formula (I):

[Compound 2]

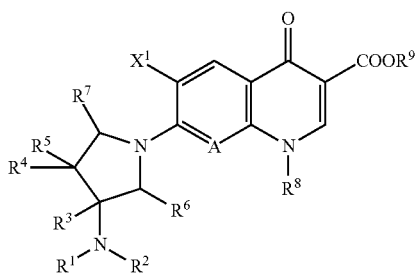

I or a salt or a hydrate thereof, wherein $R^1$ represents hydrogen atom, an alkyl group containing 1 to 6 carbon atoms, a cycloalkyl group (cyclic alkyl group) containing 3 to 6 carbon atoms, or a substituted carbonyl group derived from an amino acid, a dipeptide, or a tripeptide; the alkyl group being optionally substituted with a substituent selected from the group consisting of hydroxy group, amino group, halogen atom, an alkylthio group containing 1 to 6 carbon atoms, and an alkoxy group containing 1 to 6 carbon atoms;

$R^2$ represents hydrogen atom, an alkyl group containing 1 to 6 carbon atoms, or a cycloalkyl group containing 3 to 6 carbon atoms; the alkyl group being optionally substituted with a substituent selected from the group consisting of hydroxy group, amino group, halogen atom, an alkylthio group containing 1 to 6 carbon atoms, and an alkoxy group containing 1 to 6 carbon atoms;

$R^3$ represents an alkyl group containing 1 to 6 carbon atoms, a cycloalkyl group containing 3 to 6 carbon atoms, an alkenyl group containing 2 to 6 carbon atoms, or an alkynyl group containing 2 to 6 carbon atoms; the alkyl group being optionally substituted with a substituent selected from the group consisting of hydroxy group, amino group, halogen atom, an alkylthio group containing 1 to 6 carbon atoms, and an alkoxy group containing 1 to 6 carbon atoms;

$R^4$ and $R^5$ independently represent hydrogen atom, halogen atom, an alkyl group containing 1 to 6 carbon atoms, an alkoxy group containing 1 to 6 carbon atoms, an alkenyl group containing 2 to 6 carbon atoms, an alkynyl group containing 2 to 6 carbon atoms, or an optionally substituted cycloalkyl group containing 3 to 6 carbon atoms; the alkyl group, the alkoxy group, the alkenyl group, and the alkynyl group being either a straight chain or branched group; the alkyl group being optionally substituted with a substituent selected from the group consisting of hydroxy group, amino group, halogen atom, an alkylthio group containing 1 to 6 carbon atoms, and an alkoxy group containing 1 to 6 carbon atoms; and with the proviso that $R^4$ and $R^5$ are not simultaneously hydrogen atom; or the substituents $R^4$ and $R^5$ combine together to form (a) a 3- to 6-membered cyclic structure including the carbon atom shared by $R^4$ and $R^5$ to form a spirocyclic structure with the pyrrolidine ring, the thus formed spiro ring optionally containing oxygen atom or sulfur atom as a ring member atom, and optionally being substituted with a halogen atom or an alkyl group containing 1 to 6 carbon atoms optionally having a substituent; or (b) exomethylene group bonding to the pyrrolidine ring by double bond, the exomethylene group optionally having 1 or 2 substituents selected from hydroxy group, amino group, halogen atom, an alkylthio group containing 1 to 6 carbon atoms, and an alkoxy group containing 1 to 6 carbon atoms;

$R^6$ and $R^7$ independently represent hydrogen atom or an alkyl group containing 1 to 6 carbon atoms;

$R^8$ represents a halogen-substituted alkyl group containing 1 to 6 carbon atoms, a halogen-substituted cycloalkyl group containing 3 to 6 carbon atoms, a halogen-substituted phenyl group, or a halogen-substituted heteroaryl group;

$R^9$ represents hydrogen atom, phenyl group, acetoxymethyl group, pivaloyl oxymethyl group, ethoxycarbonyl group, choline group, dimethyl aminoethyl group, 5-indanyl group, phthalidinyl group, 5-alkyl-2-oxo-1,3-dioxol-4-ylmethyl group, 3-acetoxy-2-oxobutyl group, an alkyl group containing 1 to 6 carbon atoms, an alkoxymethyl group containing 2 to 7 carbon atoms, or a phenylalkyl group comprising an alkylene group containing 1 to 6 carbon atoms and phenyl group;

$X^1$ represents hydrogen atom or a halogen atom; and

A represents nitrogen atom or a moiety represented by formula (II):

[Compound 3]

II wherein $X^2$ represents hydrogen atom, an alkyl group containing 1 to 6 carbon atoms, an alkoxy group containing 1 to 6 carbon atoms, cyano group, halogen atom, a halogen-substituted methyl group, or a halogenomethoxy group; or $X^2$ and $R^8$ may combine together to form a cyclic structure including a part of the mother nucleus, the thus formed ring optionally containing oxygen atom, nitrogen atom, or sulfur atom as a ring constituting atom, and optionally being substituted with an alkyl group containing 1 to 6 carbon atoms optionally having a substituent.

The present invention also provides a drug containing the compound represented by the formula (E) or a salt or a hydrate thereof represented by the formula (I) as its effective ingredient.

The present invention also provides a method for treating a disease by administering the compound represented by the formula (I) or a salt or a hydrate thereof. The present invention also provides use of the compound represented by the formula (I) or a salt or a hydrate thereof for producing a drug.

The present invention provides a quinolone synthetic drug which has excellent drug properties such as strong antibacterial activity not only for Gram negative bacteria but also for Gram-positive cocci which have become less sensitive to quinolone antibacterials, high safety, and favorable pharmacokinetics.

DISCLOSURE OF THE INVENTION

Figure 1:
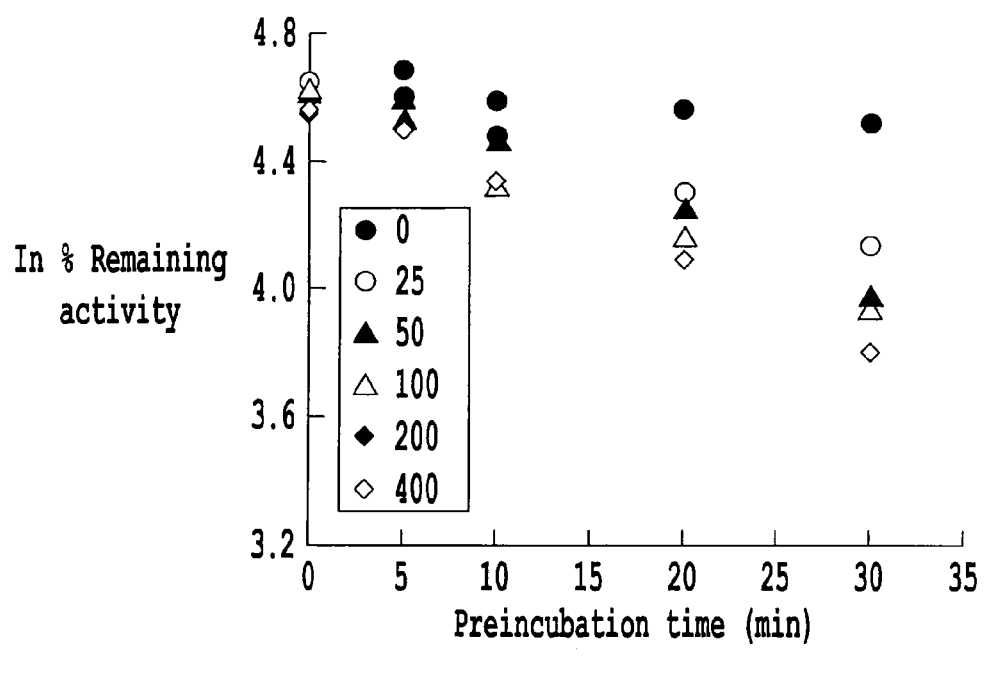
FIG. 1 is a graph showing MBI action of Comparative compound 1 and the compound of Example 9 against CYP3A4.
Figure 1:
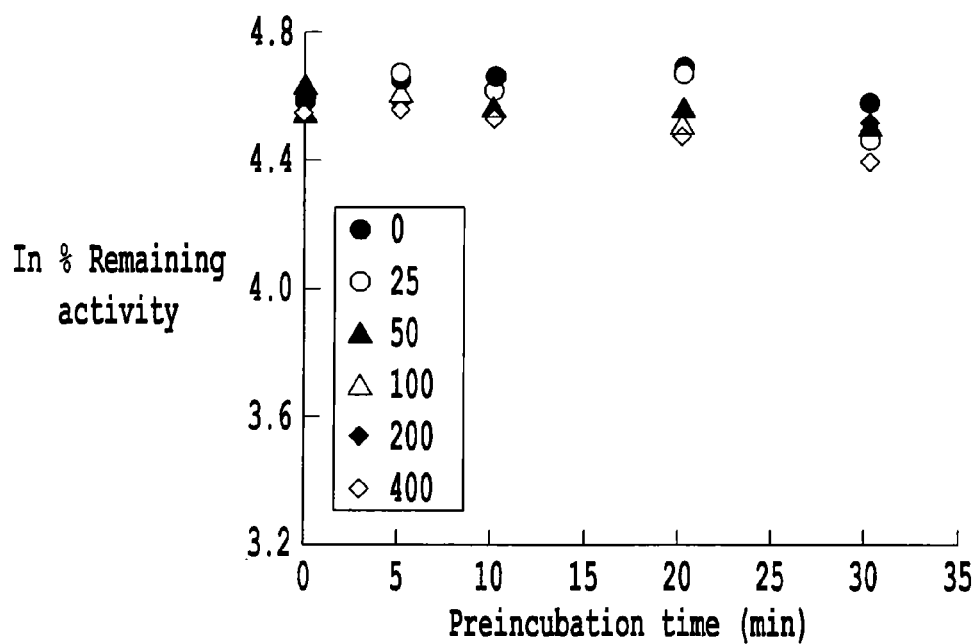

First, the substituents of the formula (I) are described.

$R^1$ represents hydrogen atom, an alkyl group containing 1 to 6 carbon atoms, a cycloalkyl group containing 3 to 6 carbon atoms, or a substituted carbonyl group derived from an amino acid, a dipeptide, or a tripeptide. When $R^1$ is an alkyl group, it may be substituted with a substituent selected from the group consisting of hydroxy group, amino group, halogen atom, an alkylthio group containing 1 to 6 carbon atoms, and an alkoxy group containing 1 to 6 carbon atoms.

$R^2$ represents hydrogen atom, an alkyl group containing 1 to 6 carbon atoms, or a cycloalkyl group containing 3 to 6 carbon atoms. When $R^2$ is an alkyl group, it may be substituted with a substituent selected from the group consisting of hydroxy group, amino group, halogen atom, an alkylthio group containing 1 to 6 carbon atoms, and an alkoxy group containing 1 to 6 carbon atoms.

When $R^1$ or $R^2$ is an alkyl group, the alkyl group may be either a straight chain or a branched alkyl group. The alkyl group is preferably methyl group, ethyl group, propyl group, or isopropyl group, and more preferably, methyl group or ethyl group, and most preferably methyl group.

When $R^1$ or $R^2$ is an alkyl group having hydroxy group or amino group as its substituent, the alkyl group may be any straight chain or branched alkyl containing 1 to 6 carbon atoms, and the alkyl group is preferably substituted with the substituent at its terminal carbon atom. The alkyl group having hydroxy group is preferably an alkyl group containing up to 3 carbon atoms, and preferable examples include hydroxymethyl group, 2-hydroxyethyl group, 2-hydroxypropyl group, and 3-hydroxypropyl group. The alkyl group having amino group is preferably an alkyl group containing up to 3 carbon atoms, and preferable examples include aminomethyl group, 2-aminoethyl group, 2-aminopropyl group, and 3-aminopropyl group.

When $R^1$ or $R^2$ is an alkyl group having a halogen atom as its substituent, the alkyl group may be any of the straight chain or branched alkyl groups containing 1 to 6 carbon atoms, and the halogen atom is preferably fluorine atom. The number of the fluorine substitution is not limited and the substitution may be mono- to perfluoro substitution. Exemplarily preferable substituents as halogenated alkyl group are halogen-substituted alkyl groups include monofluoromethyl group, difluoromethyl group, trifluoromethyl group, and 2,2,2-trifluoroethyl group.

When $R^1$ or $R^2$ is an alkyl group having an alkylthio group or an alkoxy group as its substituent, the alkyl group may be either a straight chain or a branched alkyl group, and the alkyl moiety of the alkylthio group and the alkoxy group may also be either a straight chain or a branched alkyl moiety. Exemplary alkyl groups having an alkylthio group include an alkylthiomethyl group, an alkylthioethyl group, and an alkylthiopropyl group, and the alkylthio group in such groups is preferably the one containing 1 to 3 carbon atoms. More preferable are methylthiomethyl group, ethylthiomethyl group, and methylthioethyl group. Exemplary alkyl groups having an alkoxy group include an alkoxymethyl group, an alkoxyethyl group, and an alkoxypropyl group, and the alkoxy group in such groups is preferably the one containing 1 to 3 carbon atoms. More preferable are methoxymethyl group, ethoxymethyl group, and methoxyethyl group.

When $R^1$ or $R^2$ is a cycloalkyl group, it is preferably cyclopropyl group or cyclobutyl group, and more preferably, cyclopropyl group. Substituent of the cycloalkyl group may be one or more group selected from an alkyl group containing 1 to 6 carbon atoms, halogen atom, amino group, and hydroxy group, and examples of the preferable substituent include methyl group, ethyl group, fluorine atom, chlorine atom, amino group, and hydroxy group.

Preferable combination of $R^1$ and $R^2$ include the combination wherein $R^P$ is hydrogen atom, an alkyl group, a cycloalkyl group, or a substituted carbonyl group derived from an amino acid, a dipeptide, or a tripeptide and $R^2$ is hydrogen atom. Among these, the preferable combination is the one wherein $R^1$ is hydrogen atom, an alkyl group, or a cycloalkyl group, and $R^2$ is hydrogen atom. The alkyl group in such case is preferably methyl group or ethyl group, and more preferably, methyl group. The cycloalkyl group is preferably cyclopropyl group or cyclobutyl group, and more preferably cyclopropyl group. The combination of $R^1$ and $R^2$ is more preferably the combination wherein both $R^1$ and $R^2$ are hydrogen atom, or the combination wherein one of $R^1$ and $R^2$ is hydrogen atom, and the other is methyl group, ethyl group, fluoroethyl group, or cyclopropyl group.

A quinolone derivative wherein $R^1$ is a substituted carbonyl group derived from an amino acid, a dipeptide, or a tripeptide, and $R^2$ is hydrogen atom is useful as a prodrug. The amino acid, dipeptide, or tripeptide used in producing such a prodrug is the one which is capable of producing a free amine compound by cleavage in the living body of the peptide bond between the carboxyl group and the amino group having $R^1$ and $R^2$ bonded thereto. Examples of the substituted carbonyl group used in producing such a prodrug include substituted carbonyl substituents derived from an amino acid such as glycine, alanine, or aspartic acid; a dipeptide constituted from glycine, alanine, or asparagine such as glycine-glycine, glycine-alanine, or alanine-alanine; and a tripeptide constituted from glycine, alanine, or asparagine such as glycine-glycine-alanine, or glycine-alanine-alanine.

$R^3$ represents an alkyl group containing 1 to 6 carbon atoms, a cycloalkyl group containing 3 to 6 carbon atoms, an alkenyl group containing 2 to 6 carbon atoms, or an alkynyl group containing 2 to 6 carbon atoms. When $R^3$ is an alkyl group, it may be optionally substituted with a substituent selected from the group consisting of hydroxy group, amino group, halogen atom, an alkylthio group containing 1 to 6 carbon atoms, and an alkoxy group containing 1 to 6 carbon atoms.

When $R^3$ is an alkyl group, the alkyl group may be either a straight chain or a branched alkyl group. The alkyl group is preferably methyl group, ethyl group, propyl group, or isopropyl group. Among these, the preferred is methyl group or ethyl group, and the more preferred is methyl group.

The cycloalkyl group containing 3 to 6 carbon atoms is preferably cyclopropyl group or cyclobutyl group, and more preferably cyclopropyl group.

The alkenyl group containing 2 to 6 carbon atoms is preferably the one having one double bond, which is not particularly limited for its location. The preferred are vinyl group, propenyl group, and butenyl group. The alkynyl group containing 2 to 6 carbon atoms is also preferably the one containing one triple bond, which is not particularly limited for its location. The preferred are ethynyl group, propynyl, and butynyl. Among those mentioned above, the preferred are vinyl group and ethynyl group.

When $R^3$ is an alkyl group, it may be optionally substituted with a substituent selected from the group consisting of hydroxy group, amino group, halogen atom, an alkylthio group containing 1 to 6 carbon atoms, and an alkoxy group containing 1 to 6 carbon atoms.

When the substituent of the alkyl group is hydroxy group or amino group, the alkyl group is preferably substituted with such substituent at the terminal carbon atom. Preferable examples of the alkyl group having hydroxy group are hydroxymethyl group, 2-hydroxyethyl group, 2-hydroxypropyl group, and 3-hydroxypropyl group, and preferable examples of the alkyl group having amino group are aminomethyl group, 2-aminoethyl group, 2-aminopropyl group, and 3-aminopropyl group. The alkyl group having the hydroxy group or the amino group is preferably methyl group or ethyl group having such group, and more preferably methyl group having such group, for example, hydroxymethyl group or aminomethyl group.

When the alkyl group has a halogen atom as its substituent, the alkyl group may be any of the straight chain or branched alkyl groups containing 1 to 6 carbon atoms. The preferred is methyl group or ethyl group having a halogen atom, and the more preferred is methyl group having a halogen atom. Preferable halogen atom is fluorine atom. The number of the fluorine substitution is not limited and the substitution may be mono- to perfluoro substitution. Exemplary halogen-substituted alkyl groups include monofluoromethyl group, difluoromethyl group, trifluoromethyl group, and 2,2,2-trifluoroethyl group, and the preferred is monofluoromethyl group, difluoromethyl group, and trifluoromethyl group.

When the substituent of the alkyl group is an alkylthio group or an alkoxy group, the alkyl group may be either a straight chain or a branched alkyl group, and the alkyl moiety in the alkylthio group or the alkoxy group may also be either a straight chain or a branched alkyl group. The alkyl group having an alkylthio group is preferably an alkylthiomethyl group or an alkylthioethyl group, and the alkylthio group is preferably the one containing 1 or 2 carbon atoms. The preferred are methylthiomethyl group, ethylthiomethyl group, and methylthioethyl group. The alkyl group having an alkoxy group is preferably an alkoxymethyl group or an alkoxyethyl group, and the alkoxy group is preferably the one containing 1 or 2 carbon atoms. The preferred are methoxymethyl group, ethoxymethyl group, and methoxyethyl group. The more preferred are methylthiomethyl group and methoxymethyl group.

When $R^3$ is a cycloalkyl group, the substituent is one or more group selected from the group consisting of an alkyl group containing 1 to 6 carbon atoms, halogen atom, amino group, and hydroxy group. Preferable examples of such substituent are methyl group, ethyl group, fluorine atom, and chlorine atom.

Preferable examples of $R^3$ include those containing 1 or 2 carbon atoms such as methyl group; ethyl group; vinyl group; fluoro-substituted methyl group or ethyl group; methyl group or ethyl group having amino group or hydroxy group; and methyl group having thiomethyl group or methoxy group. $R^3$ is most preferably methyl group or ethyl group.

$R^4$ and $R^5$ independently represent hydrogen atom, halogen atom, an alkyl group containing 1 to 6 carbon atoms, an alkoxy group containing 1 to 6 carbon atoms, an alkenyl group containing 2 to 6 carbon atoms, an alkynyl group containing 2 to 6 carbon atoms, or an optionally substituted cycloalkyl group containing 3 to 6 carbon atoms. When $R^4$ or $R^5$ is an alkyl group, it may be substituted with a substituent selected from the group consisting of hydroxy group, amino group, halogen atom, an alkylthio group containing 1 to 6 carbon atoms, and an alkoxy group containing 1 to 6 carbon atoms. $R^4$ and $R^5$ are not simultaneously hydrogen atom.

$R^4$ and $R^5$ may also combine together to form
(a) a 3- to 6-membered cyclic structure including the carbon atom shared by $R^4$ and $R^5$ to form a spirocyclic structure with the pyrrolidine ring, the thus formed spiro ring optionally containing oxygen atom or sulfur atom as a ring member atom, and optionally being substituted with a halogen atom or an alkyl group containing 1 to 6 carbon atoms optionally having a substituent; or
(b) exomethylene group bonding to the pyrrolidine ring by double bond, the exomethylene group optionally having 1 or 2 substituents selected from hydroxy group, amino group, halogen atom, an alkylthio group containing 1 to 6 carbon atoms, and an alkoxy group containing 1 to 6 carbon atoms.

When $R^4$ or $R^5$ is an alkyl group, it may be either a straight chain or a branched alkyl group, and it may be methyl group, ethyl group, propyl group, or isopropyl group; more preferably methyl group or ethyl group; and most preferably methyl group.

When $R^4$ or $R^5$ is an alkyl group and this alkyl has hydroxy group or amino group as its substituent, the alkyl group is preferably substituted with such substituent at its terminal carbon atom. The alkyl group having hydroxy group is preferably the one containing up to 3 carbon atoms, and preferable examples include hydroxymethyl group, 2-hydroxyethyl group, 2-hydroxypropyl group, and 3-hydroxypropyl group. The alkyl group having amino group is preferably the one containing up to 3 carbon atoms, and preferable examples include aminomethyl group, 2-aminoethyl group, 2-aminopropyl group, and 3-aminopropyl group.

When $R^4$ or $R^5$ is an alkyl group and this alkyl group has a halogen atom as its substituent, the alkyl group may be either a straight chain or a branched alkyl group containing 1 to 6 carbon atoms, and the halogen atom is preferably fluorine atom. The number of the fluorine substitution is not limited and the substitution may be mono- to perfluoro substitution. Exemplarily preferable substituents as halogenated alkyl group are halogen-substituted alkyl groups include monofluoromethyl group, difluoromethyl group, trifluoromethyl group, and 2,2,2-trifluoroethyl group.

When $R^4$ or $R^5$ is an alkyl group having an alkylthio group or an alkoxy group as its substituent, the alkyl group may be either a straight chain or a branched alkyl group, and the alkyl moiety in the alkylthio group or the alkoxy group may also be a straight chain or a branched alkyl group. The alkyl group having an alkylthio group is preferably an alkylthiomethyl group, an alkylthioethyl group, or an alkylthiopropyl group, and the alkylthio group is preferably the one containing 1 to 3 carbon atoms. More preferably, the alkyl group having an alkylthio group is methylthiomethyl group, ethylthiomethyl group, or methylthioethyl group. The alkyl group having an alkoxy group is preferably an alkoxymethyl group, an alkoxyethyl group, or an alkoxypropyl group, and the alkoxy group is preferably the one containing 1 to 3 carbon atoms.

More preferably, the alkyl group having an alkoxy group is methoxymethyl group, ethoxymethyl group, or methoxyethyl group.

When $R^4$ or $R^5$ is a cycloalkyl group, it is preferably cyclopropyl group or cyclobutyl group and more preferably cyclopropyl group. When $R^4$ or $R^5$ is a substituted cycloalkyl group, the substituent may be the same as the same case of $R^3$, and is at least one substituent selected from the group consisting of an alkyl group containing 1 to 6 carbon atoms, halogen atom, amino group, and hydroxy group. Preferable examples of such substituent are methyl group, ethyl group, fluorine atom, and chlorine atom.

When $R^4$ or $R^5$ is a halogen atom, it may be fluorine atom, chlorine atom, or iodine atom, and preferably, fluorine atom.

When $R^4$ or $R^5$ is an alkoxy group, it may be any of the alkoxy groups derived from the alkyl group as described above, and it is preferably an alkoxy group containing 1 to 3 carbon atoms. Exemplary such alkoxy groups include methoxy group and ethoxy group.

When $R^4$ or $R^5$ is an alkenyl group or an alkynyl group, these groups may be as defined above for $R^3$.

When $R^4$ and $R^5$ combine together to form a spirocyclic structure, $R^4$ and $R^5$ together form a polymethylene chain containing 2 to 5 carbon atoms and opposite ends of the thus formed polymethylene chain bind to the carbon atom having the $R^4$ and $R^5$ attached thereto to thereby for a cyclic structure. The thus formed ring may have a size of 3-membered ring to six-membered ring, and among these, the preferred are 3-membered ring or 4-membered ring, and the more preferred are 3-membered ring. The methylene group in the polymethylene chain may be replaced with oxygen atom or sulfur atom to form a saturated heterocycle. The ring formed by $R^4$ and $R^5$ is optionally substituted with a halogen atom or an optionally substituted alkyl group containing 1 to 6 carbon atoms. Exemplary halogen atoms include fluorine atom and chlorine atom. The alkyl group may be either a straight chain or a branched alkyl group, and the preferred are methyl group, ethyl group, propyl group, and isopropyl group, and the more preferred are methyl group or ethyl group. This alkyl group is optionally substituted with a substituent which is preferably a halogen atom.

When $R^4$ and $R^5$ together form an exomethylene group which binds to the pyrrolidine ring by double bond, a carbon-carbon double bond is formed by using the carbon atom at position 4 of the pyrrolidinyl group having the $R^4$ and $R^5$ attached thereto as one of the carbon atom. In such a case, the pyrrolidinyl substituent moiety has a structure represented by the following formula:

[Compound 4]

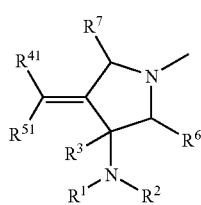

wherein $R^{41}$ and $R^{51}$, both represents hydrogen atoms, or one of them represents a hydrogen atom and the other represents a substituent selected from the group consisting of hydroxy group, amino group, halogen atom, an alkylthio group containing 1 to 6 carbon atoms, or an alkoxy group containing 1 to 6 carbon atoms.

When the substituent of the exomethylene group is alkylthio group or alkoxy group, the alkyl moiety thereof may be optionally substituted with a substituent selected from the group consisting of hydroxy group, amino group, halogen atom, an alkylthio group containing 1 to 6 carbon atoms, and an alkoxy group containing 1 to 6 carbon atoms. Among these, the an alkylthio group containing 1 to 6 carbon atoms or the an alkoxyl group containing 1 to 6 carbon atoms is preferably an alkylthio or alkoxy group containing 1 to 3 carbon atoms, more preferably, methylthio group, ethylthio group, methoxy group, or ethoxy grout, and still more preferably methylthio group or methoxy group.

Preferably, the exomethylene group is not substituted with a substituent other than hydrogen atom. However when the exomethylene group has a substituent, the substituent is preferably hydroxy group, amino group, fluorine atom, chlorine atom, methylthio group, or methoxy group.

Preferable combination of $R^4$ and $R^5$ is the one wherein one of $R^4$ and $R^5$ is hydrogen atom and the other is fluorine atom, methyl group, ethyl group, normal-propyl group, isopropyl group, normal-butyl group, cyclopropyl group, fluoromethyl group, methoxy group, vinyl group, or ethynyl group. Also preferred are $R^4$ and $R^5$ together forming cyclopropane ring or cyclobutane ring including the carbon atom shared by $R^4$ and $R^5$ to form a spirocyclic structure. Further, $R^4$ and $R^5$ preferably combine together forming an exoalkylene group containing 2 to 5 carbon atoms.

$R^4$ or $R^5$ is preferably a fluoroalkyl group, a fluoline atom, or spirocyclic structure or exomethylene group by the constructed by the combination of these $R^6$ and $R^7$ independently represent hydrogen atom or an alkyl group containing 1 to 6 carbon atoms. The alkyl group may be either a straight chain or a branched alkyl group, and the preferred are methyl group, ethyl group, propyl group, and isopropyl group. The more preferred are methyl group or ethyl group, and the most preferred is methyl group. Preferably, both $R^6$ and $R^7$ are hydrogen atom.

$R^8$ represents a halogen-substituted alkyl group containing 1 to 6 carbon atoms, a halogen-substituted cycloalkyl group containing 3 to 6 carbon atoms, a halogen-substituted phenyl group, or a halogen-substituted heteroaryl group.

When $R^8$ is a halogen-substituted alkyl group containing 1 to 6 carbon atoms, the alkyl group moiety may be either a straight chain or a branched group as exemplified by methyl group, ethyl group, propyl group, isopropyl group, butyl group, isobutyl group, sec-butyl group, and tert-butyl group. Among these, the preferred is ethyl group. The halogen atom substituting the alkyl group is preferably fluorine atom or chlorine atom, and more preferably fluorine atom. Examples of the halogen-substituted alkyl group include fluoromethyl group, 1-fluoroethyl group, and 2-fluoroethyl group, and the preferred is 2-fluoroethyl group.

When $R^8$ is a halogen-substituted cycloalkyl group containing 3 to 6 carbon atoms, exemplary cyclic alkyl group include cyclopropyl group, cyclobutyl group, and cyclopentyl group, and the preferred is cyclopropyl group. Exemplary substituent halogen atoms include fluorine atom and chlorine atom, and the preferred is fluorine atom. Mono-substitution with the halogen atom is sufficient, and the preferred is monofluorocyclopropyl group, and the more preferred is cis-monofluorocyclopropyl group.

The halogen atom in the halogen-substituted phenyl group is preferably fluorine atom or chlorine atom, and more preferably, fluorine atom. The substitution with the halogen atom is preferably a mono- or di-substitution. The halogen-substituted phenyl groups is preferably 2-fluorophenyl group, 4-fluorophenyl group, or 2,4-difluorophenyl group.

The heteroaryl group in the halogen-substituted heteroaryl group may be a five-membered or a six-membered aromatic heterocyclic group containing one or more heteroatoms selected from nitrogen atom, sulfur atom, and oxygen atom. Among such heteroaryl groups, the preferred is a five-membered or a six-membered nitrogen-containing aromatic heterocyclic group containing 1 or 2 nitrogen atoms. Exemplary such groups include pyridyl group, pyrimidyl group, piperidinyl group, pyrrolidinyl group, morpholinyl group, pyrrolyl group, imidazolyl group, pyrazolyl group, pyridyl group, pyrimidinyl group, pyridazinyl group, pyrrolidinyl group, pyrrolynyl group, imidazolidinyl group, imidazolinyl group, pyrazolidinyl group, pyrazolinyl group, piperidyl group, and piperazinyl group, and among these, the preferred is pyridyl group. The halogen atom is preferably fluorine atom or chlorine atom, and more preferably fluorine atom. The substitution with the halogen atom is preferably a mono- or di-substitution.

$R^8$ is preferably a halogen-substituted cycloalkyl group containing 3 to 6 carbon atoms, and preferably, a 2-halogenocyclopropyl group, and more preferably a 1,2-cis-2-halogenopropyl group, and particularly, a (1R,2S)-2-halogenocyclopropyl group. The more preferable is monofluorocyclopropyl group, and in particular, cis-monofluorocyclopropyl group. The most preferable is 1,2-cis-2-fluorocyclopropyl group, and in particular, (1R,2S)-2-fluorocyclopropyl group.

$R^9$ represents hydrogen atom, phenyl group, acetoxymethyl group, pivaloyl oxymethyl group, ethoxycarbonyl group, choline group, dimethyl aminoethyl group, 5-indanyl group, phthalidinyl group, 5-alkyl-2-oxo-1,3-dioxol-4-ylmethyl group, 3-acetoxy-2-oxobutyl group, an alkyl group containing 1 to 6 carbon atoms, an alkoxymethyl group containing 2 to 7 carbon atoms, or a phenylalkyl group comprising an alkylene group containing 1 to 6 carbon atoms and phenyl group.

$R^9$ is preferably hydrogen atom.

$X^1$ represents hydrogen atom or a halogen atom. Preferable halogen atom is fluorine atom or chlorine atom, and the more preferred is fluorine atom. $X^1$ is preferably fluorine atom or hydrogen atom.

A represents nitrogen atom or a moiety represented by formula (II):

[Compound 5]

II wherein $X^2$ represents an alkyl group containing 1 to 6 carbon atoms, an alkoxy group containing 1 to 6 carbon atoms, hydrogen atom, cyano group, halogen atom, a halogen-substituted methyl group, or a halogenomethoxy group. $X^2$ together with $R^8$ may combine together to form a cyclic structure including a part of the mother nucleus, and the thus formed ring may optionally contain oxygen atom, nitrogen atom, or sulfur atom as a ring member atom, and the ring may be substituted with an alkyl group containing 1 to 6 carbon atoms optionally having a substituent.

When A is a moiety represented by formula (II), and $X^2$ is an alkyl group containing 1 to 6 carbon atoms, $X^2$ may be either a straight chain or a branched alkyl group. Preferably, $X^2$ is methyl group, ethyl group, propyl group, or isopropyl group, and among these, the preferred are methyl group and ethyl group, and the more preferred is methyl group. When $X^2$ is an alkoxy group containing 1 to 6 carbon atoms, it may be any of the alkoxy group derived from the alkyl group as described above. Among those described above, $X^2$ is preferably an alkyl group containing 1 to 3 carbon atoms or an alkoxy group containing 1 to 3 carbon atoms, and more preferably methyl group or methoxy group.

When $X^2$ is a halogen atom, it is preferably fluorine atom or chlorine atom, and more preferably fluorine atom. When $X^2$ is a halogen-substituted methyl group, the halogen atom is preferably fluorine atom or chlorine atom, and more preferably fluorine atom. Exemplary halogen-substituted methyl groups include fluoromethyl group, difluoromethyl group, and trifluoromethyl group. Similarly, when $X^2$ is a halogenomethoxy group, the halogen atom is preferably fluorine atom or chlorine atom, and more preferably, fluorine atom. Exemplary halogenomethoxy groups include fluoromethoxy group, difluoromethoxy group, and trifluoromethoxy group.

When A is a moiety represented by formula (II), $X^2$ and $R^8$ may combine together to form a cyclic structure containing a part of the quinolone skeleton (3 atoms, namely, the carbon atom having $X^2$ bonded thereto; the nitrogen atom having $R^8$ bonded thereto; and the carbon atom between the nuclei having $X^2$ and $R^8$ bonded thereto). The ring formed may preferably have a size of 5 to 7-membered ring, and the ring may be either saturated or unsaturated. This cyclic structure may also contain oxygen atom, nitrogen atom, or sulfur atom as a constituent atom of the ring, and this cyclic structure may be further substituted with an alkyl group containing 1 to 6 carbon atoms as described above for $X^2$. The cyclic structure preferably contains oxygen atom, and it is preferably substituted with a methyl group. Such partial structure is preferably a structure represented by the formula: —O—$CH_2$—CH(—$CH_3$)— (the carbon atom at the right end binds to nitrogen atom).

When A is a moiety represented by formula (II), and the substituent $X^2$ does not form a cyclic structure, $X^2$ is preferably methyl group, ethyl group, methoxy group, difluoromethoxy group, cyano group, or chlorine atom, and most preferably methyl group, methoxy group, or difluoromethoxy group.

When A is a moiety represented by formula (II), and the substituent $X^2$ forms a cyclic structure, the preferred is the formation of 2,3-dihydro-3-methyl-7-oxo-7H-pyrido[1,2,3-de][1,4]benzoxazine-6-carboxylic acid skeleton, and in particular, 3-(S)-methylpyridobenzoxazine skeleton.

The compound of the present invention has a characteristic feature that it has a substituent represented by the following formula:

[Compound 6]

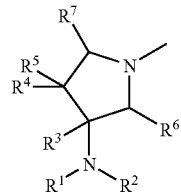

at position 7 (or at an equivalent position) of the quinoline skeleton.

In other words, compound of the present invention has a characteristic feature that amino group is present at position 3 of the pyrrolidinyl group; the carbon atom having this amino group bonded thereto has a substituent $R^3$ which is not hydrogen atom; and the carbon atom at position 4 is mono- or di-substituted. That is, position 3 of the 1-pyrrolidinyl group is di-substituted by a substituent including the 3-amino group; and position 4 is mono- or di-substituted; and accordingly, positions 3 and 4 are tri- or tetra-substituted.

This pyrrolidinyl group contains an asymmetric carbon atom, and accordingly, stereoisomers are present as described below. First, two stereoisomers:

[Compound 7]

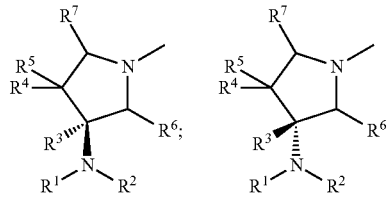

are present for the position 3.

When both $R^4$ and $R^5$ are not hydrogen atom (including the case when $R^4$ and $R^5$ together form a structure), the following structure:

[Compound 8]

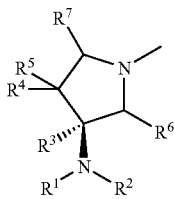

wherein the amino group is at β-configuration is preferred.

When either one of $R^4$ and $R^5$ is hydrogen atom, the following 4 types:

[Compound 9]

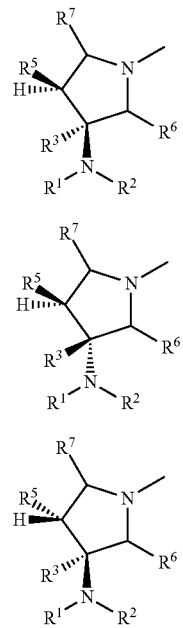

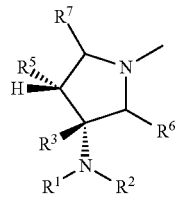

are present. The one having structure 1 is generally more preferable than the one having structure 4, while the actual preferable form changes according to the structure of the substituent $R^5$. All of the structures are within the scope of the present invention.

Preferable basic skeletons for the quinolone carboxylic acid having a substituent at position 7 are as shown below.

[Compound 10]

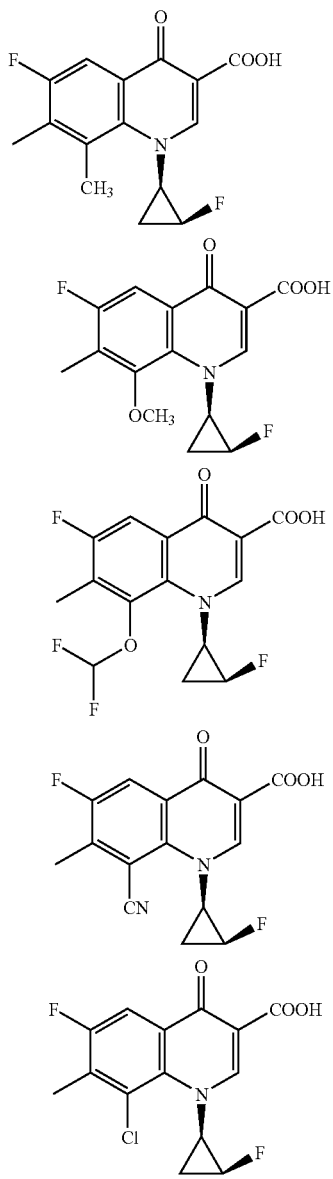

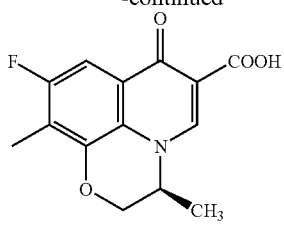

Preferable substituents at position 7 are as shown below.

[Compound 11]

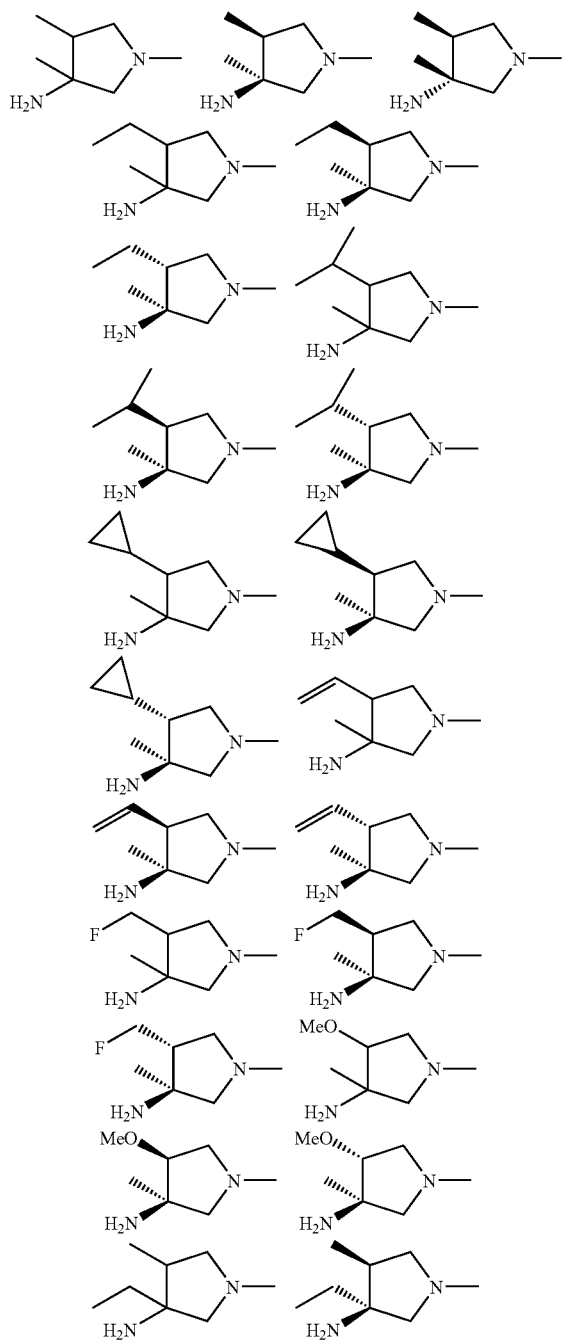
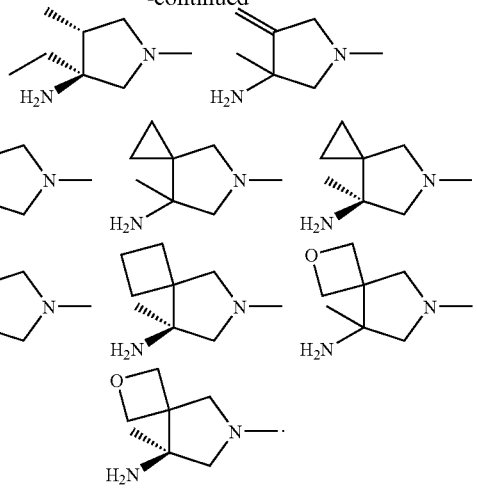

Accordingly, the preferable compound of the present invention is the quinolone carboxylic acid basic skeleton as mentioned above substituted with the substituent at position 7 as mentioned above (namely, the combination of the basic skeleton core and the substituent as mentioned above). In the formulae as shown above, absolute configuration at position 3 of the pyrrolidine ring substituted with the amino group is either 3R or 3S. Preferably, the compound of the present invention is stereochemically pure.

Preferred examples of the compound of the present invention is as described below.

7-[3-amino-3,4-dimethylpyrrolidine-1-yl]-6-fluoro-1-[(1R,2S)-2-fluorocyclopropyl]-1,4-dihydro-8-methyl-4-oxo-quinoline-3-carboxylic acid, or a salt or a hydrate thereof, 7-[3-amino-3,4-dimethylpyrrolidine-1-yl]-6-fluoro-1-[(1R,2S)-2-fluorocyclopropyl]-1,4-dihydro-8-methoxy-4-oxo-quinoline-3-carboxylic acid, or a salt or a hydrate thereof, (3S)-10-[3-amino-3,4-dimethylpyrrolidine-1-yl]-9-fluoro-2,3-dihydro-3-methyl-7-oxo-7H-pyrido[1.2.3-de][1,4]benzoxazine-6-carboxylic acid, or a salt or a hydrate thereof, 7-[3-amino-4-ethyl-3-methylpyrrolidine-1-yl]-6-fluoro-1-[(1R,2S)-2-fluorocyclopropyl]-1,4-dihydro-8-methyl-4-oxoquinoline-3-carboxylic acid, or a salt or a hydrate thereof, 7-[3-amino-4-ethyl-3-methylpyrrolidine-1-yl]-6-fluoro-1-[(1R,2S)-2-fluorocyclopropyl]-1,4-dihydro-8-methoxy-4-oxoquinoline-3-carboxylic acid, or a salt or a hydrate thereof, (3S)-10-[3-amino-4-ethyl-3-methylpyrrolidine-1-yl]-9-fluoro-2,3-dihydro-3-methyl-7-oxo-7H-pyrido[1.2.3-de][1,4]benzoxazine-6-carboxylic acid, or a salt or a hydrate thereof, 7-[3-amino-3-methyl-4-isopropyl pyrrolidine-1-yl]-6-fluoro-1-[(1R,2S)-2-fluorocyclopropyl]-1,4-dihydro-8-methyl-4-oxoquinoline-3-carboxylic acid, or a salt or a hydrate thereof, 7-[3-amino-3-methyl-4-isopropyl pyrrolidine-1-yl]-6-fluoro-1-[(1R,2S)-2-fluorocyclopropyl]-1,4-dihydro-8-methoxy-4-oxoquinoline-3-carboxylic acid, or a salt or a hydrate thereof, (3S)-10-[3-amino-3-methyl-4-isopropyl pyrrolidine-1-yl]-9-fluoro-2,3-dihydro-3-methyl-7-oxo-7H-pyrido[1.2.3-de][1,4]benzoxazine-6-carboxylic acid, or a salt or a hydrate thereof, 7-[3-amino-4-cyclopropyl-3-methylpyrrolidine-1-yl]-6-fluoro-1-[(1R,2S)-2-fluorocyclopropyl]-1,4-dihydro-8-methyl-4-oxoquinoline-3-carboxylic acid, or a salt or a hydrate thereof, 7-[3-amino-4-cyclopropyl-3-methylpyrrolidine-1-yl]-6-fluoro-1-[(1R,2S)-2-fluorocyclopropyl]-1,4-dihydro-8-methoxy-4-oxoquinoline-3-carboxylic acid, or a salt or a hydrate thereof, (3S)-10-[3-amino-4-cyclopropyl-3-methylpyrrolidine-1-yl]-9-fluoro-2,3-dihydro-3-methyl-7-oxo-7H-pyrido[1.2.3-de][1,4]benzoxazine-6-carboxylic acid, or a salt or a hydrate thereof, 7-[3-amino-3-methyl-4-vinylpyrrolidine-1-yl]-6-fluoro-1-[(1R,2S)-2-fluorocyclopropyl]-1,4-dihydro-8-methyl-4-oxoquinoline-3-carboxylic acid, or a salt or a hydrate thereof, 7-[3-amino-3-methyl-4-vinylpyrrolidine-1-yl]-6-fluoro-1-[(1R,2S)-2-fluorocyclopropyl]-1,4-dihydro-8-methoxy-4-oxoquinoline-3-carboxylic acid, or a salt or a hydrate thereof, (3S)-10-[3-amino-3-methyl-4-vinylpyrrolidine-1-yl]-9-fluoro-2,3-dihydro-3-methyl-7-oxo-7H-pyrido[1.2.3-de][1,4]benzoxazine-6-carboxylic acid, or a salt or a hydrate thereof, 7-[3-amino-4-methylene-3-methylpyrrolidine-1-yl]-6-fluoro-1-[(1R,2S)-2-fluorocyclopropyl]-1,4-dihydro-8-methyl-4-oxoquinoline-3-carboxylic acid, or a salt or a hydrate thereof, 7-[3-amino-4-methylene-3-methylpyrrolidine-1-yl]-6-fluoro-1-[(1R,2S)-2-fluorocyclopropyl]-1,4-dihydro-8-methoxy-4-oxoquinoline-3-carboxylic acid, or a salt or a hydrate thereof, (3S)-10-[3-amino-4-methylene-3-methylpyrrolidine-1-yl]-9-fluoro-2,3-dihydro-3-methyl-7-oxo-7H-pyrido[1.2.3-de][1,4]benzoxazine-6-carboxylic acid, or a salt or a hydrate thereof, 7-[3-amino-4-fluoromethyl-3-methylpyrrolidine-1-yl]-6-fluoro-1-[(1R,2S)-2-fluorocyclopropyl]-1,4-dihydro-8-methyl-4-oxoquinoline-3-carboxylic acid, or a salt or a hydrate thereof, 7-[3-amino-4-fluoromethyl-3-methylpyrrolidine-1-yl]-6-fluoro-1-[(1R,2S)-2-fluorocyclopropyl]-1,4-dihydro-8-methoxy-4-oxoquinoline-3-carboxylic acid, or a salt or a hydrate thereof, (3S)-10-[3-amino-4-fluoromethyl-3-methylpyrrolidine-1-yl]-9-fluoro-2,3-dihydro-3-methyl-7-oxo-7H-pyrido[1.2.3-de][1,4]benzoxazine-6-carboxylic acid, or a salt or a hydrate thereof, 7-[(3R)-3-amino-3-methyl-4-methylene pyrrolidine-1-yl]-6-fluoro-1-[(1R,2S)-2-fluorocyclopropyl]-8-methoxy-1,4-dihydro-4-oxoquinoline-3-carboxylic acid, or a salt or a hydrate thereof, 7-(3-amino-4-methoxy-3-methylpyrrolidine-1-yl)-6-fluoro-1-[(1R,2S)-2-fluorocyclopropyl]-8-methyl-1,4-dihydro-4-oxoquinoline-3-carboxylic acid, or a salt or a hydrate thereof, 7-(3-amino-4-methoxy-3-methylpyrrolidine-1-yl)-6-fluoro-1-[(1R,2S)-2-fluorocyclopropyl]-8-methoxy-1,4-dihydro-4-oxoquinoline-3-carboxylic acid, or a salt or a hydrate thereof, 7-[(3S,4S)-3-amino-4-fluoromethyl-3-methylpyrrolidine-1-yl]-6-fluoro-1-[(1R,2S)-2-fluoro-1-cyclopropyl]-8-methoxy-1,4-dihydro-4-oxoquinoline-3-carboxylic acid, or a salt or a hydrate thereof, 7-[(3S,4S)-3-amino-4-fluoromethyl-3-methylpyrrolidine-1-yl]-1-cyclopropyl-6-fluoro-8-methoxy-1,4-dihydro-4-oxoquinoline-3-carboxylic acid, or a salt or a hydrate thereof, 7-[(3S,4S)-3-amino-4-fluoromethyl-3-methylpyrrolidine-1-yl]-6-fluoro-1-[(1R,2S)-2-fluoro-1-cyclopropyl]-8-methyl-1,4-dihydro-4-oxoquinoline-3-carboxylic acid, or a salt or a hydrate thereof, 7-[(3S,4S)-3-amino-4-fluoromethyl-3-methylpyrrolidine-1-yl]-1-cyclopropyl-6-fluoro-8-methyl-1,4-dihydro-4-oxoquinoline-3-carboxylic acid, or a salt or a hydrate thereof, 7-[(3R)-3-amino-4-fluoro-3-methylpyrrolidine-1-yl]-6-fluoro-1-[(1R,2S)-2-fluoro-1-cyclopropyl]-8-methoxy-1,4-dihydro-4-oxoquinoline-3-carboxylic acid, or a salt or a hydrate thereof, 7-[(3R)-3-amino-4-fluoro-3-methylpyrrolidine-1-yl]-6-fluoro-1-[(1R,2S)-2-fluoro-1-cyclopropyl]-8-methyl-1,4-dihydro-4-oxoquinoline-3-carboxylic acid, or a salt or a hydrate thereof, 7-[(3S)-3-amino-3-fluoromethyl-4-methylpyrrolidine-1-yl]-6-fluoro-1-[(1R,2S)-2-fluoro-1-cyclopropyl]-8-methoxy-1,4-dihydro-4-oxoquinoline-3-carboxylic acid, or a salt or a hydrate thereof, 7-[(3S)-3-amino-3-fluoromethyl-4-methylpyrrolidine-1-yl]-6-fluoro-1-[(1R,2S)-2-fluoro-1-cyclopropyl]-8-methyl-1,4-dihydro-4-oxoquinoline-3-carboxylic acid, or a salt or a hydrate thereof, 7-[7-amino-7-methyl-5-azaspiro[2.4]heptane-5-yl]-6-fluoro-1-[(1R,2S)-2-fluorocyclopropyl]-1,4-dihydro-8-methyl-4-oxoquinoline-3-carboxylic acid, or a salt or a hydrate thereof, 7-[7-amino-7-methyl-5-azaspiro[2.4]heptane-5-yl]-6-fluoro-1-[(1R,2S)-2-fluorocyclopropyl]-1,4-dihydro-8-methoxy-4-oxoquinoline-3-carboxylic acid, or a salt or a hydrate thereof, (3S)-10-[7-amino-7-methyl-5-azaspiro[2.4]heptane-5-yl]-9-benzoxazine-6-carboxylic acid, or a salt or a hydrate thereof, 7-[8-amino-8-methyl-6-azaspiro[3.4]octane-5-yl]-6-fluoro-1-[(1R,2S)-2-fluorocyclopropyl]-1,4-dihydro-8-methyl-4-oxoquinoline-3-carboxylic acid, or a salt or a hydrate thereof, 7-[8-amino-8-methyl-6-azaspiro[3.4]octane-5-yl]-6-fluoro-1-[(1R,2S)-2-fluorocyclopropyl]-1,4-dihydro-8-methoxy-4-oxoquinoline-3-carboxylic acid, or a salt or a hydrate thereof, (3S)-10-[8-amino-8-methyl-6-azaspiro[3.4]octane-5-yl]-9fluoro-2,3-dihydro-3-methyl-7-oxo-7H-pyrido[1.2.3-de][1,4]-benzoxazine-6-carboxylic acid, or a salt or a hydrate thereof, 7-[(7S)-7-amino-7-methyl-5-azaspiro[2.4]heptane-5-yl]-1-[(1R,2S)-2-fluorocyclopropyl]-8-methyl-1,4-dihydro-4-oxoquinoline-3-carboxylic acid, or a salt or a hydrate thereof, 7-[(7S)-7-amino-7-methyl-5-azaspiro[2.4]heptane-5-yl]-1-cyclopropyl-8-methyl-1,4-dihydro-4-oxoquinoline-3-carboxylic acid, or a salt or a hydrate thereof, 7-[(7S)-7-amino-7-methyl-5-azaspiro[2.4]heptane-5-yl]-1-[(1R,2S)-2-fluorocyclopropyl]-8-methoxy-1,4-dihydro-4-oxoquinoline-3-carboxylic acid, or a salt or a hydrate thereof, 7-[(7S)-7-amino-7-methoxy-5-azaspiro[2.4]heptane-5-yl]-1-cyclopropyl-8-methyl-1,4-dihydro-4-oxoquinoline-3-carboxylic acid, or a salt or a hydrate thereof.

Next, method for synthesizing 3-amino-3-aliphatic hydrocarbon-substituted-4-aliphatic hydrocarbon-substituted pyrrolidine derivative which is relevant with the present invention is described. Typical example of the 3-amino-3-aliphatic hydrocarbon-substituted-4-aliphatic hydrocarbon-substituted pyrrolidine derivative is 3-amino-3-aliphatic hydrocarbon-substituted-4-aliphatic hydrocarbon-substituted pyrrolidine-1-yl group such as 3-amino-3-methyl-4-alkyl-substituted pyrrolidine-1-yl group.

3-Amino-3-methyl-4-alkyl-substituted pyrrolidine derivative (8) which is a typical substituent compound in the present invention can be produced by synthesizing an important intermediate by 1,3-dipolar cycloaddition using 3-substituted crotonate ester (1) and azomethine ylide (2) for the reaction block, followed by hydrolysis of the ester moiety and conversion into amine. Although the inventors of the present invention selected tertiary butoxycarbonyl group for the protective group of the amine moiety at position 3, the protective group of the amine moiety at position 3 is not limited to the tertiary butoxycarbonyl group as long as the selected protective group does not affect the subsequent reaction steps and is easily deprotected later, and a protective group which is the same as the protective group at position 1 may also be used. Synthesis of the optically active compound can be conducted, for example, by optical resolution using an appropriate intermediate, for example, by HPLC resolution using a chiral column of the appropriate intermediate, preferential crystallization of the diastereomer salt, or by bonding chiral building block to an appropriate intermediate to produce a diastereomer, separating the diastereomer by using an appropriate separation technique such as silica gel chromatography, and removing the chiral building block to produce an optically active substance. Alternatively, the optically active compound may be synthesized by using the chiral building block for the starting material.

[Compound 12]

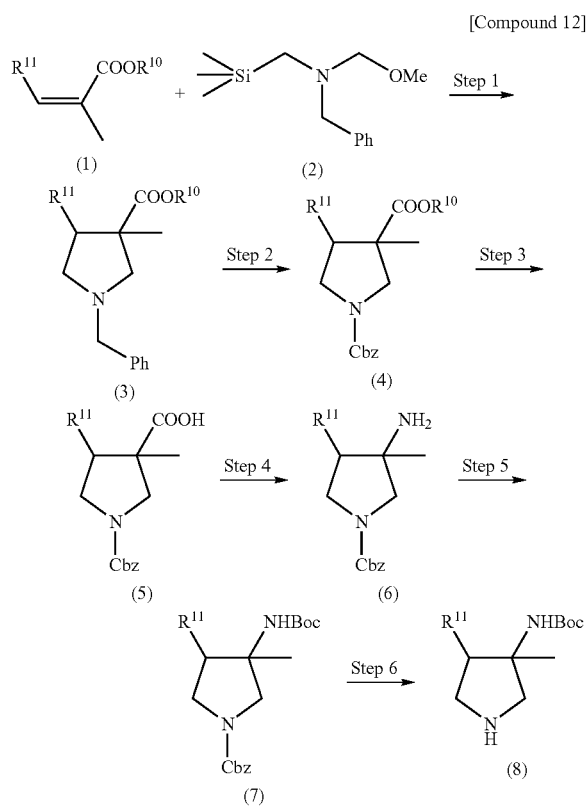

In the formula, Boc represents tertiary butoxycarbonyl group, Cbz represents benzyloxycarbonyl group, $R^{10}$ represents an alkyl group containing 1 to 6 carbon atoms, and $R^{11}$ represents $R^4$ or $R^5$ described for the formula (I) excluding hydrogen atom.

Step 1 is a step wherein 3-alkoxycarbonyl-3-methyl-4-substituted pyrrolidine derivative (3) is synthesized by 1,3-dipolar cycloaddition by using 3-substituted crotonate ester (1) and azomethine ylide (2) for the reaction blocks. The azomethine ylide used for producing the azomethine ylide may be produced, for example, by adding a catalytic amount of trifluoroacetic acid or a catalytic amount of silver fluoride to N-benzyl-N-(methoxymethyl) trimethylsilyl methylamine (See Journal of Organic Chemistry, vol. 52, No. 2, page 235, 1987). The reaction solvent is not particularly limited as long as it produces azomethine ylide without inhibiting the 1,3-dipolar cycloaddition. The solvent, however, is preferably dichloromethane or 1,2-dichloroethane. The reaction may be conducted at a temperature of from −20° C. to the reflux temperature of the solvent, and preferably, at room temperature to the reflux temperature of the solvent.

Step 2 is the step in which protective group at position 1 of the pyrrolidine ring is converted. This step is preferably conducted in order to enable separation and purification by extraction of the carboxylic acid derivative produced by the hydrolysis of the ester at position 3. The protective group at position 1 is preferably the one which is distinguishable in the deprotection step from the protective group of the amino group at position 3 generated in the subsequent conversion although use of the same protective group is allowable. Preferable protective group at position 1 is benzyloxycarbonyl group. The reaction for introducing this benzyloxycarbonyl is generally conducted by direct conversion by von Braun reaction using benzyl chloroformate in a solvent such as dichloromethane; by catalytic hydrolysis using a catalyst such as palladium-carbon followed by reaction with benzyl chloroformate in an appropriate solvent and in the presence of a base.

Step 3 is the step of hydrolyzing the ester at position 3 of the pyrrolidine ring. The ester is an alkyl ester containing 1 to 6 carbon atoms, and preferably, methyl ester, ethyl ester, or tertiary butyl ester. The hydrolysis is can be conducted by any method commonly used in the art as long as the protective group at position 1 is not affected, and typically by hydrolysis using a base or an acid. Hydrolysis of the methyl ester and the ethyl ester is conducted by reaction with are alkaline aqueous solution such as aqueous solution of sodium hydroxide, aqueous solution of potassium hydroxide, or aqueous solution of barium hydroxide in ethanol or water followed by acidification by an appropriate acid which does not affect the protective group at position 1 for separation and purification. In the case of hydrolysis of the tertiary butyl ester, the hydrolysis is conducted under acidic conditions or in the presence of an acid catalyst in an appropriate solvent in which the ester is soluble. Preferable acids include hydrochloric acid, formic acid, acetic acid, trifluoroacetic acid, and toluenesulfonic acid.

Step 4 is the step of converting the carboxyl group at position 3 of the pyrrolidine ring to amino group. This step is generally carried out by rearrangement of carboxylic acid to amine. For example, when the rearrangement is accomplished by Curtius rearrangement, the carboxylic acid is converted to acid azide by using a reagent such as sodium azide, trimethylsilyl azide, or diphenylphosphoryl azide (DPPA) in an appropriate solvent such as toluene, and converting the acid azide to isocyanate by heating the reaction mixture, and then converting the isocyanate to amine by hydrolysis using hydrochloric acid or the like.

Step 5 is the step of protecting the amino group at position 3 of the pyrrolidine ring. However, the subsequent steps may also be conducted without protecting the amino group. The protective group of the amino group at position 3 may be an amino protecting group commonly used in the art. However, use of a protective group which is distinguishable in the deprotection step from the protective group at position 1 is preferable. Examples include tertiary butoxycarbonyl group, acetyl group, and trifluoroacetyl group, and the preferred is tertiary butoxycarbonyl group.

It should be noted that Step 4 and Step 5 can be accomplished in one step when the rearrangement is conducted in an appropriate solvent. For example, Curtis rearrangement may be carried out by using diphenylphosphoryl azide (DPPA) in tertiary butyl alcohol to produce 3-(tertiary butoxycarbonyl) aminopyrrolidine derivative.

Step 6 is the step of deprotection of position 1 of the pyrrolidine ring, and the deprotection reaction may be conducted under any conditions as long as other functional groups and configuration are not affected. Since the protective group at position 1 is benzyloxycarbonyl group with regard to the compound of the present invention, the decomposition is conducted under deprotection conditions commonly used in the art, for example, by catalytic hydrolysis in the presence of a catalyst such as palladium-carbon or by using ammonium formate in a protic polar solvent. When carbon-carbon unsaturated bond is present at position 4 of the pyrrolidine ring due to the presence of the substituent such as vinyl group or methylene group, the decomposition should be accomplished while maintaining the carbon-carbon unsaturated bond. Since the protective group at position 1 is benzyloxycarbonyl group with regard to the compound of the present invention, the decomposition condition capable of maintaining the carbon-carbon unsaturated bond of the vinyl group, methylene group, or the like at position 4 of the pyrrolidine ring is provided by the method using sodium-liquid ammonia (Birch reduction conditions) in the presence of a strong acid (for example, hydrobromic acid-acetic acid, trifluoroacetic acid, and trifluoromethanesulfonic acid-trifluoroacetic acid), the method using barium hydroxide, and the like.

Next, synthesis of pyrrolidine derivative which is typically 7-amino-7-methyl-5-azaspiro[2.4]heptane-5-yl group is described.

7-amino-7-methyl-5-azaspiro[2.4]-heptane derivative (17) which is another typical compound of the present invention can be synthesized by converting ketone moiety of acetoacetate derivative into aminonitrile derivative by Strecker reaction, converting cyano group to aminomethyl group by reduction, and condensing the aminomethyl group with ester moiety (carboxylic acid unit) to produce a pyrrolidone derivative which is an important intermediate.

Although the inventors of the present invention selected tertiary butoxycarbonyl group for the protective group of the amine moiety at position 3, the protective group of the amine moiety at position 3 is not limited to the tertiary butoxycarbonyl group as long as the selected protective group does not affect the subsequent reaction steps and is easily deprotected later, and a protective group which is the same as the protective group at position 1 may also be used. Synthesis of the optically active compound can be conducted, for example, by optical resolution using an appropriate intermediate, for example, by HPLC resolution using a chiral column of the appropriate intermediate, preferential crystallization of the diastereomer salt, or by bonding chiral building block to an appropriate intermediate to produce a diastereomer, separating the diastereomer by using an appropriate separation technique such as silica gel chromatography, and removing the chiral building block to produce an optically active substance. Alternatively, the optically active compound may be synthesized by using the chiral building block for the starting material.

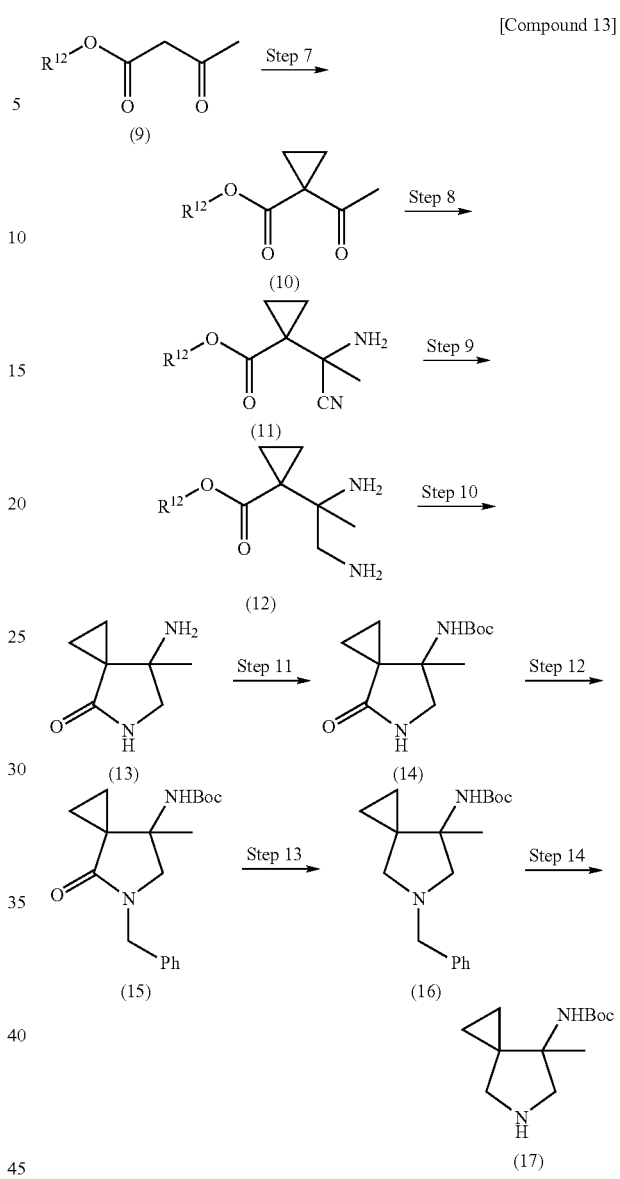

[Compound 13]

In the formula, Boc represents tertiary butoxycarbonyl group, and $R^{12}$ represents an alkyl group containing 1 to 6 carbon atoms.

Step 7 is the step of constructing a cyclic structure at methylene moiety of the acetoacetate derivative. This step can be generally accomplished by using a 1,2-dihalogeno ethane such as dibromoethane as an alkylating agent in the presence of a base. Exemplary bases include potassium carbonate, sodium hydride, and metal sodium, and the exemplary reaction solvents include acetone and N,N-dimethylformamide. After completing the reaction, the cyclo compound may be separated and purified by distillation under a reduced pressure.

Step 8 is the step of converting methylketone moiety to aminonitrile derivative by Strecker reaction. This Strecker reaction is conducted by reacting ammonia with a cyanating agent such as potassium cyanide optionally in the presence of ammonium chloride. The reaction conditions may be adequately selected by referring to the Strecker reaction commonly used in the amino acid synthesis.

Step 9 is the step of reducing cyano group for conversion into methylamine. The reduction of nitrile can be generally accomplished by catalytic reduction in the presence of a catalyst in an appropriate solvent such as ethanol. Examples of the catalyst include palladium-carbon catalyst, Raney nickel, Raney cobalt, and platinum oxide. When secondary amine is produced as a byproduct in the catalytic reduction of nitrile, the reduction may be conducted in the presence of ammonia. The reduction may be carried out by a metal hydride if other functional groups in the reaction system, for example, ester group which is the typical example in the compound of the present invention is not reduced. A typical example of the metal hydride is sodium borohydride-cobalt chloride (II). If the ester moiety is reduced, the reaction may be conducted after converting the ester moiety to a bulky ester such as tertiary butyl ester which is not reduced.

Step 10 is the step of condensing ester moiety (carboxylic acid unit) and methylamine in the molecule to produce the pyrrolidone derivative. When the ester moiety is methyl ester or ethyl ester, the condensation can be generally accomplished by heating the reaction solution from the room temperature in an appropriated solvent. When the ester moiety is methyl ester or ethyl ester, the pyrrolidone derivative can be directly produced from the reaction of Step 9. On the other hand, when the ester is a bulky ester such as tertiary butyl ester, the condensation is accomplished by hydrolyzing the ester by a method commonly used in the art, and then converting the hydrolyzate into the pyrrolidone derivative by using a condensing agent such as DCC.

Step 11 is the step of protecting the amino group at position 3 of the pyrrolidine ring. However, the subsequent steps may also be conducted without protecting the amino group. The protective group of the amino group at position 3 may be an amino protecting group commonly used in the art which is stable under the reaction conditions of the subsequent step 13. However, use of a protective group which is distinguishable in the deprotection step from the protective group at position 1 is preferable. Examples include tertiary butoxycarbonyl group, acetyl group, and trifluoroacetyl group, and the preferred is tertiary butoxycarbonyl group.

Step 12 is the step of protecting position 1 of the pyrrolidine ring. However, the subsequent steps may also be conducted without protecting the amino group. The protective group of position 1 may be an amino protecting group commonly used in the art which is stable under the reaction conditions of the subsequent step 13. However, use of a protective group which is distinguishable in the deprotection step from the amino group protective group at position 3 is preferable. The inventors of the present invention selected benzyl group for the protective group. The reaction of introducing the benzyl group is conducted by using benzyl halide in the presence of a base such as sodium hydride or potassium carbonate. The reaction solvent used may be acetone, N,N-dimethylformamide, tetrahydrofuran, or a mixture thereof.

Step 13 is the step of reducing carbonyl group of the pyrrolidone. The reduction is conducted by using a reducing agent. Exemplary reducing agents include metal hydrides such as lithium aluminum hydride, and sodium bis(2-methoxyethoxy) aluminum hydride, boron hydride compounds such as diborane and borane-tetrahydrofuran complex. The solvent used is typically ether solvent such as tetrahydrofuran, and the reaction may be carried out at a temperature of −78° C. to 100°.

Step 14 is the step or deprotecting position 1 of the pyrrolidine ring, and the deprotection reaction may be conducted under any conditions as long as other functional groups and configuration are not affected. Since the protective group at position 1 is benzyl group with regard to the compound of the present invention, the decomposition is conducted under deprotection conditions commonly used in the art, for example, by catalytic hydrolysis in the presence of a catalyst such as palladium-carbon or by using ammonium formate in a protic polar solvent. When carbon to carbon unsaturated bond is present at position 4 of the pyrrolidine ring due to the presence of the substituent such as vinyl group or methylene group, the decomposition should be accomplished while maintaining the carbon to carbon unsaturated bond. Since the protective group at position 1 is benzyl group with regard to the compound of the present invention, the decomposition condition capable of maintaining the carbon to carbon unsaturated bond of the vinyl group, methylene group, or the like at position 4 of the pyrrolidine ring is provided, for example, by the method using sodium-liquid ammonia (Birch reduction conditions).

In the foregoing, the reactions have been described in terms of examples. Those skilled in the art will be able to find a new synthetic method by taking such reactions into consideration. The scope of the present invention is not limited by the reactions as described above.

When the compound of the present invention (I) is produced by using the thus produced Compound (8) or Compound (17), a compound having the quinolone skeleton represented by the following formula (18):

[Compound 14]

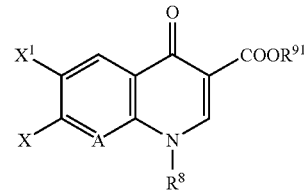

(18)

wherein $R^8$, $X^1$, and A are as defined above; and $R^{91}$ represents hydrogen atom, dihalogenoboron, or diacyloxy boron; and $X^2$ represents a leaving group may be reacted with Compound (8) or Compound (17).

$R^{91}$ of the compound having the quinolone skeleton is hydrogen atom or a boron substituent capable of producing a boron chelate. The boron substituents may be a dihalogenoboron or a diacyloxy boron. Preferable dihalogenoboron is difluoroboron ($—BF_2$), and preferable diacyloxy boron is diacetyloxy boron [$—B(OAc)_2$], and these compound can be produced by the method commonly used in the art.

The production method is described by using the compound of Example 9 as an example.

[Compound 15]

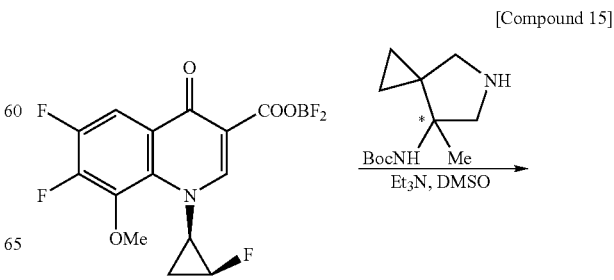

-continued

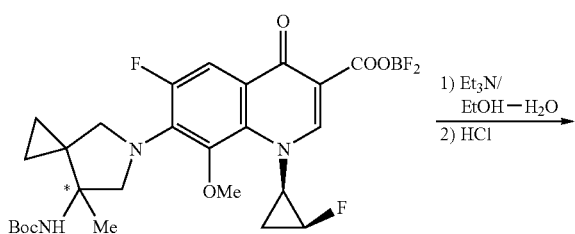

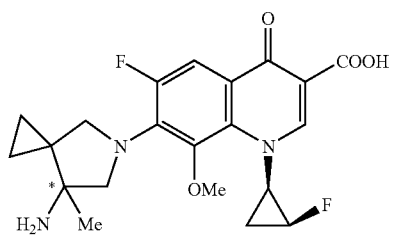

The target compound can be produced by dissolving the compound having the quinolone skeleton in an appropriate solvent and reacting the compound having the quinolone skeleton with Compound (8) or (17) for introducing the substituent at position 7 in the presence of a base. The amino group of the compound for introducing the substituent at position 7 may be protected with a protective group, and exemplary protective groups other than tert-butyl oxycarbonyl (Boc) include benzyloxycarbonyl group, p-methoxy benzyloxycarbonyl group, acetyl group, methoxyacetyl group, trifluoroacetyl group, pivaloyl group, formyl group, benzoyl group, tert-butyl group, benzyl group, trimethylsilyl group, and isopropyl dimethylsilyl. Exemplary bases include carbonate, hydrogen carbonate, or hydroxide of an alkaline metal or an alkaline earth metal; a trialkylamine such as triethylamine and N,N-diisopropylethylamine; and nitrogen-containing heterocyclic group compounds such as pyridine, 1,8-diazabicycloundecene, and N-methylpiperidine, and the preferred are trialkylamines, and in particular triethylamine. The solvent used is not particularly limited as long as it does not inhibit the reaction, and preferable examples include N,N-dimethylformamide, dimethyl sulfoxide, sulfolane, acetonitrile, ethanol, dimethyl acetamide, tetrahydrofuran, and N-methylpyrrolidone, and the more preferred are dimethyl sulfoxide or sulfolane.

When the compound having the quinolone skeleton is a boron chelate compound, the target compound can be produced by cleaving the boron substituent moiety by hydrolysis, and deprotecting the protective group of the amino group. The hydrolysis of the boron substituent can be conducted under conditions commonly used in the art, for example, by reacting with a base in an alcohol solvent such as methanol and ethanol. The base is preferably triethylamine, and the reaction is preferably conducted in an ice bath. The deprotection is conducted under the conditions suitable for the protective group used, for example, by treating the hydrolyzate with concentrated hydrochloric acid. After the reaction, the reaction solution is alkalized by adding an aqueous solution of sodium hydroxide.

Accordingly, the compounds represented by the following formulae (19) and (20) are useful as an intermediate for producing the compound (I) of the present invention.

[Compound 16]

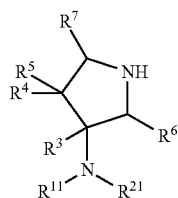

(19)

In the formulae, $R^{11}$ represents a group comprising $R^1$ as defined above (hydrogen atom, an alkyl group containing 1 to 6 carbon atoms, a cycloalkyl group containing 3 to 6 carbon atoms, or a substituted carbonyl group derived from an amino acid, a dipeptide, or a tripeptide; the alkyl group being optionally substituted with a substituent selected from the group consisting of hydroxy group, amino group, halogen atom, an alkylthio group containing 1 to 6 carbon atoms, and an alkoxy group containing 1 to 6 carbon atoms) and the protective group of the amino acid;

$R^{21}$ represents a group comprising $R^2$ as defined above (hydrogen atom, an alkyl group containing 1 to 6 carbon atoms, or a cycloalkyl group containing 3 to 6 carbon atoms; the alkyl group being optionally substituted with a substituent selected from the group consisting of hydroxy group, amino group, halogen atom, an alkylthio group containing 1 to 6 carbon atoms, and an alkoxy group containing 1 to 6 carbon atoms) and the protective group of the amino acid; and $R^3$, $R^4$, $R^5$, $R^6$, and $R^7$ are as defined above.

Next, the protective group of the amino group represented by $R^{11}$ and $R^{21}$ is described. The protective group is not particularly limited as long the protective group is the one widely used in the art, and exemplary protective groups include alkoxycarbonyl groups such as tartiary butlxycarbonyl group, and 2,2,2-trichloroethoxycarbonyl group; aralkyloxycarbonyl groups such as benzyloxycarbonyl group, paramethoxybenzyloxycarbonyl group, and paranitrobenzyloxycarbonyl group; acyl groups such as acetyl group, methoxyacetyl group, trifluoroacetyl group, chloroacetyl group, pivaloyl group, formyl group, and benzoyl group; alkyl groups or aralkyl groups such as tertiary butyl group, benzyl group, paranitrobenzyl group, paramethoxybenzyl group, and triphenylmethyl group; ethers such as methoxymethyl group, tertiary butoxymethyl group, tetrahydropyranyl group, and 2,2,2-trichloroethoxymethyl group; (alkyl and/or aralkyl)-substituted silyl groups such as trimethylsilyl group, isopropyldimethylsilyl group, tertiary butyldimethylsilyl group, tribenzylsilyl group, and tertiary butyldiphenylsilyl group.

[Compound 17]

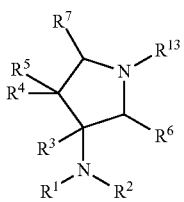

(20)

In the formula $R^{13}$ represents protective group of the amino group, and $R^{11}$, $R^{21}$, $R^3$, $R^4$, $R^5$, $R^6$ and $R^7$ are as defined above.

The protective group represented by $R^{13}$ is not particularly limited as long the protective group is the one widely used in the art. Exemplary protective groups include alkoxycarbonyl groups such as tartiary butlxycarbonyl group, and 2,2,2-trichloroethoxycarbonyl group; aralkyloxycarbonyl groups such as benzyloxycarbonyl group, paramethoxybenzyloxycarbonyl group, and paranitrobenzyloxycarbonyl group; acyl groups such as acetyl group, methoxyacetyl group, trifluoroacetyl group, chloroacetyl group, pivaloyl group, formyl group, and benzoyl group; alkyl groups or aralkyl groups such as tertiary butyl group, benzyl group, paranitrobenzyl group, paramethoxybenzyl group, and triphenylmethyl group; ethers such as methoxymethyl group, tertiary butoxymethyl group, tetrahydropyranyl group, and 2,2,2-trichloroethoxymethyl group; (alkyl and/or aralkyl)-substituted silyl groups such as trimethylsilyl group, isopropyldimethylsilyl group, tertiary butyldimethylsilyl group, tribenzylsilyl group, and tertiary butyldiphenylsilyl group.

When more than two of $R^{11}$, $R^{12}$ and $R^{13}$ are protective groups, the actual protective groups should be chosen is able to be determined according to the knowledge of the present field of the art to be selectively removed at the synthesis of compound 19 or 20.

The thus produced compound of Example 9 shows strong antibacterial activity as well as excellent stability and pharmacokinetics as will be evident from the Test Examples as presented below. When this compound was evaluated by X ray crystallography, absolute configuration at the part of the asymmetric carbon at position 7 (the site of the amino group substitution) of 5-azaspiro[2.4]heptane-5-yl group was (7S). This confirmed that the preferable compound is the one in which the spirobicyclic substituent at position 7 has an absolute configuration (S).

Since the compound of the present invention has strong antibacterial activity, it can be used as a drug for human, animals, and fish, or as a preservative of agricultural chemicals and foods. The typical dose of the compound of the present invention when it is used as a human drug is 50 mg to 1 g, and more preferably 100 mg to 500 mg per day per adult. When the compound of the invention is administered to an animal, the dose is typically 1 mg to 200 mg, and more preferably 5 mg to 100 mg per day per kg weight of the animal although the dose may vary according to the size of the animal to be treated, type of the pathogenic microorganism, and seriousness of the condition. Such daily dose may be administered in a single dose or in 2 to 4 divided doses. If necessary, a dose exceeding such daily dose may be administered.

The compound of the present invention has excellent antibacterial activity for a broad range of microorganisms causing various infections, and therefore, the present compound is capable of treating, preventing, or ameliorating the diseases caused by such pathogenic microorganisms. The compound of the present invention is effective for bacteria and the bacteria-like microorganisms including *Staphylococcus, Streptococcus pyogenes*, hemolytic *streptococcus, enterococcus, pneumococcus, Peptostreptococcus, Neisseria gonorrhoeae, Escherichia coli, Citrobacter, Shigella, Klebsiella pneumoniae, Enterobacter, Serratia, Proteus, Pseudomonas aerugimosa, Haemophilus influenzae, Acinetobacter, Campylobacter*, and *Chlamydia trachomatis*.

The diseases caused by such pathogenic microorganisms include superficial secondary infections such as folliculitis, furuncle, carbuncle, erysipelas, cellulitis, lymphangitis, whitlow, subepidermal abscess, hidradenitis, acne conglobata, infectious atheroma, perianal abscess, mastitis, and injury, burn and operative wounds; secondary infections of laryngopharyngitis, acute bronchitis, tonsillitis, chromic bronchitis, bronchiectasis, diffuse panbronchiolitis, and chronic respiratory diseases; pneumonia, pyelonephritis, cystitis, prostatitis, epididymitis, gonorrheal urethritis, nongonococcal urethritis, cholecystitis, cholangitis, shigellosis, enteritis, adnexitis, intrautarine infection, bartholinitis, blepharitis, hordeolum, dacryocystitis, meibomianitis, corneal ulcer, middle otitis, sinusitis, periodontal inflammations, pericoronitis, jaw inflammation, peritonitis, endocarditis, sepsis, meningitis, and skin infections.

The compound of the present invention is also effective for acid fast bacteria such as *M. tuberculosis* complex (*Mycobacterium tuberculosis, M. bovis*, and *M. africans*) and atypical mycobacteria (*M. kansasii, M. marianum, M. scrofulaceum, M. avium, M. intracellulare, M. xenopi, M. fortuitum*, and *M. chelonae*). The mycobacterial infections caused by such pathogenic microorganisms are divided into three categories of tuberculosis, atypical mycobacteriosis, and leprosy. Mycobacterial infections affect not only the lung but also thoracic cavity, trachea and bronchus, lymph nodes, by systemic dissemination, joints and bones, meninges and brain, digestive organs (intestine and liver), skin, mammary gland, eyes, auris media and throat, urinary tract, male genitalia, and female genitalia. The main organ affected by the atypical mycobacteriosis (non-tuberculous mycobacteriosis) is lung. The atypical mycobacteriosis, however, also affects by topical lymphadenitis, skin soft tissues, bones and joints, and by systemic dissemination.

The compound of the present invention is also effective for various microorganisms causing animal infections such as *Escherichia, Salmonella, Pasteurella, Haemophilus, Bordetella, Staphylococcus*, and mycoplasma. Exemplary diseases include, colibacillosis, pullorum disease, avian paratyphoid, fowl cholera, infectious diarrhea, staphylococcosis mycoplasma infection, and the like for fowls; colibacillosis, salmonellosis, pasteurellosis, hemophilosis, atrophic rhinitis, exudative epidermitis, mycoplasma infection and the like for pigs; colibacillosis, salmonellosis, hemorrhagic septicemia, mycoplasma infection, pleuropneumonia, and mastitis for cows; *Escherichia coli* sepsis, salmonella infection, hemorrhagic septicemia, pyometra, cystitis, and the like for dogs; and exudative pleurisy, cystitis, chronic rhinitis, hemophilosis, kitten's diarrhea, mycoplasma infection, and the like for cats.

The antibacterial drug containing the compound of the present invention may be prepared by selecting a dosage form appropriate for the administration rcute, and preparing the drug by a method commonly used in the art for producing the selected dosage form. Exemplary dosage forms for the antibacterial drug containing the compound of the present invention as its main ingredient include tablet, powder, granules, capsule, solution, syrup, elixir, and oil-base and water-base suspension. In the case of an injection, the preparation may contain a stabilizer, an antiseptic, a solubilizer, and the like and the preparation optionally supplemented with such additives may be filled in a container, and then freeze dried to produce a solid preparation to be hydrated immediately before use. The container may be filled either with a single dose or multiple doses. In the case of a solid preparation, the preparation may contain a pharmaceutically acceptable carrier with the compound (1), and exemplary carries include fillers, expanders, binders, disintegrants, solubilizers, wetting agents, and lubricants. The liquid preparation may be a solution, a suspension, an emulsion, or the like which may contain a suspending agent or emulsifier as an additive.

In the case of a solid preparation, the preparation may contain a pharmaceutically acceptable carrier with the active compound, and exemplary carriers include fillers, binders, disintegrants, solubilizers, wetting agents, and lubricants. The liquid preparation may be a solution, a suspension, an emulsion, or the like which may contain a suspending agent or emulsifier as an additive.

Next, exemplary preparations are described.

| Preparation 1 (Capsule) | |
|---|---|
| Compound of Example 9 | 100.0 mg |
| Corn starch | 23.0 mg |
| Carboxymethlcellulose calcium | 22.5 mg |
| Hydroxymethylcellulose | 3.0 mg |
| Magnesium stearate | 1.5 mg |
| Total | 150.0 mg |

| Preparation 2 (Solution) | |
|---|---|
| Compound of Example 9 | 1 to 10 g |
| Acetic acid or sodium hydroxide | 0.5 to 2 g |
| Ethyl paraoxybenzoate | 0.1 g |
| Purified water | 87.9 to 98.4 g |
| Total | 100.0 g |

| Preparation 3 (Powder for animal feed) | |
|---|---|
| Compound of Example 9 | 1 to 10 g |
| Corn starch | 89.5 to 98.5 g |
| Light anhydrous silicic acid | 0.5 g |
| Total | 100.0 g |

EXAMPLES

Next, the present invention is described in further detail by referring to Reference Examples and Examples which by no means limit the scope of the present invention.

Reference Example 1

Ethyl (3R*,4R*)-1-benzyl-3,4-dimethylpyrrolidine-3-carboxylate

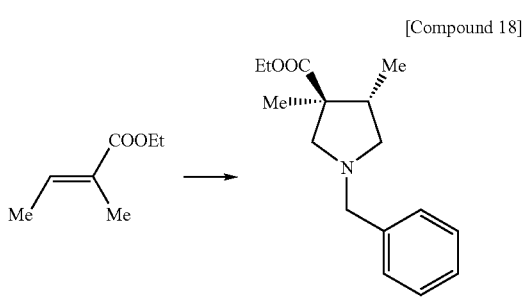

[Compound 18]

To a solution of tiglic acid ethyl ester (6.41 g, 50.0 mmol) and N-benzyl-N-(methoxy-methyl)-N-trimethylsilyl methylamine (15.35 g, 60.0 mmol) in dichloromethane (150 mL), a catalytic amount of trifluoroacetic acid was added at room temperature, and the mixture was stirred in an oil bath at 40° C. for 10 hours. The reaction mixture was diluted by adding ethyl acetate (500 mL), and the solution was washed with saturated aqueous solution of sodium hydrogencarbonate (200 mL) and saturated aqueous solution of sodium chloride (200 mL), and dried with anhydrous sodium sulfate. After removing the dessicating agent by filtration, the solvent was removed by distillation under reduced pressure. The resulting residue was purified by silica gel column chromatography (chloroform : methanol, 49:1→19:1→9:1) to obtain 13.73 g of crude title compound as a pale yellow oil. The crude product was used in the subsequent reaction with no further purification.

$^1$H-NMR (400 MHz, CDCl$_3$) δ ppm: 0.96 (3H, d, J=7.1 Hz), 1.17 (3H, s), 1.22 (3H, t, J=7.1 Hz), 2.16 (1H, t, J=8.8 Hz), 2.25 (1H, d, J=9.6 Hz), 2.61-2.67 (1H, m), 2.91 (1H, t, J=8.2 Hz), 3.28 (1H, d, J=10.0 Hz), 3.53 (1H, d, J=13.5 Hz), 3.64 (1H, d, J=13.2 Hz), 4.11 (2H, q, J=7.1 Hz), 7.19-7.38 (5H, m).

MS (ESI) m/z: 262 (M+H)$^+$.

Reference Example 2

Ethyl (3R*,4R*)-1-benzyloxycarbonyl-3,4-dimethylpyrrolidine-3-carboxylate

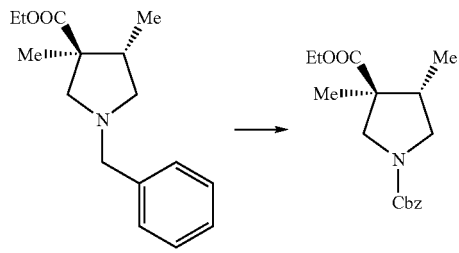

[Compound 19]

To a solution of ethyl (3R*,4R*)-1-benzyl-3,4-dimethylpyrrolidine-3-carboxylate (2.75 g, 10.0 mmol) in dichloromethane (30 mL), benzyl chloroformate (2.14 mL, 15.0 mmol) was added at room temperature, and the mixture was stirred at room temperature for 6 hours. Benzyl chloroformate (2.14 mL, 15.0 mmol) was also added to the mixture, and the mixture was stirred at room temperature for another 14 hours. The solvent was removed by distillation under reduced pressure, and the residue was purified by silica gel column chromatography (hexane : ethyl acetate, 9:1→4:1→2:1) to obtain 1.64 g of the title compound (5.37 mmol, 2 steps, 54%) as a colorless transparent oil.

$^1$H-NMR (400 MHz, CDCl$_3$) δ ppm: 0.99 (1.5H, d, J=7.1 Hz), 1.02 (1.5H, d, J=7.1 Hz), 1.18 (3H, s), 1.26 (3H, t, J=7.1 Hz), 2.57-2.66 (1H, m), 3.01-3.10 (1H, m), 3.39 (0.5H, d, J=10.7 Hz), 3.45 (0.5H, d, J=11.0 Hz), 3.66 (1H, td, J=11.0, 8.0 Hz), 3.77 (1H, dd, J=10.9, 4.8 Hz), 4.11-4.19 (2H, m), 5.09-5.17 (2H, m), 7.26-7.38 (5H, m).

MS (ESI) m/z: 306 (M+H)$^+$.

Reference Example 3

(3R*,4S*)-1-Benzyloxycarbonyl-3-(tert-butoxycarbonylamino)-3,4-dimethylpyrrolidine

[Compound 20]

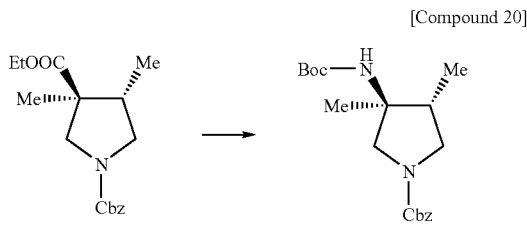

To a solution of ethyl (3R*,4R*)-1-benzyloxycarbonyl-3,4-dimethylpyrrolidine-3-carboxylate (1.63 g, 5.34 mmol) in ethanol (16 mL), 1N aqueous solution of sodium hydroxide (16.0 mL, 16.0 mmol) was added at room temperature, and the mixture was stirred at room temperature for 3.5 hours. After concentrating the solvent under reduced pressure, 1N hydrochloric acid was added to the mixture for acidification, and the mixture was extracted with ethyl acetate (150 mL). The resulting organic layer was dried with anhydrous sodium sulfate, and after removing the dessicating agent by filtration, the solvent was removed by distillation under reduced pressure to obtain crude product in the form of carboxylic acid. The crude product in the form of a carboxylic acid was used in the subsequent reaction with no further purification.

To a solution of the thus obtained crude product in the form of a carboxylic acid and triethylamine (1.488 mL, 10.68 mmol) in toluene (30 mL), diphenylphosphoryl azide (1.495 mL, 6.94 mmol) was added in an ice bath, and the mixture was stirred at room temperature for 30 minutes, and further stirred in an oil bath at 80° C. for 2 hours. The reaction mixture was diluted by adding ethyl acetate (150 mL), and the solution was washed with saturated aqueous solution of sodium hydrogencarbonate (80 mL), water (80 mL), and saturated aqueous solution of sodium chloride (80 mL) in this order. The resulting organic layer was dried with anhydrous sodium sulfate, and after removing the dessicating agent by filtration, the solvent was removed by distillation under reduced pressure to obtain crude product in the form of isocyanate. The thus obtained crude product in the form of isocyanate was dissolved in 1,4-dioxane (15 mL), and after adding 6N hydrochloric acid (15 mL), the mixture was stirred for 1 hour in an oil bath at 50° C. The reaction mixture was concentrated under reduced pressure, and after azeotropically distilling with ethanol (5 times), the residue was dissolved in dichloromethane (30 mL), and to this solution at room temperature was added triethylamine (3.72 mL, 26.69 mmol), and then di-tert-butyl dicarbonate (2.33 g, 10.68 mmol). The reaction mixture was stirred at room temperature for 3 hours, and the solvent was removed by distillation under reduced pressure. The residue was purified by silica gel column chromatography (hexane : ethyl acetate, 9:1→4:1) to obtain 1.10 g (3.16 mmol, 4 steps, 59%) of the title compound as a colorless gummy solid.

$^1$H-NMR (400 MHz, CDCl$_3$) δ ppm: 0.94-0.98 (3H, m), 1.24-1.26 (3H, m) 1.42-1.44 (9H, m), 2.44-2.62 (1H, m), 2.99-3.05 (1H, m), 3.63-3.70 (3H, m), 4.54-4.56 (1H, m), 5.08-5.17 (2H, m), 7.28-7.37 (5H, m)

MS (ESI) m/z: 371 (M+Na)$^+$.

Reference Example 4

(+)-(3R*,4S*)-1-Benzyloxycarbonyl-3-(tert-butoxycarbonylamino)-3,4-dimethylpyrrolidine and (−)-(3R*,4S*)-1-benzyloxycarbonyl-3-(tert-butoxycarbonylamino)-3,4-dimethylpyrrolidine The racemic compound of (3R*,4S*)-1-benzyloxycarbonyl-3-(tert-butoxycarbonylamino)-3,4-dimethylpyrrolidine (1.10 g, 3.16 mmol) produced in Reference Example 3 was optically resolved by using an optically active column (CHIRALPAK AD, 20 mm diam.×250 mm; hexane : isopropyl alcohol, 95:5; flow rate, 25 mL/minute; resolution, 30 mg per run) to produce (+)-(3R*,4S*)-1-benzyloxycarbonyl-3-(tert-butoxycarbonylamino)-3,4-dimethylpyrrolidine (528 mg; 1.52 mmol; retention time=12.8 minutes, [α]D25.1=+8.1° (c=0.161, chloroform)) and (−)-(3R*,4S*)-1-benzyloxycarbonyl-3-(tert-butoxycarbonylamino)-3,4-dimethylpyrrolidine (532 mg; 1.53 mmol; retention time=15.8 minutes; [α]D25.1=−6.3° (c=0.175, chloroform)).

Example 1

7-[(3R*,4S*)-3-Amino-3,4-dimethylpyrrolidine-1-yl]-6-fluoro-1-[(1R,2S)-2-fluorocyclopropyl]-8-methoxy-1,4-dihydro-4-oxoquinoline-3-carboxylic acid

[Compound 21]

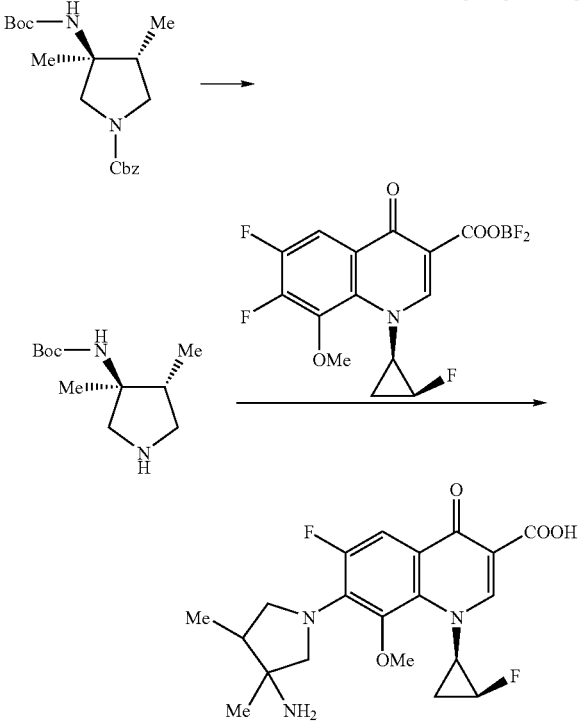

To a solution of (+)-(3R*,4S*)-1-benzyloxycarbonyl-3-(tert-butoxycarbonylamino)-3,4-dimethylpyrrolidine (490 mg, 1.406 mmol) in methanol (20 mL) was added 10% palladium-carbon catalyst (M; water content, about 50%; 147 mg), and the suspension was stirred in hydrogen atmosphere at room temperature for 2 hours. After removing the catalyst by filtration, the solvent was removed by distillation under reduced pressure to obtain crude product (314 mg, quantitative) of (3R*,4S*)-3-(tert-butoxycarbonylamino)-3,4-dimethylpyrrolidine as a colorless gummy solid.

The thus obtained (3R*,4S*)-3-(tert-butoxycarbonylamino)-3,4-dimethylpyrrolidine crude product (314 mg), 6,7-difluoro-1-[(1R,2S)-2-fluorocyclopropyl]-8-methoxy-1,4-dihydro-4-oxoquinoline-3-carboxylic acid—difluoroboron complex (461 mg, 1.277 mmol), and triethylamine (0.534 mL, 3.83 mmol) were dissolved in dimethyl sulfoxide (4 mL), and the mixture was stirred in an oil bath at 35° C. for 18 hours. To this reaction mixture were added a mixed solution of ethanol and water (ethanol : water=4:1) (20 mL) and triethylamine (2 mL), and the mixture was heated under reflux in an oil bath at 100° C. for 2 hours. After concentrating the reaction mixture under reduced pressure, the residue was dissolved in ethyl acetate (150 mL), and washed with 10% aqueous solution of citric acid (80 mL), water (80 mL×2), and saturated aqueous solution of sodium chloride (80 mL). The organic layer was dried with anhydrous sodium sulfate, and the solvent was removed by distillation under reduced pressure. The residue was dissolved in concentrated hydrochloric acid (20 mL) in an ice bath, and solution was stirred at room temperature for 10 minutes. The reaction mixture was washed with chloroform (30 mL×3). To the aqueous layer was added 10 mol/l aqueous solution of sodium hydroxide in an ice bath to adjust the pH to 12.0, and the solution was further adjusted to pH 7.4 with hydrochloric acid. The solution was then extracted with a mixed solution of chloroform and methanol (chloroform : methanol=9:1) (150 mL×2). The organic layer was dried with anhydrous sodium sulfate, and the solvent was removed by distillation under reduced pressure. The residue was purified by recrystallization from ethanol, and the crystals were dried under reduced pressure to obtain the title compound 328 mg (0.805 mmol, 63%) as a pale yellow powder.

mp: 200-203° C.

$[\alpha]_D^{25.1}$=+213.7° (c=0.204, 0.1N NaOH).

$^1$H-NMR (400 MHz, 0.1N NaOD) δ ppm: 1.00 (3H, d, J=6.6 Hz), 1.12 (3H, s), 1.55-1.70 (2H, m), 2.07 (1H, m), 3.39 (1H, d, J=10.0 Hz), 3.48-3.69 (6H, m), 4.04 (1H, m), 4.93 (1H, dd, J=39.1, 1.5 Hz), 7.64 (1H, d, J=14.6 Hz), 8.47 (1H, s).

Elementary analysis for $C_{20}H_{23}F_2N_3O_4 \cdot 1.5H_2O$:

Calculated: C, 55.29; H, 6.03; F, 8.75; N, 9.67.

Found: C, 55.55; H, 6.03; F, 8.45; N, 9.56.

MS (FAB) m/z: 408 (M+H)$^+$.

IR (ATR): 2974, 2935, 2879, 1722, 1614, 1572, 1537, 1502, 1456, 1390, 1356, 1323, 1271, 1207 cm$^{-1}$.

Example 2

7-[(3R*,4S*)-3-Amino-3,4-dimethylpyrrolidin-1-yl]-6-fluoro-1-[(1R,2S)-2-fluorocyclopropyl]-8-methoxy-1,4-dihydro-4-oxoquinoline-3-carboxylic acid

[Compound 22]

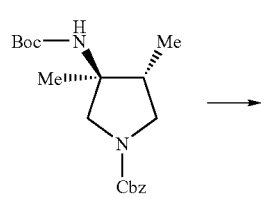

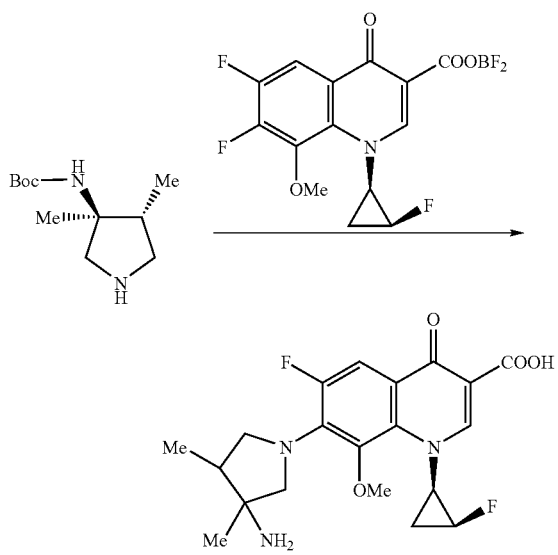

By using a procedure similar to Example 1, (−)-(3R*,4S*)-1-benzyloxycarbonyl-3-(tert-butoxycarbonylamino)-3,4-dimethylpyrrolidine (480 mg, 1.378 mmol) was converted to (3R*,4S*)-3-(tert-butoxycarbonylamino-3,4-dimethylpyrrolidine crude product (311 mg, quantitative), and the product was reacted with 6,7-difluoro-1-[(1R,2S)-2-fluorocyclopropyl]-8-methoxy-1,4-dihydro-4-oxoquinoline-3-carboxylic acid—difluoroboron complex (452 mg, 1.252 mmol) to obtain 348 mg (0.854 mmol, 68%) of the title compound as a pale yellow powder.

mp: 195-196° C.

$[\alpha]_D^{25.1}$=−118.3° (c=0.224, 0.1N NaOH).

$^1$H-NMR (400 MHz, 0.1N NaOD) δ ppm: 1.00 (3H, d, J=6.6 Hz), 1.14 (3H, s), 1.31-1.44 (1H, m), 1.49-1.59 (1H, m), 2.09 (1H, m), 3.39-3.57 (6H, m), 3.71 (1H, m), 3.97-4.02 (1H, m), 5.00 (1H, dm, J=63.7 Hz), 7.63 (1H, d, J=14.6 Hz), 8.39 (1H, d, J=2.4 Hz).

Elementary analysis for $C_{20}H_{23}F_2N_3O_4 \cdot 0.75H_2O$:

Calculated: C, 57.07; H, 5.87; F, 9.03; N, 9.98.

Found: C, 57.30; H, 5.90; F, 9.13; N, 9.92.

MS (FAB) m/z: 408 (M+H)$^+$.

IR (ATR): 2962, 2873, 1724, 1616, 1513, 1435, 1362, 1321, 1271 cm$^{-1}$.

Reference Example 5

Methyl (3R*,4S*)-1-benzyl-3,4-dimethylpyrrolidine-3-carboxylate

[Compound 23]

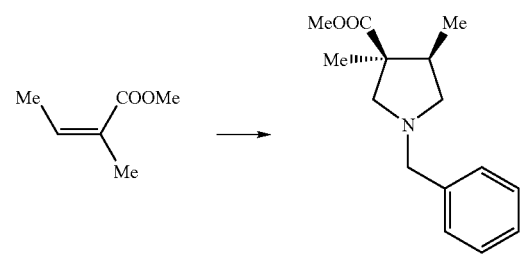

The procedure of Reference Example 1 was repeated by using methyl angelate (12.01 mL, 100.0 mmol) and N-benzyl-N-(n-butoxy methyl)-N-trimethylsilyl methylamine (36.0 g, 128.9 mmol) to obtain 12.28 g of the crude title compound as a yellow oil. The thus obtained crude product was used in the subsequent reaction with no further purification.

MS (ESI) m/z: 248 (M+H)$^+$.

Reference Example 6

Methyl (3R*,4S*)-1-benzyloxycarbonyl-3,4-dimethylpyrrolidine-3-carboxylate

[Compound 24]

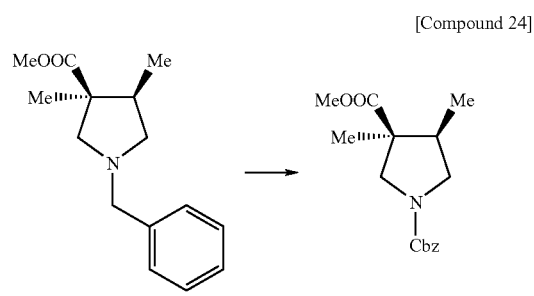

The procedure of Reference Example 2 was repeated by using the thus synthesized methyl (3R*,4S*)-1-benzyl-3,4-dimethylpyrrolidine-3-carboxylate crude product (12.28 g) and benzyl chloroformate (21.3 mL, 149.3 mmol) to obtain 4.23 g (14.52 mmol, 2 steps, 15%) of the title compound as a colorless oil.

$^1$H-NMR (400 MHz, CDCl$_3$) δ ppm: 0.94 (1.5H, d, J=6.8 Hz), 0.96 (1.5H, d, J=6.7 Hz), 1.30 (1.5H, s), 1.31 (1.5H, s), 2.14 (1H, m), 3.16-3.28 (2H, m), 3.64-3.71 (4H, m), 3.92 (1H, dd, J=14.6, 11.5 Hz), 5.16 (2H, m), 7.26-7.37 (5H, m).

MS (ESI) m/z: 292 (M+H)$^+$.

Reference Example 7

(3R*,4R*)-1-Benzyloxycarbonyl-3-(tert-butoxycarbonylamino)-3,4-dimethylpyrrolidine

[Compound 25]

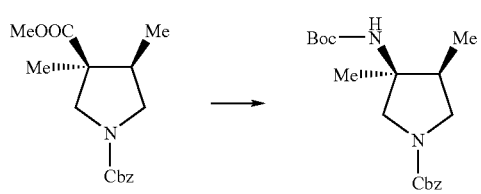

To a solution of methyl (3R*,4S*)-1-benzyloxycarbonyl-3,4-dimethylpyrrolidine-3-carboxylate (4.23 g, 14.52 mmol) in methanol (88 mL), 1N aqueous solution of sodium hydroxide (44.0 mL, 44.0 mmol) was added at room temperature, and the mixture was stirred at room temperature for 5 hours, and in an oil bath at 50° C. for another 19 hours. To the mixture was added sodium hydroxide (1.742 g, 43.6 mmol), and this mixture was also stirred in an oil bath at 50° C. for 8 hours. After concentrating the solvent under reduced pressure, concentrated hydrochloric acid was added to the concentrate in an ice bath for acidification, and the solution was extracted with ethyl acetate (300 mL). The resulting organic layer was dried with anhydrous sodium sulfate, and the dessicating agent was removed by filtration. The solvent was removed by distillation under reduced pressure to obtain the crude product in the form of a carboxylic acid. The crude product in the form of a carboxylic acid was used in the subsequent reaction with no further purification.

To a solution of the thus obtained crude product in the form of a carboxylic acid and triethylamine (6.06 mL, 43.5 mmol) in toluene (70 mL), diphenylphosphoryl azide (4.06 mL, 18.84 mmol) was added in an ice bath, and the mixture was stirred at room temperature for 2 hours, and in an oil bath at 90° C. for another 1 hour. To the heated and stirred reaction mixture was added tert-butyl alcohol (70 mL), and the mixture was heated under reflux in an oil bath at 120° C. for 93 hours, and the reaction mixture was then cooled to room temperature. After removing the solvent by distillation under reduced pressure, the residue was purified by silica gel column chromatography (hexane-ethyl acetate 90:10→85:15→80:20→75:25) to obtain 1.205 g (3.46 mmol, 2 steps, 24%) of the title compound as a colorless gummy solid.

$^1$H-NMR (400 MHz, CDCl$_3$) δ ppm: 0.99 (1.5H, d, J=7.3 Hz), 1.01 (1.5H, d, J=7.1 Hz), 1.43-1.46 (12H, m), 2.06-2.22 (1H, m), 3.11-3.17 (1H, m), 3.24 (0.5H, d, J=11.5 Hz), 3.30 (0.5H, d, J=11.2 Hz), 3.60-3.67 (1H, m), 3.88 (0.3H, d, J=11.2 Hz), 4.02 (0.5H, d, J=11.0 Hz), 4.43 (1H, brs), 5.09-5.17 (2H, m), 7.26-7.37 (5H, m).

MS (ESI) m/z: 293 (M-tBu)$^+$.

Reference Example 8

(+)-(3R*,4R*)-1-Benzyloxycarbonyl-3-(tert-butoxycarbonylamino)-3,4-dimethylpyrrolidine and (−)-(3R*,4R*)-1-benzyloxycarbonyl-3-(tert-butoxycarbonylamino)-3,4-dimethylpyrrolidine The racemic compound of (3R*,4R*)-1-benzyloxycarbonyl-3-(tert-butoxycarbonylamino)-3,4-dimethylpyrrolidine (1.205 g, 3.46 mmol) produced in Reference Example 7 was optically resolved in an optically active column (CHIRALPAK AS, 20 mm diam.×250 mm; hexane : isopropyl alcohol, 95:5; flow rate, 20 mL/minute; resolution, 40 mg per run) to obtain (+)-(3R*,4R*)-1-benzyloxycarbonyl-3-(tert-butoxycarbonylamino)-3,4-dimethylpyrrolidine (468 mg, 1.34 mmol, retention time=9.0 minutes, [α]D25.1=+10.3° (c=0.165, chloroform)) and (−)-(3R*,4R*)-1-benzyloxycarbonyl-3-(tert-butoxycarbonylamino)-3,4-dimethylpyrrolidine (591 mg, 1.70 mmol, retention time=11.4 minutes, [α]D25.1=−12.0° (c=0.150, chloroform)).

Example 3

7-[(3R*,4R*)-3-Amino-3,4-dimethylpyrrolidin-1-yl]-6-fluoro-1-[(1R,2S)-2-fluorocyclopropyl]-8-methoxy-1,4-dihydro-4-oxoquinoline-3-carboxylic acid

[Compound 26]

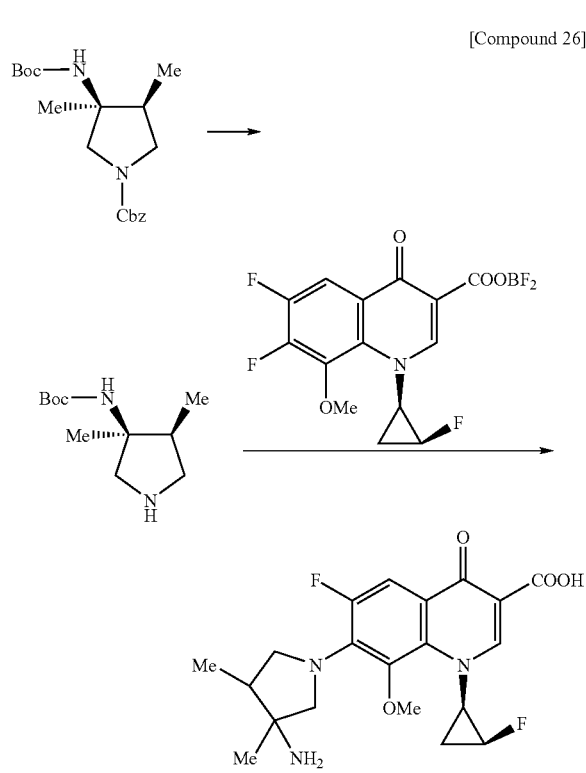

By using a procedure similar to Example 1, (+)-(3R*,4R*)-1-benzyloxycarbonyl-3-(tert-butoxycarbonylamino)-3,4-dimethylpyrrolidine (468 mg, 1.343 mmol) was converted to (3R*,4R*)-3-(tert-butoxycarbonylamino)-3,4-dimethylpyrrolidine crude product (280 mg, 1.307 mmol, 97%), and the product was reacted with 6,7-difluoro-1-[(1R,2S)-2-fluorocyclopropyl]-8-methoxy-1,4-dihydro-4-oxoquinoline-3-carboxylic acid -difluoroboron complex (429 mg, 1.188 mmol) to obtain 370 mg (0.834 mmol, 68%) of the title compound as a white powder.

mp: 175-179° C.

$[\alpha]_D^{23.8}=-107.1°$ (c=0.240, 0.1N NaOH)

$^1$H-NMR (400 MHz, 0.1N NaOD) δ ppm: 1.00 (3H, d, J=6.8 Hz), 1.25 (3H, s), 1.31-1.43 (1H, m), 1.48-1.59 (1H, m), 2.03-2.13 (1H, m), 3.41 (1H, dd, J=10.5, 1.7 Hz), 3.46-3.52 (4H, m), 3.62-3.70 (2H, m), 3.99 (1H, dt, J=10.2, 4.5 Hz), 5.01 (1H, ddd, J=63.8, 8.7, 5.5 Hz), 7.63 (1H, d, J=14.6 Hz), 8.39 (1H, d, J=2.9 Hz).

Elementary analysis for $C_{20}H_{23}F_2N_3O_4 \cdot 2H_2O$:

Calculated: C, 54.17; H, 6.14; F, 8.57; N, 9.48.

Found: C, 54.41; H, 5.81; F, 8.63; N, 9.37.

MS (EI) m/z: 407 (M$^+$).

IR (ATR): 2962, 2881, 2833, 1726, 1614, 1577, 1510, 1435, 1387, 1354, 1306, 1267 cm$^{-1}$.

Example 4

7-[(3R*,4R*)-3-Amino-3,4-dimethylpyrrolidine-1-yl]-6-fluoro-1-[(1R,2S)-2-fluorocyclopropyl]-8-methoxy-1,4-dihydro-4-oxoquinoline-3-carboxylic acid

[Compound 27]

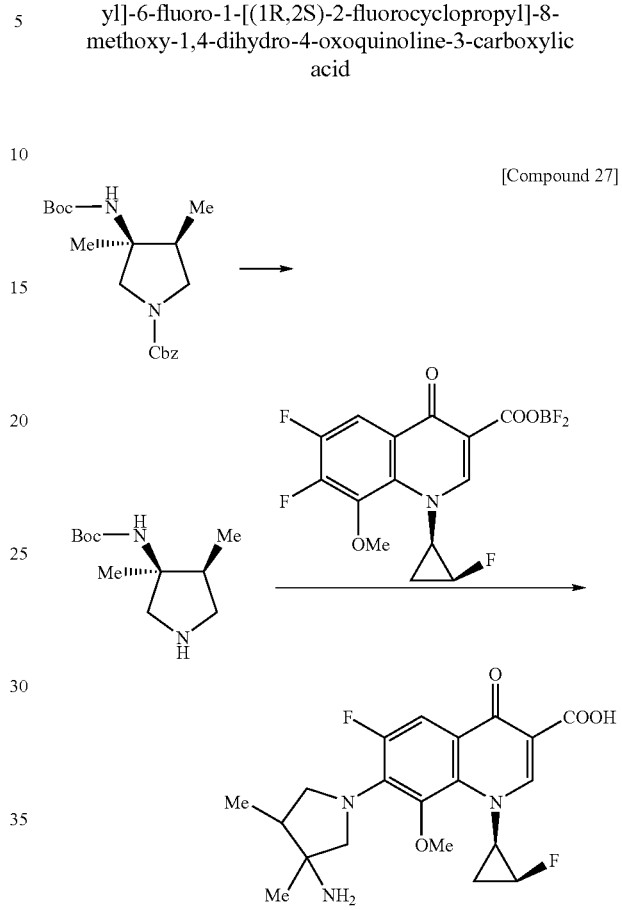

By using a procedure similar to Example 1, (−)-(3R*,4R*)-1-benzyloxycarbonyl-3-(tert-butoxycarbonylamino)-3,4-dimethylpyrrolidine (169 mg, 0.485 mmol) was converted to (3R*,4R*)-3-(tert-butoxycarbonylamino)-3,4-dimethylpyrrolidine crude product (95 mg, 0.443 mmol, 91%), and the product was reacted with 6,7-difluoro-1-[(1R,2S)-2-fluorocyclopropyl]-8-methoxy-1,4-dihydro-4-oxoquinoline-3-carboxylic acid -difluoroboron complex (145 mg, 0.402 mmol) to obtain 65 mg (0.146 mmol, 36%) of the title compound as a white powder.

mp: 209-211° C.

$[\alpha]_D^{23.7}=+186.0°$ (c=0.162, 0.1N NaCH).

$^1$H-NMR (400 MHz, 0.1N NaOD) δ ppm: 1.01 (3H, d, J=6.8 Hz), 1.26 (3H, s), 1.53-1.71 (2H, m), 2.10 (1H, m), 3.34 (1H, d, J=7.5 Hz), 3.54-3.62 (5H, m), 3.76 (1H, dd, J=10.5, 2.9 Hz), 4.05 (1H, m), 4.80-5.02 (1H, m), 7.64 (1H, d, J=14.6 Hz), 8.48 (1H, s).

Elementary analysis for $C_{20}H_{23}F_2N_3O_4 \cdot 0.5EtOH \cdot 0.75H_2O$:

Calculated: C, 56.81; H, 6.24; F, 8.56; N, 9.46.

Found: C, 56.72; H, 6.26; F, 8.44; N, 9.30.

MS (EI) m/z: 407 (M$^+$).

IR (ATR): 2964, 2870, 2833, 1726, 1616, 1577, 1537, 1495, 1456, 1392, 1358, 1298, 1265, 1203 cm$^{-1}$.

Reference Example 9

Methyl (3R*,4R*)-1-benzyl-4-ethyl-3-methylpyrrolidine-3-carboxylate

[Compound 28]

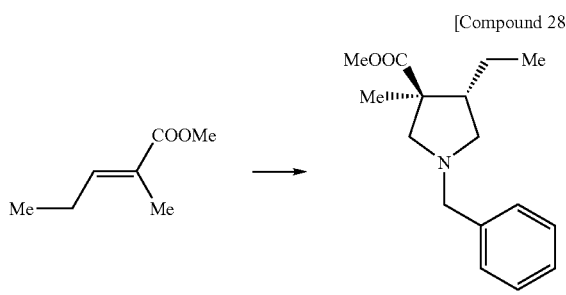

The procedure of Reference Example 1 was repeated by using methyl trans-2-methyl-2-pentenate (2.70 g, 21.1 mmol) and N-benzyl-N-(methoxy methyl)-N-trimethylsilyl methylamine (5.00 g, 21.1 mmol) to obtain 3.70 g (14.06 mmol, 67%) of the title compound as a pale yellow oil.

$^1$H-NMR (400 MHz, CDCl$_3$) δ ppm: 0.81 (3H, t, J=7.4 Hz), 1.14 (3H, s), 1.15-1.24 (1H, m), 1.44-1.54 (1H, m), 2.16 (1H, t, J=9.1 Hz), 2.22 (1H, d, J=9.6 Hz), 2.38-2.46 (1H, m), 2.92 (1H, dd, J=8.8, 7.8 Hz), 3.21 (1H, d, J=9.3 Hz), 3.51 (1H, d, J=13.2 Hz), 3.62 (3H, s), 3.62 (1H, d, J=13.2 Hz), 7.15-7.27 (5H, m).

MS (ESI) m/z: 262 (M+H)$^+$.

Reference Example 10

Methyl (3R*,4R*)-1-benzyloxycarbonyl-4-ethyl-3-methylpyrrolidine-3-carboxylate

[Compound 29]

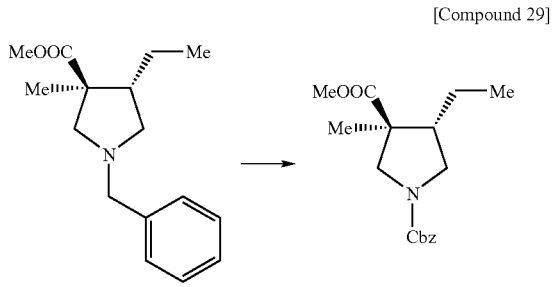

The procedure of Reference Example 2 was repeated by using methyl (3R*,4R*)-1-benzyl-4-ethyl-3-methylpyrrolidine-3-carboxylate (3.68 g, 14.08 mmol) to obtain 3.68 g (12.05 mmol, 86%) of the title compound as a colorless transparent oil.

$^1$H-NMR (400 MHz, CDCl$_3$) δ ppm: 0.86-0.92 (3H, m), 1.18 (3H, s), 1.23-1.34 (1H, m), 1.51-1.59 (1H, m), 2.42-2.54 (1H, m), 3.06 (1H, m), 3.40 (0.5H, d, J=10.7 Hz), 3.47 (0.5H, d, J=11.0 Hz), 3.68-3.79 (5H, m), 5.09-5.19 (2H, m), 7.28-7.38 (5H, m).

MS (ESI) m/z: 306 (M+H)$^+$.

Reference Example 11

(3R*,4S*)-1-Benzyloxycarbonyl-3-(tert-butoxycarbonylamino)-4-ethyl-3-methylpyrrolidine

[Compound 30]

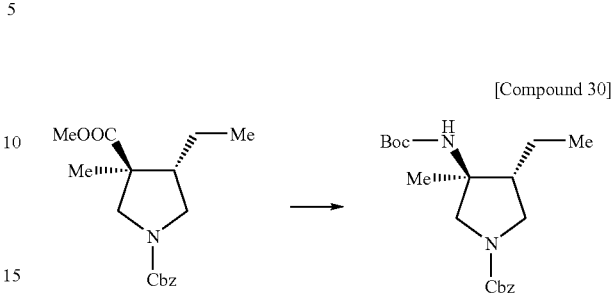

The procedure of Reference Example 3 was repeated by using methyl (3R*,4R*)-1-benzyloxycarbonyl-4-ethyl-3-methylpyrrolidine-3-carboxylate (3.68 g, 12.05 mmol) to obtain 3.25 g (8.97 mmol, 4 steps, 74%) of the title compound as a colorless transparent gummy solid.

$^1$H-NMR (400 MHz, CDCl$_3$) δ ppm: 0.91-0.98 (3H, m), 1.23-1.31 (4H, m) 1.41-1.54 (10H, m), 2.25-2.42 (1H, m), 2.99-3.06 (1H, m), 3.57-3.75 (3H, m), 4.55-4.59 (1H, m), 5.08-5.17 (2H, m), 7.27-7.38 (5H, m).

MS (ESI) m/z: 307 (M-tBu)$^+$.

Reference Example 12

(+)-(3R*,4S*)-1-Benzyloxycarbonyl-3-(tert-butoxycarbonylamino)-4-ethyl-3-methylpyrrolidine and (−)-(3R*,4S*)-1-benzyloxycarbonyl-3-(tert-butoxycarbonylamino)-4-ethyl-3-methylpyrrolidine The racemic body of (3R*,4S*)-1-benzyloxycarbonyl-3-(tert-butoxycarbonylamino)-4-ethyl-3-methylpyrrolidine (800 mg, 2.21 mmol) produced in Reference Example 11 was optically resolved in an optically active column (CHIRAL-PAK IA, 20 mm diam.×250 mm; hexane : dichloromethane, 75:25; flow rate, 20 mL/minute; resolution, 10 mg per run) to obtain (+)-(3R*,4S*)-1-benzyloxycarbonyl-3-(tert-butoxycarborylamino)-4-ethyl-3-methylpyrrolidine (393 mg, 1.084 mmol, retention time=11.3 minutes, [α]D25.1=+15.2° (c=0.230, chloroform)) and (−)-(3R*,4S*)-1-benzyloxycarbonyl-3-(tert-butoxycarbonylamino)-4-ethyl-3-methylpyrrolidine (396 mg, 1.093 mmol, retention time=13.1 minutes, [α]D25.1=−10.4 (c=0.125, chloroform)).

Example 5

7-[(3R*,4S*)-3-Amino-4-ethyl-3-methylpyrrolidin-1-yl]-6-fluoro-1-[(1R,2S)-2-fluorocyclopropyl]-8-methoxy-1,4-dihydro-4-oxoquinoline-3-carboxylic acid

[Compound 31]

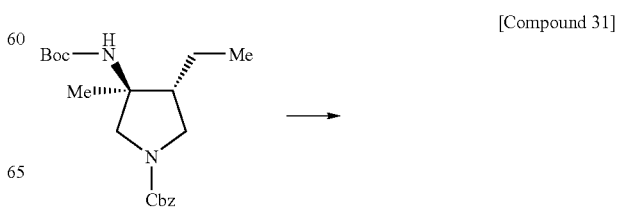

41

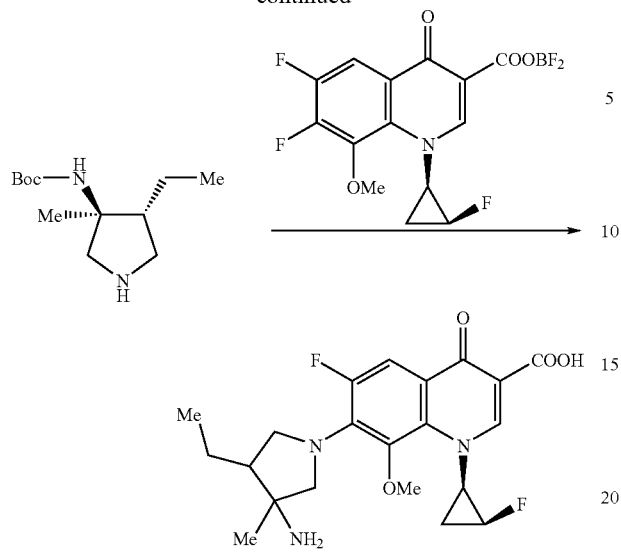

By using a procedure similar to Example 1, (+)-(3R*,4S*)-1-benzyloxycarbonyl-3-(tert-butoxycarbonylamino)-4-ethyl-3-methylpyrrolidine (383 mg, 1.057 mmol) was converted to crude (3R*,4S*)-3-(tert-butoxycarbonylamino)-4-ethyl-3-methylpyrrolidine, and the product was reacted with 6,7-difluoro-1-[(1R,2S)-2-fluorocyclopropyl]-8-methoxy-1,4-dihydro-4-oxoquinoline-3-carboxylic acid-difluoroboron complex (361 mg, 1.000 mmol) to obtain 260 mg (0.618 mmol, 62%) of the title compound as a white powder.

mp: 209-211° C.
$[\alpha]_D^{25.1}=-154.2°$ (c=0.144, 0.1N NaOH)
$^1$H-NMR (400 MHz, 0.1N NaOD) δ ppm: 0.94 (3H, t, J=7.3 Hz), 1.14 (3H, s), 1.19-1.41 (2H, m), 1.53 (1H, m), 1.61-1.67 (1H, m), 1.88-1.95 (1H, m), 3.40-3.42 (1H, m), 3.47-3.53 (1H, m), 3.54 (3H, s), 3.60 (1H, dd, J=10.0, 3.4 Hz), 3.73 (1H, t, J=9.2 Hz), 3.96-4.01 (1H, m), 5.02 (1H, ddd, J=63.8, 8.5, 5.4 Hz), 7.64 (1H, d, J=14.4 Hz), 8.38 (1H, d, J=3.2 Hz).

Elementary analysis for $C_{21}H_{25}F_2N_3O_4 \cdot 0.5H_2O$:
Calculated: C, 58.60; H, 6.09; F, 8.83; N, 9.76.
Found: C, 58.68; H, 5.94; F, 9.03; N, 9.69.
MS (FAB) m/z: 422 (M+H)$^+$.
IR (ATR): 2964, 2931, 2875, 1716, 1618, 1514, 1448, 1439, 1371, 1325, 1279, 1234 cm$^{-1}$.

Example 6

7-[(3R*,4S*)-3-Amino-4-ethyl-3-methylpyrrolidin-1-yl]-6-fluoro-1-[(1R,2S)-2-fluorocyclopropyl]-8-methoxy-1,4-dihydro-4-oxoquinoline-3-carboxylic acid

[Compound 32]

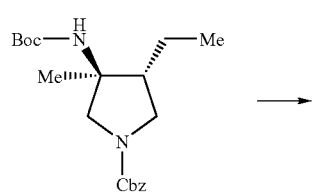

42

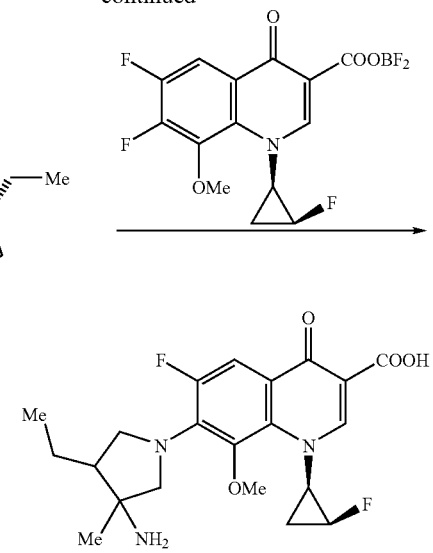

By using a procedure similar to Example 1, (−)-(3R*,4S*)-1-benzyloxycarbonyl-3-(tert-butoxycarbonylamino)-4-ethyl-3-methylpyrrolidine (386 mg, 1.065 mmol) was converted to crude (3R*,4S*)-3-(tert-butoxycarbonylamino)-4-ethyl-3-methylpyrrolidine, and the product was reacted with 6,7-difluoro-1-[(1R,2S)-2-fluorocyclopropyl]-8-methoxy-1,4-dihydro-4-oxoquinoline-3-carboxylic acid—difluoroboron complex (361 mg, 1.000 mmol) to obtain 263 mg (0.625 mmol, 63%) of the title compound as a white powder.

mp: 113-115° C.
$[\alpha]_D^{25.1}=+234.5°$ (c=0.310, 0.1N NaOE)
$^1$H-NMR (400 MHz, 0.1N NaOD) δ ppm: 0.91 (3H, t, J=7.3 Hz), 1.09 (3H, s), 1.17-1.28 (1H, m), 1.52-1.70 (3H, m), 1.80-1.88 (1H, m), 3.31 (1H, d, J=9.8 Hz), 3.49-3.53 (5H, m), 3.63-3.69 (1H, m), 4.02 (1H, m), 4.80-4.98 (1H, m), 7.64 (1H, d, J=14.6 Hz), 8.48 (1H, s).

Elementary analysis for $C_{21}H_{25}F_2N_3O_4 \cdot 0.25EtOH \cdot 0.5H_2O$:
Calculated: C, 58.43; H, 6.27; F, 8.60; N, 9.51.
Found: C, 58.36; H, 6.26; F, 8.68; N, 9.49.
MS (FAB) m/z: 422 (M+H)$^+$.
IR (ATR): 2960, 2929, 2873, 1728, 1614, 1579, 1541, 1510, 1433, 1392, 1352, 1296, 1275 cm$^{-1}$.

Reference Example 13

Ethyl Trans-4-fluoro-2-methyl-2-butenate

[Compound 33]

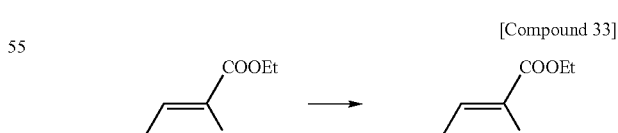

To a solution of ethyl trans-4-hydroxy-2-methyl-2-butenate synthesized by the method of Wolff, M. (Tetrahedron Letters, vol. 43, pages 2555-2559, 2002) (2.73 g, 18.94 mmol) in dichloromethane (100 mL), diethylaminosulfur trifluoride (7.45 mL, 56.9 mmol) was added dropwise in an ice bath in 10 minutes, and the mixture was stirred at the same temperature for 2 hours. To the reaction mixture was added saturated aqueous solution of sodium hydrogencarbonate (80 mL), and the solution was extracted with dichloromethane (200 mL+2×100 mL). The organic layer was dried with anhydrous sodium sulfate, and the dessicating agent was removed by using a short silica gel column. The solvent was removed by distillation under reduced pressure to obtain 2.43 g (16.63 mmol, 88%) of the target compound as a pale yellow oil.

$^1$H-NMR (400 MHz, CDCl$_3$) δ ppm: 1.31 (3H, t, J=7.2 Hz), 1.86-1.87 (3H, m), 4.22 (2H, q, J=7.2 Hz), 5.09 (2H, ddd, J=46.5, 5.9, 1.1 Hz), 6.82-6.89 (1H, m).

Reference Example 14

Ethyl (3R*,4R*)-1-benzyl-4-fluoromethyl-3-methylpyrrolidine-3-carboxylate

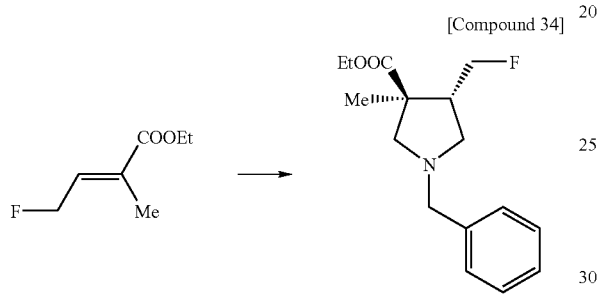

[Compound 34]

The procedure of Reference Example 1 was repeated by using ethyl trans-4-fluoro-2-methyl-2-butenate (2.43 g, 16.63 mmol) and N-benzyl-N-(methoxy methyl)-N-trimethylsilyl methylamine (5.11 mL, 19.97 mmol) to obtain 2.57 g (9.20 mmol, 55%) of the title compound as a pale yellow.

$^1$H-NMR (400 MHz, CDCl$_3$) δ ppm: 1.25 (3H, t, J=7.2 Hz), 1.30 (3H, s), 2.33 (1H, d, J=9.3 Hz), 2.46 (1H, dd, J=9.0, 7.1 Hz), 2.89-3.06 (2H, m), 3.16 (1H, d, J=9.3 Hz), 3.57 (1H, d, J=13.2 Hz), 3.64 (1H, d, J=13.2 Hz), 4.16 (2H, ddd, J=14.3, 7.1, 2.6 Hz), 4.44 (1H, ddd, J=34.9, 9.3, 6.0 Hz), 4.56 (1H, ddd, J=34.7, 9.3, 6.1 Hz), 7.21-7.35 (5H, m).

MS (ESI) m/z: 280 (M+H)$^+$.

Reference Example 15

Ethyl (3R*,4R*)-1-benzyloxycarbonyl-4-fluoromethyl-3-methylpyrrolidine-3-carboxylate

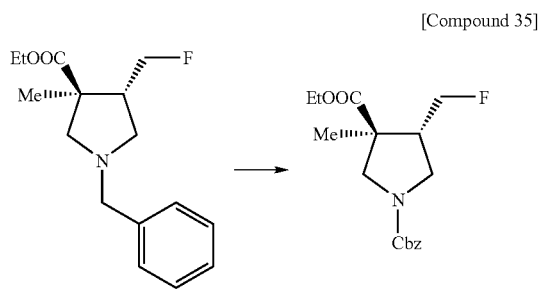

[Compound 35]

The procedure of Reference Example 2 was repeated by using ethyl (3R*,4R*)-1-benzyl-4-fluoromethyl-3-methylpyrrolidine-3-carboxylate (2.56 g, 9.16 mmol) to obtain 2.56 g (7.92 mmol, 86%) of the title compound as a colorless transparent oil.

$^1$H-NMR (400 MHz, CDCl$_3$) δ ppm: 1.26 (3H, t, J=7.2 Hz), 1.29 (3H, s), 2.91-3.00 (1H, m), 3.35-3.48 (2H, m), 3.71-3.77 (1H, m), 3.81 (1H, d, J=11.0 Hz), 4.11-4.21 (2H, m), 4.41-4.68 (2H, m), 5.10-5.18 (2H, m), 7.29-7.37 (5H, m).

MS (ESI) m/z: 324 (M+H)$^+$.

Reference Example 16

(3R*,4S*)-1-Benzyloxycarbonyl-3-(tert-butoxycarbonylamino)-4-fluoromethyl-3-methylpyrrolidine

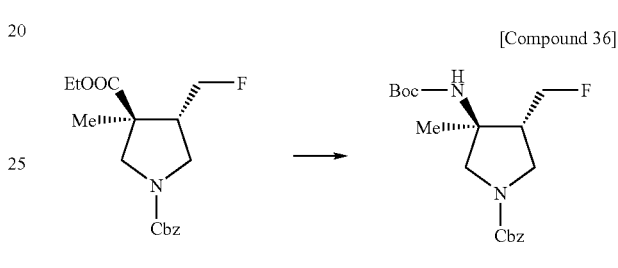

[Compound 36]

The procedure of Reference Example 3 was repeated by using ethyl (3R*,4R*)-1-benzyloxycarbonyl-4-fluoromethyl-3-methylpyrrolidine-3-carboxylate (2.55 g, 7.89 mmol) to obtain 2.14 g (5.84 mmol, 4 steps, 74%) of the title compound as a colorless transparent gummy solid.

$^1$H-NMR (400 MHz, CDCl$_3$) δ ppm: 1.37 (1.8H, s), 1.39 (1.2H, s), 1.42 (9H, m), 2.79-3.13 (1H, m), 3.19-3.31 (1H, m), 3.60-3.72 (3H, m), 4.41-4.62 (2H, m), 4.77 (0.4H, brs), 4.85 (0.6H, brs), 5.09-5.17 (2H, m), 7.28-7.37 (5H, m).

MS (ESI) m/z: 311 (M-tBu)$^+$.

Reference Example 17

(−)-(3R*,4S*)-1-Benzyloxycarbonyl-3-(tert-butoxycarbonylamino)-4-fluoromethyl-3-methylpyrrolidine and (+)-(3R*,4S*)-1-benzyloxycarbonyl-3-(tert-butoxycarbonylamino)-4-fluoromethyl-3-methylpyrrolidine The racemic body of (3R*,4S*)-1-benzyloxycarbonyl-3-(tert-butoxycarbonylamino) -4-fluoromethyl-3-methylpyrrolidine (1.454 g, 3.97 mmol) produced in Reference Example 16 was optically resolved in an active column (CHIRALPAK AS, 20 mm diam.×250 mm; hexane : isopropyl alcohol, 93:7; flow rate, 215 mL/minute; resolution, 60 mg per run) to obtain (−)-(3R*,4S*)-1-benzyloxycarbonyl-3-(tert-butoxycarbonylamino) -4-fluoromethyl-3-methylpyrrolidine (624 mg, 1.703 mmol, retention time=11.8 minutes, [α]D25.1=−15.0° (c=0.645, chloroform)) and (+)-(3R*,4S*)-1-benzyloxycarbonyl-3-(tert-butoxycarbonylamino) -4-fluoromethyl-3-methylpyrrolidine (623 mg, 1.700 mmol, retention time=15.5 minutes, [α]D25.1=+13.8° (c=1.230, chloroform)).

Example 7

7-[(3R*,4S*)-3-Amino-4-fluoromethyl-3-methylpyrrolidin-1-yl]-6-fluoro-1-[(1R,2S)-2-fluorocyclopropyl]-8-methoxy-1,4-dihydro-4-oxoquinoline-3-carboxylic acid

Example 8

7-[(3R*,4S*)-3-Amino-4-fluoromethyl-3-methylpyrrolidin-1-yl]-6-fluoro-1-[(1R,2S)-2-fluorocyclopropyl]-8-methoxy-1,4-dihydro-4-oxoquinoline-3-carboxylic acid

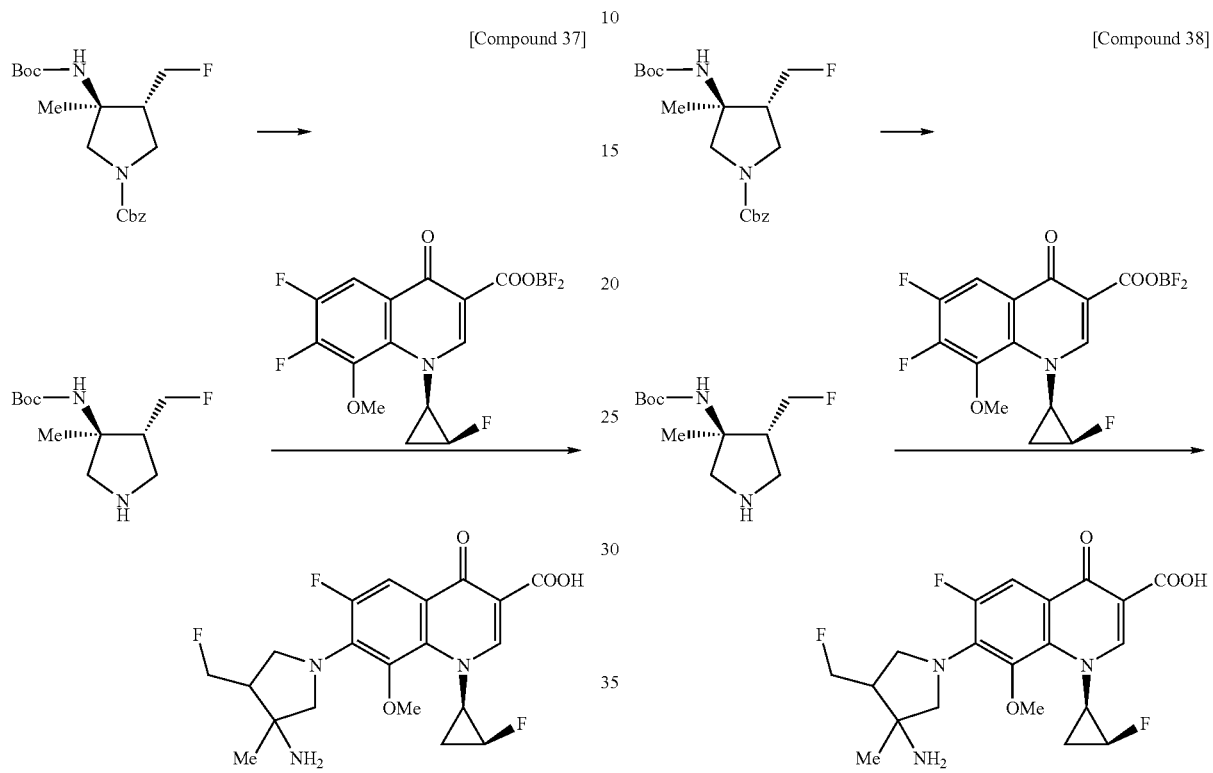

By using a procedure similar to Example 1, (−)-(3R*,4S*)-1-benzyloxycarbonyl-3-(tert-butoxycarbonylamino)-4-fluoromethyl-3-methylpyrrolidine (303 mg, 0.827 mmol) was converted to crude (3R*,4S*)-3-(tert-butoxycarbonylamino)-4-fluoromethyl-3-methylpyrrolidine, and the product was reacted with 6,7-difluoro-1-[(1R,2S)-2-fluorocyclopropyl]-8-methoxy-1,4-dihydro-4-oxoquinoline-3-carboxylic acid—difluoroboron complex (299 mg, 0.827 mmol) to obtain 231 mg (0.521 mmol, 63%) of the title compound as a white powder.

mp: 195-198° C.

$[\alpha]_D^{25.1}=-36.8°$ (c=0.125, 0.1N NaOH)

$^1$H-NMR (400 MHz, 0.1N NaOD) δ ppm: 1.29 (3H, s), 1.45 (1H, d, J=27.2 Hz), 1.52-1.64 (1H, m), 2.50 (1H, td, J=13.5, 6.9 Hz), 3.54-3.57 (2H, m), 3.58 (3H, s), 3.63 (1H, t, J=9.2 Hz), 3.94 (1H, t, J=9.2 Hz), 3.99-4.05 (1H, m), 4.63 (1H, ddd, J=37.6, 9.2, 6.5 Hz), 4.98 (2H, d, J=64.2 Hz), 7.66 (1H, d, J=14.5 Hz), 8.42 (1H, d, J=2.0 Hz).

Elementary analysis for $C_{20}H_{22}F_3N_3O_4 \cdot 1H_2O$):

Calculated: C, 54.17; H, 5.46; F, 12.85; N, 9.48.

Found: C, 54.34; H, 5.41; F, 13.13; N, 9.21.

MS (EI) m/z: 426 (M+H)$^+$.

IR (ATR): 3541, 3089, 2972, 2881, 1716, 1622, 1514, 1456, 1365, 1327, 1279, 1238 cm$^{-1}$.

By using a procedure similar to Example 1, (+)-(3R*,4S*)-1-benzyloxycarbonyl-3-(tert-butoxycarbonylamino)-4-fluoromethyl-3-methylpyrrolidine (310 mg, 0.846 mmol) was converted to crude (3R*,4S*)-3-(tert-butoxycarbonylamino)-4-fluoromethyl-3-methylpyrrolidine, and the product was reacted with 6,7-difluoro-1-[(1R,2S)-2-fluorocyclopropyl]-8-methoxy-1,4-dihydro-4-oxoquinoline-3-carboxylic acid—difluoroboron complex (305 mg, 0.846 mmol) to obtain 257 mg (0.516 mmol, 61%) of the title compound as a white powder.

mp: 186-189° C.

$[\alpha]_D^{25.1}=+132.0°$ (c=0.103, 0.1N NaOH).

$^1$H-NMR (400 MHz, 0.1N NaOD) δ ppm: 1.28 (3H, s), 1.51-1.70 (2H, m), 2.45-2.59 (1H, m), 3.46 (1H, d, J=9.8 Hz), 3.60 (3H, s), 3.66 (2H, q, J=7.1 Hz), 3.69 (1H, dd, J=10.0, 3.2 Hz), 3.74-3.79 (2H, m), 4.03-4.09 (1H, m), 4.66 (1H, ddd, J=37.3, 9.6, 6.4 Hz), 4.93 (2H, d, J=71.6 Hz), 7.67 (1H, d, J=14.5 Hz), 8.47 (1H, s).

Elementary analysis for $C_{20}H_{22}F_3N_3O_4 \cdot 1EtOH \cdot 1.5H_2O$:

Calculated: C, 53.01; H, 6.27; F, 11.43; N, 8.43.

Found: C, 53.03; H, 6.02; F, 11.86; N, 8.08.

MS (EI) m/z: 426 (M+H)$^+$.

IR (ATR): 2970, 2883, 1728, 1616, 1560, 1456, 1390, 1350, 1336, 1315, 1298, 1267, 1203 cm$^{-1}$.

Reference Example 18 tert-Butyl 1-acetyl-1-cyclopropanecarboxylate

[Compound 39]

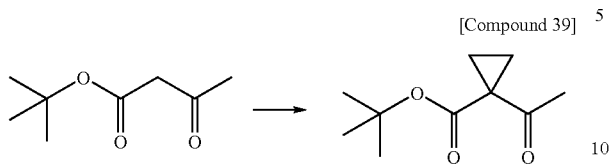

A mixture of tert-butyl acetoacetate (497 mL, 3.00 mol), 1,2-dibromoethane (310 mL, 3.60 mmol), potassium carbonate (1.106 k g, 8.00 mmol), and dimethylformamide (2.0 L) was stirred in a water bath at 30° C. for 1.5 hours, in a water bath at 60° C. for 3.5 hours, and in a water bath at 30° C. for 4 days. The reaction mixture was separated by filtration through celite, and the residue on the celite was washed with diethylether (3.5 L). The filtrate and the diethylether used for the washing were combined and added to water (2 L), and the organic layer was separated. The aqueous layer was extracted with diethylether (2 L), and water (1 L) was added to the resulting aqueous layer, and further extraction was conducted by adding diethylether (2 L). All organic layers were combined, and washed with 10% aqueous solution of citric acid (2 L), water (2 L×3), and saturated aqueous solution of sodium chloride (2 L×3), and dried by adding anhydrous sodium sulfate. After removing the dessicating agent by filtration, the solvent was removed by distillation under reduced pressure, and the residue was distilled under reduced pressure to obtain 371.8 g of the target compound (10 mmHg, distillation fraction of 72 to 78° C., 2.02 mol, 67%) as a colorless transparent oil.

$^1$H-NMR (400 MHz, CDCl$_3$) δ ppm: 1.37-1.40 (4H, m), 1.49 (9H, s), 2.44 (3H, s).

Reference Example 19 tert-Butyl 1-(1-amino-1-cyanoethyl)-1-cyclopropanecarboxylate

[Compound 40]

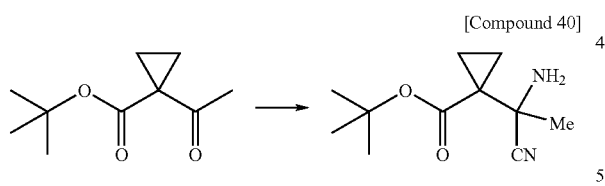

tert-Butyl 1-acetyl-1-cyclopropanecarboxylate (9.21 g, 50.0 mmol) was dissolved in a 7N solution of ammonia in methanol (300 mL), and to this solution in an ice bath were added concentrated ammonia solution (90 mL), ammonium chloride (53.5 g, 1.00 mol), and sodium cyanide (4.90 g, 100.0 mmol). The mixture was stirred at room temperature for 18 hours, and the solvent was concentrated under reduced pressure. To the concentrate was added water (100 mL), and the solution was extracted with dichloromethane (300 mL+2×100 mL). The organic layers were combined, and dried by adding anhydrous sodium sulfate. After removing the dessicating agent by filtration, the solvent was removed by distillation under reduced pressure to obtain 10.15 g (48.3 mmol, 97%) of the crude target compound as a pale brown oil. The thus obtained crude product was used in the subsequent reaction with no further purification.

$^1$H-NMR (400 MHz, CDCl$_3$) δ ppm: 1.02-1.12 (2H, m), 1.19-1.17 (2H, m), 1.48 (9H, s), 1.50 (3H, s), 2.13 (2H, brs).
MS (ESI) m/z: 155 (M-tBu)$^+$.

Reference Example 20 tert-Butyl 1-(1,2-diamino-1-methylethyl)-1-cyclopropane carboxylate

[Compound 41]

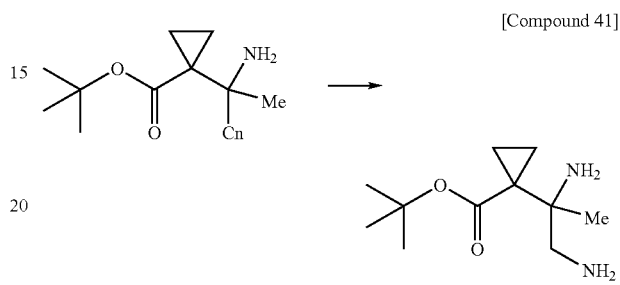

To a solution (50 mL) of tert-butyl 1-(1-amino-1-cyanoethyl)-1-cyclopropanecarboxylate (1.12 g, 5.30 mmol) in ethanol was added a suspension (30 mL) of Raney nickel catalyst (R-100 manufactured by Nikko Rica Corporation, 10 mL) in ethanol, and the suspension was vigorously stirred at room temperature for 6 hours in hydrogen gas atmosphere. The catalyst was removed by filtration through celite, and the solvent was removed by distillation under reduced pressure to obtain 0.84 g (3.92 mmol, 74%) of the crude target compound as a colorless transparent oil. The thus obtained crude product was used in the subsequent reaction with no further purification.

MS (ESI) m/z: 215 (M+H)$^+$.

Reference Example 21

1-(1,2-Diamino-1-methylethyl)-1-cyclopropanecarboxylic acid dihydrochloride

[Compound 42]

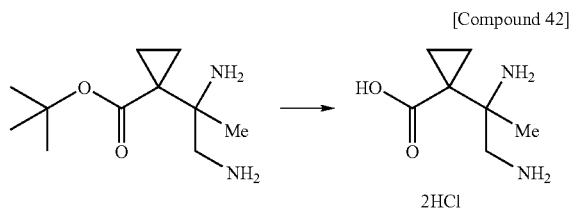

2HCl 0.82 g (3.83 mmol) of the crude tert-butyl 1-(1,2-diamino-1-methyl ethyl)-1-cyclopropanecarboxylate was dissolved in concentrated hydrochloric acid (5 mL) at room temperature, and the solution was stirred at the same temperature for 30 minutes. After adding water to the reaction solution, the solvent was removed by distillation under reduced pressure. The residue was azeotropically distilled with ethanol (twice) to obtain 0.82 g (3.55 mmol, 93%) of the crude target compound as a pale yellow foam solid. The thus obtained crude product was used in the subsequent reaction with no further purification.

$^1$H-NMR (400 MHz, CD$_3$OD) δ ppm: 1.20-1.26 (1H, m), 1.28 (3H, s), 1.32-1.43 (2H, m), 1.58-1.62 (1H, m), 3.46 (1H, d, J=13.4 Hz), 3.80 (1H, d, J=13.4 Hz).
MS (ESI) m/z: 159 (M+H)$^+$.

Reference Example 22

7-(tert-Butoxycarbonylamino)-7-methyl-5-azaspiro[2.4]heptan-4-one

[Compound 43]

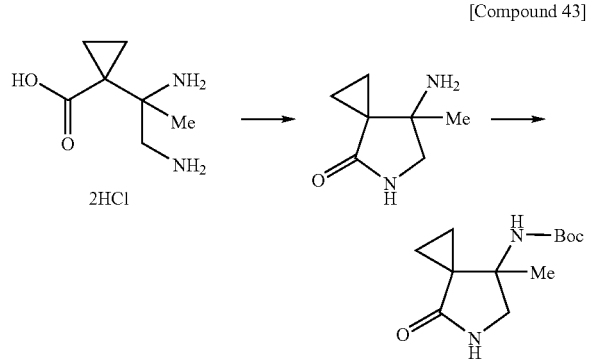

To a solution (70 mL) of the crude 1-(1,2-diamino-1-methyl ethyl)-1-cyclopropanecarboxylic acid dihydrochloride (800 mg, 3.46 mmol) in acetonitrile was added 1,1,1,3,3,3-hexamethyldisilazane (7.38 mL, 34.6 mmol), and the mixture was heated under reflux in an oil bath at 100° C. for 4 hours under nitrogen atmosphere. The mixture was cooled to room temperature, and after adding methanol (70 mL), the solvent was removed by distillation under reduced pressure to obtain crude 7-amino-7-methyl-5-azaspiro[2.4]heptan-4-one as a pale brown gummy solid.

MS (ESI) m/z: 141 (M+H)$^+$.

To the thus obtained crude 7-amino-7-methyl-5-azaspiro[2.4]heptan-4-one were added 1,4-dioxane (20 mL) and di-tert-butyl dicarbonate (1.528 g, 7.00 mmol) at room temperature, and the mixture was stirred at the temperature for 5 hours. Water (50 mL) was added to this reaction mixture, and the mixture was extracted with chloroform (100 mL+50 mL). The organic layers were combined and dried with anhydrous sodium sulfate. The dessicating agent was removed by filtration through a short silica gel column, and the solvent was removed by distillation under reduced pressure. Diethylether was added to the residue, and the resulting suspension was filtered to obtain 502 mg (2.09 mmol, 2 steps, 60%) of the target compound as a white powder.

$^1$H-NMR (400 MHz, CDCl$_3$) δ ppm: 0.77-0.82 (1H, m), 0.94-1.04 (2H, m) 1.16-1.23 (1H, m), 1.28 (3H, s), 1.43 (9H, s), 3.29 (1H, d, J=10.3 Hz), 4.12 (1H, m), 4.60 (1H, brs), 5.82 (1H, brs).

MS (ESI) m/z: 185 (M-tBu)$^+$.

Reference Example 23

5-Benzyl-7-(tert-butoxycarbonylamino)-7-methyl-5-azaspiro[2.4]heptan-4-one

[Compound 44]

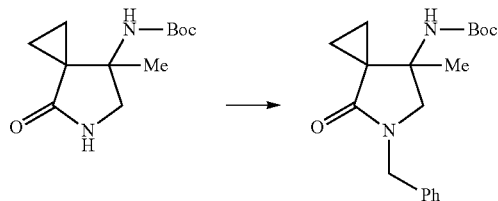

To a solution (65 mL) of 7-(tert-butoxycarbonylamino)-7-methyl-5-azaspiro[2.4]heptan-4-one (3.12 g, 12.97 mmol) in dimethylformamide in an ice bath was gradually added sodium hydride (55%, dispersion in a mineral oil, 538 mg, 12.33 mmol) in 5 minutes, and the mixture was stirred at the same temperature for 40 minutes. Benzyl bromide (1.851 mL, 15.56 mmol) was added, and the mixture was stirred at room temperature for 1.5 hours. The reaction mixture was diluted by adding ethyl acetate (300 mL), and the solution was washed with water (100 mL×2) and saturated aqueous solution of sodium chloride (100 mL). After drying the solution with anhydrous sodium sulfate and removing the dessicating agent by filtration, the solvent was removed by distillation under reduced pressure. The residue was purified by silica gel column chromatography (hexane : ethyl acetate, 9:1→4:1→2:1) to obtain 4.20 g (12.71 mmol, 98%) of the target compound as a colorless transparent gummy solid.

$^1$H-NMR (400 MHz, CDCl$_3$) δ ppm: 0.76-0.81 (1H, m), 0.93-1.06 (2H, m), 1.21-1.29 (4H, m), 1.37 (9H, m), 3.14 (1H, d, J=10.3 Hz), 3.92-3.98 (1H, m), 4.44 (1H, d, J=15.1 Hz), 4.56 (1H, d, J=14.6 Hz), 4.56 (1H, brs), 7.22-7.33 (5H, m).

MS (ESI) m/z: 331 (M+H)$^+$.

Reference Example 24

(−)-5-Benzyl-7-(tert-butoxycarbonylamino)-7-methyl-5-azaspiro[2.4]heptan-4-one and (+)-5-benzyl-7-(tert-butoxycarbonylamino)-7-methyl-5-azaspiro[2.4]heptan-4-one The racemic body of 5-benzyl-7-(tert-butoxycarbonylamino)-7-methyl-5-azaspiro[2.4]heptan-4-one produced in Reference Example 23 (2.254 g, 6.82 mmol) was optically resolved in an optically active column (CHIRALPAK AD, 20 mm diam.×250 mm; hexane: isopropyl alcohol, 90:10; flow rate, 20 mL/minute; resolution, 50 mg per run) to obtain (−)-5-benzyl-7-(tert-butoxycarbonylamino)-7-methyl-5-azaspiro[2.4]heptan-4-one (997 mg, 3.02 mmol, retention time=7.0 minutes, $[α]_D^{25.1}$=−113.9°(c=0.180, chloroform)) and (+)-5-benzyl-7-(tert-butoxycarbonylamino)-7-methyl-5-azaspiro[2.4]heptan-4-one (957 mg, 2.90 mmol, retention time=11.3 minutes, $[α]_D$=+108.8° (c=0.249, chloroform)).

Reference Example 25

(−)-5-Benzyl-7-(tert-butoxycarbonylamino)-7-methyl-5-azaspiro[2.4]heptane

[Compound 45]

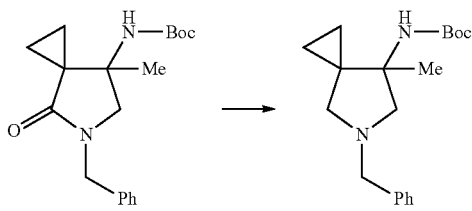

To a solution (15 mL) of (−)-5-benzyl-7-(tert-butoxycarbonylamino)-7-methyl-5-azaspiro[2.4]heptan-4-one (950 mg, 2.88 mmol) in dichloromethane at room temperature was added trifluoroacetic acid (7.5 mL), and the mixture was stirred at the same temperature for 40 minutes. The solvent was removed by distillation under reduced pressure. After azeotropically distilling the solution with toluene (twice), saturated aqueous solution of sodium hydrogencarbonate (30 mL) was added, and the solution was extracted with chloroform (100 mL+2×50 mL). The organic layers were combined, and dried with anhydrous sodium sulfate. After removing the dessicating agent by filtration, the solvent was removed by distillation under reduced pressure. The residue was dissolved in tetrahydrofuran (30 mL), and while stirring the solution in an ice bath. Lithium aluminum hydride (218 mg, 5.74 mmol) was added to the solution, and the solution was stirred at the same temperature for 1 hour. After adding another portion of lithium aluminum hydride (109 mg, 2.87 mmol) and stirring the solution at room temperature for 2.5 hours, the solution was ice cooled, and water (0.31 mL), 15% aqueous solution of sodium hydroxide (0.31 mL), and water (0.93 mL) were carefully added in this order. The resulting mixture was stirred overnight at room temperature, dried with magnesium sulfate, and subjected to filtration through celite. The filtrate was concentrated under reduced pressure to obtain the crude 7-amino-5-benzyl-7-methyl-5-azaspiro[2.4]heptane as a colorless transparent oil. The thus obtained crude product was used in the subsequent reaction with no further purification.

$^1$H-NMR (400 MHz, CDCl$_3$) δ ppm: 0.37-0.45 (2H, m), 0.56-0.66 (2H, m), 0.96 (3H, s), 2.48 (1H, d, J=9.0 Hz), 2.55 (1H, d, J=8.8 Hz), 2.74 (2H, d, J=9.0 Hz), 3.59 (2H, s), 7.21-7.37 (5H, m).

MS (ESI) m/z: 217 (M+H)$^+$.

The crude 7-amino-5-benzyl-7-methyl-5-azaspiro[2.4]heptane was dissolved in dichloromethane (15 mL), and after adding di-tert-butyl dicarbonate (1.255 g, 5.75 mmol), the mixture was stirred at room temperature for 22 hours. The solvent was removed by distillation under reduced pressure, and the residue was purified by silica gel column chromatography (chloroform : methanol : triethylamine, 98:2:1→95:5:1) to obtain 586 mg (1.852 mmol, 3 steps, 64%) of the target compound as a colorless transparent gummy solid.

$^1$H-NMR (400 MHz, CDCl$_3$) δ ppm: 0.40-0.45 (1H, m), 0.50-0.55 (1H, m), 0.63-0.69 (1H, m), 0.80-0.85 (1H, m), 1.20 (3H, s), 1.43 (9H, s), 2.44 (1H, d, J=8.8 Hz), 2.59 (1H, d, J=9.5 Hz), 2.83 (1H, d, J=8.8 Hz), 3.33 (1H, m), 3.57 (1H, d, J=13.2 Hz), 3.68 (1H, d, J=13.2 Hz), 4.75 (1H, brs), 7.20-7.37 (5H, m).

MS (ESI) m/z: 317 (M+H)$^+$.

$[α]_D^{25.1}$=−63.6° (c=0.129, chloroform)

Reference Example 26

(+)-5-Benzyl-7-(tert-butoxycarbonylamino)-7-methyl-5-azaspiro[2.4]heptane

[Compound 46]

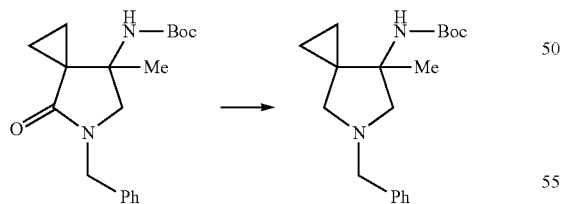

The procedure of Reference Example 25 was repeated by using (+)-5-benzyl-7-(tert-butoxycarbonylamino)-7-methyl-5-azaspiro[2.4]heptan-4-one (950 mg, 2.88 mmol) to obtain crude 7-amino-5-benzyl-7-methyl-5-azaspiro[2.4]heptane as a colorless transparent oil.

$^1$H-NMR (400 MHz, CDCl$_3$) δ ppm: 0.37-0.45 (2H, m), 0.56-0.66 (2H, m), 0.96 (3H, s), 2.48 (1H, d, J=9.0 Hz), 2.55 (1H, d, J=8.8 Hz), 2.74 (2H, d, J=9.0 Hz), 3.59 (2H, s), 7.21-7.37 (5H, m).

MS (ESI) m/z: 217 (M+H)$^+$.

By using the crude 7-amino-5-benzyl-7-methyl-5-azaspiro[2.4]heptane, the procedure of Reference Example 28 was repeated to obtain 629 mg (1.985 mmol, 3 steps, 69%) of the target compound as a colorless transparent gummy solid.

$^1$H-NMR (400 MHz, CDCl$_3$) δ ppm: 0.40-0.45 (1H, m), 0.50-0.55 (1H, m), 0.63-0.69 (1H, m), 0.80-0.85 (1H, m), 1.20 (3H, s), 1.43 (9H, s), 2.44 (1H, d, J=8.8 Hz), 2.59 (1H, d, J=9.5 Hz), 2.83 (1H, d, J=8.8 Hz), 3.33 (1H, m), 3.57 (1H, d, J=13.2 Hz), 3.68 (1H, d, J=13.2 Hz), 4.75 (1H, brs), 7.20-7.37 (5H, m)

MS (ESI) m/z: 317 (M+H)$^+$.

$[α]_D^{25.1}$=+76.2° (c=0.290, chloroform)

Reference Example 27

(−)-7-(tert-Butoxycarbonylamino)-7-methyl-5-azaspiro[2.4]heptane

[Compound 47]

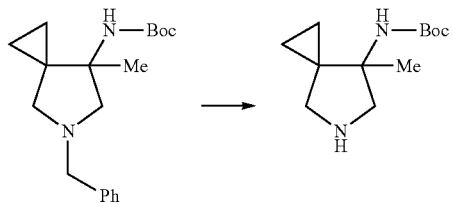

To a solution of (−)-5-benzyl-7-(tert-butoxycarbonylamino)-7-methyl-5-azaspiro[2.4]heptane (581 mg, 1.836 mmol) in methanol (40 mL) was added 10% palladium-carbon catalyst (M; water content, about 50%; 349 mg), and the suspension was stirred at room temperature for 2.5 hours in hydrogen atmosphere. After removing the catalyst by filtration, the solvent was removed by distillation under reduced pressure to obtain 434 mg (quantitative) of the crude target compound as a colorless transparent gummy solid.

$^1$H-NMR (400 MHz, CDCl$_3$) δ ppm: 0.38-0.43 (1H, m), 0.55-0.60 (2H, m), 0.74-0.80 (1H, m), 1.08 (3H, s), 1.44 (9H, s), 2.75 (1H, d, J=12.0 Hz), 2.77 (1H, d, J=11.5 Hz), 3.13 (1H, d, J=11.5 Hz), 3.75 (1H, brd, J=12.0 Hz), 4.44 (1H, brs).

MS (ESI) m/z: 227 (M+H)$^+$.

$[α]_D^{25.1}$=−63.5° (c=0.277, chloroform)

Reference Example 28

(+)-7-(tert-Butoxycarbonylamino)-7-methyl-5-azaspiro[2.4]heptane

[Compound 48]

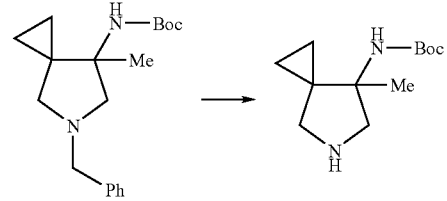

To a solution of (+)-5-benzyl-7-(tert-butoxycarbonylamino)-7-methyl-5-azaspiro[2.4]heptane (627 mg, 1.981 mmol) in methanol (40 mL) was added 10% palladium-carbon catalyst (M; water content, about 50%; 376 mg), and the suspension was stirred at room temperature for 5 hours in hydrogen atmosphere. After removing the catalyst, the solvent was removed by distillation under reduced pressure to obtain 452 mg (quantitative) of the crude target compound as a colorless transparent gummy solid.

$^1$H-NMR (400 MHz, CDCl$_3$) δ ppm: 0.38-0.43 (1H, m), 0.55-0.60 (2H, m), 0.74-0.80 (1H, m), 1.08 (3H, s), 1.44 (9H, s), 2.75 (1H, d, J=12.0 Hz), 2.77 (1H, d, J=11.5 Hz), 3.13 (1H, d, J=11.5 Hz), 3.75 (1H, brd, J=12.0 Hz), 4.44 (1H, brs).

MS (ESI) m/z: 227 (M+H)$^+$.

$[α]_D^{25.1}$=+59.5° (c=0.185, chloroform)

Reference Example 29

7-[7-(tert-Butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid under reduced pressure to obtain 870 mg (1.676 mmol, 91%) of the crude target compound as a yellow foam solid.

$^1$H-NMR (400 MHz, CDCl$_3$) δ ppm: 0.55-0.60 (1H, m), 0.68-0.73 (1H, m), 0.74-0.80 (1H, m), 0.92-0.97 (1H, m), 1.22 (3H, s), 1.40 (9H, s), 1.43-1.59 (2H, m), 3.13 (1H, d, J=9.8 Hz), 3.60 (3H, s), 3.75 (1H, dd, J=11.0, 3.7 Hz), 3.85 (1H, dt, J=10.2, 4.5 Hz), 4.18 (1H, d, J=10.0 Hz), 4.47 (1H, m), 4.62 (1H, s), 4.79-4.99 (1H, dm), 7.83 (1H, d, J=13.7 Hz), 8.68 (1H, d, J=2.7 Hz), 14.88 (0.7H, brs).

MS (ESI) m/z: 520 (M+H)$^+$.

$[α]_D^{25.1}$=128.5° (c=1.240, chloroform)

Reference Example 30

7-[7-(tert-Butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid

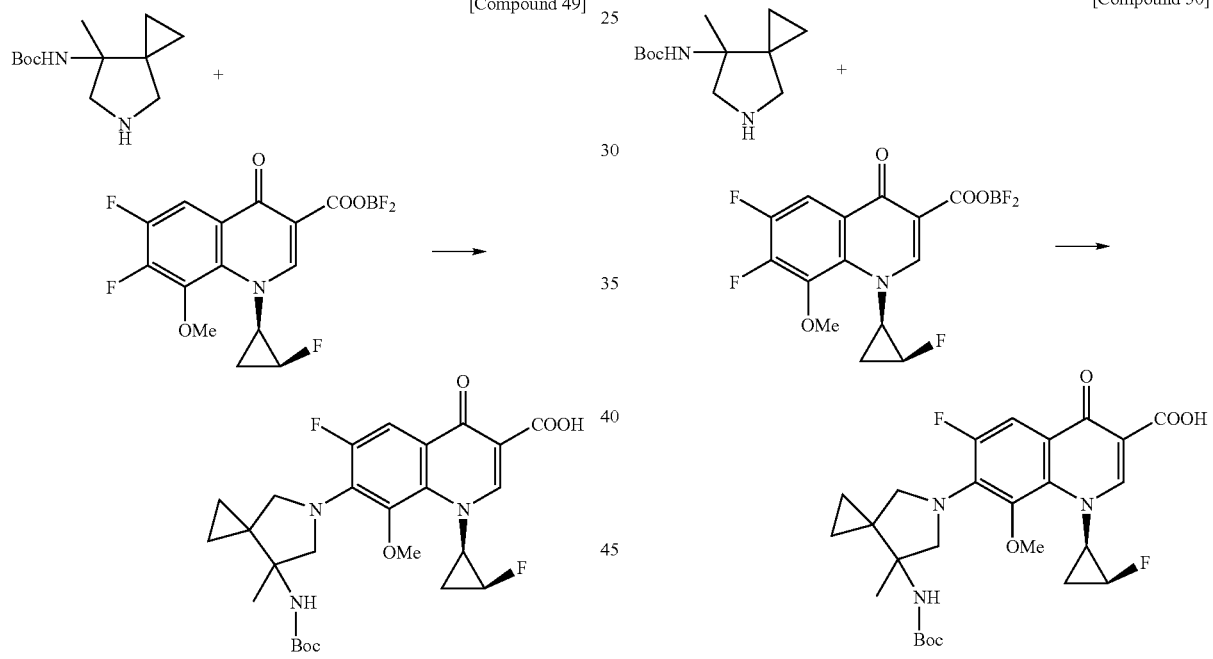

The crude (−)-7-(tert-butoxycarbonylamino)-7-methyl-5-azaspiro[2.4]heptane produced in Reference Example 27 (434 mg, 1.836 mmol), 6,7-difluoro-1-[(1R,2S)-2-fluorocyclopropyl]-8-methoxy-1,4-dihydro-4-oxoquinoline-3-carboxylic acid -difluoroboron complex (663 mg, 1.836 mmol), and triethylamine (0.768 mL, 5.510 mmol) were dissolved in dimethyl sulfoxide (5 mL), and the mixture was stirred in an oil bath at 40° C. for 14 hours. To the reaction mixture were added a mixed solution (50 mL) of ethanol and water (ethanol : water, 4:1) and triethylamine (5 mL), and the mixture was heated under reflux in an oil bath at 100° C. for 2 hours. The reaction mixture was then concentrated under reduced pressure, and the residue was dissolved in ethyl acetate (200 mL), and washed with 10% aqueous solution of citric acid (50 mL), water (50 mL×2), and saturated aqueous solution of sodium chloride (50 mL). The organic layer was dried with anhydrous sodium sulfate, and the solvent was removed by distillation The procedure of Reference Example 29 was repeated by using the crude (+)-7-(tert-butoxycarbonylamino)-7-methyl-5-azaspiro[2.4]heptane produced in Reference Example 28 (452 mg, 1.981 mmol) and 6,7-difluoro-1-[(1R,2S)-2-fluorocyclopropyl]-8-methoxy-1,4-dihydro-4-oxoquinoline-3-carboxylic acid -difluoroboron complex (715 mg, 1.981 mmol) to obtain 1.00 g (1.925 mmol, 97%) of the crude target compound as a yellow foam solid.

$^1$H-NMR (400 MHz, CDCl$_3$) δ ppm: 0.55-0.60 (1H, m), 0.68-0.80 (2H, m), 0.91-0.97 (1H, m), 1.21 (3H, s), 1.40 (9H, s), 1.53-1.68 (2H, m), 3.04 (1H, d, J=10.0 Hz), 3.61 (3H, s), 3.81 (1H, dd, J=10.7, 4.4 Hz), 3.87-3.93 (1H, m), 4.24 (1H, d, J=9.8 Hz), 4.46 (1H, m), 4.65-4.85 (2H, m), 7.83 (1H, d, J=13.4 Hz), 8.76 (1H, s).

MS (ESI) m/z: 520 (M+H)$^+$.

$[α]_D^{25.1}$=+133.2° (c=2.230, chloroform)

Example 9

7-(7-Amino-7-methyl-5-azaspiro[2.4]heptan-5-yl)-6-fluoro-1-[(1R,2S)-2-fluorocyclopropyl]-8-methoxy-1,4-dihydro-4-oxoquinoline-3-carboxylic acid

[Compound 51]

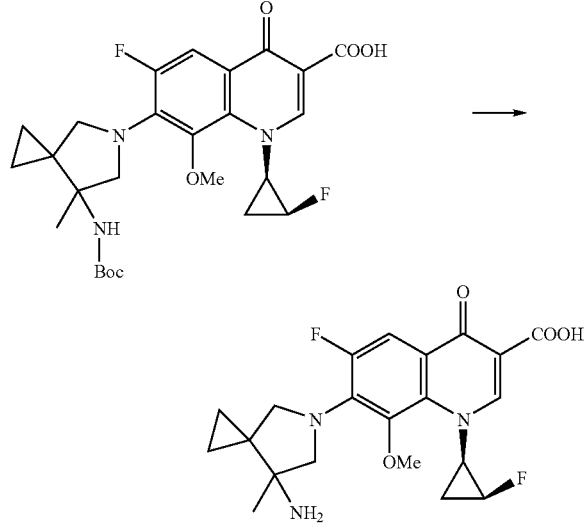

The 7-[7-(tert-butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid produced in Reference Example 29 (870 mg, 1.676 mmol) was dissolved in concentrated hydrochloric acid (10 mL) in an ice bath, and the mixture was stirred at room temperature for 20 minutes and washed chloroform (20 mL×5). Saturated aqueous solution of sodium hydroxide was added to the aqueous layer in an ice bath to adjust the pH to 12.0, and the pH was further adjusted to 7.4 by adding hydrochloric acid. The solution was extracted with a mixed solution (chloroform : methanol, 10:1) (200 mL×2), and then, with lower layer of a mixed solution (200 mL) (chloroform : methanol : water, 7:3:1). The organic layers were combined and dried with anhydrous sodium sulfate, and the solvent was removed by distillation. The residue was purified by recrystallization from ethanol, and the crystals were dried under reduced pressure to obtain 644 mg (1.535 mmol, 92%) of the title compound as a pale pink powder.

mp: 195-200° C.

$[\alpha]_D^{25.1}$=+40.8° (c=0.147, 0.1N NaOH)

$^1$H-NMR (400 MHz, 0.1N NaOD) δ ppm: 0.49-0.56 (2H, m), 0.67-0.76 (2H, m), 1.12 (3H, s), 1.43-1.64 (2H, m), 3.56 (3H, s), 3.59-3.71 (4H, m), 3.99-4.04 (1H, m), 4.80-5.03 (1H, m), 7.65 (1H, d, J=13.9 Hz), 8.45 (1H, s).

Elementary analysis for $C_{21}H_{23}F_2N_3O_4 \cdot 0.75EtOH \cdot 0.5H_2O$:

Calculated: C, 58.37; H, 6.20; F, 8.21; N, 9.08.

Found: C, 58.23; H, 5.99; F, 8.09; N, 9.02.

MS (EI) m/z: 419 (M$^+$).

IR (ATR): 2964, 2843, 1726, 1612, 1572, 1537, 1452, 1439, 1387, 1360, 1346, 1311, 1294, 1265, 1207 cm$^{-1}$.

Example 10

7-(7-Amino-7-methyl-5-azaspiro[2.4]heptan-5-yl)-6-fluoro-1-[(1R,2S)-2-fluorocyclopropyl]-8-methoxy-1,4-dihydro-4-oxoquinoline-3-carboxylic acid

[Compound 52]

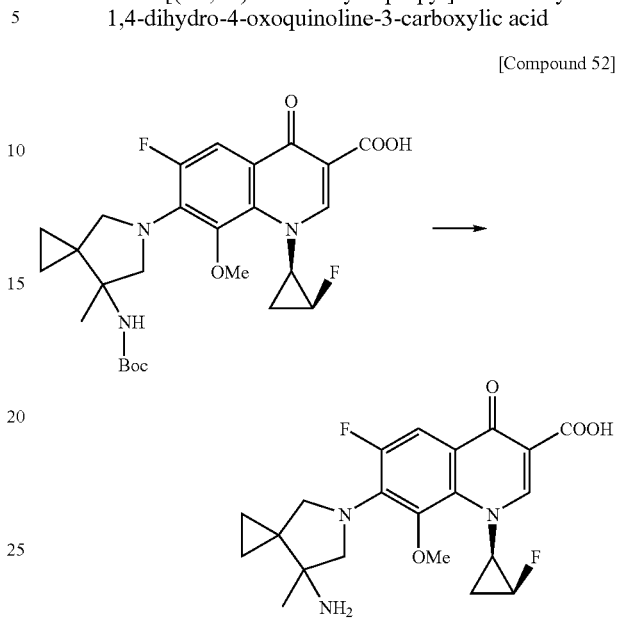

The procedure of Example 9 was repeated by using the 7-[7-(tert-butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid produced in Reference Example 30 (1000 mg, 1.925 mmol) to obtain 649 mg (1.546 mmol, 80%) of the title compound as a pale pink powder.

mp: 211-214° C.

$[\alpha]_D^{25.1}$=+128.8° (c=0.163, 0.1N NaOH).

$^1$H-NMR (400 MHz, 0.1N NaOD) δ ppm: 0.52 (2H, m), 0.73 (2H, m), 1.07 (3H, s), 1.42-1.64 (2H, m), 3.45 (1H, d, J=10.3 Hz), 3.52-3.56 (1H, m), 3.55 (3H, s), 3.73 (1H, dd, J=10.0, 2.2 Hz), 3.85 (1H, d, J=9.0 Hz), 3.99-4.04 (1H, m), 4.82-5.02 (1H, m), 7.64 (1H, d, J=14.4 Hz), 8.45 (1H, s).

Elementary analysis for $C_{21}H_{23}F_2N_3O_4 \cdot 1.0EtOH \cdot 0.5H_2O$:

Calculated: C, 58.22; H, 6.37; F, 8.01; N, 8.86.

Found: C, 58.02; H, 6.13; F, 8.05; N, 9.02.

MS (EI) m/z: 419 (M$^+$).

IR (ATR): 2970, 2848, 1726, 1614, 1577, 1537, 1452, 1439, 1389, 1360, 1354, 1317, 1296, 1265, 1215, 1203 cm$^{-1}$.

Example 11

7-(7-Amino-7-methyl-5-azaspiro[2.4]heptan-5-yl)-6-fluoro-1-[(1R,2S)-2-fluorocyclopropyl]-8-methoxy-1,4-dihydro-4-oxoquinoline-3-carboxylic acid Hydrochloride

[Compound 53]

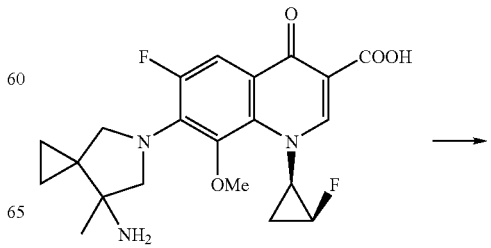

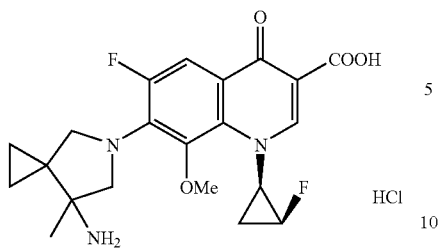
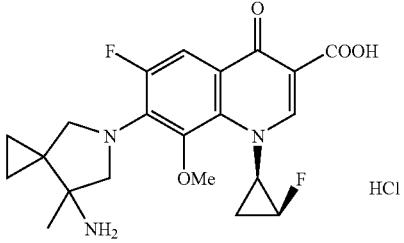

7-[7-amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid in which configuration of the amino group in the substituent at position 7 is the same as the one produced in Example 9 (18.07 g, 39.4 mmol) was suspended in methanol (54 mL), and 1N hydrochloric acid (43.4 mL, 43.4 mmol) was added to the suspension at room temperature. Isopropyl alcohol (180 mL) was then added, and the mixture was stirred in a water bath at 50° C. for some time until precipitated gummy material thoroughly turned to crystal. After allowing to stand at room temperature for 1 hour, the crystals were collected by filtration, and washed with a small amount of isopropyl alcohol (twice). The crystals were then dried under reduced pressure to obtain the title compound 12.91 g (27.2 mmol, 69%) as a yellow powder.

mp: 226-228° C.

$[\alpha]_D^{25.1}$=+41.1° (c=0.347, 0.1N NaOH)

$^1$H-NMR (400 MHz, 0.1N NaOD) δ ppm: 0.49-0.56 (2H, m), 0.67-0.76 (2H, m), 1.12 (3H, s), 1.43-1.64 (2H, m), 3.56 (3H, s), 3.59-3.71 (4H, m), 3.99-4.04 (1H, m), 4.80-5.03 (1H, m), 7.65 (1H, d, J=13.9 Hz), 8.45 (1H, s)

Elementary analysis for $C_{21}H_{23}F_2N_3O_4 \cdot 1HCl \cdot 1H_2O$:

Calculated: C, 53.22; H, 5.53; F, 8.02; N, 8.87; Cl, 7.48.

Found: C, 53.01; H, 5.52; F, 7.90; N, 8.71; Cl, 7.53.

Example 12

7-(7-Amino-7-methyl-5-azaspiro[2.4]heptan-5-yl)-6-fluoro-1-[(1R,2S)-2-fluorocyclopropyl]-8-methoxy-1,4-dihydro-4-oxoquinoline-3-carboxylic acid hydrochloride

[Compound 54]

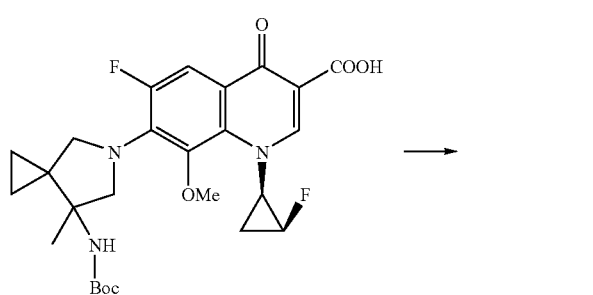

7-[7-(tert-Butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid in which configuration of the tert-butoxycarbonylamino group in the substituent at position 7 is the same as the one produced in Example 9 (267.2 g) was suspended in isopropyl alcohol (1.6 L), and 6N hydrochloric acid (405 mL, 2.43 mol) was added to the suspension while the suspension was stirred in an oil bath at 55° C. The mixture was stirred at the same temperature for 3.5 hours, and after allowing to cool to room temperature, isopropyl alcohol (2.4 L) was added. The reaction vessel was cooled in a water bath at 5° C., and the mixture was stirred at the same temperature for 13 hours. The precipitated crystals were collected by filtration and after air drying for several hours, the crystals were dried under reduced pressure at 40° C. to obtain 223.3 g (471 mmol, 92%) of the target compound as a yellow powder.

Reference Example 31

Methyl 3-methyl-5-oxo-1-[(R)-1-phenylethyl]pyrrolidin-3-yl -carboxylate

[Compound 55]

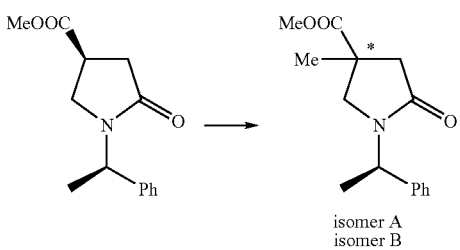

isomer A
isomer B

To a solution of methyl (3R)-5-oxo-1-[(R)-1-phenylethyl]pyrrolidin-3-yl-carboxylate (49.5 g, 200 mmol) and methyl iodide (37.4 mL, 600 mmol) in dimethylformamide (1 L), sodium hydride (in oil; content, 55%; 11.35 g: 260 mmol) was gradually added in 5 minutes at room temperature. After stirring at room temperature for 2 hours, methyl iodide (24.9 mL, 400 mmol) and sodium hydride (in oil; content, 55%; 6.11 g; 140 mmol) were further added, and the mixture was stirred for another 4 hours. The reaction mixture was added to 0.5N hydrochloric acid (1 L) in an ice bath, and extracted with ethyl acetate (2 L+1 L). The organic layers were combined and washed with water (1 L×2) and saturated aqueous solution of sodium chloride (1 L), and dried with anhydrous sodium sulfate. After removing the dessicating agent by filtration, the solvent was removed by distillation under reduced pressure. The thus obtained crude product was purified by silica gel column chromatography (hexane : ethyl acetate, 80:20→67:33→50:50→33:67) to obtain stereoisomers at position 3 of the title compound (stereoisomer A: 19.86 g (76.0 mmol, 38%) as a pale yellow oil, stereoisomer B: 20.22 g (77.4 mmol, 39%) as a pale yellow solid, and a mixture of stereoisomers A and B: 9.69 g (37.1 mmol, 19%) as a pale yellow oil.

Stereoisomer A:

$^1$H-NMR (400 MHz, CDCl$_3$) δ ppm: 1.21 (3H, s), 1.52 (3H, d, J=7.1 Hz), 2.31 (1H, d, J=16.8 Hz), 2.73 (1H, d, J=10.0 Hz), 2.95 (1H, d, J=16.9 Hz), 3.69 (1H, d, J=10.0 Hz), 3.72 (3H, s), 5.51 (1H, q, J=7.2 Hz), 7.26-7.37 (5H, m).

MS (ESI) m/z: 262 (M+H)$^+$.

$[α]_D^{25.1}$=+90.1° (c=0.350, chloroform)

Stereoisomer B:

$^1$H-NMR (400 MHz, CDCl$_3$) δ ppm: 1.39 (3H, s), 1.52 (3H, d, J=7.1 Hz), 2.33 (1H, d, J=16.9 Hz), 2.93 (1H, d, J=16.8 Hz), 3.09 (1H, d, J=10.0 Hz), 3.30 (1H, d, J=10.3 Hz), 3.61 (3H, s), 5.51 (1H, q, J=6.8 Hz), 7.25-7.36 (5H, m).

MS (ESI) m/z: 262 (M+H)$^+$.

$[α]_D^{25.1}$=+120.8° (c=0.190, chloroform)

Reference Example 32

Methyl 4-ethyl-3-methyl-5-oxo-1-[(R)-1-phenyl-ethyl]pyrrolidin-3-yl-carboxylate

[Compound 56]

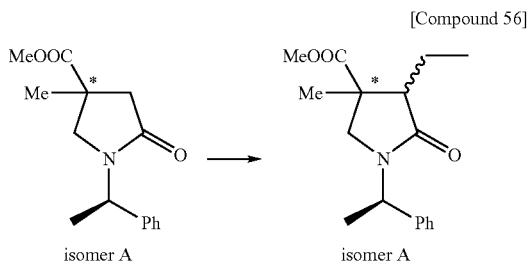

isomer A     isomer A

To a solution of the methyl 3-methyl-5-oxo-1-[(R)-1-phenylethyl]pyrrolidin-3-yl-carboxylate (stereoisomer A) produced in Reference Example 31 (19.86 g, 76.0 mmol) and hexamethylphosphoric triamide (30 mL) in tetrahydrofuran (300 mL), a solution of lithium diisopropyl amide in heptane, tetrahydrofuran, and ethylbenzene (1.8M, 63.3 mL, 113.9 mmol) was gradually added in 15 minutes at −78° C. After stirring the mixture at −78° C. for 30 minutes, ethyl iodide (12.2 mL, 152.0 mmol) was added dropwise at the same temperature in 10 minutes. After stirring at −78° C. for 1 hour, the mixture was quenched by adding saturated aqueous solution of ammonium chloride (100 mL). The reaction mixture was extracted with ethyl acetate (300 mL), and the organic layer was washed with water (200 mL×2) and saturated aqueous solution of sodium chloride (200 mL). After drying with anhydrous sodium sulfate, the dessicating agent was removed by filtration, and the solvent was removed by distillation under reduced pressure. The resulting crude product was purified by silica gel column chromatography (hexane : ethyl acetate, 90:10→85:15→80:20) to obtain 10.63 g of the title compound (a mixture of stereoisomers of position 4, 36.7 mmol, 48%) as a pale yellow oil.

$^1$H-NMR (400 MHz, CDCl$_3$) δ ppm: 1.01-1.07 (3.6H, m), 1.22 (2.4H, s), 1.45-1.56 (3.8H, m), 1.64-1.75 (1H, m), 1.80-1.85 (0.2H, m), 2.24 (0.8H, t, J=6.7 Hz), 2.61-2.65 (1H, m), 2.81 (0.2H, t, J=7.2 Hz), 3.55 (0.2H, d, J=9.5 Hz), 3.62 (0.8H, d, J=10.0 Hz), 3.699 (2.4H, s), 3.704 (0.6H, s), 5.50-5.56 (1H, m), 7.26-7.36 (5H, m).

MS (ESI) m/z: 290 (M+H)$^+$.

Reference Example 33

4-Ethyl-3-methyl-5-oxo-1-[(R)-1-phenylethyl]pyrrolidin-3-yl -carboxylic acid

[Compound 57]

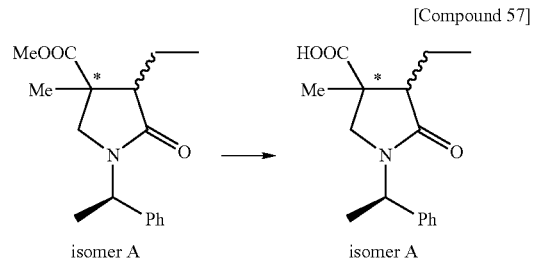

isomer A     isomer A

To a solution of the methyl 4-ethyl-3-methyl-5-oxo-1-[(R)-1-phenylethyl]pyrrolidin-3-yl-carboxylate (stereoisomer A) produced in Reference Example 32 (10.63 g, 36.7 mmol) in tetrahydrofuran (330 mL) and methanol (110 mL), 2N aqueous solution of sodium hydroxide (110 mL, 220 mmol) was added at room temperature, and the mixture was stirred in an oil bath at 60° C. for 5.5 hours. The reaction mixture was concentrated under reduced pressure, and after adding concentrated hydrochloric acid to the concentrate in an ice bath for acidification, the mixture was extracted with chloroform (300 mL+2×100 mL). The organic layers were combined, and dried with anhydrous sodium sulfate. After removing the dessicating agent by filtration, the solvent was removed by distillation under reduced pressure to obtain 11.46 g (quantitative) of the crude title compound as a pale brown solid. The crude product was used in the subsequent reaction with no further purification.

$^1$H-NMR (400 MHz, CDCl$_3$) δ ppm: 1.03-1.08 (3.6H, m), 1.25 (2.4H, s), 1.50-1.54 (3.2H, m), 1.59-1.70 (0.8H, m), 1.73-1.87 (1H, m), 2.30 (0.8H, t, J=6.6 Hz), 2.63 (0.8H, d, J=10.3 Hz), 2.67 (0.2H, d, J=9.8 Hz), 2.86 (0.2H, t, J=7.2 Hz), 3.60 (0.2H, d, J=9.8 Hz), 3.69 (0.8H, d, J=10.3 Hz), 5.48-5.56 (1H, m), 7.26-7.36 (5H, m).

MS (ESI) m/z: 276 (M+H)$^+$.

Reference Example 34

(3R*,4S*)-3-Amino-4-ethyl-3-methyl-5-oxo-1-[(R)-1-phenylethyl]pyrrolidine and (3R*,4R*)-3-amino-4-ethyl-3-methyl-5-oxo-1-[(R)-1-phenylethyl]pyrrolidine

[Compound 58]

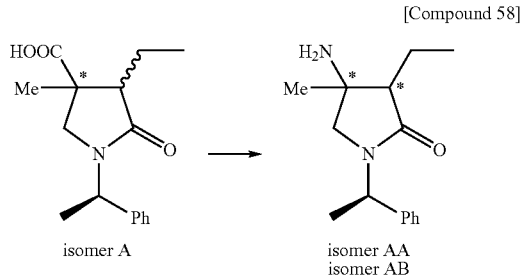

isomer A     isomer AA
                isomer AB

To a solution of the crude 4-ethyl-3-methyl-5-oxo-1-[(R)-1-phenylethyl]pyrrolidin-3-yl-carboxylic acid (stereoisomer A) (11.46 g) produced in Reference Example 33 and triethylamine (10.24 mL, 73.4 mmol) in toluene (150 mL), diphenylphosphoryl azide (10.29 mL, 47.7 mmol) was added at room temperature, and the mixture was stirred at room temperature for 15 minutes, and in an oil bath at 90° C. for 3 hours. The reaction mixture was diluted by adding ethyl acetate (500 mL), and the solution was washed with saturated aqueous solution of sodium hydrogencarbonate (200 mL), water (200 mL), and saturated aqueous solution of sodium chloride (200 mL) in this order. The resulting organic layer was dried with anhydrous sodium sulfate, and after removing the dessicating agent by filtration, the solvent was removed by distillation under reduced pressure to obtain the crude product in the form of an isocyanate. The crude product in the form of an isocyanate was dissolved in 1,4-dioxane (80 mL), and after adding 6N hydrochloric acid (80 mL), the mixture was stirred in an oil bath at 60° C. for 2 hours. The reaction mixture was concentrated under reduced pressure, and the concentrate was azeotropically distilled with ethanol. Water (100 mL) was added to the residue, and after stirring in an ice bath, saturated aqueous solution of sodium hydroxide was added for alkalization. The resulting mixture was extracted with dichloromethane (600 mL+100 mL), and the organic layers were combined. After drying with anhydrous sodium sulfate, the dessicating agent was removed by filtration, and the solvent was removed by distillation under reduced pressure. The resulting isomer mixture was separated and purified by silica gel column chromatography (chloroform : methanol : triethylamine, 100:0:1→99:1:1→98:2:1) to obtain 7.00 g of stereoisomer AA of the title compound ((3R*,4S*) configuration, 28.4 mmol, 2 steps, 77%) as a pale brown gummy solid, and 1.41 g of the stereoisomer AB of the title compound ((3R*,4R*) configuration, 5.72 mmol, 2 steps, 16%) as a pale brown gummy solid.

Stereoisomer AA:
$^1$H-NMR (400 MHz, CDCl$_3$) δ ppm: 1.14 (3H, t, J=7.6 Hz), 1.19 (3H, s), 1.43-1.55 (4H, m), 1.72-1.83 (1H, m), 2.05 (1H, t, J=6.8 Hz), 2.77 (1H, d, J=10.0 Hz), 2.99 (1H, d, J=9.8 Hz), 5.53 (1H, q, J=7.1 Hz), 7.24-7.35 (5H, m).
MS (ESI) m/z: 247 (M+H)$^+$.
$[α]_D^{25.1}$=+126.6° (c=0.470, chloroform)

Stereoisomer AB:
$^1$H-NMR (400 MHz, CDCl$_3$) δ ppm: 0.93 (3H, s), 1.13 (3H, t, J=7.4 Hz), 1.46-1.62 (4H, m), 1.65-1.74 (1H, m), 2.11 (1H, t, J=7.1 Hz), 2.70 (1H, d, J=9.5 Hz), 3.00 (1H, d, J=9.3 Hz), 5.52 (1H, q, J=7.1 Hz), 7.24-7.35 (5H, m).
MS (ESI) m/z: 247 (M+H)$^+$.
$[α]_D^{25}$ 1=+132.5° (c=0.260, chloroform)

Reference Example 35

(3R*,4R*)-3-(tert-Butoxycarbonylamino)-4-ethyl-3-methyl-1-[(R)-1-phenylethyl]pyrrolidine

[Compound 59]

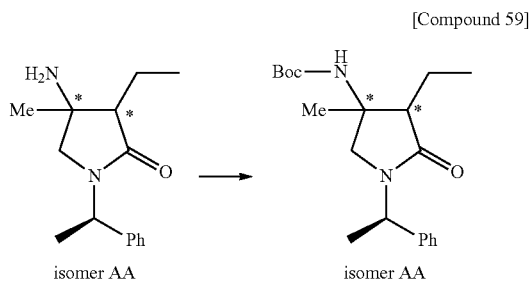

isomer AA     isomer AA

To a solution of (3R*,4S*)-3-amino-4-ethyl-3-methyl-5-oxo-1-[(R)-1-phenylethyl]pyrrolidine (isomer AA, 4.16 g, 16.89 mmol) in tetrahydrofuran (100 mL) produced in Reference Example 34, lithium aluminum hydride (1.282 g, 33.8 mmol) was gradually added in 5 minutes in an ice bath, and the mixture was stirred at room temperature for 2 hours. The reaction mixture was cooled in an ice bath, and after carefully adding water (1.22 mL, 67.7 mmol), 15% aqueous solution of sodium hydroxide (1.22 mL), and water (3.66 mL) in this order, the mixture was stirred overnight at room temperature. The insoluble content was removed by filtration, and the residue on the filter was washed with tetrahydrofuran (3 times), and the filtrate and the tetrahydrofuran used for the washing were combine. The solvent was removed by distillation under reduced pressure, and the residue was dissolved in dichloromethane (70 mL). Di-tert-butyl dicarbonate (5.53 g, 25.3 mmol) was added, and the mixture was stirred at room temperature for 25 hours. The solvent was removed by distillation under reduced pressure, and the residue was purified by silica gel column chromatography (hexane : ethyl acetate, 90:10→80:20→67:33) to obtain 4.45 g (13.37 mmol, 2 steps, 79%) of the title compound as a pale brown oil.

$^1$H-NMR (400 MHz, CDCl$_3$) δ ppm: 0.87 (3H, t, J=7.3 Hz), 1.14-1.22 (1H, m), 1.33 (3H, d, J=6.3 Hz), 1.44 (9H, s), 1.45 (3H, s), 1.55-1.65 (1H, m), 1.74-1.82 (1H, m), 2.36 (1H, t, J=8.8 Hz), 2.63 (1H, d, J=9.5 Hz), 2.71 (1H, d, J=8.1 Hz), 2.75 (1H, d, J=9.0 Hz), 3.28 (1H, q, J=6.5 Hz), 4.73 (1H, brs), 7.19-7.33 (5H, m).
MS (ESI) M/Z: 333 (M+H)$^+$.
$[α]_D^{25.1}$=+5.4° (c=0.410, chloroform.)

Reference Example 36

(3R*,4R*)-1-Benzyloxycarbonyl-3-(tert-butoxycarbonylamino)-4-ethyl-3-methylpyrrolidine

[Compound 60]

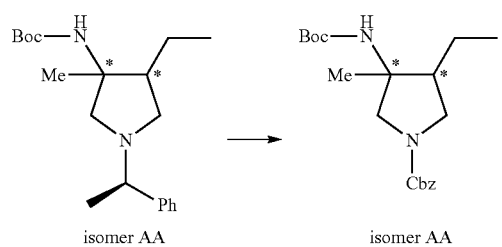

isomer AA     isomer AA

To a solution of (3R*,4R*)-3-(tert-butoxycarbonylamino)-4-ethyl-3-methyl-1-[(R)-1-phenylethyl]pyrrolidine (4.43 g, 13.33 mmol) produced in Reference Example 35 in dichloromethane (40 mL), benzyl chloroformate (5.71 mL, 39.9 mmol) was added at room temperature, and the mixture was stirred at the same temperature for 5 days. The solvent was removed by distillation under reduced pressure, and the residue was purified by silica gel column chromatography (hexane : ethyl acetate, 90:10→80:20→67:33) to obtain 3.94 g (10.86 mmol, 81%) of the title compound as a colorless transparent gummy solid.

$^1$H-NMR (400 MHz, CDCl$_3$) δ ppm: 0.94-1.00 (3H, m), 1.12-1.22 (1H, m), 1.41-1.47 (12H, m), 1.59-1.69 (1H, m), 1.82-1.95 (1H, m), 3.12-3.26 (2H, m), 3.65-3.75 (1H, m), 3.96 (0.3H, d, J=11.5 Hz), 4.10 (0.7H, m), 4.43 (1H, brs), 5.09-5.18 (2H, m), 7.27-7.38 (5H, m).
MS (ESI) m/z: 307 (M-tBu)$^+$.
$[α]_D^{25.1}$=−13.3° (c=0.120, chloroform)

Example 13

7-[(3R*,4R*)-3-Amino-4-ethyl-3-methylpyrrolidin-1-yl]-6-fluoro-1-[(1R,2S)-2-fluorocyclopropyl]-8-methoxy-1,4-dihydro-4-oxoquinoline-3-carboxylic acid

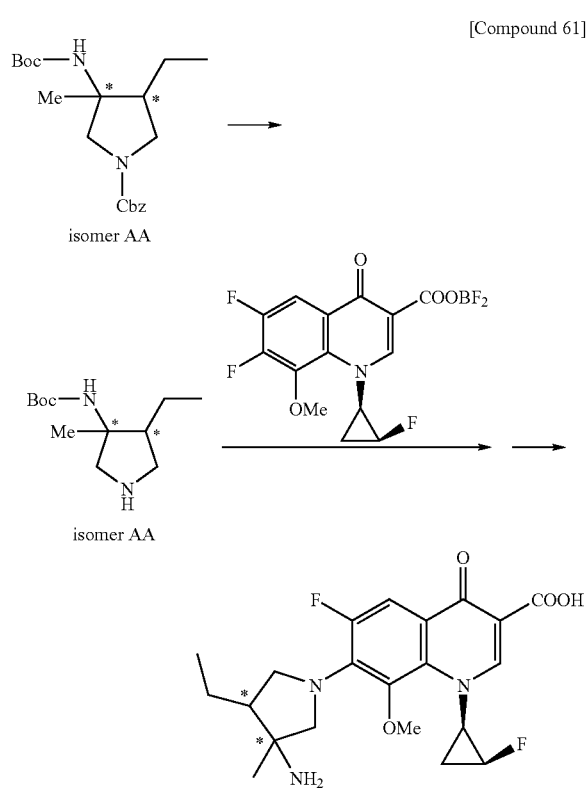

[Compound 61]

By using a procedure similar to Example 1, the crude (3R*,4R*)-1-benzyloxycarbonyl-3-(tert-butoxycarbonylamino)-4-ethyl-3-methylpyrrolidine (450 mg, 1.242 mmol) produced in Reference Example 36 was converted to (3R*,4R*)-3-(tert-butoxycarbonylamino)-4-ethyl-3-methylpyrrolidine (304 mg, quantitative), and 294 mg of the product was reacted with 6,7-difluoro-1-[(1R,2S)-2-fluorocyclopropyl]-8-methoxy-1,4-dihydro-4-oxoquinoline-3-carboxylic acid—difluoroboron complex (434 mg, 1.201 mmol) to obtain 282 mg (0.662 mmol, 55%) of the title compound as a white powder.

mp: 90-93° C.

$[\alpha]_D^{25.1}$=+220.2° (c=0.113, 0.1N NaOH).

$^1$H-NMR (400 MHz, 0.1N NaOD) δ ppm: 0.96 (3H, t, J=7.4 Hz), 1.27-1.34 (4H, m), 1.56-1.72 (3H, m), 1.89-1.97 (1H, m), 3.30 (1H, d, J=10.7 Hz), 3.56 (3H, s), 3.61-3.70 (2H, m), 3.78 (1H, dd, J=10.6, 2.8 Hz), 4.06 (1H, dd, J=13.1, 6.0 Hz), 4.82-5.01 (1H, m), 7.65 (1H, d, J=14.4 Hz), 8.48 (1H, s).

Elementary analysis for $C_{21}H_{25}F_2N_3O_4 \cdot 0.125H_2O$:

Calculated: C, 59.22; H, 6.03; F, 8.92; N, 9.87.

Found: C, 59.09; H, 5.84; F, 8.79; N, 9.89.

MS (FAB) m/z: 422 (M+H)$^+$.

IR (ATR): 2958, 2873, 1724, 1618, 1541, 1508, 1431, 1363, 1313, 1277, 1234 cm$^{-1}$.

Reference Example 37

Methyl (3R*,4R*)-4-ethyl-3-methyl-5-oxo-1-[(R)-1-phenylethyl]pyrrolidin-3-yl-carboxylate and methyl (3R*,4S*)-4-ethyl-3-methyl-5-oxo-1-[(R)-1-phenylethyl]pyrrolidin-3-yl-carboxylate

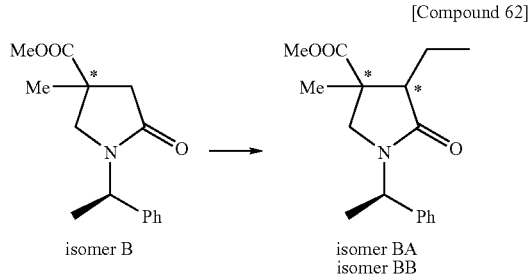

[Compound 62]

The procedure of Reference Example 32 was repeated by using the methyl 3-methyl-5-oxo-1-[(R)-1-phenylethyl]pyrrolidin-3-yl-carboxylate (stereoisomer B) produced in Reference Example 31 (20.22 g, 77.4 mmol) to obtain 2.27 g of stereoisomers BA at position 4 of the title compound ((3R*,4R*) configuration, 7.84 mmol, 10%) as a pale yellow oil and 7.40 g of stereoisomer BB ((3R*,4S*) configuration, 25.6 mmol, 33%) as a pale yellow oil.

Stereoisomer BA:

$^1$H-NMR (400 MHz, CDCl$_3$) δ ppm: 1.03 (3H, t, J=7.5 Hz), 1.25 (3H, s), 1.39-1.55 (4H, m), 1.79-1.90 (1H, m), 2.78 (1H, dd, J=8.0, 6.5 Hz), 2.95 (1H, d, J=9.8 Hz), 3.17 (1H, d, J=9.8 Hz), 3.64 (3H, s), 5.52 (1H, q, J=7.1 Hz), 7.25-7.35 (5H, m).

MS (ESI) m/z: 290 (M+H)$^+$.

$[\alpha]_D^{25.1}$=+106.7° (c=0.520, chloroform)

Stereoisomer BB:

$^1$H-NMR (400 MHz, CDCl$_3$) δ ppm: 1.00 (3H, t, J=7.6 Hz), 1.38-1.47 (4H, m), 1.51 (3H, d, J=7.4 Hz), 1.63-1.70 (1H, m), 2.26 (1H, dd, J=7.4, 6.4 Hz), 2.98 (1H, d, J=10.3 Hz), 3.29 (1H, d, J=10.3 Hz), 3.53 (3H, s), 5.52 (1H, q, J=7.1 Hz), 7.25-7.35 (5H, m).

MS (ESI) m/z: 290 (M+H)$^+$.

$[\alpha]_D^{25.1}$+130.0° (c=0.110, chloroform)

Reference Example 38

(3R*,4S*)-4-Ethyl-3-methyl-5-oxo-1-[(R)-1-phenylethyl]pyrrolidin-3-yl-carboxylic acid

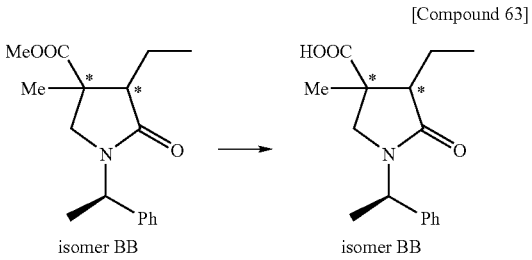

[Compound 63]

The procedure of Reference Example 33 was repeated by using the methyl (3R*,4S*)-4-ethyl-3-methyl-5-oxo-1-[(R)-1-phenylethyl]pyrrolidin-3-yl-carboxylate (stereoisomer BB, 2.04 g, 7.03 mmol) produced in Reference Example 37 to obtain 2.15 g (quantitative) of the crude target compound as a pale brown solid. The thus obtained crude product was used in the subsequent reaction with no further purification.

$^1$H-NMR (400 MHz, CDCl$_3$) δ ppm: 0.98 (3H, t, J=7.6 Hz), 1.41 (3H, s), 1.50-1.73 (5H, m), 2.30 (1H, dd, J=7.6, 5.9 Hz), 2.96 (1H, d, J=10.1 Hz), 3.32 (1H, d, J=10.5 Hz), 5.51 (1H, q, J=7.0 Hz), 7.23-7.34 (5H, m).

MS (ESI) m/z: 276 (M+H)$^+$.

Reference Example 39

(3R*,4S*)-3-Amino-4-ethyl-3-methyl-5-oxo-1-[(R)-1-phenylethyl]pyrrolidine

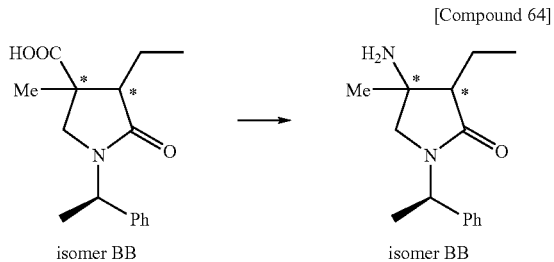

[Compound 64]

To a solution of the crude (3R*,4S*)-4-ethyl-3-methyl-5-oxo-1-[(R)-1-phenylethyl]pyrrolidin-3-yl-carboxylic acid produced in Reference Example 38 (stereoisomer BB, 2.15 g, 7.03 mmol) and triethylamine (1.96 mL, 14.06 mmol) in toluene (30 mL), diphenylphosphoryl azide (1.97 mL, 9.14 mmol) was added room temperature, and the mixture was stirred at room temperature for 15 minutes, and in an oil bath at 90° C. for 3 hours. The reaction mixture was diluted by adding ethyl acetate (200 mL), and the solution was washed with saturated aqueous solution of sodium hydrogencarbonate (50 mL), water (50 mL), and saturated aqueous solution of sodium chloride (50 mL) in this order. The resulting organic layer was dried with anhydrous sodium sulfate, and after removing the dessicating solution by filtration, the solvent was removed by distillation under reduced pressure to obtain the crude product in the form of an isocyanate. The thus obtained crude product in the form of an isocyanate was dissolved in 1,4-dioxane (16 mL), and 6N hydrochloric acid (16 mL) was added to the solution, and the mixture was stirred in an oil bath at 60° C. for 3.5 hours. The reaction mixture was concentrated under reduced pressure, and the concentrate was azeotropically distilled with ethanol. To the residue was added water (30 mL), and saturated aqueous solution of sodium hydroxide was added in an ice bath with stirring for alkalinization. The resulting mixture was extracted with dichloromethane (150 mL+2×50 mL), and the organic layers were combined and dried with anhydrous sodium sulfate. After removing the dessicating agent by filtration, the solvent was removed by distillation under reduced pressure to obtain 1.79 g (quantitative) of the crude target compound as a greenish brown oil. The thus obtained crude product was used in the subsequent reaction with no further purification.

$^1$H-NMR (400 MHz, CDCl$_3$) δ ppm: 1.13 (3H, t, J=7.6 Hz), 1.27 (3H, s), 1.46-1.58 (1H, m), 1.49 (3H, d, J=7.1 Hz), 1.68-1.80 (1H, m) 2.10 (1H, t, J=7.0 Hz), 2.68 (1H, d J=9.8 Hz), 3.13 (1H, d, J =9.8 Hz), 5.51 (1H, q, J=7.2 Hz), 7.24-7.35 (5H, m). MS (ESI) m/z: 247 (M+H)$^+$.

Reference Example 40

(3R*,4R*)-3-(tert-Butoxycarbonylamino-4-ethyl-3-methyl-1-[(R)-1-phenylethyl]pyrrolidine

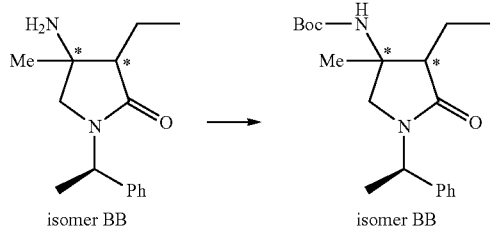

[Compound 65]

The procedure of Reference Example 35 was repeated by using the crude (3R*,4S*)-3-amino-4-ethyl-3-methyl-5-oxo-1-[(R)-1-phenylethyl]pyrrolidine produced in Reference Example 39 (stereoisomer BB, 1.79 g, 7.03 mmol) to obtain 2.03 g (6.11 mmol, steps, 87%) of the target compound as a pale red oil.

$^1$H-NMR (400 MHz, CDCl$_3$) δ ppm: 0.86 (3H, t, J=8.1 Hz), 1.11-1.21 (1H, m), 1.31 (3H, d, J=6.3 Hz), 1.42 (9H, s), 1.52 (3H, s), 1.55-1.65 (1H, m), 1.78-1.86 (1H, m), 2.27 (1H, t, J=9.2 Hz), 2.55 (1H, d, J=9.5 Hz), 2.81 (1H, c, J=9.5 Hz), 2.92 (1H, t, J =8.7 Hz), 3.33 (1H, q, J=6.5 Hz), 4.70 (1H, brs), 7.19-7.31 (5H, m).

MS (ESI) m/z: 333 (M+H)$^+$.

$[α]_D^{25.1}$=+30.3° (c=0.405, chloroform)

Reference Example 41

(3R*,4R*)-1-Benzyloxycarbonyl-3-(tert-butoxycarbonylamino)-4-ethyl-3-methylpyrrolidine

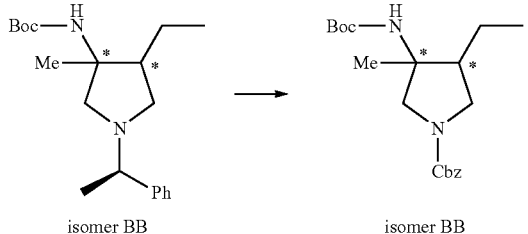

[Compound 66]

The procedure of Reference Example 36 was repeated by using the (3R*,4R*)-3-(tert-butoxycarbonylamino)-4-ethyl-3-methyl-1-[(R)-1-phenylethyl]pyrrolidine produced in Reference Example 40 (stereoisomer BB, 2.03 g, 6.11 mmol) to obtain 1.752 g (4.83 mmol, 79%) of the target compound as a pale pink gummy solid.

$^1$H-NMR (400 MHz, CDCl$_3$) δ ppm: 0.94-1.00 (3H, m), 1.12-1.22 (1H, m), 1.41-1.47 (12H, m), 1.59-1.69 (1H, m), 1.82-1.95 (1H, m), 3.12-3.26 (2H, m), 3.65-3.75 (1H, m), 3.96 (0.3H, d, J=11.5 Hz), 4.10 (0.7H, m), 4.43 (1H, brs), 5.09-5.18 (2H, m), 7.27-7.38 (5H, m).

MS (ESI) m/z: 307 (M-tBu)$^+$.

$[α]_D^{25.1}$=+10.5° (c=0.260, chloroform)

Example 14

7-[(3R*,4R*)-3-Amino-4-ethyl-3-methylpyrrolidin-1-yl]-6-fluoro-1-[(1R,2S)-2-fluorocyclopropyl]-8-methoxy-1,4-dihydro-4-oxoquinoline-3-carboxylic acid

[Compound 67]

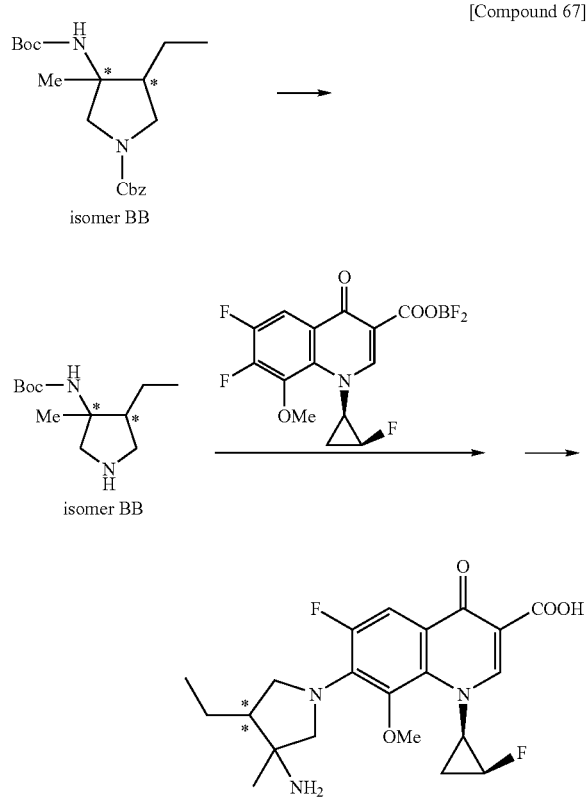

By using a procedure similar to Example 1, the (3R*,4R*)-1-benzyloxycarbonyl-3-(tert-butoxycarbonylamino)-4-ethyl-3-methylpyrrolidine produced in Reference Example 41 (439 mg, 1.211 mmol) was converted to crude (3R*,4R*)-3-(tert -butoxycarbonylamino)-4-ethyl-3-methylpyrrolidine (285 mg, quantitative), and 283 mg of the product was reacted with 6,7-difluoro-1-[(1R,2S)-2-fluorocyclopropyl]-8-methoxy-1,4-dihydro-4-oxoquinoline-3-carboxylic acid—difluoroboron complex (434 mg, 1.201 mmol) to obtain 256 mg (0.565 mmol, 47%) of the title compound as a white powder.

mp: 167-169° C.

$[\alpha]_D^{25.1}$=-97.6° (c=0.127, 0.1N NaOH)

$^1$H-NMR (400 MHz, 0.1N NaOD) δ ppm: 0.96 (3H, t, J=6.9 Hz), 1.25-1.44 (5H, m), 1.49-1.68 (2H, m), 1.94 (1H, m), 3.37 (1H, d, J=10.5 Hz), 3.54-3.76 (6H, m), 3.97-4.02 (1H, m), 5.02 (1H, dm, J=66.4 Hz), 7.65 (1H, d, J=14.6 Hz), 8.39 (1H, s)

Elementary analysis for $C_{21}H_{25}F_2N_3O_4 \cdot 0.5H_2O \cdot 0.5EtOH$:

Calculated: C, 58.27; H, 6.45; F, 8.38; N, 9.27.

Found: C, 58.31; H, 6.46; F, 8.23; N, 9.08.

MS (FAB) m/z: 422 (M+H)$^+$.

IR (ATR): 2967, 2939, 2883, 2831, 1728, 1612, 1577, 1537, 1493, 1456, 1439, 1389, 1358, 1302, 1284, 1261 cm$^{-1}$.

Reference Example 42 tert-Butyl 2-oxo-1-[(1R)-1-phenylethyl]pyrrolidine-4-carboxylate

[Compound 68]

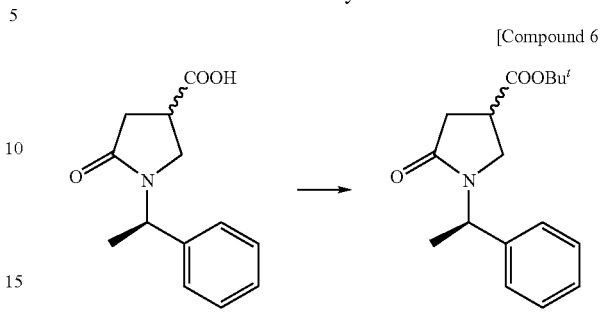

To a suspension of 2-oxo-1-[(1R)-1-phenylethyl]pyrrolidine-4-carboxylic acid (1165 g, 4.994 mol) in dichloromethane (10 L) was added O-tert-butyl-N,N'-diisopropylurea (3020 g, 15.00 mol) at room temperature with stirring, and the reaction system was cooled by adding ice water to outer bath when increase of inner temperature and start of the refluxing were noted. When the temperature decreased to room temperature, the reaction mixture was stirred for 1 hour after removing the ice bath, and for 3 hours by heating to 40° C. After stirring the reaction mixture in an ice bath for 1 hour, the insoluble content was separated by filtration, and the solvent was removed by distillation under reduced pressure. The residue was purified by silica gel column chromatography (silica gel, 4 kg; elution solution, hexane : ethyl acetate, 3:1) to obtain 925.2 g (64%) of a mixture of isomers at position 4 as a pale yellow syrup. Although separation of the isomers was easy, the isomers were used without separation since the subsequent step involved racemization. $^1$H-NMR spectrum of the isomers authentic sample is shown below.

Low Polarity Isomer:

$^1$H-NMR (400 MHz, CDCl$_3$) δ ppm: 1.45 (9H, s), 1.54 (3H, d, J=7.08), 2.59-2.74 (2H, m), 2.95-3.03 (1H, m), 3.14 (1H, dd, J=9.77, 8.79 Hz), 3.49 (1H, dd, J=9.77, 6.35 Hz), 7.26-7.36 (5H, m).

High Polarity Isomer:

$^1$H-NMR (400 MHz, CDCl$_3$) δ ppm: 1.36 (9H, s), 1.53 (3H, d, J=7.32), 2.59-2.75 (2H, m), 3.02-3.11 (1H, m), 3.16 (1H, dd, J=10.01, 5.62 Hz), 3.51 (1H, dd, J=10.01, 8.54 Hz), 7.24-7.36 (5H, m)

Reference Example 43 tert-Butyl (3S)-3-methyl-5-oxo-1-[(1R)-1-phenylethyl]pyrrolidine-3-carboxylate

[Compound 69]

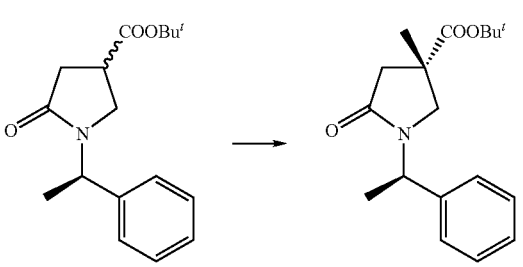

To a solution of tert-butyl 2-oxo-1-[(1R)-1-phenylethyl]pyrrolidine-4-carboxylate (30.05 g, 0.104 mol) in N,N'-dimethylformamide (210 mL), iodomethane 26.0 mL (59.28 g, 0.418 mol), and then sodium hydride 155%, in oil, 11.35 g, 0.260 mol) was added at room temperature in nitrogen atmosphere while stirring the mixture. When inner temperature increased to about 50° C., the reaction mixture was cooled to 30° C. by adding ice water to the outer bath. After changing the bath to a water bath at an outer temperature of 17° C., the mixture was stirred for 23 hours. The reaction mixture was poured into cold aqueous solution of citric acid (1 L of 10% citric acid and 500 g of ice), and after stirring the mixture for 30 minutes, the mixture was extracted with ethyl acetate (800 mL, 500 mL). The organic layers were combined, and washed with saturated aqueous solution of sodium chloride. After drying with anhydrous sodium sulfate, the mixture was subjected to filtration, and the filtrate was concentrated under reduced pressure. The concentrate was purified by flash silica gel column chromatography (elution was started at hexane ethyl acetate of 5:1, and after elution of the low polarity isomer, hexane : ethyl acetate was changed to 4:1) to obtain 10.63 g (33.7%) of high polarity isomer the title compound as a white solid. 14.91 g (47.3%) of low polarity isomer of tert-butyl (4R)-4-methyl-2-oxo-1-[(1R)-1-phenylethyl]pyrrolidine-4-carboxylate was also obtained.

$^1$H-NMR (400 MHz, CDCl$_3$) δ ppm: 1.34 (12H, s), 1.52 (3H, d, J=7.10 Hz), 2.27 (1H, d, J=17.0 Hz), 2.93 (1H, d, J=17.0 Hz), 3.05 (1H, d, J=10.1 Hz), 3.32 (1H, d, J=10.1 Hz), 5.50 (1H, q, J=7.1 Hz), 7.23-7.38 (5H, m).

Reference Example 44 tert-Butyl (3R)-4-hydroxy-3-methyl-5-oxo-1-[(1R)-1-phenylethyl]pyrrolidine-3-carboxylate

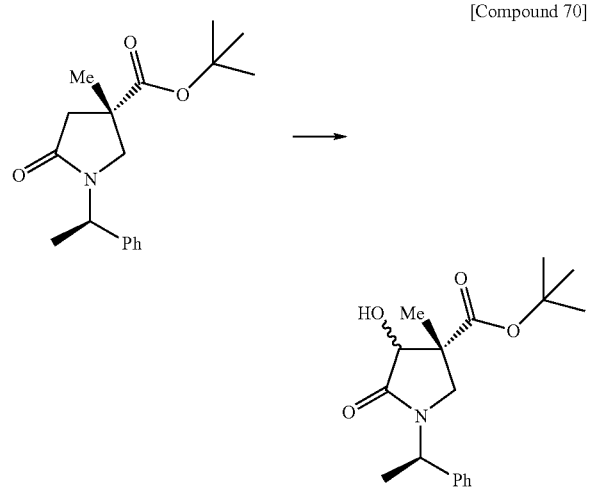

[Compound 70]

To a solution of tert-butyl (3S)-3-methyl-5-oxo-1-[(1R)-1-phenylethyl]pyrrolidine-3-carboxylate (10.0 g, 33.0 mmol) and triethyl phosphite (6.78 mL, 39.6 mmol) in anhydrous tetrahydrofuran (165 mL), lithium bistrimethylsilylamide (46.1 mL, 46.1 mmol, 1.0M solution in tetrahydrofuran) was added at −5° C., and the mixture was stirred at the same temperature for 30 minutes. After bubbling oxygen gas into the reaction mixture for 2 hours, saturated aqueous solution of ammonium chloride (150 mL) was added to the mixture in an ice bath, and the mixture was concentrated under reduced pressure. Water (100 mL) was added to the residue and the mixture was extracted with ethyl acetate (200 mL×2). The organic layer was washed with saturated aqueous solution of sodium chloride (200 mL), and dried with anhydrous sodium sulfate. After removing the solvent by distillation under reduced pressure, the residue was purified by silica gel column chromatography (hexane : ethyl acetate=1:1→1:4) to obtain 9.61 g (91.3%) of the title compound as a pale yellow oily substance.

$^1$H-NMR (400 MHz, CDCl$_3$) δ ppm: 1.24-1.54 (15H, m), 2.64-4.54 (3H, m), 5.44-5.51 (1H, m), 7.26-7.37 (5H, m)

MS (FAB$^+$) m/z: 320 (M+H)$^+$.

HRMS (FAB$^+$) m/z: Calcd for C$_{18}$H$_{26}$NO$_4$: δ 320.1862; Found: 320.1853.

IR (ATR) ν: 3363, 2978, 2935, 2360, 1716, 1684, 1489, 1456, 1369, 1304, 1269, 1230, 1167 cm$^{-1}$.

Reference Example 45 tert-Butyl (3R)-4-hydroxy-3-methyl-1-[(1R)-1-phenylethyl]pyrrolidine-3-carboxylate

[Compound 71]

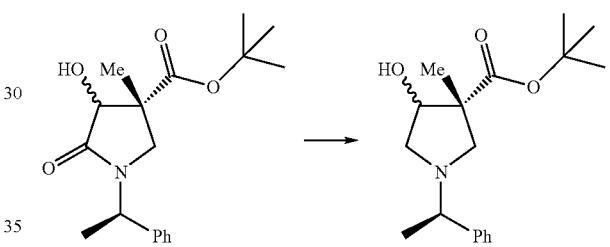

To a solution of tert-butyl (3R)-4-hydroxy-3-methyl-5-oxo-1-[(1R)-1-phenylethyl]pyrrolidine-3-carboxylate (9.35 g, 29.3 mmol) in tetrahydrofuran (150 mL), a solution of borane in tetrahydrofuran (82.6 mL, 96.6 mmol, 1.17M solution in tetrahydrofuran) was added in an ice bath, and the mixture was stirred room temperature for 14 hours. Water (20 mL), ethanol (80 mL), and triethylamine (20 mL) were added to the reaction mixture in an ice bath, and the mixture was heated under reflux in an oil bath at 88° C. for 2 hours. After concentrating the reaction mixture under reduced pressure, water (200 mL) was added and the mixture was extracted with ethyl acetate (200 mL×2). The organic layer was washed with saturated aqueous solution of sodium chloride (200 mL), and dried with anhydrous sodium sulfate. The solvent was removed by distillation under reduced pressure, and the residue was purified by silica gel column chromatography (hexane : ethyl acetate=3:1→1:2) to obtain 4.75 g (53.1%) of the title compound as a colorless oily substance.

$^1$H-NMR (400 MHz, CDCl$_3$) δ ppm: 1.25 (3H, s), 1.32 (3H, d, J=6.6 Hz), 1.44 (9H, s), 1.92 (1H, d, J=6.6 Hz), 2.39 (1H, d, J=9.5 Hz), 2.69 (1H, dd, J=9.8, 3.9 Hz), 2.75-2.82 (1H, m), 2.92 (1H, d, J=9.8 Hz), 3.31 (1H, q, J=6.6 Hz), 4.38-4.45 (1H, m), 7.20-7.30 (5H, m).

MS (FAB$^+$) m/z: 306 (M+H)$^+$.

HRMS (FAB$^+$) m/z: Calcd for C$_{18}$H$_{28}$NO$_3$: 306.2069; Found: 306.2064.

IR (ATR) ν: 3450, 2976, 2931, 2785, 2359, 1790, 1720, 1603, 1493, 1477, 1454, 1367, 1281, 1255, 1211 cm$^{-1}$.

Reference Example 46 tert-Butyl (3R)-1-benzyloxycarbonyl-4-hydroxy-3-methylpyrrolidine-3-carboxylate

[Compound 72]

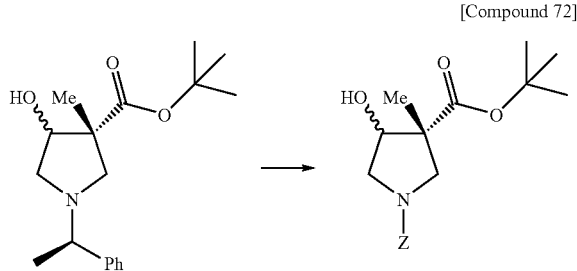

To a solution of tert-butyl (3R)-4-hydroxy-3-methyl-1-[(1R)-1-phenylethyl]pyrrolidine-3-carboxylate (2.00 g, 6.55 mmol) in ethanol (10 mL), 1N hydrochloric acid (6.88 mL, 6.88 mmol) was added at room temperature, and the mixture was stirred for 10 minutes. After concentrating the reaction mixture under reduced pressure and dissolving the residue in ethanol (50 mL), 10% palladium-carbon catalyst (200 mg) was added, and the suspension was stirred in an oil bath at 50° C. for 14 hours in hydrogen atmosphere. After filtering the reaction mixture, the filtrate was concentrated, and the diethylether (30 mL) and saturated sodium hydrogencarbonate (30 mL) were added to the residue, and benzyloxycarbonyl chloride (982 μl, 6.88 mmol) was added in an ice bath. The mixture was stirred at room temperature for 3 hours, and the reaction mixture was extracted with ethyl acetate (100 mL×2). The organic layer was washed with saturated aqueous solution of sodium chloride (20 mL), and dried with anhydrous sodium sulfate. The solvent was removed by distillation under reduced pressure and the residue was purified by silica gel column chromatography (hexane : ethyl acetate=2:1→1:2) to obtain 2.00 g (91.1%) of the title compound as a colorless oily substance.

$^1$H-NMR (400 MHz, CDCl$_3$) δ ppm: 1.30 (3H, s), 1.44 (9H, s), 2.10 (1H, dd, J=30.9, 3.8 Hz), 3.26-3.45 (2H, m), 3.68-3.79 (2H, m), 4.45-4.51 (1H, m), 5.13 (2H, s), 7.28-7.38 (5H, m)

MS (FAB$^+$) m/z: 336 (M+H)$^+$.

HRMS (FAB$^+$) m/z: Calcd for C$_{18}$H$_{26}$NO$_5$: 336.1811; Found: 336.1789.

IR (ATR) ν: 3421, 2978, 2941, 2885, 2364, 1788, 1707, 1687, 1498, 1456, 1423, 1367, 1319, 1257, 1213, 1161 cm$^{-1}$.

Reference Example 47 tert-Butyl (R)-1-benzyloxycarbonyl-3-methyl-4-oxopyrrolidine-3-carboxylate

[Compound 73]

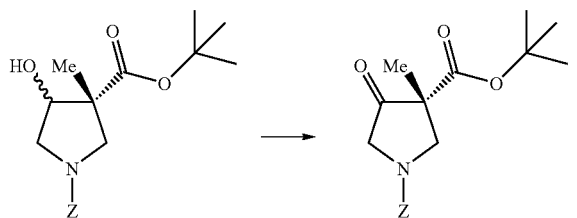

To a solution of oxalyl chloride (1.01 mL, 11.7 mmol) in dichloromethane (40 mL), a solution of dimethyl sulfoxide (1.11 mL, 15.6 mmol) in dichloromethane (5 mL) was added at −78° C., and the mixture was stirred for 10 minutes. After adding a solution of tert-butyl (R)-1-benzyloxycarbonyl-4-hydroxy-3-methylpyrrolidine-3-carboxylate (1.97 g, 5.87 mmol) in dichloromethane (15 mL) and stirring the mixture for 1 hour, triethylamine (5.98 mL, 42.9 mmol) was added, and the mixture was stirred −78° C. for 30 minutes and in an ice bath for 30 minutes. To the reaction mixture were added saturated aqueous solution of ammonium chloride (50 mL) and water (100 mL), and the mixture was extracted with ethyl acetate (200 mL×2). The organic layer was washed with water (100 mL) and saturated aqueous solution of sodium chloride (100 mL), and dried with anhydrous sodium sulfate. The solvent was removed by distillation under reduced pressure, and the residue was purified by silica gel column chromatography (hexane-ethyl acetate=10:1→3:2) to obtain 1.68 g (85.8%) of the title compound as a colorless oily substance.

$^1$H-NMR (400 MHz, CDCl$_3$) δ ppm: 1.34 (3H, d, J=4.9 Hz), 1.38 (9H, s), 3.46 (1H, d, J=12.0 Hz), 3.81 (1H, d, J=19.0 Hz), 4.10-4.19 (1H, m), 4.35 (1H, dd, J=5.9, 12.0 Hz), 5.19 (2H, s), 7.30-7.40 (5H, m).

MS (FAB$^+$) m/z: 334 (M+H)$^+$.

HRMS (FAB$^+$) m/z: Calcd for C$_{18}$H$_{24}$NO$_5$: 334.1654; Found: 334.1643.

IR (ATR) ν: 2981, 2941, 2889, 1768, 1711, 1498, 1454, 1421, 1369, 1290, 1269, 1196, 1134 cm$^{-1}$.

Reference Example 48 tert-Butyl (S)-1-benzyloxycarbonyl-3-methyl-4-methylene pyrrolidine-3-carboxylate

[Compound 74]

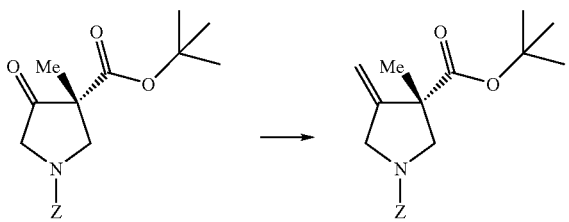

To a solution of methyltriphenylphosphonium bromide (2.02 g, 5.65 mmol) in anhydrous tetrahydrofuran (30 mL), n-butyl lithium (3.11 mL, 4.78 mmol, 1.54M solution in hexane) was added at −78° C., and the mixture was stirred for 20 minutes. At the same temperature, a solution of tert-butyl (R)-1-benzyloxycarbonyl-3-methyl-4-oxopyrrolidine-3-carboxylate (1.45 g, 4.35 mmol) in anhydrous tetrahydrofuran (15 mL) was added, and after gradually increasing the temperature, the mixture was stirred at 55° C. for 3 hours. To the reaction mixture was added 10% aqueous solution of citric acid (30 mL) in an ice bath, and the solution was concentrated under reduced pressure. Water (100 mL) was added to the concentrate, and the mixture was extracted with ethyl acetate (100 mL×2). The organic layer was washed with saturated aqueous solution of sodium hydrogencarbonate (50 mL) and saturated aqueous solution of sodium chloride (50 mL), and dried with anhydrous sodium sulfate. The solvent was removed by distillation under reduced pressure to obtain 710 mg (49.3%) of the title compound as a colorless oily substance.

¹H-NMR (400 MHz, CDCl₃) δ ppm: 1.36 (3H, d, J=6.6 Hz), 1.39 (9H, d, J=2.0 Hz), 3.24 (1H, dd, J=13.7, 11.2 Hz), 4.05-4.16 (2H, m), 4.19-4.29 (1H, m), 5.04-5.18 (4H, m), 7.29-7.38 (5H, m)

MS (FAB⁺) m/z: 332 (M+H)⁺.

HRMS (FAB⁺) m/z: Calc for $C_{19}H_{26}NO_4$: 332.1862; Found: 332.1869.

IR (ATR)ν: 2976, 2935, 2873, 1705, 1498, 1450, 1417, 1362, 1308, 1275, 1257, 1213, 1159 cm⁻¹.

Reference Example 49

(S)-1-Benzyloxycarbonyl-3-methyl-4-methylene pyrrolidine-3-carboxylic Acid

[Compound 75]

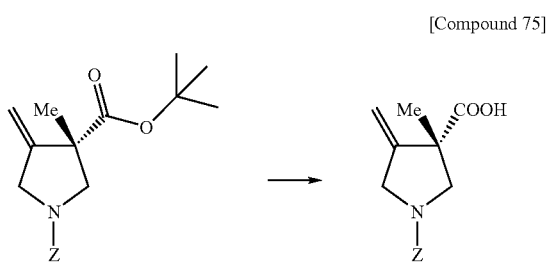

To a solution of tert-butyl (S)-1-benzyloxycarbonyl-3-methyl-4-methylene pyrrolidine-3-carboxylate (710 mg, 2.14 mmol) in dichloromethane (8 mL), trifluoroacetic acid (4 mL) was added in an ice bath, and the mixture was stirred at room temperature for 2 hours. Saturated aqueous solution of sodium hydrogencarbonate (20 mL) was added to the reaction mixture, and the mixture was washed with diethylether (20 mL). After adding 1N hydrochloric acid to the aqueous layer, the mixture was extracted with chloroform (100 mL×2), and the organic layer was dried with anhydrous sodium sulfate. The solvent was removed by distillation under reduced pressure to obtain 590 mg (100%) of the title compound as a colorless oily substance.

¹H-NMR (400 MHz, CDCl₃) δ ppm: 1.44 (3H, s), 3.23-3.36 (1H, m), 4.11-4.30 (3H, m), 5.09-5.25 (4H, m), 7.27-7.39 (5H, m).

MS (FAB⁺) m/z: 276 (M+H)⁺.

HRMS (FAB⁺) m/z: Calcd for $C_{15}H_{18}NO_4$: 276.1236, Found: 276.1222

IR (ATR) ν: 3064, 3032, 2979, 2945, 2877, 2362, 1705, 1672, 1498, 1423, 1362, 1309, 1257, 1213, 1167, 1124 cm⁻¹.

Reference Example 50

(S)-1-Benzyloxycarbonyl-3-(tert-butoxycarbonylamino)-3-methyl-4-methylene Pyrrolidine

[Compound 76]

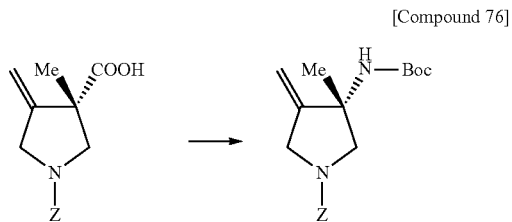

To a solution of (S)-1-benzyloxycarbonyl-3-methyl-4-methylene pyrrolidine-3-carboxylic acid (590 mg, 2.14 mmol) in toluene (21 mL), triethylamine (597 μl, 4.29 mmol) and diphenyl phosphoryl azide (508 μl, 2.36 mmol) was added, and the mixture was stirred at room temperature for 1 hour. The mixture was then heated under reflux in an oil bath at 125° C. for 1 hour, and concentrated. The concentrate was dissolved in 1,4-dioxane (8 mL) and 6N hydrochloric acid (4 mL) was added. After stirring for 1 hour, water (20 mL) was added to the reaction mixture, and the mixture was washed with diethylether (50 mL). The aqueous layer was alkalized with saturated aqueous solution of sodium hydrogencarbonate, and extracted with chloroform (100 mL×2). The organic layer was dried with anhydrous sodium sulfate, and the solvent was removed by distillation under reduced pressure. The residue was dissolved in dichloromethane (8 mL), and di-tert-butyl dicarbonate (936 mg, 4.29 mmol) was added in an ice bath. The solvent was stirred at 25° C. for 19 hours, and the reaction mixture was concentrated under reduced pressure. The concentrate was purified by silica gel column chromatography (hexane:ethyl acetate=5:1→3:1) to obtain 514 mg (69.2%) of the title compound as a colorless oily substance.

¹H-NMR (400 MHz, CDCl₃) δ ppm: 1.42 (3H, s), 1.46 (3H, s), 3.56 (1H, t, J=9.2 Hz), 3.85-3.98 (1H, m), 4.13-4.26 (2H, m), 4.62-4.74 (1H, m), 5.01-5.17 (4H, m), 7.27-7.38 (5H, m).

MS (FAB⁺) m/z: 347 (M+H)⁺.

HRMS (FAB⁺) m/z: Calcd for $C_{19}H_{27}N_2O_4$: 347.1971, Found: 347.1954

IR (ATR) ν: 3334, 2976, 2931, 2873, 1695, 1498, 1448, 1419, 1390, 1363, 1282, 1244, 1215, 1165 cm⁻¹.

Reference Example 51

(S)-3-(tert-Butoxycarbonylamino)-3-methyl-4-methylene Pyrrolidine

[Compound 77]

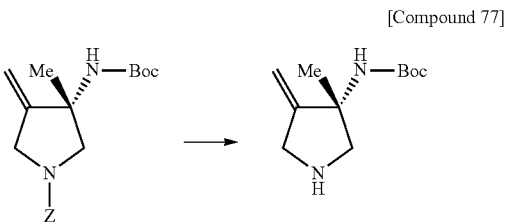

Ammonia gas was bubbled into a solution of (S)-1-benzyloxycarbonyl-3-(tert-butoxycarborylamino)-3-methyl-4-methylene pyrrolidine (488 mg, 1.41 mmol) in tetrahydrofuran (7 mL) at −78° C. to produce a mixed solution of liquid ammonia and tetrahydrofuran (20 mL), and sodium (162 mg, 7.04 mmol) was added. The mixture was stirred at the same temperature for 10 minutes. Saturated aqueous solution of ammonium chloride (20 mL) was added at −78° C., and the mixture was stirred at room temperature for 30 minutes. To the reaction mixture was added saturated aqueous solution of sodium hydrogencarbonate (50 mL), and the solution was extracted with chloroform (200 mL×2). The organic layer was dried with anhydrous sodium sulfate, and the solvent was removed by distillation under reduced pressure to obtain 218 mg (72.9%) of the title compound as a colorless crystals.

$[\alpha]_D^{25.1}$=−74.09° (c=1.04, CHCl₃)

¹H-NMR (400 MHz, CDCl₃) δ ppm: 1.41-1.416 (12H, m), 2.90 (1H, d, J=11.7 Hz), 3.45 (1H, d, J=14.2 Hz), 3.50-3.57

(1H, m), 3.69 (1H, d, J=16.1 Hz), 4.64 (1H, brs), 5.01 (1H, t, J=2.2 Hz), 5.04 (1H, t, J=2.2 Hz).

MS (FAB+) m/z: 213 (M+H)+.

HRMS (FAB+) m/z: Calcd for $C_{11}H_{21}N_2O_2$: 213.1603; Found: 213.1600.

IR (ATR) ν: 3284, 3199, 2978, 2922, 28329, 1695, 1660, 1556, 1441, 1365, 1333, 1288, 1279, 1248, 1176 cm$^{-1}$.

Example 15

7-[(3S)-3-Amino-3-methyl-4-methylene pyrrolidine-1-yl]-6-fluoro-1-[(1R,2S)-2-fluorocyclopropyl]-8-methoxy-1,4-dihydro-4-oxoquinoline-3-carboxylic Acid

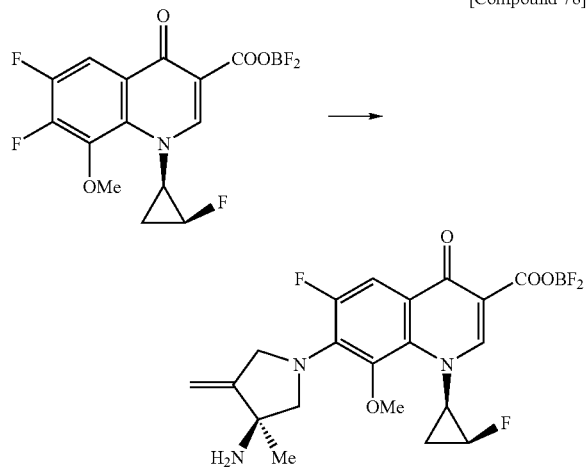

[Compound 78]

To a solution of (3S)-3-(tert-butoxycarbonylamino)-3-methyl-4-methylene pyrrolidine (218 mg, 1.03 mmol) in dimethyl sulfoxide (3.1 mL), triethylamine (156 μl, 1.12 mmol) and 6,7-difluoro-1-[(1R,2S)-2-fluorocyclopropyl]-8-methoxy-1,4-dihydro-4-oxoquinoline-3-carboxylic acid—difluoroborane complex (337 mg, 934 μmol) were added, and the mixture was stirred at room temperature for 3 days. The reaction mixture was concentrated, and to the concentrate were added a mixed solution of ethanol and water (ethanol:water, 4:1) (25 mL) and triethylamine (5 mL), and the mixture was heated under reflux in an oil bath at 90° C. for 3 hours. The reaction mixture was concentrated under reduced pressure, and 10% aqueous solution of citric acid (50 mL) and water (50 mL) were added to the residue, and the mixture was extracted with ethyl acetate (100 mL×2). The organic layer was washed with water (50 mL) and saturated aqueous solution of sodium chloride (50 mL). The organic layer was dried with anhydrous sodium sulfate, and the solvent was removed by distillation under reduced pressure. The residue was dissolved in concentrated hydrochloric acid (10 mL) in an ice bath, and the solution was stirred at room temperature for 10 minutes. Water (50 mL) was added to the reaction mixture, and the mixture was washed with chloroform (50 mL×2). In an ice bath, 10 mol/l aqueous solution of sodium hydroxide was added to the aqueous layer to pH 12.0, and the pH was adjusted to 7.4 by adding concentrated hydrochloric acid. The solution was extracted with chloroform (100 mL×2). The organic layer was dried with anhydrous sodium sulfate, and the solvent was removed by distillation under reduced pressure. The residue was purified by recrystallization from ethanol, and the crystals were dried under reduced pressure to obtain 224 mg (57.9%) of the title compound as a pale yellow crystals.

mp: 100-102° C.

$[\alpha]_D^{25.1}$=118.9° (c=0.39, 0.1N NaOH).

$^1$H-NMR (400 MHz, 0.1N NaOD) δ ppm: 1.40 (3H, s), 1.49-1.72 (2H, m) 3.51-3.67 (5H, m), 4.00-4.09 (1H, m), 4.46-4.53 (1H, m), 4.21 (1H, d, J=14.9 Hz), 4.97 (1H, d, J=64.5 Hz), 5.07 (1H, s), 5.18 (1H, s), 7.71 (1H, d, J=14.4 Hz), 8.47 (1H, d, J=1.2 Hz).

Elementary analysis for $C_{20}H_{21}F_2N_3O_4 \cdot 0.5E_2O$:
Calculated: C, 57.97; H, 5.35; F, 9.17; N, 10.14.
Found: C, 57.91; H, 5.42; F, 9.41; M, 10.15.

MS (ESI) m/z: 406 (M+H)+.

IR (ATR) ν: 2839, 1724, 1614, 1577, 1541, 1508, 1435, 1396, 1356, 1338, 1323, 1271, 1188 cm$^{-1}$.

Reference Example 52

(3S)-10-[7-(tert-Butoxycarbonylamino)-7-methyl-5-azaspiro[2.4]heptane-5-yl]-9-fluoro-2,3-dihydro-3-methyl-7-oxo-7H-pyrido[1,2,3-de][1,4]benzoxazine-6-carboxylic acid

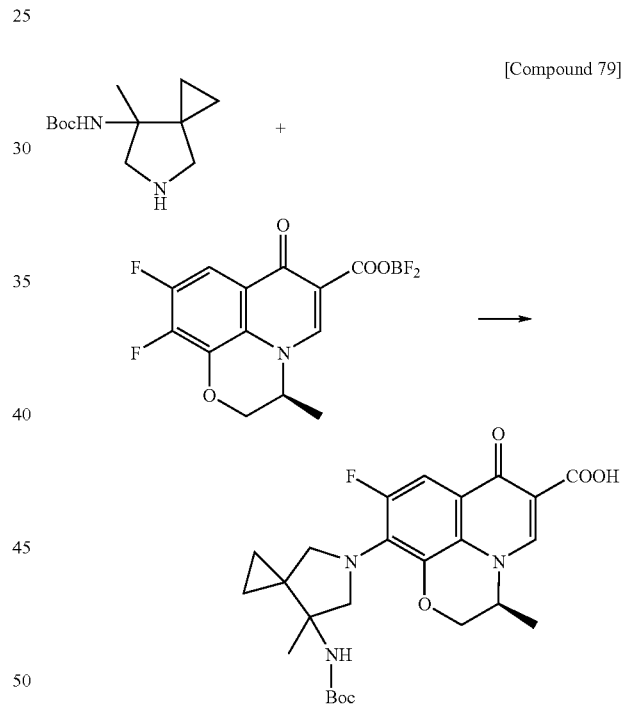

[Compound 79]

(−)-7-(tert-butoxycarbonylamino)-7-methyl-5-azaspiro[2.4]heptane (391 mg, 1.73 mmol), (3S)-9,10-difluoro-2,3-dihydro-3-methyl-7-oxo-7H-pyrido[1.2.3-de][1,4]benzoxazine-6-carboxylic acid—difluoroborane complex (580 mg, 1.76 mmol), and triethylamine (0.490 mL, 3.52 mmol) were dissolved in dimethyl sulfoxide (5 mL), and the solution was stirred in an oil bath at 40° C. for 24 hours. To the reaction mixture were added a mixed solution of ethanol and water (ethanol:water, 5:2) (7 mL) and triethylamine (2 mL), and the mixture was heated under reflux in an oil bath at 100° C. for 3.5 hours. The reaction mixture was concentrated under reduced pressure, and the concentrate was dissolved in ethyl acetate. The solution was washed with 10% aqueous solution of citric acid, water, and saturated aqueous solution of sodium chloride. The organic layer was dried with anhydrous sodium sulfate, and the solvent was removed by distillation under reduced pressure. The residue was purified by silica gel column chromatography (dichloromethane:methanol, 98:2) to obtain 761 mg (5.37 mmol, 90%) of the title compound as a yellow oily product.

1H-NMR (400 MHz, CDCl$_3$) δ ppm: 0.53-0.60 (1H, m), 0.63-0.71 (1H, m), 0.71-0.79 (1H, m), 0.87-0.96 (1H, m), 1.21 (3H, s), 1.42 (9H, s), 1.61 (3H, d, J=6.8 Hz), 3.32 (1H, dd, J=10.3, 2.2 Hz), 3.89 (1H, dd, J=11.0, 2.2 Hz), 4.15-4.69 (5H, m), 7.68 (1H, d, J=14.2 Hz), 8.54 (1H, s).

MS (ESI) m/z: 488 (M+H)$^+$.

Example 16

(3S)-10-(7-Amino-7-methyl-5-azaspiro[2.4]heptane-5-yl)-9-fluoro-2,3-dihydro-3-methyl-7-oxo-7H-pyrido[1,2,3-de][1,4]benzoxazine-6-carboxylic Acid

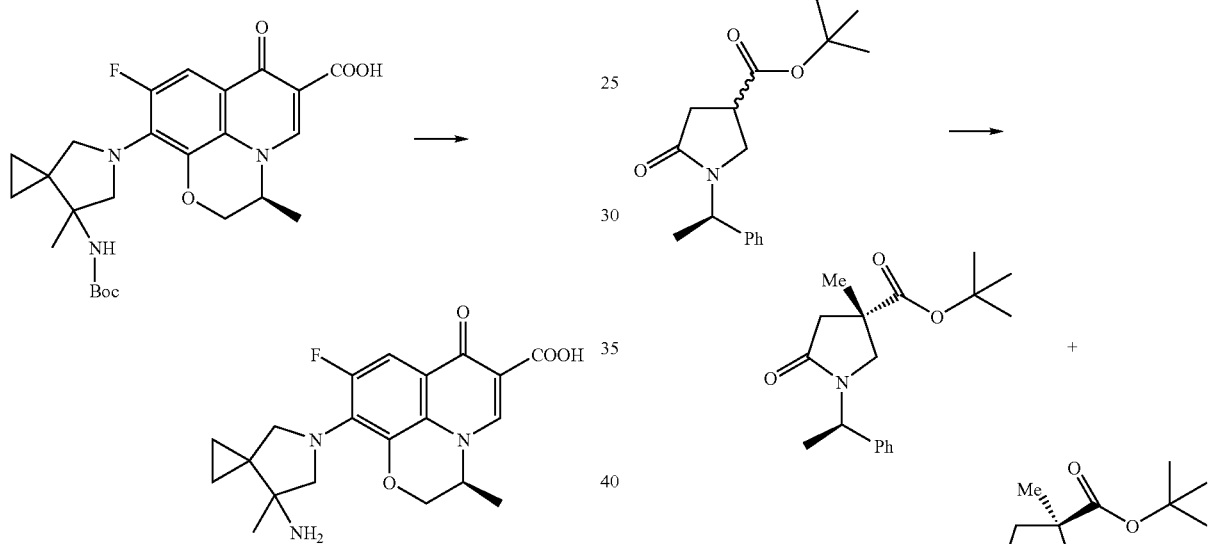

(3S)-10-[7-(tert-butoxycarbonylamino)-7-methyl-5-azaspiro[2.4]heptane-5-yl]-9-fluoro-2,3-dihydro-3-methyl-7-oxo-7H-pyrido[1,2,3-de][1,4]benzoxazine-6-carboxylic acid (761 mg, 1.56 mmol) was dissolved in concentrated hydrochloric acid (6.5 mL) in an ice bath, and the mixture was stirred at room temperature for 120 minutes. The reaction mixture was washed with chloroform, and saturated aqueous solution of sodium hydroxide was added to the aqueous layer in an ice bath to a pH of 12.0. Hydrochloric acid was then added to adjust pH to 7.4, end the solution was extracted with lower layer of a mixed solution (chloroform:methanol water, 7:3:1). After combining the organic layers, and drying with anhydrous sodium sulfate, the solvent was removed by distillation under reduced pressure. Chloroform was added to the residue, and the insoluble content was removed by filtration. The filtrate distilled under reduced pressure. The residue was purified by crystallization from ethanol, and dried under reduced pressure to obtain 260 mg (0.68 mmol, 43%) of the title compound as a yellow powder.

mp: 268-270° C.

[α]$_D^{25}$=−114° (c=0.200, 0.1N NaOH).

1H-NMR (400 MHz, 0.1N NaOD) δ ppm: 0.52-0.58 (2H, m), 0.70-0.76 (2H, m), 1.08 (3H, s), 1.49 (3H, d, J=6.8 Hz), 3.55-3.68 (2H, m), 3.73-3.85 (2H, m), 4.28 (1H, d, J=9.3 Hz), 4.42-4.48 (1H, m), 4.52-4.61 (1H, m), 7.48 (1H, d, J=14.4 Hz), 8.29 (1H, s).

Elementary analysis for C$_{20}$H$_{22}$FN$_3$O$_4$:
Calculated: C, 62.01; H, 5.72; F, 4.90; N, 10.85.
Found: C, 62.00; H, 5.65; F, 4.85; N, 10.69.
MS (FAB) m/z: 388 (M+H)$^+$.
IR (ATR) ν: 3365, 2979, 2877, 1619, 1572, 1519, 1444, 1413, 1398, 1376, 1359, 1338, 1328, 1307, 1280, 1108, 1081, 867 cm$^{-1}$.

Reference Example 53 tert-Butyl (3S)-3-methyl-5-oxo-1-[(1R)-1-phenylethyl]pyrrolidine-3-carboxylate and tert-butyl (3R)-3-methyl-5-oxo-1-[(1R)-1-phenylethyl]pyrrolidine-3-carboxylate

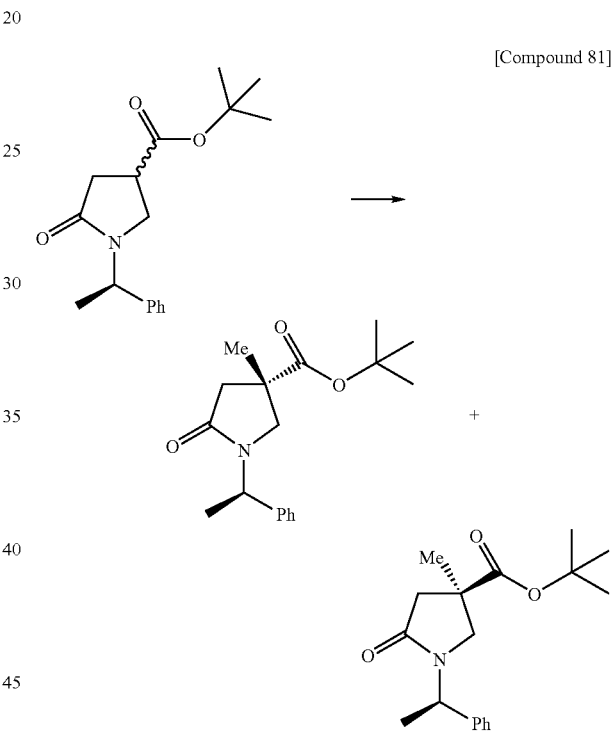

To a solution of tert-butyl 2-oxo-1-[(1R)-1-phenylethyl] pyrrolidine-4-carboxylate (30.05 g, 0.104 mol) in N,N-dimethylformamide (210 mL), iodomethane (26.0 mL, 59.28 g, 0.418 mol), and then, sodium hydride (55%, in oil, 11.35 g, 0.260 mol) was added at room temperature in nitrogen atmosphere while stirring the mixture. When inner temperature increased to about 50° C., the reaction mixture was cooled to 30° C. by adding ice water to the outer bath. After changing the bath to a water bath at an outer temperature of 17° C., the mixture was stirred for 23 hours. The reaction mixture was poured into cold aqueous solution of citric acid (1 L of 10% citric acid and 500 g of ice), and after stirring the mixture for 30 minutes, the mixture was extracted with ethyl acetate (800 mL, 500 mL). The organic layers were combined, and washed with saturated aqueous solution of sodium chloride. After drying with anhydrous sodium sulfate, the mixture was subjected to filtration, and the filtrate was concentrated under reduced pressure. The concentrate was purified by flash silica gel column chromatography (elution was started at hexane ethyl acetate of 5:1, and after elution of the low polarity isomer, hexane:ethyl acetate was changed to 4:1) to obtain 10.63 g (33.7%) of high polarity isomer of tert-butyl (3S)-3-methyl-5-oxo-1-[(1R)-1-phenylethyl]pyrrolidine-3-carboxylate as a white solid. 14.91 g (47.3%) of low polarity isomer of tert-butyl (3R)-3-methyl-5-oxo-1-[(1R)-1-phenylethyl]pyrrolidine-3-carboxylate was also obtained.

High Polarity Isomer:

$^1$H-NMR (400 MHz, CDCl$_3$) δ ppm: 1.34 (9H, s), 1.52 (3H, d, J=7.10 Hz), 2.27 (1H, d, J=17.0 Hz), 2.93 (1H, d, J=17.0 Hz), 3.05 (1H, d, J=10.1 Hz), 3.32 (1H, d, J=10.1 Hz), 5.50 (1H, q, J=7.1 Hz), 7.23-7.38 (5H, m).

Low Polarity Isomer:

$^1$H-NMR (400 MHz, CDCl$_3$) δ ppm: 1.18 (3H, s), 1.44 (9H, s), 1.52 (3H, d, J=7.1 Hz), 2.26 (1H, d, J=16.9 Hz), 2.63-2.69 (1H, m), 2.91 (1H, d, J=16.9 Hz), 3.63 (1H, d, J=10.0 Hz), 5.51 (1H, q, J=7.1 Hz), 7.26-7.37 (5H, m).

Reference Example 54 tert-Butyl (3S)-4-hydroxy-3-methyl-5-oxo-1-[(1R)-1-phenylethyl]pyrrolidine-3-carboxylate

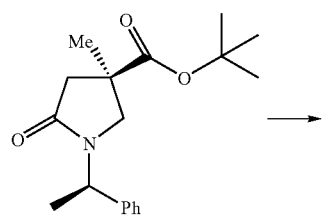

[Compound 82]

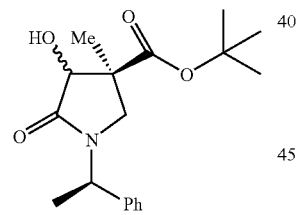

To a solution of tert-butyl (3R)-3-methyl-5-oxo-1-[(1R)-1-phenylethyl]pyrrolidine-3-carboxylate (9.90 g, 32.6 mmol) and tri ethyl phosphite (6.71 mL, 39.1 mmol) in anhydrous tetrahydrofuran (165 mL), lithium bistrimethylsilyl amide (45.7 mL, 45.7 mmol, 1.0M solution in tetrahydrofuran) was added at −5° C., and the mixture was stirred at the same temperature for 30 minutes. After bubbling oxygen gas into the reaction mixture for 30 minutes, saturated aqueous solution of ammonium chloride (150 mL) was added in an ice bath, and the mixture was concentrated under reduced pressure. Water (100 mL) was added to the residue and the mixture was extracted with ethyl acetate (200 mL×2). The organic layer was washed with saturated aqueous solution of sodium chloride (200 mL), and dried with anhydrous sodium sulfate. After the filtration, the filtrate was concentrated under reduced pressure, and the residue was purified by silica gel column chromatography (hexane ethyl acetate, 1:1→1:4) to obtain 7.73 g (74%) of the title compound as a pale yellow oily substance.

$^1$H-NMR (400 MHz, CDCl$_3$) δ ppm: 1.24-1.56 (15H, m), 2.61-2.73 (1H, m), 3.43-3.57 (1H, m), 4.02-4.15 (2H, m), 5.45-5.54 (1H, m), 7.26-7.38 (5H, m).

Reference Example 55 tert-Butyl (3S)-4-hydroxy-3-methyl-1-[(1R)-1-phenylethyl]pyrrolidine-3-carboxylate

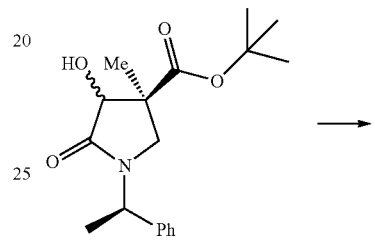

[Compound 83]

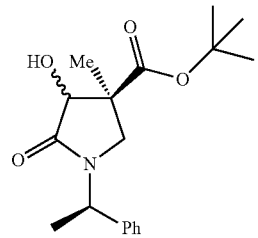

To a solution of tert-butyl (3S)-4-hydroxy-3-methyl-5-oxo-1-[(1R)-1-phenylethyl]pyrrolidine-3-carboxylate (5.13 g, 16.1 mmol) in tetrahydrofuran (100 mL), 1.17M solution of borane in tetrahydrofuran (45.3 mL, 53.1 mmol) was added in an ice bath, and the mixture was stirred at room temperature for 13 hours. After concentrating the reaction mixture under reduced pressure, water (10 mL), ethanol (100 mL), and triethylamine (5 mL) were added to the concentrate, and the mixture was heated under reflux in an oil bath at 90° C. for 2 hours. The reaction mixture was concentrated under reduced pressure, and water (200 mL) was added to the concentrate. The mixture was extracted with ethyl acetate (200 mL×2). The resulting organic layer was washed with saturated aqueous solution of sodium chloride (200 mL), and dried with anhydrous sodium sulfate. After the filtration, the filtrate was concentrated under reduced pressure, and the residue was purified by silica gel column chromatography (hexane:ethyl acetate, 3:1→1:2) to obtain 1.50 g (31%) of the title compound as a colorless oily substance.

$^1$H-NMR (400 MHz, CDCl$_3$) δ ppm: 1.26 (3H, s), 1.33 (3H, d, J=6.6 Hz), 1.44 (9H, s), 2.42 (1H, dd, J=3.8, 3.9 Hz), 2.49 (1H, d, J=10.0 Hz), 2.94 (2H, dd, J=10.0, 5.9 Hz), 3.30 (1H, q, J=6.6 Hz), 4.45 (1H, br s), 7.20-7.30 (5H, m)

MS (ESI) m/z: 306 (M+H)$^+$.

Reference Example 56 tert-Butyl (3S)-1-benzyloxycarbonyl-4-hydroxy-3-methylpyrrolidine-3-carboxylate

[Compound 84]

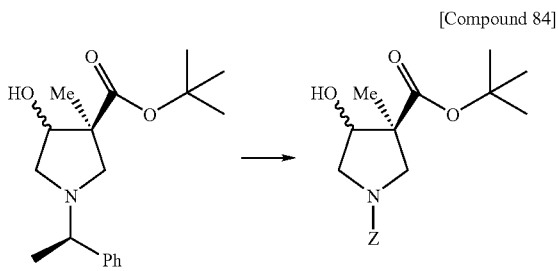

To a solution of tert-butyl (3S)-4-hydroxy-3-methyl-1-[(1R)-1-phenylethyl]pyrrolidine-3-carboxylate (1.49 g, 4.88 mmol) in ethanol (30 mL), 1N hydrochloric acid (5.12 mL, 5.12 mmol) was added at room temperature, and the mixture was stirred at 10 minutes. 10% palladium-carbon catalyst (1.40 g) was added to the reaction mixture, and the suspension was stirred in an oil bath at 40° C. for 2 hours in hydrogen atmosphere at normal pressure. After filtering the reaction mixture and concentrating the filtrate, tetrahydrofuran (20 mL), water (20 mL), and sodium hydrogencarbonate (2.05 g, 24.4 mmol) were added to the residue, and benzyloxycarbonyl chloride (836 µl, 5.86 mmol) was further added in an ice bath. The reaction mixture was stirred at room temperature for 2 hours, and extracted with ethyl acetate (100 mL×2). The resulting organic layer was washed with saturated aqueous solution of sodium chloride (20 mL), and dried with anhydrous sodium sulfate. After the filtration, the filtrate was concentrated under reduced pressure, and the residue was purified by silica gel column chromatography (hexane:ethyl acetate, 2:1→1:2) to obtain 1.48 g (90%) of the title compound as a colorless oily substance.

$^1$H-NMR (400 MHz, CDCl$_3$) δ ppm: 1.30 (3H, s), 1.44 (9H, s), 2.10 (1H, dd, J=30.9, 3.8 Hz), 3.26-3.45 (2H, m), 3.68-3.79 (2H, m), 4.45-4.51 (1H, m), 5.13 (2H, s), 7.28-7.38 (5H, m).

MS (ESI) m/z: 358 (M+Na)$^+$.

Reference Example 57 tert-Butyl (3S)-1-benzyloxycarbonyl-3-methyl-4-oxopyrrolidine-3-carboxylate

[Compound 85]

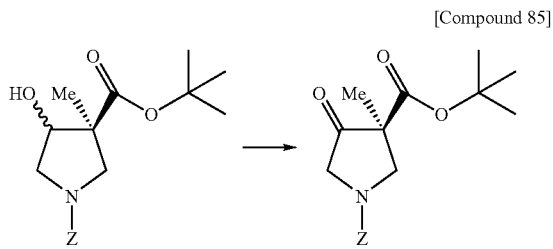

To a solution of oxalyl chloride (736 µl, 8.58 mmol) in dichloromethane (30 mL), a solution of dimethyl sulfoxide (811 µl, 11.4 mmol) in dichloromethane (5 mL) was added at −78° C., and the mixture was stirred for 10 minutes. A solution of (3S)-1-tert-butyl tert-butyl benzyloxycarbonyl-4-hydroxy-3-methylpyrrolidine-3-carboxylate (1.44 g, 4.29 mmol) in dichloromethane (10 mL) was added, and the mixture was stirred for 1 hour. Triethylamine (4.37 mL, 31.4 mmol) was then added, and the mixture was stirred at −78° C. for 30 minutes, and in an ice bath, for 30 minutes. To reaction mixture were added saturated aqueous solution of ammonium chloride (50 mL) and water (100 mL), and the mixture was extracted with ethyl acetate (200 mL×2). The organic layer was washed with water (100 mL) and saturated aqueous solution of sodium chloride (100 mL), and dried with anhydrous sodium sulfate. After the filtration, the filtrate was concentrated under reduced pressure by silica gel column chromatography (hexane-ethyl acetate, 10:1→3:2) to obtain 1.37 g (96%) of the title compound as a colorless oily substance.

$^1$H-NMR (400 MHz, CDCl$_3$) δ ppm: 1.34 (3H, d, J=4.9 Hz), 1.38 (9H, s), 3.46 (1H, d, J=12.0 Hz), 3.81 (1H, d, J=19.0 Hz), 4.10-4.19 (1H, m), 4.35 (1H, dd, J=5.9, 12.0 Hz), 5.19 (2H, s), 7.30-7.40 (5H, m).

Reference Example 58 tert-Butyl (3R)-1-benzyloxycarbonyl-3-methyl-4-methylene pyrrolidine-3-carboxylate

[Compound 86]

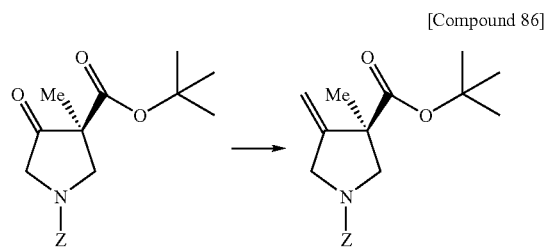

To a solution of methyltriphenylphosphonium bromide (1.67 g, 4.68 mmol) in anhydrous tetrahydrofuran (20 mL), n-butyl lithium (2.54 mL, 3.96 mmol, 1.56M solution in hexane) was added at −78° C., and the mixture was stirred for 20 minutes. A solution of tert-butyl (3S)-1-benzyloxycarbonyl-3-methyl-4-oxopyrrolidine-3-carboxylate (1.20 g, 3.60 mmol) in anhydrous tetrahydrofuran (4 mL) was added at the same temperature, and the temperature was gradually increased, and the mixture was stirred at 55° C. for 3 hours. To the reaction mixture was added 10% aqueous solution of citric acid (50 mL) in an ice bath, and the mixture was concentrated under reduced pressure. Water (100 mL) was added to the concentrate, and the mixture was extracted with ethyl acetate (100 mL×2). The organic layer was washed with saturated aqueous solution of sodium chloride (50 mL), and dried with anhydrous sodium sulfate. After the filtration, the filtrate was concentrated under reduced pressure, and the residue was purified by silica gel column chromatography (hexane-ethyl acetate, 10:1→5:1) to obtain 750 mg (63%) of the title compound as a colorless oily substance.

$^1$H-NMR (400 MHz, CDCl$_3$) δ ppm: 1.36 (3E, d, J=6.6 Hz), 1.39 (9H, d, J=2.0 Hz), 3.24 (1H, dd, J=13.7, 11.2 Hz), 4.05-4.16 (2H, m), 4.19-4.29 (1H, m), 5.04-5.18 (4H, m), 7.29-7.38 (5H, m).

Reference Example 59

(3R)-1-Benzyloxycarbonyl-3-methyl-4-methylene pyrrolidine-3-carboxylic Acid

[Compound 87]

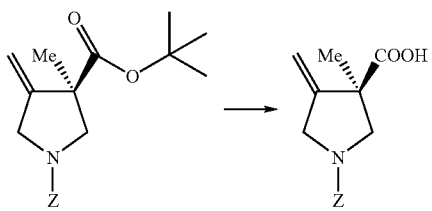

To a solution of tert-butyl (3R)-1-benzyloxycarbonyl-3-methyl-4-methylene pyrrolidine-3-carboxylate (750 mg, 2.26 mmol) in dichloromethane (8 mL), trifluoroacetic acid (4 mL) was added in an ice bath, and the mixture was stirred at room temperature for 4 hours. After concentrating the reaction mixture under reduced pressure, saturated aqueous solution of sodium hydrogencarbonate (20 mL) was added to the residue, and the mixture was washed with diethylether (20 mL). To the aqueous layer was added 1N hydrochloric acid for acidification, and the solution was extracted with chloroform (100 mL×2). After drying the organic layer with anhydrous sodium sulfate and filtering, the filtrate was concentrated under reduced pressure to obtain 665 mg of the unpurified title compound as a colorless oily substance.

$^1$H-NMR (400 MHz, CDCl$_3$) δ ppm: 1.44 (3H, s), 3.23-3.36 (1H, m), 4.11-4.30 (3H, m), 5.09-5.25 (4H, m), 7.27-7.39 (5H, m).

Reference Example 60

(3R)-1-Benzyloxycarbonyl-3-(tert-butoxy-carbonylamino)-3-methyl-4-methylene Pyrrolidine

[Compound 88]

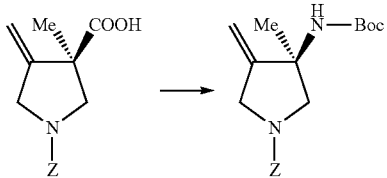

To a solution of (3R)-1-benzyloxycarbonyl-3-methyl-4-methylene pyrrolidine-3-carboxylic acid (2.26 mmol) in toluene (20 mL), triethylamine (630 μl, 4.53 mmol) and diphenyl phosphoryl azide (536 μl, 2.49 mmol) were added, and the mixture was stirred at room temperature for 1 hour. The mixture was heated under reflux in an oil bath at 110° C. for 1 hour. After concentrating the reaction mixture, the concentrate was dissolved in 1,4-dioxane (8 mL). 6N hydrochloric acid (4 mL) was added, and the mixture was stirred for 2 hours. Water (20 mL) was added to the reaction mixture, and the mixture was washed with diethylether (50 mL). The aqueous layer was alkalized by adding saturated aqueous solution of sodium hydrogencarbonate, and extracted with chloroform (100 mL×2). After drying the organic layer with anhydrous sodium sulfate and filtration, the filtrate was concentrated under reduced pressure, and the residue was dissolved in toluene (8 mL). Di-tert-butyl dicarbonate (592 mg, 2.71 mmol) was added in an ice bath, and the mixture was stirred at room temperature for 67 hours. The reaction mixture was concentrated under reduced pressure, and the residue was purified by silica gel column chromatography (hexane ethyl acetate, 5:1→3:1) to obtain 437 mg (62%) of the title compound as a colorless oily substance.

$^1$H-NMR (400 MHz, CDCl$_3$) δ ppm: 1.42 (9H, s), 1.46 (3H, s), 3.56 (1H, t, J=9.2 Hz), 3.85-3.98 (1H, m), 4.13-4.26 (2H, m), 4.62-4.74 (1H, m), 5.01-5.17 (4H, m), 7.27-7.38 (5H, m).

Reference Example 61

(3R)-3-(tert-Butoxycarbonylamino)-3-methyl-4-methylene Pyrrolidine

[Compound 89]

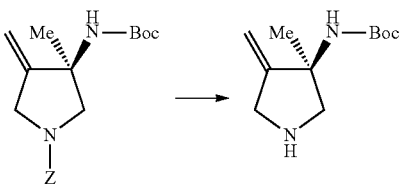

Ammonia gas was bubbled into a solution of (3R)-1-benzyloxycarbonyl-3-(tert-butoxycarbonylamino)-3-methyl-4-methylene pyrrolidine (469 mg, 1.41 mmol) in tetrahydrofuran (7 mL) at −78° C. to produce a mixed solution of liquid ammonia and tetrahydrofuran (20 mL), and sodium (154 mg, 6.70 mmol) was added to this solution. The mixture was stirred at the same temperature for 10 minutes. Saturated aqueous solution of ammonium chloride (10 mL) was added at −78° C., and the mixture was stirred at room temperature for 30 minutes. To the reaction mixture was added saturated aqueous solution of sodium hydrogencarbonate (30 mL), and the mixture was extracted with chloroform (100 mL×2). The organic layer was dried by anhydrous sodium sulfate, after filtration, the filtrate was concentrated under reduced pressure to obtain 255 mg (85%) of the title compound as colorless crystals.

$^1$H-NMR (400 MHz, CDCl$_3$) δ ppm: 1.41-1.46 (12H, m), 2.90 (1H, d, J=11.7 Hz), 3.45 (1H, d, J=14.2 Hz), 3.50-3.57 (1H, m), 3.69 (1H, d, J=16.1 Hz), 4.64 (1H, br s), 5.01 (1H, t, J=2.2 Hz), 5.04 (1H, t, J=2.2 Hz).

Example 17

7-[(3R)-3-Amino-3-methyl-4-methylene pyrrolidine-1-yl]-6-fluoro-1-[(1R,2S)-2-fluorocyclopropyl]-8-methoxy-1,4-dihydro-4-oxoquinoline-3-carboxylic Acid

[Compound 90]

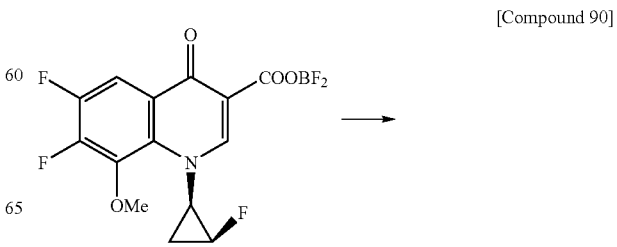

85
-continued

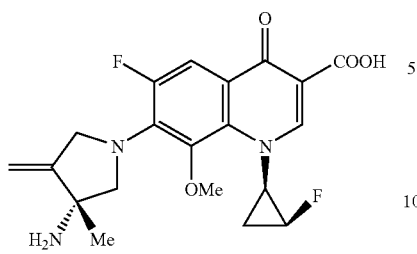

To a solution of (3R)-3-(tert-butoxycarbonylamino)-3-methyl-4-methylene pyrrolidine (255 mg, 1.20 mmol) in dimethyl sulfoxide (3 mL), triethylamine (201 μl, 1.44 mmol) and 6,7-difluoro-1-[(1R,2S)-2-fluorocyclopropyl]-8-methoxy-1,4-dihydro-4-oxoquinoline-3-carboxylic acid—difluoroboron complex (433 mg, 1.20 mmol) were added, and the mixture was stirred at 35° C. for 15 hours. After concentrating the reaction mixture, a mixed solution of ethanol and water (ethanol:water, 9:1) (15 mL) and triethylamine (0.5 mL) were added to the residue, and the mixture was heated under reflux in an oil bath at 90° C. for 2 hours. The reaction mixture was concentrated under reduced pressure, and 10% aqueous solution of citric acid (50 mL) and water (50 mL) were added to the residue. The mixture was extracted with ethyl acetate (100 mL×2), and the organic layer was washed with water (50 mL×3) and saturated aqueous solution of sodium chloride (50 mL). The organic layer was dried with anhydrous sodium sulfate and filtered, and the filtrate was concentrated under reduced pressure. The concentrate was dissolved in concentrated hydrochloric acid (5 mL) in an ice bath, and the solution was stirred at room temperature for 10 minutes. Water (50 mL) was added to the reaction mixture, and the mixture was washed with chloroform (100 mL×3). 10 mol/l aqueous solution of sodium hydroxide was added to the aqueous layer in an ice bath to pH 11.0, and concentrated hydrochloric acid was added to adjust the pH to 7.4. The solution was then extracted with chloroform (100 mL×5). The organic layer was dried with anhydrous sodium sulfate and filtered, and the filtrate was concentrated under reduced pressure. The concentrate was purified by recrystallization from ethanol, and the crystals were dried under reduced pressure to obtain 210 mg (43%) of the title compound as pale yellow crystals.

mp: 236-239° C. (decomposition).

$[\alpha]_D$ $^1$H-NMR (400 MHz, 0.1N NaOD) δ ppm: 1.39 (3H, s), 1.41-1.66 (2H, m) 3.55 (1H, dd, J=9.6, 3.2 Hz), 3.61 (3H, s), 3.63 (1H, d, J=10.0 Hz), 4.02-4.07 (1H, m), 4.33 (2H, dd, J=25.9, 15.1 Hz), 4.99 (1H, d, J=63.7 Hz), 5.05 (2H, t, J=1.7 Hz), 5.16 (2H, t, J=2.2 Hz), 7.68 (1H, d, J=14.2 Hz), 8.45 (1H, d, J=2.0 Hz)

Elementary analysis for $C_{20}H_{21}F_2N_3O_4$:

Calculated: C, 59.25; H, 5.22; F, 9.37; N, 10.37.

Found: C, 59.14; H, 5.20; F, 9.62; N, 10.50.

IR (ATR) ν: 2960, 2856, 1716, 1618, 1547, 1514, 1452, 1369, 1327, 1306, 1269, 1230, 1190, 1111 cm$^{-1}$.

Reference Example 62

Ethyl 3-[N-benzyloxycarbonyl-N-(ethoxycarbonyl methyl)amino]propionate

[Compound 91]

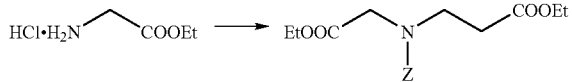

To a suspension of glycine ethyl ester hydrochloride (41.9 g, 0.3 mol) in ethanol (300 mL) was added triethylamine (41.8 mL, 0.3 mol) and ethyl acrylate (10.8 mL, 0.1 mol) in an ice bath, and the mixture was stirred at 80° C. for 1 hour. The reaction mixture was concentrated under reduced pressure, and water (400 mL) was added to the residue, and the mixture was extracted with ethyl acetate (200 mL×3). The extract was washed with water (200 mL×2) and saturated aqueous solution of sodium chloride (200 mL) in this order, an the dried with anhydrous sodium sulfate. After the filtration, the filtrate was concentrated under reduced pressure, and the residue was dissolved in acetone (150 mL). To this solution were added aqueous solution of sodium carbonate (11.5 g, 108 mmol) (50 mL) and a solution of benzyloxycarbonyl chloride (18.4 g, 108 mmol) in acetone (50 mL) in an ice bath, and the mixture was stirred at room temperature for 2 hours. The reaction mixture was concentrated under reduced pressure, and water (400 mL) was added to the residue. The mixture was extracted with ethyl acetate (200 mL×3), and the extract was washed with saturated aqueous solution of sodium chloride (200 mL), and dried with anhydrous sodium sulfate. After the filtration, the filtrate was concentrated under reduced pressure, and the residue was purified by silica gel column chromatography (hexane:ethyl acetate, 5:1) to obtain 31.1 g (92%) of the title compound as a colorless oily product.

$^1$H-NMR (400 MHz, CDCl$_3$) δ ppm: 1.16-1.29 (6H, m), 2.58-2.70 (2H, m), 3.59-3.66 (2H, m), 4.04-4.22 (6H, m), 5.10-5.18 (2H, m), 7.26-7.38 (5H, m).

MS (ESI) m/z: 338 (M+H)$^+$.

Reference Example 63

Ethyl 1-benzyloxycarbonyl-4-oxopyrrolidine-3-carboxylate

[Compound 92]

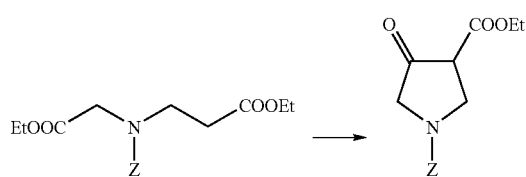

To a solution of ethyl 3-[N-benzyloxycarbonyl-N-(ethoxycarbonyl methyl)amino]ethylpropionate (26.8 g, 79.5 mmol) in ethanol (200 mL), sodium ethoxide (20% solution in ethanol, 40.6 mL, 119.3 mmol) was added, and the mixture was heated under reflux for 2 hours. After concentrating the reaction mixture under reduced pressure, the residue was dissolved in water (100 mL). Concentrated hydrochloric acid was added to this solution in an ice bath for acidification, and the solution was extracted with chloroform (100 mL×3). The extract was washed with saturated aqueous solution of sodium chloride (100 mL), and dried with anhydrous sodium sulfate. After the filtration, the filtrate was concentrated under reduced pressure, and the residue was purified by silica gel column chromatography (hexane:ethyl acetate, 2:1) to obtain 16.7 g (72%) of the title compound as a pale brown oily product.

$^1$H-NMR (400 MHz, CDCl$_3$) δ ppm: 1.25-1.33 (3H, m), 3.87-4.37 (7H, m), 5.16-5.22 (2H, m), 7.23-7.41 (5H, m).

MS (ESI) m/z: 314 (M+Na)$^+$.

Reference Example 64

Ethyl 1-benzyloxycarbonyl-3-methyl-4-oxopyrrolidine-3-carboxylate

[Compound 93]

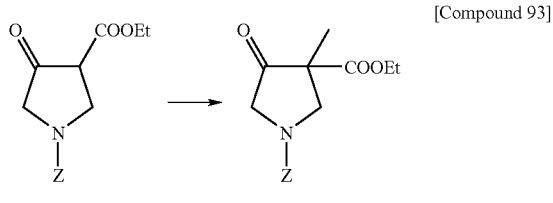

To a solution of ethyl 1-benzyloxycarbonyl-4-oxopyrrolidine-3-carboxylate (1.0 g, 3.4 mmol) in acetone (30 mL), potassium carbonate (0.95 g, 6.9 mmol) and methyl iodide (1 mL) were added, and the mixture was stirred at 45° C. for 1 hour. The reaction mixture was concentrated under reduced pressure, and water (20 mL) was added to the concentrate. The mixture was extracted with ethyl acetate (20 mL×3). The extract was washed with 10% aqueous solution of sodium thiosulfate (20 mL) and saturated aqueous solution of sodium chloride (20 mL) in this order, and dried with anhydrous sodium sulfate. After the filtration, the filtrate was concentrated under reduced pressure, and the residue was purified by silica gel column chromatography (hexane:ethyl acetate, 4:1) to obtain 1.0 g (95%) of the title compound as a pale yellow oily product.

$^1$H-NMR (400 MHz, CDCl$_3$) δ ppm: 1.21 (3E, t, J=7.1 Hz), 1.55 (3H, s), 3.53 (1H, d, J=11.7 Hz), 3.88 (1H, d, J=19.3 Hz), 4.07-4.20 (3H, m), 4.37 (1H, d, J=12.0 Hz), 5.19 (2H, s), 7.30-7.40 (5H, m).

MS (ESI) m/z: 306 (M+H)$^+$, 328 (M+Na)$^+$.

Reference Example 65

Ethyl 1-benzyloxycarbonyl-4-hydroxy-3-methylpyrrolidine-3-carboxylate

[Compound 94]

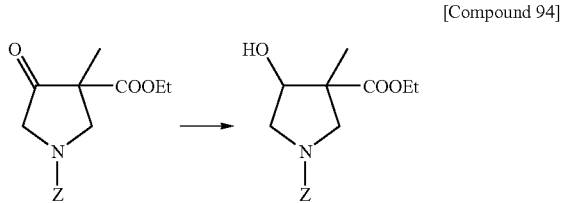

To a solution of ethyl 1-benzyloxycarbonyl-3-methyl-4-oxopyrrolidine-3-carboxylate (1.0 g, 3.28 mmol) in methanol (20 mL), sodium borohydride (0.19 g, 4.92 mmol) was added at −20° C., and the mixture was stirred at the same temperature for 20 minutes. To the reaction mixture were added saturated aqueous solution of ammonium chloride (20 mL) and water (20 mL), and the mixture was extracted by ethyl acetate (20 mL×3). The extract was washed with saturated aqueous solution of sodium chloride (20 mL), and dried with anhydrous sodium sulfate. After filtration, the filtrate was concentrated under reduced pressure, and the residue was purified by silica gel column chromatography (hexane:ethyl acetate, 3:1) to obtain 0.57 g (57%) of the title compound as a colorless oily product.

$^1$H-NMR (400 MHz, CDCl$_3$) δ ppm: 1.23-1.34 (6H, m), 2.90-3.87 (4H, m), 4.11-4.56 (3H, m), 5.14 (2H, d, J=4.2 Hz), 7.24-7.40 (5H, m).

MS (ESI) m/z: 308 (M+H)$^+$.

Reference Example 66

Ethyl 1-benzyloxycarbonyl-4-methoxy-3-methylpyrrolidine-3-carboxylate

[Compound 95]

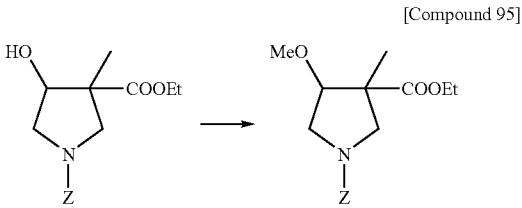

To a solution of ethyl 1-benzyloxycarbonyl-4-hydroxy-3-methylpyrrolidine-3-carboxylate (0.55 g, 1.8 mmol) in N,N-dimethylformamide (10 mL), methyl iodide (0.22 mL, 3.6 mmol) and sodium hydride (55% in oil, 117 mg, 2.7 mmol) were added in an ice bath, and the mixture was stirred at room temperature for 1 hour. Ice water was added to the reaction mixture, and the mixture was extracted with ethyl acetate (20 mL×3). The extract was washed with water (20 mL×3) and saturated aqueous solution of sodium chloride (20 mL) in this order, and dried with anhydrous sodium sulfate. After filtration, the filtrate was concentrated under reduced pressure, and the residue was purified by silica gel column chromatography (hexane:ethyl acetate, 2:1) to obtain 0.38 g (66%) of the title compound as a pale yellow oily product.

$^1$H-NMR (400 MHz, CDCl$_3$) δ ppm: 1.24-1.29 (6H, m), 3.19-3.73 (3H, m), 3.30 (3H, s), 3.80-4.28 (4H, m), 5.14 (2H, s), 7.29-7.39 (5H, m).

MS (ESI) m/z: 322 (M+H)$^+$.

Reference Example 67

1-Benzyloxycarbonyl-4-methoxy-3-methylpyrrolidine-3-carboxylic Acid

[Compound 96]

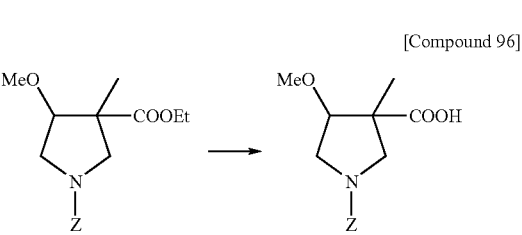

To a solution of ethyl 1-benzyloxycarbonyl-4-methoxy-3-methylpyrrolidine-3-carboxylate (0.38 g, 1.18 mmol) in ethanol (4 mL) was added 1N aqueous solution of sodium hydroxide (4 mL), and the mixture was stirred at 40° C. for 17.5 hours. Water (10 mL) was added to the reaction mixture, and the mixture was washed with ethyl acetate (10 mL×2). To the aqueous layer was added 1N hydrochloric acid (10 mL), and the mixture was extracted by chloroform (20 mL×3). The extract was washed with saturated aqueous solution of sodium chloride (20 mL), and dried with anhydrous sodium sulfate. After filtration, the filtrate was concentrated under reduced pressure to obtain 0.31 g (89%) of the title compound as a colorless oily product.

$^1$H-NMR (400 MHz, CDCl$_3$) δ ppm: 1.33 (3H, s), 3.34-3.47 (1H, m), 3.36 (3H, s), 3.53-3.75 (2H, m), 3.85-3.95 (1H, m), 4.09-4.18 (1H, m), 5.14 (1H, s), 7.25-7.40 (5H, m).

MS (ESI) m/z: 294 (M+H)$^+$, 316 (M+Na)$^+$.

Reference Example 68

1-Benzyloxycarbonyl-3-(tert-butoxycarbonylamino)-4-methoxy-3-methylpyrrolidine

[Compound 97]

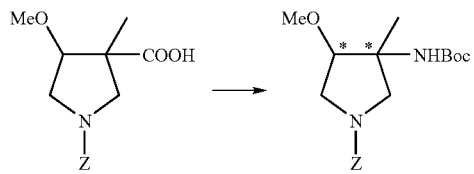

To a solution of 1-benzyloxycarbonyl-4-methoxy-3-methylpyrrolidine-3-carboxylic acid (0.3 g, 1.02 mmol) in toluene (10 mL), triethylamine (0.29 mL, 2.05 mmol) and diphenyl phosphoryl azide (0.24 mL, 1.13 mmol) were added, and the mixture was stirred at 125° C. for 2 hours. After concentrating the reaction mixture under reduced pressure, 1,4-dioxane (4 mL), water (4 mL) and concentrated hydrochloric acid (1 mL) were added to the residue, and the mixture was stirred at 50° C. for 2 hours. Water (10 mL) was added to the reaction mixture, and the mixture was washed with ethyl acetate (10 mL). The aqueous layer was alkalized with 10N sodium hydroxide aqueous solution, and extracted by chloroform (20 mL×3). The extract was washed with saturated aqueous solution of sodium chloride (20 mL), and dried with anhydrous sodium sulfate. After filtration, the filtrate was concentrated under reduced pressure, and the residue was dissolved in ethanol (10 mL). Di-tert-butyl dicarbonate (0.27 g, 1.22 mmol) was added to the solution, and the mixture was stirred at 50° C. for 1 hour. The reaction mixture was concentrated under reduced pressure, and the residue was purified by silica gel column chromatography (hexane:ethyl acetate, 6:1) to obtain 0.27 g (72%) of racemic body of the title compound as a colorless oily product.

$^1$H-NMR (400 MHz, CDCl$_3$) δ ppm: 1.41-1.45 (12H, m), 3.30-3.82 (7H, m), 4.12 (1H, q, J=7.1 Hz), 5.09-5.26 (3H, m), 7.24-7.38 (5H, m).

MS (ESI) m/z: 387 (M+Na)$^+$.

Next, the racemic body of the title compound (0.68 g, 1.87 mmol) was subjected to high-performance liquid chromatography using an optically active column, and fraction α (0.29 g, 43%) and fraction β (0.28 g, 41%) which are enantiomers of the title compound were respectively obtained as colorless oily products.

Conditions of the Optical Resolution:
  Column: CHIRALPAK AD (DAICEL, 20 mm×250 mm)
  solvent: 2-propanol:hexane, 1:9
  Flow rate: 10 ml/min
  Detection: UV (254 nm)

Retention time: about 18.1 minutes (fraction α), about 23.5 minutes (fraction β)

Reference Example 69

3-(tert-Butoxycarbonylamino)-4-methoxy-3-methylpyrrolidine (Derived from Fraction α)

[Compound 98]

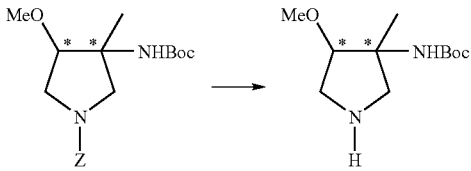

To a solution of 1-benzyloxycarbonyl-3-(tert-butoxycarbonylamino)-4-methoxy-3-methylpyrrolidine (fraction α) (0.29 g, 0.8 mmol) in methanol (10 mL), 5% palladium-carbon catalyst (water content, 50%; 0.15 g) was added, and the suspension was stirred at room temperature for 16.5 hours in hydrogen atmosphere. The reaction mixture was filtered through celite, and the filtrate was concentrated under reduced pressure to obtain the title compound as a colorless oily product. This product was used in the subsequent reaction with no further purification.

MS (ESI) m/z: 231 (M+H)$^+$.

Example 18

7-(3-Amino-4-methoxy-3-methylpyrrolidine-1-yl)-6-fluoro-1-[(1R,2S)-2-fluorocyclopropyl]-8-methoxy-1,4-dihydro-4-oxoquinoline-3-carboxylic Acid (Substituent at Position 7 Derived from Fraction α)

[Compound 99]

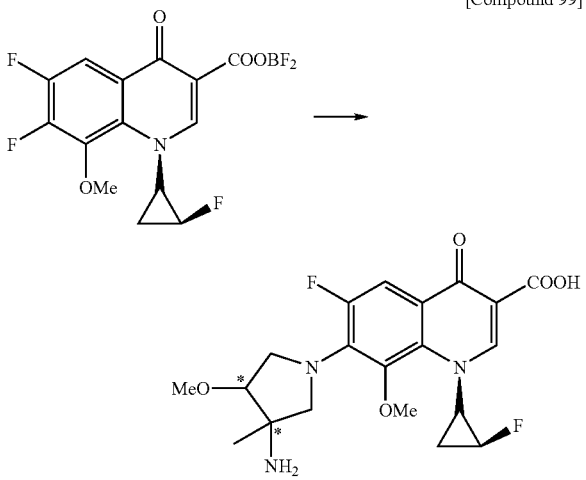

To a solution of 3-(tert-butoxycarbonylamino)-4-methoxy-3-methylpyrrolidine in dimethyl sulfoxide (2 mL), triethylamine (0.33 mL, 2.4 mmol) and 6,7-difluoro-1-[(1R,2S)-2-fluorocyclopropyl]-8-methoxy-1,4-dihydro-4-oxoquinoline-3-carboxylic acid—difluoroboron complex (0.19 g, 0.53 mmol) were added, and the mixture was stirred at 40° C. for 21.5 hours in nitrogen atmosphere. To the reaction mixture were added ethanol containing 10% water (10 mL) and triethylamine (1 mL), and the mixture was heated under reflux for 1 hour. The reaction mixture was concentrated under reduced pressure, and ethyl acetate (20 mL) and 10% aqueous solution of citric acid (20 mL) were added to the concentrate for separation into two layers. The aqueous layer was extracted with ethyl acetate (20 mL×2), and the organic layers were combined and washed with water (20 mL×3) and saturated aqueous solution of sodium chloride (20 mL) in this order and dried with anhydrous sodium sulfate. After filtration, the filtrate was concentrated under reduced pressure, and the residue was purified by silica gel column chromatography (chloroform methanol, 50:1). The eluate was concentrated under reduced pressure, and to the concentrate was added concentrated hydrochloric acid (1 mL) in an ice bath. The reaction mixture was stirred at room temperature for 15 minutes, and washed with chloroform (10 mL×5). 10N aqueous solution of sodium hydroxide was added to the aqueous layer to pH 12.0, and hydrochloric acid was then added to adjust the pH to 7.4. The mixture was extracted with chloroform (30 mL×5) and dried with anhydrous sodium sulfate. After filtration, the filtrate was concentrated under reduced pressure. The concentrate was purified by recrystallization from ethanol-diethylether, and the crystals were dried under reduced pressure to obtain 103 mg (46%) of the title compound as a colorless crystalline powder.

mp: 150-151° C.

$^1$H-NMR (400 MHz, DMSO-$d_6$) δ ppm: 1.21 (3H, s), 1.47-1.58 (2H, m) 3.24-3.64 (4H, m), 3.31 (3H, s), 3.37 (3H, s), 3.87-3.94 (1H, m) 4.08 (1H, dd, J=12.3, 7.2 Hz), 4.96-5.18 (1H, m), 7.67 (1H, d, J=13.9 Hz), 8.63 (1H, d, J=2.7 Hz).

Elementary analysis for $C_{20}H_{23}F_2N_3O_5$:

Calculated: C, 56.73; H, 5.48; F, 8.97; N, 9.92.

Found: C, 56.71; H, 5.54; F, 9.03; N, 9.73.

IR (ATR) ν: 2931, 1718, 1617, 1513, 1450, 1438 cm$^{-1}$.

MS (FAB) m/z: 424 (M+H)$^+$.

Reference Example 70

3-(tert-Butoxycarbonylamino)-4-methoxy-3-methylpyrrolidine (Derived from Fraction β)

[Compound 100]

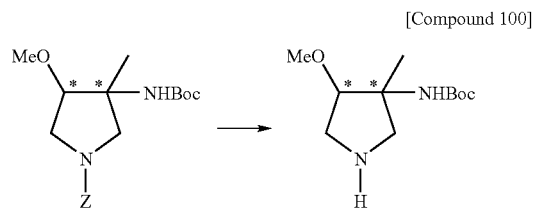

To a solution of 1-benzyloxycarbonyl-3-(tert-butoxycarbonylamino)-4-methoxy-3-methylpyrrolidine (fraction β) (0.28 g, 0.77 mmol) in methanol (10 mL) was added 5% palladium-carbon (containing water, 0.14 g), and the mixture was stirred at room temperature for 18 hours in hydrogen atmosphere. The reaction mixture was filtered through celite, and the filtrate was concentrated under reduced pressure to obtain the title compound as a colorless oily product. This product was used in the subsequent reaction without further purification.

(ESI) m/z: 231 (M+H)$^+$.

Example 19

7-(3-Amino-4-methoxy-3-methylpyrrolidine-1-yl)-6-fluoro-1-[(1R,2S)-2-fluorocyclopropyl]-8-methoxy-1,4-dihydro-4-oxoquinoline-3-carboxylic Acid (Substituent at Position 7 Derived from Fraction β)

[Compound 101]

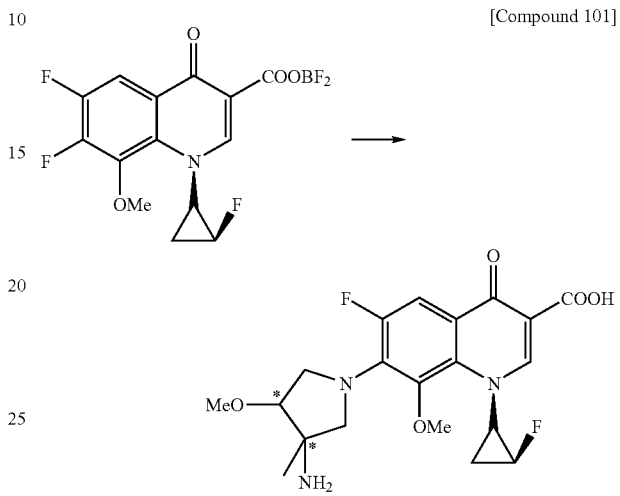

To a solution of 3-(tert-butoxycarbonylamino)-4-methoxy-3-methylpyrrolidine in dimethyl sulfoxide (1 mL), triethylamine (0.33 mL, 2.4 mmol) and 6,7-difluoro-1-[(1R, 2S)-2-fluorocyclopropyl]-8-methoxy-1,4-dihydro-4-oxoquinoline-3-carboxylic acid—difluoroboron complex (0.19 g, 0.53 mmol) were added, and the mixture was stirred at 40° C. for 3 days in nitrogen atmosphere. To the reaction mixture were ethanol containing 10% water (10 mL) and triethylamine (1 mL), and the mixture was heated under reflux for 1 hour. After concentrating the reaction mixture under reduced pressure, ethyl acetate (20 mL) and 10% aqueous solution of citric acid (20 mL) were added to the concentrate for separation into two layers. The aqueous layer was extracted with ethyl acetate (20 mL×2), and the organic layers were combined and washed with water (20 mL×3) and saturated aqueous solution of sodium chloride (20 mL) in this order, and dried with anhydrous sodium sulfate. After filtration, the filtrate was concentrated under reduced pressure, and the residue was purified by silica gel column chromatography (chloroform:methanol, 100:1). The eluate was concentrated under reduced pressure, and concentrated hydrochloric acid (2 mL) was added to the residue in an ice bath. The mixture was stirred at room temperature for 20 minutes, and the reaction mixture was washed with chloroform (10 mL×5). 10N aqueous solution of sodium hydroxide was added to the aqueous layer to pH 12.0, and hydrochloric acid was then added to adjust the pH to 7.4. The solution was extracted with chloroform (30 mL×5) and dried with anhydrous sodium sulfate. After filtration, the filtrate was concentrated under reduced pressure, and the residue was purified by recrystallization from ethanol-diethylether-hexane. The crystals were dried under reduced pressure to obtain 56 mg (25%) of the title compound as a pale yellow crystalline powder.

mp: 162-163° C.

$^1$H-NMR (400 MHz, DMSO-$d_6$) δ ppm: 1.20 (3H, s), 1.54-1.66 (2H, m), 3.19-3.59 (4H, m), 3.30 (3H, s), 3.56 (3H, s), 3.87-3.96 (1H, m), 4.05-4.14 (1H, m), 4.82-5.06 (1H, m), 7.66 (1H, d, J=13.9 Hz), 8.68 (1H, s).

Reference Example 71

Ethyl (3R,4R)-4-fluoromethyl-2-oxo-1-[(1R)-1-phenylethyl]pyrrolidine-3-carboxylate

[Compound 102]

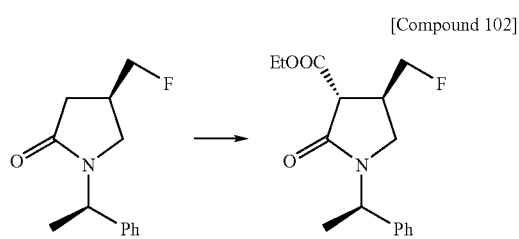

To a solution of (4R)-4-fluoromethyl-2-oxo-1-[(1R)-1-phenylethyl]pyrrolidine (34.1 g, 154 mmol) and ethyl chloroformate (16.1 mL, 169 mmol) in tetrahydrofuran (500 mL), lithium bistrimethylsilyl amide (323 mL, 323 mmol, 1.0M solution in tetrahydrofuran) was added at 0° C., and the mixture was stirred at the same temperature for 30 minutes. Saturated aqueous solution of ammonium chloride (700 mL) was added to reaction mixture at the same temperature, and the mixture was extracted with ethyl acetate (700 mL×2). The organic layer was washed with saturated aqueous solution of sodium chloride (500 mL), and dried with anhydrous sodium sulfate. After filtration, the filtrate was concentrated under reduced pressure, and the residue was purified by silica gel column chromatography (elution with hexane:ethyl acetate, 5:1→2:3) to obtain 35.0 g (77%) of the title compound as a pale yellow oily substance.

$^1$H-NMR (400 MHz, CDCl$_3$) δ ppm: 1.31 (3H, t, J=7.1 Hz), 1.55 (3H, d, J=7.1 Hz), 2.88-3.01 (1H, m), 3.17 (1H, d, J=7.4 Hz), 3.39 (1H, d, J=7.4 Hz), 3.74 (1H, t, J=6.1 Hz), 4.26 (2H, q, J=7.1 Hz), 4.42 (2H, dd, J=47.1, 5.1 Hz), 5.49 (1H, q, J=7.1 Hz), 7.26-7.38 (5H, m)

Reference Example 72

Ethyl (3S,4R)-4-fluoromethyl-3-methyl-2-oxo-1-[(1R)-1-phenylethyl]pyrrolidine-3-carboxylate

[Compound 103]

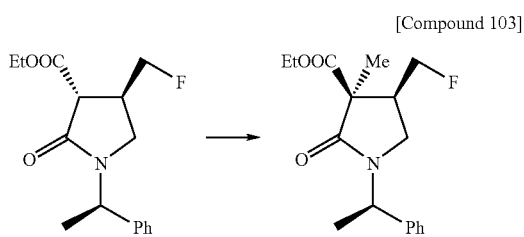

To a solution of ethyl (3R,4R)-4-fluoromethyl-3-methyl-2-oxo-1-[(1R)-1-phenylethyl]pyrrolidine-3-carboxylate (33.4 g, 114 mmol) and iodomethane (9.94 mL, 159 mmol) in tetrahydrofuran (670 mL), potassium bistrimethylsilyl amide (274 mL, 137 mmol, 0.5M solution in toluene) was added at −78° C., and the mixture was stirred at the same temperature for 10 minutes. The temperature was gradually increased in 30 minutes with stirring to −10° C., and saturated aqueous solution of ammonium chloride (700 mL) was added to the reaction mixture. The mixture was extracted with ethyl acetate (700 mL×2), and the organic layer was washed with saturated aqueous solution of sodium chloride (500 mL), and dried with anhydrous sodium sulfate. After filtration, the filtrate was concentrated under reduced pressure, and the residue was purified by silica gel column chromatography (elution by hexane:ethyl acetate, 7:1→1:1) to obtain 29.1 g (83%) of the title compound as a pale yellow oily substance.

$^1$H-NMR (400 MHz, CDCl$_3$) δ ppm: 1.29 (3H, t, J=7.1 Hz), 1.49 (3H, s), 1.56 (3H, t, J=8.8 Hz), 2.34-2.47 (1H, m), 3.04 (1H, dd, J=9.3, 8.1 Hz), 3.29 (1H, t, J=9.5 Hz), 4.19 (2H, q, J=7.1 Hz), 4.34-4.59 (2H, m), 5.52 (1H, q, J=7.0 Hz), 7.28-7.39 (5H, m)

Reference Example 73

(3S,4R)-4-Fluoromethyl-3-methyl-2-oxo-1-[(1R)-1-phenylethyl]pyrrolidine-3-carboxylic Acid

[Compound 104]

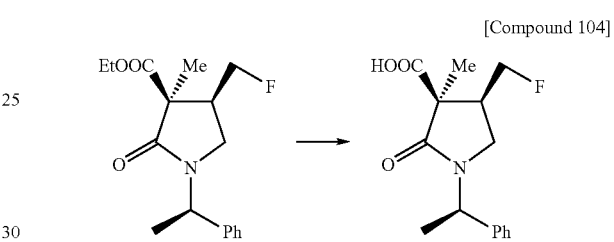

To a solution of ethyl (3S,4R)-4-fluoromethyl-3-methyl-2-oxo-1-[(1R)-1-phenylethyl]pyrrolidine-3-carboxylate (20.0 g, 65.1 mmol) in ethanol (400 mL), 10 mol/l aqueous solution of sodium hydroxide (65.1 mL, 651 mmol) was added dropwise, and the mixture was stirred for 30 minutes. Water (400 mL) was added to the reaction mixture in an ice bath, and the aqueous solution was washed with diethylether (500 mL). Concentrated hydrochloric acid was added to the aqueous layer in an ice bath to pH 2 to 3, and the mixture was extracted with chloroform (500 mL×3). The organic layer was dried with anhydrous sodium sulfate, and after filtration, the filtrate was concentrated under reduced pressure. The concentrate was azeotropically distilled by adding toluene (20 mL), and dried under reduced pressure to obtain 19.16 g (quantitative) of the title compound as a white solid.

$^1$H-NMR (400 MHz, CDCl$_3$) δ ppm: 1.51 (3H, s), 1.59 (3H, d, J=7.1 Hz), 2.42-2.54 (1H, m), 3.12 (1H, dd, J=10.5, 7.1 Hz), 3.33 (1H, dd, J=10.5, 3.9 Hz), 4.60 (2H, dd, J=46.8, 5.1 Hz), 5.49 (1H, q, J=7.0 Hz), 7.26-7.40 (5H, m).

Reference Example 74

(3S,4S)-3-(tert-Butoxycarbonylamino)-4-fluoromethyl-3-methyl-1-[(1R)-1-phenylethyl]pyrrolidine

[Compound 105]

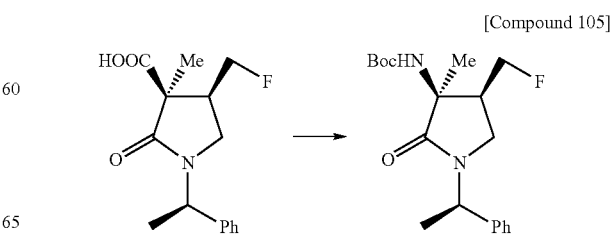

Elementary analysis for C$_{20}$H$_{23}$F$_2$N$_3$O$_5$:
Calculated: C, 56.73; H, 5.48; F, 8.97; N, 9.92.
Found: C, 56.56; H, 5.49; F, 9.09; N, 9.80.
IR (ATR) ν: 2937, 1725, 1621, 1511, 1436 cm$^{-1}$.
MS (FAB) m/z: 424 (M+H)$^+$.

To a solution of (3S,4R)-4-fluoromethyl-3-methyl-2-oxo-1-[(1R)-1-phenylethyl]-pyrrolidine-3-carboxylic acid (65.1 mmol) and diphenylphosphoryl azide (15.4 mL, 71.6 mmol) in toluene (380 mL), triethylamine (18.2 mL, 130 mmol) was added, and the mixture was stirred in an oil bath at 110° C. for 1 hour. The reaction mixture was concentrated under reduced pressure to obtain the crude product in the form of an isocyanate.

MS (ESI) m/z: 277 (M+H)+

The resulting crude product in the form of an isocyanate was dissolved in 1,4-dioxane (90 mL), and water (45 mL) and concentrated hydrochloric acid (45 mL) was added in an ice bath, and the mixture was stirred at room temperature for 3 hours. Water (180 mL) was added to the reaction mixture, and the mixture was washed with diethylether (200 mL). 10 mol/l aqueous solution of sodium hydroxide was added to the aqueous layer to pH 9 to 10 in an ice bath, and the mixture was extracted with chloroform (500 mL×2). The organic layer was washed with saturated aqueous solution of sodium chloride (100 mL), and after drying with anhydrous sodium sulfate and filtration, the filtrate was concentrated under reduced pressure to obtain the crude product in the form of an amine (10.1 g, DM041701).

$^1$H-NMR (400 MHz, CDCl$_3$) δ ppm: 1.30 (3H, s), 1.55 (3H, d, J=7.1 Hz), 2.18-2.32 (1H, m), 2.98 (1H, dd, J=10.3, 7.3 Hz), 3.17 (1H, dd, J=10.4, 4.3 Hz), 4.48-4.72 (2H, m), 5.48 (1H, q, J=7.1 Hz), 7.15-7.37 (5H, m).

MS (ESI) m/z: 251 (M+H)$^+$.

The crude product in the form of an amine (10.1 g, 40.2 mmol) was dissolved in toluene (200 mL), and a solution of 65% (by weight) solution of sodium bis(2-methoxyethoxy) aluminum hydride in toluene (48.3 mL, 161 mmol) in toluene (6 mL) was added dropwise in 15 minutes in an ice bath so that the inner temperature does not exceed 50° C., and the mixture was stirred at room temperature for 10 minutes. The reaction mixture was cooled in an ice bath, and 25% (by weight) aqueous solution of sodium hydroxide (160 mL) was added dropwise. After quenching the solution, the solution was extracted with toluene (135 mL). The organic layer was washed with saturated aqueous solution of sodium chloride (100 mL), and the organic layer was dried with anhydrous sodium sulfate. After filtration, the filtrate was concentrated under reduced pressure to obtain the crude product in the form of an amine (10.0 g).

MS (ESI) m/z: 237 (M+H)+

To the crude product in the form of an amine (10.0 g, 40.2 mmol) was added di-tert-butyl dicarbonate (9.65 g, 44.2 mmol), and the reaction mixture was stirred at room temperature for 10 hours. After stirring, the solvent was removed by distillation under reduced pressure, and the residue was purified by silica gel column chromatography (eluted with hexane:ethyl acetate; 19:1→5:4) to obtain 1.78 g (5 steps, 8%) of the title compound as a colorless transparent syrup substance.

$^1$H-NMR (400 MHz, CDCl$_3$) δ ppm: 1.32 (3H, d, J=6.6 Hz), 1.42 (9H, s), 1.52 (3H, s), 2.35 (1H, td, J=14.2, 7.1 Hz), 2.45 (1H, t, J=8.3 Hz), 2.57 (1H, d, J=9.3 Hz), 2.70 (1H, d, J=9.3 Hz), 2.92 (1H, t, J=8.8 Hz), 3.31 (1H, q, J=6.6 Hz), 4.42 (1H, ddd, J=47.1, 9.3, 6.1 Hz), 4.63 (1H, ddd, J=47.4, 9.3, 6.1 Hz), 4.94 (1H, s), 7.19-7.31 (5H, m).

MS (ESI) m/z: 337 (M+H)$^+$.

Reference Example 75

(3S,4S)-3-(tert-Butoxycarbonylamino)-4-fluoromethyl-3-methylpyrrolidine

[Compound 106]

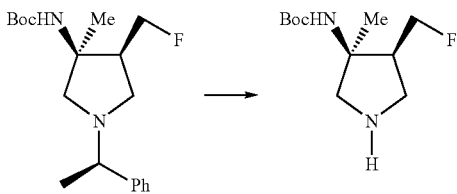

To a solution of (3S,4S)-3-(tert-butoxycarbonylamino)-4-fluoromethyl-3-methyl-1-[(1R)-1-phenylethyl]pyrrolidine (1.35 g, 4.01 mmol) in ethanol (30 mL) was added 10% palladium-carbon catalyst (containing 52.8% water, 1.30 g), and the suspension was stirred in an oil bath at 40° C. for 12 hours in hydrogen gas atmosphere. After removing the catalyst by filtration, the filtrate was concentrated under reduced pressure to obtain 932 mg (quantitative) of the crude target compound as a colorless transparent syrup substance.

$^1$H-NMR (400 MHz, CDCl$_3$) δ ppm: 1.44 (9H, s), 1.47 (3H, s), 2.16-2.30 (1H, m), 2.85 (1H, d, J=11.5 Hz), 3.01 (1H, dd, J=11.3, 7.4 Hz), 3.20 (1H, dd, J=11.3, 8.6 Hz), 3.29 (1H, d, J=11.8 Hz), 4.49-4.69 (2H, m), 4.98 (1H, s).

MS (ESI) m/z: 233 (M+H)$^+$.

Example 20

7-[(3S,4S)-3-Amino-4-fluoromethyl-3-methylpyrrolidin-1-yl]-6-fluoro-1-[(1R,2S)-2-fluoro-1-cyclopropyl]-8-methoxy-1,4-dihydro-4-oxoquinoline-3-carboxylic Acid

[Compound 107]

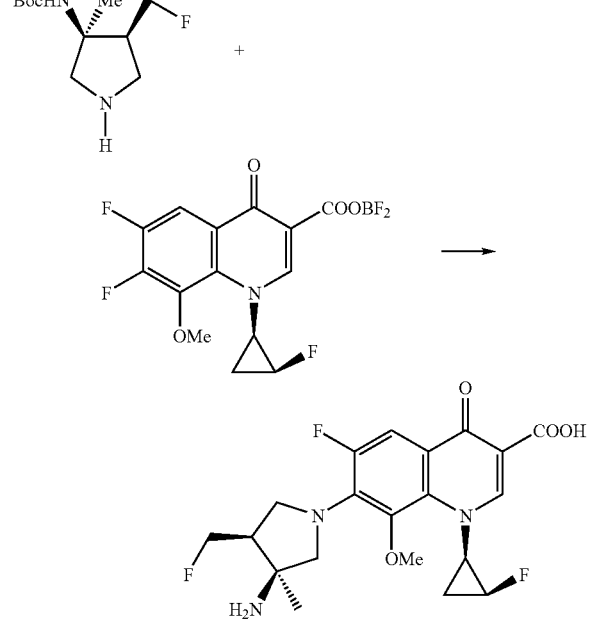

(3S,4S)-3-(tert-butoxycarbonylamino)-4-fluoromethyl-3-methylpyrrolidine (221 mg, 0.951 mmol), 6,7-difluoro-1-[(1R,2S)-2-fluoro-1-cyclopropyl]-8-methoxy-1,4-dihydro- 4-oxoquinoline-3-carboxylic acid—difluoroboron complex (343 mg, 0.951 mmol), and triethylamine (0.159 mL, 1.14 mmol) were dissolved in dimethyl sulfoxide (3 mL), and stirred in an oil bath at 35° C. for 18 hours. After concentrating the reaction mixture, a mixed solution of ethanol and water (ethanol:water, 9:1) (40 mL) and triethylamine (1 mL) were added to the concentrate, and the mixture was heated under reflux for 2 hours. The reaction mixture was concentrated under reduced pressure. The concentrate was dissolved in ethyl acetate (100 mL×2), and the solution was washed with 10% aqueous solution of citric acid (50 mL), water (50 m×3), and saturated aqueous solution of sodium chloride (100 mL). The organic layer was dried with anhydrous sodium sulfate, and after filtering the residue, the filtrate was concentrated under reduced pressure. The concentrate was dissolved in concentrated hydrochloric acid (20 mL), and the solution was stirred at room temperature for 30 minutes. The reaction mixture was washed with chloroform (100 mL×5), and to the aqueous layer was added 10 mol/l aqueous solution of sodium hydroxide to pH 12 in an ice bath. Hydrochloric acid was added to adjust the pH to 7.4, and the solution was extracted with chloroform (150 mL×4). The organic layer was dried with anhydrous sodium sulfate, and after filtration, the filtrate was concentrated under reduced pressure. The concentrate was purified by recrystallization from ethanol, and the crystals were dried under reduced pressure to obtain 269 mg (24%) of the title compound as a pale yellow powder.

mp: 187-189° C.

$^1$H-NMR (400 MHz, 0.1N NaOD) δ ppm: 1.33 (3H, s), 1.40-1.51 (1H, m), 1.51-1.63 (1H, m), 2.45-2.58 (1H, m), 3.49 (1H, d, J=9.6 Hz), 3.58 (3H, s), 3.64-3.73 (2H, m), 3.85 (1H, t, J=9.4 Hz), 4.00-4.05 (1H, m), 4.69 (1H, ddd, J=37.3, 10.0, 5.9 Hz), 4.80-4.84 (1H, m), 5.00 (1H, d, J=64.0 Hz), 7.66 (1H, d, J=14.5 Hz), 8.42 (1H, d, J=2.7 Hz).

Elementary analysis for $C_{20}H_{22}F_3N_3O_4 \cdot 0.25H_2O$:

Calculated: C, 55.88; H, 5.28; F, 13.26; N, 9.77.

Found: C, 55.58; H, 5.29; F, 13.17; N, 9.84.

IR (ATR) ν: 2962, 2873, 1720, 1618, 1510, 1435, 1363, 1311, 1275, 1234, 1186, 1122 cm$^{-1}$.

Example 21

7-[(3S,4S)-3-Amino-4-fluoromethyl-3-methylpyrrolidin-1-yl]-1-cyclopropyl-6-fluoro-8-methoxy-1,4-dihydro-4-oxoquinoline-3-carboxylic Acid

[Compound 108]

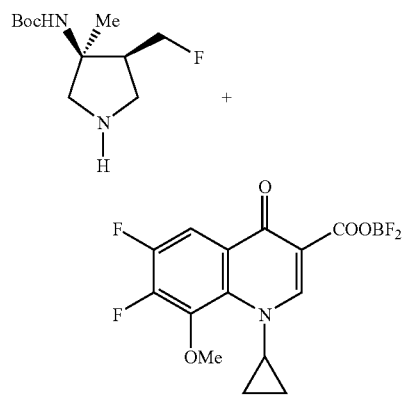

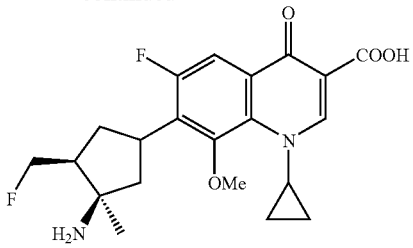

(3S,4S)-3-(tert-butoxycarbonylamino)-4-fluoromethyl-3-methylpyrrolidine (46.5 mg, 0.200 mmol), 1-cyclopropyl-6,7-difluoro-8-methoxy-1,4-dihydro-4-oxoquinoline-3-carboxylic acid—difluoroboron complex (68.6 mg, 0.200 mmol), and triethylamine (0.0335 mL, 0.240 mmol) were dissolved in dimethyl sulfoxide (0.5 mL), and the mixture was stirred in an oil bath at 35° C. for 19 hours. After concentrating the mixture, a mixed solution of ethanol and water (ethanol:water, 9:1) (20 mL) and triethylamine (0.5 mL) added to the concentrate, and the mixture was heated under reflux for 2 hours. The reaction mixture was concentrated under reduced pressure, and the residue was dissolved in ethyl acetate (50 mL×2), and the solution was washed with 10% aqueous solution of citric acid (50 mL), water (50 m×3), and saturated aqueous solution of sodium chloride (50 mL). The organic layer was dried with anhydrous sodium sulfate, and the solvent was removed by distillation under reduced pressure. The residue was dissolved in concentrated hydrochloric acid (5 µL) in an ice bath, and the solution was stirred at room temperature for 30 minutes. The reaction mixture was washed with chloroform (100 mL×5), and to the aqueous layer was added 10 mol/l aqueous solution of sodium hydroxide to pH 12 in an ice bath, and the hydrochloric acid was added to adjust the pH to 7.4. The solution was extracted with chloroform (100 mL×3), and the organic layer was dried with anhydrous sodium sulfate, and after filtration, the filtrate was concentrated under reduced pressure. The concentrate was purified by recrystallization from ethanol, and the crystals were dried under reduced pressure to obtain 42.6 mg (52%) of the title compound as a white powder.

mp: 226-229° C.

$^1$H-NMR (400 MHz, 0.1N NaOD) δ ppm: 0.32-0.90 (1H, m), 0.98-1.11 (2H, m), 1.14-1.22 (1H, m), 1.39 (3H, s), 2.47-2.60 (1H, m), 3.44 (1H, d, J=10.0 Hz), 3.58 (3H, s), 3.73 (1H, dd, J=10.4, 2.6 Hz), 3.78 (2H, d, J=8.3 Hz), 4.04-4.11 (1H, m), 4.79-4.88 (2H, m), 7.65 (1H, d, J=14.4 Hz), 8.49 (1H, s).

Elementary analysis for $C_{20}H_{23}F_2N_3O_4$:

Calculated: C, 58.96; H, 5.69; F, 9.33; N, 10.31.

Found: C, 58.90; H, 5.70; F, 9.33; M, 10.19.

IR (ATR) ν: 3450, 3374, 3079, 2962, 2873, 1724, 1620, 1508, 1439, 1373, 1315, 1273, 1228, 1186, 1153, 1109 cm$^1$.

Example 22

7-[(3S,4S)-3-Amino-4-fluoromethyl-3-methylpyrrolidin-1-yl]-6-fluoro-1-[(1R,2S)-2-fluoro-1-cyclopropyl]-8-methyl-1,4-dihydro-4-oxoquinoline-3-carboxylic Acid

[Compound 109]

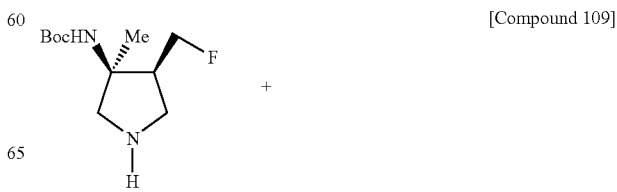

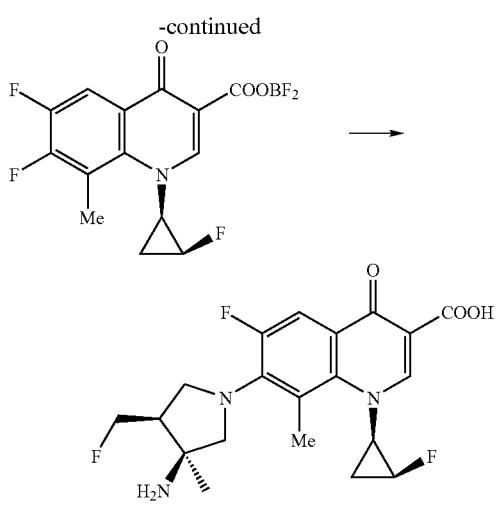

(3S,4S)-3-(tert-butoxycarbonylamino)-4-fluoromethyl-3-methylpyrrolidine (932 mg, 4.01 mmol), 6,7-difluoro-1-[(1R,2S)-2-fluoro-1-cyclopropyl]-8-methyl-1,4-dihydro-4-oxoquinoline-3-carboxylic acid—difluoroboron complex (922 mg, 2.67 mmol), and triethylamine (0.447 mL, 3.20 mmol) was dissolved in sulfolane (5 mL), and the mixture was stirred in an oil bath at 35° C. for 166 hours. After concentrating the reaction mixture, a mixed solution of ethanol and water (ethanol:water, 9:1) (80 mL) and triethylamine (1 mL) were added to the concentrate, and the mixture was stirred in an oil bath at 90° C. for 30 minutes. The reaction mixture was concentrated under reduced pressure, and the concentrate was dissolved in ethyl acetate (200 mL×2), and washed with 10% aqueous solution of citric acid (100 mL), water (100 m×3), and saturated aqueous solution of sodium chloride (100 mL). The organic layer was dried with anhydrous sodium sulfate, and the solvent was removed by distillation under reduced pressure. The residue was purified by short silica gel column chromatography (elusion by chloroform:methanol, 49:1→9:1). The residue was dissolved in concentrated hydrochloric acid (20 mL) in an ice bath, and the mixture was stirred at room temperature for 30 minutes, and washed with chloroform (100 mL×5). To the aqueous layer was added 10 mol/l aqueous solution of sodium hydroxide to pH 12 in an ice bath, and hydrochloric acid was added to adjust the pH to 7.4. The solution was extracted with chloroform (150 mL×4), and the organic layer was dried with anhydrous sodium sulfate. After filtration, the filtrate was concentrated under reduced pressure, and the residue was purified by recrystallization from ethanol. The crystals were dried under reduced pressure to obtain 97.7 mg (9%) of the title compound as a pale yellow powder.

mp: 135-137° C.

$^1$H-NMR (400 MHz, 0.1N NaOD) δ ppm: 1.18-1.32 (1H, m), 1.38 (3H, s), 1.55-1.66 (1H, m), 2.52 (3H, s), 2.53-2.65 (1H, m), 3.20 (1H, d, J=9.8 Hz), 3.49 (1H, t, J=9.2 Hz), 3.70 (1H, t, J=8.9 Hz), 3.78 (1H, dd, J=9.8, 3.2 Hz), 4.09 (1H, dt, J=9.9, 4.4 Hz), 4.70 (1H, ddd, J=41.9, 9.4, 6.0 Hz), 4.80-4.86 (1H, m), 5.01 (1H, d, J=67.9 Hz), 7.69 (1H, d, J=14.0 Hz), 8.45 (1H, d, J=3.2 Hz).

Elementary analysis for $C_{20}H_{22}F_3N_3O_4 \cdot 0.7H_2O$:

Calculated: C, 56.80; H, 5.60; N, 9.94.

Found: C, 56.52; H, 5.53; N, 10.06.

IR (ATR) ν: 2968, 2873, 1718, 1614, 1508, 1462, 1431, 1396, 1358, 1319, 1282, 1163, 1128, 1101 cm$^{-1}$.

Example 23

7-[(3S,4S)-3-Amino-4-fluoromethyl-3-methylpyrrolidin-1-yl]-1-cyclopropyl-6-fluoro-8-methyl-1,4-dihydro-4-oxoquinoline-3-carboxylic Acid

[Compound 110]

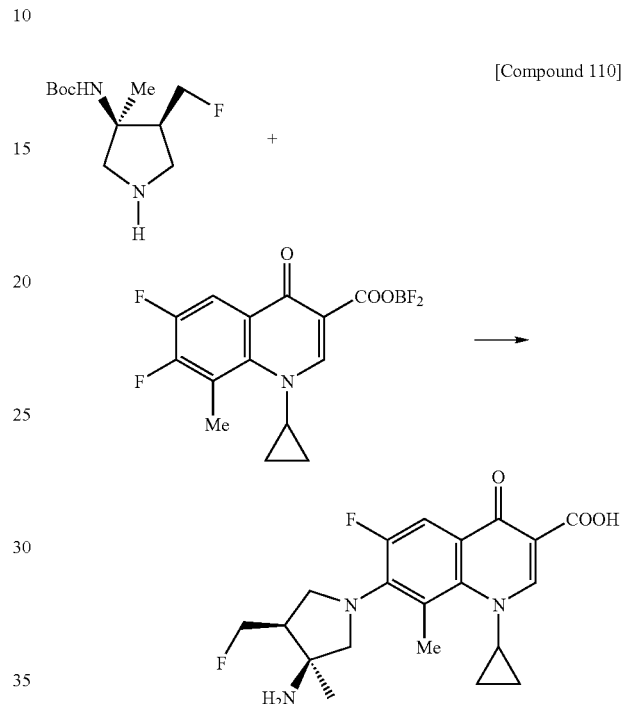

(3S,4S)-3-(tert-butoxycarbonylamino)-4-fluoromethyl-3-methylpyrrolidine (298 mg, 1.28 mmol), 1-cyclopropyl-6,7-difluoro-8-methyl-1,4-dihydro-4-oxoquinoline-3-carboxylic acid—difluoroboron complex (280 mg, 0.855 mmol), and triethylamine (0.143 mL, 1.03 mmol) were dissolved in sulfolane (1.5 mL), and the mixture was stirred in an oil bath at 35° C. for 142 hours. The reaction mixture was concentrated, and a mixed solution of ethanol and water (ethanol:water, 9:1) (40 μL) and triethylamine (1 mL) were added to the concentrate, and the mixture was stirred in an oil bath at 90° C. for 30 minutes. The reaction mixture was concentrated under reduced pressure, and the residue was dissolved in ethyl acetate (100 mL×2), and washed with 10% aqueous solution of citric acid (50 mL), water (50 m×3) and saturated aqueous solution of sodium chloride (50 mL). The organic layer was dried with anhydrous sodium sulfate, and after filtration, the filtrate was concentrated under reduced pressure. The concentrate was purified by short silica gel column chromatography (elusion by chloroform-methanol, 49:1→9:1), and the residue was dissolved in concentrated hydrochloric acid (10 mL). After stirring the solution at room temperature for 30 minutes, the reaction mixture was washed with chloroform (50 mL×5). To the aqueous layer was added 10 mol/l aqueous solution of sodium hydroxide to pH 12 in an ice bath, and hydrochloric acid was added to adjust the pH to 7.4. The solution was extracted with chloroform (100 mL×4), and the organic layer was dried with anhydrous sodium sulfate. After filtration, the filtrate was concentrated under reduced pressure. The concentrate was purified by recrystallization from ethanol, and the crystals were dried under reduced pressure to obtain 109 mg (33%) of the title compound as a pale yellow powder.

mp: 212-215° C.

$^1$H-NMR (400 MHz, 0.1N NaOD) δ ppm: 0.75-0.90 (2H, m), 1.10-1.25 (2H, m), 1.38 (3H, s), 2.56-2.61 (1H, m), 2.58 (3H, s), 3.29 (1H, d, J=9.6 Hz), 3.53-3.63 (2H, m), 3.64 (1H, dd, J=9.8, 2.7 Hz), 4.10-4.17 (1H, m), 4.68 (1H, ddd, J=34.7, 10.2, 5.3 Hz), 4.80-4.82 (1H, m), 7.67 (1H, d, J=14.0 Hz), 8.57 (1H, s).

Elementary analysis for $C_{20}H_{23}F_2N_3O_3$:

Calculated: C, 61.37; H, 5.92; F, 9.71; N, 10.74.

Found: C, 61.26; H, 5.91; F, 9.86; N, 10.72.

IR (ATR) ν: 3361, 3087, 2974, 2873, 171:2, 1616, 1545, 1508, 1458, 1431, 1358, 1315, 1228, 1188, 1151, 1109 cm$^{-1}$.

Reference Example 76

(3S,4S)-3-Ethoxycarbonyl-4-fluoromethyl-1-[(1R)-1-phenylethyl]-2-pyrrolidone

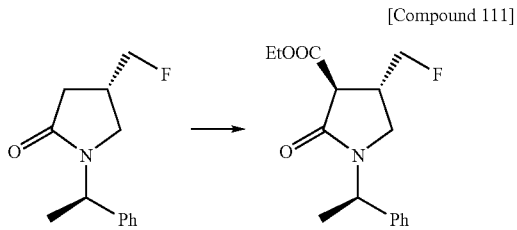

[Compound 111]

To a solution of (4S)-4-fluoromethyl-1-[(1R)-1-phenylethyl]-2-pyrrolidone (7.59 g, 34.3 mmol) and ethyl chloroformate (3.92 mL, 41.2 mmol) in tetrahydrofuran (150 mL), lithium bistrimethylsilyl amide (75.5 mL, 75.5 mmol, 1.0M solution in tetrahydrofuran) was added at 0° C., and the mixture was stirred the same temperature for 20 minutes. Saturated aqueous solution of ammonium chloride (200 mL) was added to the reaction mixture at the same temperature, and the mixture was extracted with ethyl acetate (200 mL×2). The organic layer was washed with saturated aqueous solution of sodium chloride (100 mL), and dried with anhydrous sodium sulfate. After filtration, the filtrate was concentrated under reduced pressure, and the residue was purified by silica gel column chromatography (elusion by hexane:ethyl acetate, 5:1→2:3) to obtain 8.50 g (85%) of the title compound as a pale yellow oily substance.

$^1$H-NMR (400 MHz, CDCl$_3$) δ ppm: 1.33 (3H, t, J=7.2 Hz), 1.56 (3H, d, J=7.4 Hz), 2.80 (1H, dd, J=9.8, 6.1 Hz), 2.94-3.11 (1H, m), 3.34 (1H, d, J=7.1 Hz), 3.53 (1H, t, J=9.1 Hz), 4.23-4.31 (3H, m), 4.37 (1H, dd, J=5.6, 2.7 Hz), 5.49 (1H, q, J=7.1 Hz), 7.26-7.37 (5H, m).

Reference Example 77

(3R,4S)-3-Ethoxycarbonyl-4-fluoromethyl-3-methyl-1-[(1R)-1-phenylethyl]-2-pyrrolidone

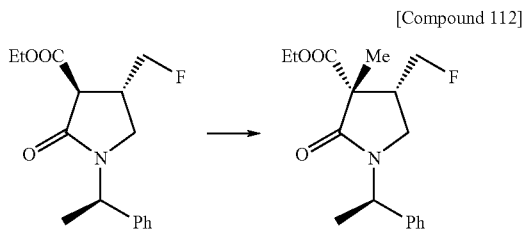

[Compound 112]

To a solution of (3S,4S)-3-ethoxycarbonyl-4-fluoromethyl-1-[(1R)-1-phenylethyl]-2-pyrrolidone (8.30 g, 28.3 mmol) and iodomethane (2.47 mL, 39.6 mmol) in tetrahydrofuran (170 mL), potassium bistrimethylsilyl amide (67.9 mL, 34.0 mmol, 0.5M solution in toluene) was added at −78° C., and the mixture was stirred at the same temperature for 10 minutes. While stirring, the temperature was gradually increased to −10° C. in 30 minutes. Saturated aqueous solution of ammonium chloride (200 mL) was added to the reaction mixture, and the mixture was extracted with ethyl acetate (200 mL×2), and the organic layer was washed with saturated aqueous solution of sodium chloride (150 mL) and dried with anhydrous sodium sulfate. After filtration, the filtrate was concentrated under reduced pressure, and the residue was purified by silica gel column chromatography (elusion by hexane:ethyl acetate, 7:1→1:1) to obtain 7.91 g (91%) of the title compound as a pale yellow oily substance.

$^1$H-NMR (400 MHz, CDCl$_3$) δ ppm: 1.10 (3H, t, J=7.2 Hz), 1.50 (3H, s), 1.57 (3H, dd, J=7.1, 2.4 Hz), 2.46-2.60 (1H, m), 2.89 (1H, t, J=9.5 Hz), 3.35 (1H, dd, J=9.4, 7.9 Hz), 4.00-4.15 (2H, m), 4.20-4.45 (2H, m), 5.56 (1H, q, J=7.3 Hz), 7.26-7.37 (5H, m)

Reference Example 78

(3R,4S)-4-Fluoromethyl-3-methyl-2-oxo-1-[(1R)-1-phenylethyl]-pyrrolidine-3-carboxylic Acid

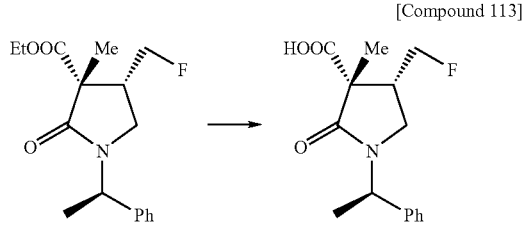

[Compound 113]

To a solution of (3R,4S)-3-ethoxycarbonyl-4-fluoromethyl-3-methyl-1-[(1R)-1-phenylethyl]-2-pyrrolidone (1.05 g, 3.42 mmol) in ethanol (20 mL), 10 mol/l aqueous solution of sodium hydroxide (3.42 mL, 34.2 mmol) was added dropwise in an ice bath, and the mixture was stirred for 30 minutes. Water (20 mL) was added to the reaction mixture in an ice bath, and the aqueous solution was washed with diethylether (50 mL). To the aqueous layer was added concentrated hydrochloric acid to pH 2 to 3 in an ice bath, and the solution was extracted with chloroform (50 mL×3). The organic layer was washed with saturated aqueous solution of sodium chloride (50 mL), and dried with anhydrous sodium sulfate. After filtration, the filtrate was concentrated under reduced pressure. The concentrate was azeotropically distilled by adding toluene (20 mL), and dried under reduced pressure to obtain 950 mg (99%) of the title compound as a colorless oily substance.

$^1$H-NMR (400 MHz, CDCl$_3$) δ ppm: 1.53-1.61 (6H, m), 2.50-2.61 (1H, m), 3.02 (1H, dd, J=10.5, 3.4 Hz), 3.49 (1H, dd, J=10.5, 7.1 Hz), 4.34-4.56 (2H, m), 5.49 (1H, q, J=7.0 Hz), 7.14-7.36 (5H, m).

MS ESI) m/z: 280 (M+H)$^+$.

Reference Example 79

(3R,4R)-3-(tert-Butoxycarbonylamino)-4-fluoromethyl-3-methyl-1-[(1R)-1-phenylethyl]pyrrolidine

[Compound 114]

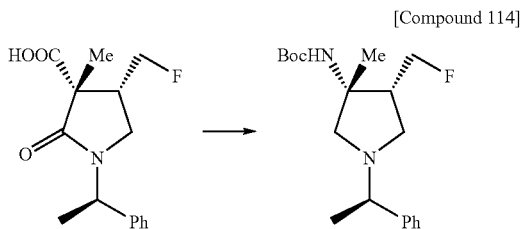

To a solution of (3R,4S)-4-fluoromethyl-3-methyl-2-oxo-1-[(1R)-1-phenylethyl]-pyrrolidine-3-carboxylic acid (950 mg, 3.40 mmol) and diphenylphosphoryl azide (0.806 mL, 3.74 mmol) in toluene (20 mL), triethylamine (0.948 mL, 6.80 mmol) was added, and the mixture was stirred in an oil bath at 110° C. for 1 hour. The reaction mixture was concentrated under reduced pressure to obtain the crude product in the form of an isocyanate.

MS (ESI) m/z: 277 (M+H)+

The crude product in the form of an isocyanate was dissolved in 1,4-dioxane (5 mL), and water (2.5 mL) and concentrated hydrochloric acid (2.5 mL) were added to this solution in an ice bath. After stirring the mixture at room temperature for 13 hours, water (10 mL) was added to the reaction mixture, and the mixture was washed with diethyl-ether (50 mL). To the aqueous layer was added 10 mol/l aqueous solution of sodium hydroxide to pH 9 to 10 in an ice bath, and the solution was extracted with chloroform (100 mL×3). The organic layer was washed with saturated aqueous solution of sodium chloride (100 mL), and dried with anhydrous sodium sulfate. After filtration, the filtrate was concentrated under reduced pressure to obtain the crude product in the form of an amine (470 mg)

$^1$H-NMR (400 MHz, CDCl$_3$) δ ppm: 1.36 (3H, s), 1.54 (3H, d, J=7.1 Hz), 2.29-2.42 (1H, m), 2.82 (1H, dd, J=10.3, 4.4 Hz), 3.35 (1H, dd, J=10.1, 7.4 Hz), 4.32-4.62 (2H, m), 5.47 (1H, q, J=7.0 Hz), 7.26-7.37 (5H, m).

MS (ESI) m/z: 251 (M+H)$^+$.

The crude product in the form of an amine (470 mg, 1.88 mmol) was dissolved in toluene (10 mL), and a solution of 65% (by weight) solution of sodium bis(2-methoxyethoxy) aluminum hydride in toluene (2.25 mL, 7.52 mmol) in toluene (2 mL) was added dropwise in 15 minutes in an ice bath so that the inner temperature does not exceed 50° C., and the mixture was stirred at room temperature for 10 minutes. The reaction mixture was cooled in an ice bath, and 25% (by weight) aqueous solution of sodium hydroxide (5 mL) was added dropwise. After quenching the solution, the solution was extracted with toluene (40 mL). The organic layer was dried with anhydrous sodium sulfate, and the organic layer was dried with anhydrous sodium sulfate. After filtration, the filtrate was concentrated under reduced pressure to obtain the crude product in the form of an amine (490 mg).

MS (ESI) m/z: 237 (M+H)+

To the crude product in the form of an amine (490 mg, 1.88 mmol) was added di-tert-butyl dicarbonate (451 mg, 2.07 mmol), and the reaction mixture was stirred at room temperature for 17 hours. After concentrating the reaction mixture under reduced pressure, the residue was purified by silica gel column chromatography (elusion by hexane:ethyl acetate, 19:1→5:4) to obtain 404 mg (5 steps, 35%) of the title compound as a colorless transparent syrup substance.

$^1$H-NMR (400 MHz, CDCl$_3$) δ ppm: 1.34 (3H, d, J=6.6 Hz), 1.44 (9H, s), 1.53 (3H, s), 2.31 (1H, td, J=14.3, 7.2 Hz), 2.52 (1H, t, J=8.4 Hz), 2.59 (1H, d, J=9.0 Hz), 2.69-2.77 (2H, m), 3.28 (1H, q, J=6.6 Hz), 4.42 (1H, ddd, J=47.2, 9.4, 6.1 Hz), 4.62 (1H, ddd, J=47.4, 9.4, 6.2 Hz), 4.98 (1H, s), 7.22-7.30 (5H, m).

MS (ESI) m/z: 337 (M+H)$^+$.

Reference Example 80

(3R,4R)-3-(tert-Butoxycarbonylamino)-4-fluoromethyl-3-methylpyrrolidine

[Compound 115]

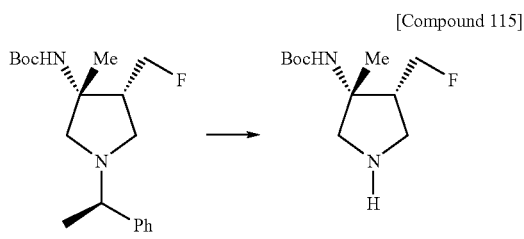

To a solution of (3R,4R)-3-(tert-butoxycarbonylamino)-4-fluoromethyl-3-methyl-1-[(1R)-1-phenylethyl]pyrrolidine (250 mg, 0.743 mmol) in ethanol (10 mL) was added 10% palladium-carbon catalyst (containing 52.8% water, 250 mg), and the suspension was stirred in an oil bath at 40° C. for 1.5 hours in hydrogen gas atmosphere. After removing the catalyst by filtration, the filtrate was concentrated under reduced pressure to obtain 169 mg (98%) of the crude target compound as a colorless transparent syrup substance.

$^1$H-NMR (400 MHz, CDCl$_3$) δ ppm: 1.44 (9H, s), 1.47 (3H, s), 2.16-2.30 (1H, m), 2.85 (1H, d, J=11.5 Hz), 3.01 (1H, dd, J=11.3, 7.4 Hz), 3.20 (1H, dd, J=11.3, 8.6 Hz), 3.29 (1H, d, J=11.8 Hz), 4.49-4.69 (2H, m), 4.98 (1H, s).

MS (ESI) m/z: 233 (M+H)$^+$.

Example 24

7-[(3R,4R)-3-Amino-4-fluoromethyl-3-methylpyrrolidin-1-yl]-6-fluoro-1-[(1R,2S)-2-fluoro-1-cyclopropyl]-8-methoxy-1,4-dihydro-4-oxoquinoline-3-carboxylic Acid

[Compound 116]

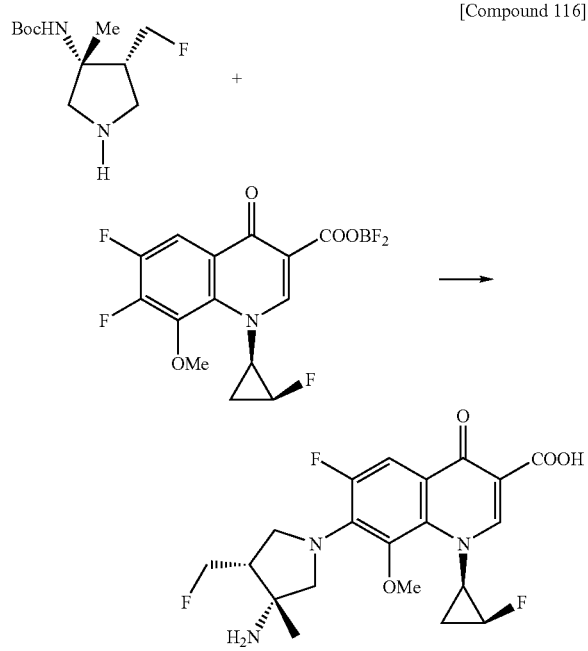

(3R,4R)-3-(tert-butoxycarbonylamino)-4-fluoromethyl-3-methylpyrrolidine (169 mg, 0.728 mmol), 6,7-difluoro-1-[(1R,2S)-2-fluoro-1-cyclopropyl]-8-methoxy-1,4-dihydro-4-oxoquinoline-3-carboxylic acid—difluoroborane complex (268 mg, 0.742 mmol) and triethylamine (0.124 mL, 0.891 mmol) were dissolved in dimethyl sulfoxide (2 mL), and the solution was stirred in an oil bath at 35° C. for 16 hours. After concentrating the reaction mixture, a mixed solution of ethanol and water (Ethanol:water, 9:1) (55 mL) and triethylamine (1 mL) were added, and the mixture was heated under reflux for 2 hours. After concentrating the reaction mixture under reduced pressure, the residue was dissolved in ethyl acetate (100 mL×2) and washed with 10% aqueous solution of citric acid (100 mL), water (100 m×3) and saturated aqueous solution of sodium chloride (100 mL). The organic layer was dried with anhydrous sodium sulfate, and after filtration, the filtrate was concentrated under reduced pressure. The concentrate was dissolved in concentrated hydrochloric acid (10 mL) in an ice bath, and the mixture was stirred at room temperature for 30 minutes and washed with chloroform (100 mL×4). To the aqueous layer was added 10 mol×1 aqueous solution of sodium hydroxide to pH 12 in an ice bath, and hydrochloric acid was added to adjust the pH to 7.4. The solution was extracted with chloroform (150 mL×3), and the organic layer was dried with anhydrous sodium sulfate. After filtration, the filtrate was concentrated under reduced pressure, and the concentrate was purified by recrystallization from ethanol. The crystals were dried under reduced pressure to obtain 216 mg (67%) of the title compound as a pale yellow powder.

mp: 185-188° C.

$^1$H-NMR (400 MHz, 0.1N NaOD) δ ppm: 1.38 (3H, s), 1.50-1.62 (1H, m) 1.61-1.70 (1H, m), 2.45-2.58 (1H, m), 3.39 (1H, d, J=10.5 Hz), 3.59 (3H, s), 3.70 (1H, t, J=9.3 Hz), 3.75-3.84 (2H, m), 4.02-4.09 (1H, m), 4.70 (1H, ddd, J=40.7, 9.6, 6.1 Hz), 4.78-4.81 (1H, m), 4.94 (1H, ddd, J=56.6, 9.1, 6.1 Hz), 7.67 (1H, d, J=14.7 Hz), 8.48 (1H, s).

Elementary analysis for $C_{20}H_{22}F_3N_3O_4 \cdot 1H_2O$:
Calculated: C, 54.17; H, 5.46; F, 12.85; N, 9.48
Found: C, 54.20; H, 5.52; F, 12.25; N, 8.99.

IR (ATR) ν: 2970, 2868, 1724, 1616, 1574, 1512, 1437, 1390, 1354, 1317, 1298, 1271, 1192, 1142 cm$^{-1}$.

Reference Example 81 tert-Butyl (3S)-4-fluoro-3-methyl-5-oxo-1-[(1R)-1-phenylethyl]pyrrolidine-3-carboxylate (Isomer A)

[Compound 117]

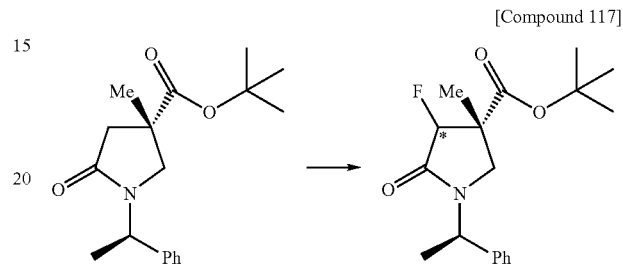

To a solution of tert-butyl (3S)-3-methyl-5-oxo-1-[(1R)-1-phenylethyl]-pyrrolidine-3-carboxylates (6.83 g, 22.5 mmol) in tetrahydrofuran (135 mL), lithium bistrimethylsilyl amide (27.0 mL, 27.0 mmol, 1.0M solution in tetrahydrofuran) was added at 0° C., and the mixture was stirred at the same temperature for 15 minutes. To the reaction mixture, N-fluorobenzenesulfoneimide (13.3 g, 42.2 mmol) was added at the same temperature, and the mixture was stirred for 2 hours. Saturated aqueous solution of ammonium chloride (300 mL) was added to the reaction mixture, and the mixture was extracted with ethyl acetate (300 mL×2). The organic layer was washed with saturated aqueous solution of sodium chloride (300 mL), and dried with anhydrous sodium sulfate. After the filtration, the filtrate was concentrated under reduced pressure, and the residue was purified by silica gel column chromatography (elusion by hexane:ethyl acetate, 5:1→2:3) to obtain 5.80 g (80%) of the title compound (isomer A) as a white solid.

$^1$H-NMR (400 MHz, CDCl$_3$) δ ppm: 1.35 (3H, d, J=2.9 Hz), 1.37 (9H, s), 1.56 (3H, d, J=7.1 Hz), 3.10 (1H dd, J=10.2, 1.1 Hz), 3.17 (1H, d, J=10.3 Hz), 5.23 (1H, d J=51.7 Hz), 5.50 (1H, q, J=7.1 Hz), 7.26-7.39 (5H, m).

MS (ESI) m/z: 322 (M+H)$^+$.

Reference Example 82 tert-Butyl (3S)-4-fluoro-3-methyl-5-oxo-1-[(1R)-1-phenylethyl]-pyrrolidine-3-carboxylate (Isomer B)

[Compound 118]

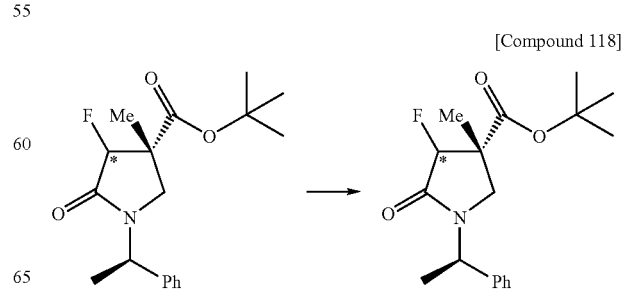

To a solution of tert-butyl (3S)-4-fluoro-3-methyl-5-oxo-1-[(1R)-1-phenylethyl]-pyrrolidine-3-carboxylate isomer A (3.85 g, 12.0 mmol) in tetrahydrofuran (70 mL), lithium diisopropyl amide (6.66 mL, 12.0 mmol, 1.8M solution in tetrahydrofuran) was added at −78° C., and the mixture was stirred at the same temperature for 15 minutes. At the same temperature, 2,6-di-tert-butyl phenol (2.97 g, 14.4 mmol) was added to the reaction mixture, and the temperature was gradually increased with stirring in 2 hours. Saturated aqueous solution of ammonium chloride (200 mL) was added to the reaction mixture, and the mixture was extracted with ethyl acetate (200 mL×2). The organic layer was washed with saturated aqueous solution of sodium chloride (200 mL), and dried with anhydrous sodium sulfate. After filtration, the filtrate was concentrated under reduced pressure, and the concentrate was purified by silica gel column chromatography (elusion by hexane ethyl acetate, 5:1→2:3) to obtain 2.32 g (60%) of the title compound (isomer B having a polarity higher than isomer A) as a white solid. 1.53 g (40%) of isomer A was also recovered.

$^1$H-NMR (400 MHz, CDCl$_3$) δ ppm: 1.38 (12E, s), 1.53 (3H, d, J=7.1 Hz), 2.97 (1H, d, J=10.5 Hz), 3.52 (1H, d, J=10.3 Hz), 4.68 (1H, d, J=51.7 Hz), 5.49 (1H, q, J=7.1 Hz), 7.26-7.39 (5H, m).

MS (ESI) m/z: 322 (M+H)$^+$.

Reference Example 83 tert-Butyl (3S)-4-fluoro-3-methyl-1-[(1R)-1-phenylethyl]-pyrrolidine-3-carboxylate (Isomer A)

[Compound 119]

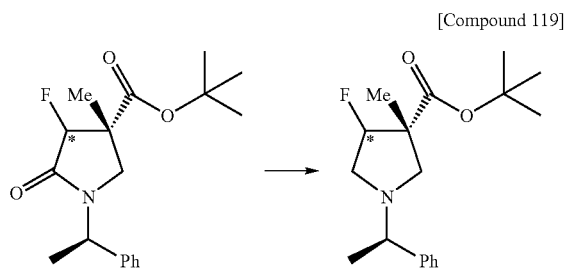

To a solution of tert-butyl (3S)-4-fluoro-3-methyl-5-oxo-1-[(1R)-1-phenylethyl]-pyrrolidine-3-carboxylate (isomer A) (2.58 g, 8.03 mmol) in tetrahydrofuran (50 mL) was added 1.01M solution of borane in tetrahydrofuran (26.2 mL, 26.5 mmol) in an ice bath and the mixture was stirred at room temperature for 15 hours. The reaction mixture was concentrated under reduced pressure, and water (5 mL), ethanol (45 ml), and triethylamine (3 mL) were added in an ice bath, and the mixture was heated under reflux for 1.5 hours. After concentrating the reaction mixture under reduced pressure, water (100 mL) was added, and the mixture was extracted with chloroform (200 mL×2). The organic layer was washed with saturated aqueous solution of sodium chloride (100 mL), and dried with anhydrous sodium sulfate. After filtration, the filtrate was concentrated under reduced pressure, and the concentrate was purified by silica gel column chromatography (elusion by hexane ethyl acetate, 12:1→2:1) to obtain 2.15 g (87%) of the title compound (isomer A) as a colorless oily substance.

$^1$H-NMR (400 MHz, CDCl$_3$) δ ppm: 1.29 (3H, d, J=3.7 Hz), 1.32 (3H, d, J=6.6 Hz), 1.46 (9H, s), 2.44 (H, d, J=8.8 Hz), 2.68 (1H, dd, J=31.7, 11.9 Hz), 2.96 (1H, dq, J=31.0, 5.7 Hz), 3.06 (1H, d, J=8.8 Hz), 3.32 (1H, q, J=6.5 Hz), 5.22 (1H, dd, J=55.2, 4.9 Hz), 7.14-7.31 (5H, m).

MS (ESI) m/z: 308 (M+H)$^+$.

Reference Example 84 tert-Butyl (3S)-4-fluoro-3-methyl-1-[(1R)-1-phenylethyl]-pyrrolidine-3-carboxylate (Isomer B)

[Compound 120]

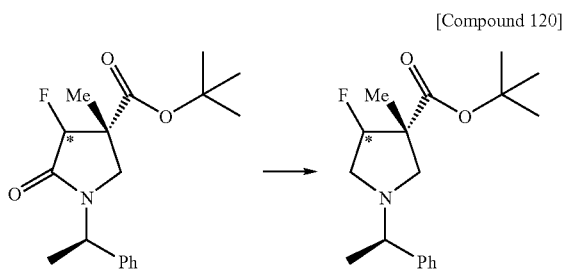

To a solution of tert-butyl (3S)-4-fluoro-3-methyl-5-oxo-1-[(1R)-1-phenylethyl]-pyrrolidine-3-carboxylate (isomer B) (1.64 g, 5.10 mmol) in tetrahydrofuran (30 mL), 1.01M solution of borane in tetrahydrofuran (16.7 mL, 16.9 mmol) was added in an ice bath, and the mixture was stirred at room temperature for 15 hours. After concentrating the reaction mixture under reduced pressure, water (5 mL), ethanol (45 mL), and triethylamine (2 mL) were added in an ice bath, and the mixture was heated under reflux for 1.5 hours. After concentrating the reaction mixture under reduced pressure, water (100 mL) was added, and the mixture was extracted with chloroform (200 mL×2). The organic layer was washed with saturated aqueous solution of sodium chloride (100 mL), and dried with anhydrous sodium sulfate. After the filtration, the filtrate was concentrated under reduced pressure, and the concentrate was purified by silica gel column chromatography (elusion by hexane ethyl acetate, 12:1→2:1) to obtain 1.55 g (99%) of the title compound (isomer B) as a colorless oily substance.

$^1$H-NMR (400 MHz, CDCl$_3$) δ ppm: 1.29 (3H, d, J=1.2 Hz), 1.34 (3H, d, J=6.6 Hz), 1.43 (9H, s), 2.39 (1H, d, J=9.5 Hz), 2.74 (1H, ddd, J=34.4, 12.0, 1.7 Hz), 3.02 (1H, d, J=9.5 Hz), 3.35 (1H, ddd, J=31.5, 12.2, 4.6 Hz), 3.44 (1H, q, J=6.6 Hz), 4.78 (1H, ddd, J=54.2, 4.8, 1.6 Hz), 7.19-7.32 (5H, m).

MS (ESI) m/z: 308 (M+H)$^+$.

Reference Example 85 tert-Butyl (3S)-1-benzyloxycarbonyl-4-fluoro-3-methylpyrrolidine-3-carboxylate (Isomer A)

[Compound 121]

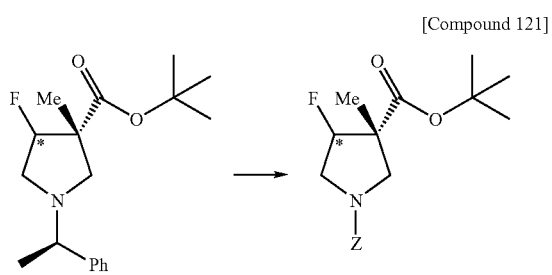

To a solution of tert-butyl (3S)-4-fluoro-3-methyl-1-[(1R)-1-phenylethyl]-pyrrolidine-3-carboxylate (isomer A) (2.15 g, 6.99 mmol) in dichloromethane (40 mL), benzyloxycarbonyl chloride (1.50 mL, 10.5 mmol) was added, and the mixture was stirred in an oil bath at 60° C. for 20 hours. After concentrating the reaction mixture under reduced pressure, the concentrate was purified by silica gel column chromatography (elusion by hexane:ethyl acetate, 12:1→2:1) to obtain 1.81 g (77%) of the title compound (isomer A) as a colorless oily substance.

$^1$H-NMR (400 MHz, CDCl$_3$) δ ppm: 1.35 (3H, dd, J=7.8, 2.2 Hz), 1.41 (9H, br s), 3.24 (1H, dd, J=17.0, 10.9 Hz), 3.61-3.75 (2H, m), 4.08 (1H, dd, J=10.7, 2.7 Hz), 5.14 (2H, d, J=4.6 Hz), 5.17 (1H, d, J=51.0 Hz), 7.26-7.38 (5H, m).

Reference Example 86 tert-Butyl (3S)-1-benzyloxycarbonyl-4-fluoro-3-methylpyrrolidine-3-carboxylate (Isomer B)

[Compound 122]

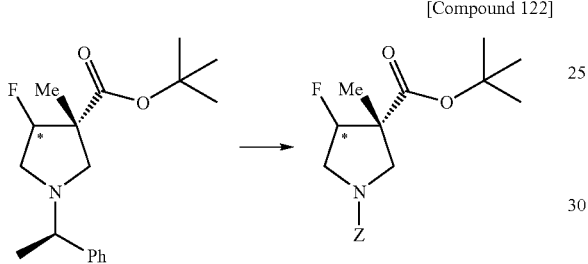

To a solution of tert-butyl (3S)-4-fluoro-3-methyl-1-[(1R)-1-phenylethyl]-pyrrolidine-3-carboxylate isomer B (1.55 g, 5.04 mmol) in dichloromethane (30 mL), benzyloxycarbonyl chloride (1.08 mL, 7.56 mmol) was added, and the mixture was stirred in an oil bath at 60° C. for 24 hours. After concentrating the reaction mixture under reduced pressure, the residue was purified by silica gel column chromatography (elusion by hexane:ethyl acetate, 20:1→3:2) to obtain 1.38 g (81%) of the title compound (isomer B) as a colorless oily substance.

$^1$H-NMR (400 MHz, CDCl$_3$) δ ppm: 1.24 (3H, s), 1.47 (9H, s), 3.49 (1H, dd, J=26.9, 11.0 Hz), 3.60-3.80 (2H, m), 3.90 (1H, dd, J=11.0, 3.7 Hz), 4.90 (1H, dd, J=51.8, 2.9 Hz), 5.14 (2H, dd, J=16.6, 11.7 Hz), 7.22-7.38 (5H, m).

MS (ESI) m/z: 360 (M+Na)$^+$.

Reference Example 87

(3S)-1-Benzyloxycarbonyl-4-fluoro-3-methylpyrrolidine-3-carboxylic Acid (Isomer A)

[Compound 123]

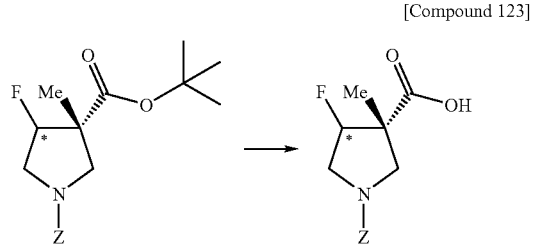

To a solution of tert-butyl (3S)-1-benzyloxycarbonyl-4-fluoro-3-methylpyrrolidine-3-carboxylate (isomer A) (1.80 g, 5.33 mmol) in dichloromethane (10 mL), trifluoroacetic acid (10 mL) was added dropwise and, and the mixture was stirred for 2 hours. The reaction mixture was concentrated under reduced pressure, and saturated aqueous solution of sodium hydrogencarbonate (30 mL) was added to the concentrate under reduced pressure. The aqueous solution was washed with diethylether (50 mL), and to the aqueous layer was added 1 mol/l hydrochloric acid to pH 2 to 3, and the mixture was extracted with chloroform (200 mL×2). The organic layer was dried with anhydrous sodium sulfate, and after filtration, the filtrate was concentrated under reduced pressure. The concentrate was azeotropically distilled by adding toluene (20 mL), and dried under reduced pressure to obtain 1.86 g (quantitative) of the title compound (isomer A) as a colorless oily substance.

$^1$H-NMR (400 MHz, CDCl$_3$) δ ppm: 1.44 (3H, d, J=4.9 Hz), 3.32 (1H, t, J=12.0 Hz), 3.67-3.83 (2H, m), 4.14 (1H, t, J=10.3 Hz), 5.09-5.17 (2H, m), 5.22 (1H, d, J=43.9 Hz), 7.27-7.38 (5H, m).

MS (ESI) m/z: 304 (M+Na)$^+$.

Reference Example 88

(3S)-1-Benzyloxycarbonyl-4-fluoro-3-methylpyrrolidine-3-carboxylic Acid (Isomer B)

[Compound 124]

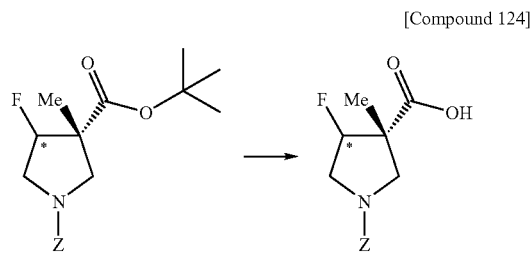

To a solution of tert-butyl (3S)-1-benzyloxycarbonyl-4-fluoro-3-methylpyrrolidine-3-carboxylate isomer B (1.35 g, 4.00 mmol) in dichloromethane (7 mL), trifluoroacetic acid (7 mL) was added dropwise in an ice bath, and the mixture was stirred for 2 hours. After concentrating the reaction mixture under reduced pressure, saturated aqueous solution of sodium hydrogencarbonate (30 mL) was added to the concentrate in an ice bath, and the aqueous solution was washed with diethylether (50 mL). To the aqueous layer was added 1 mol/l hydrochloric acid to pH 2 to 3, and the solution was extracted with chloroform (150 mL×2). The organic layer was dried with anhydrous sodium sulfate, and after filtration, the filtrate was concentrated under reduced pressure. The concentrate was azeotropically distilled by adding toluene (20 mL), and dried under reduced pressure to obtain 1.25 g (quantitative) of the title compound (isomer B) as a colorless oily substance.

$^1$H-NMR (400 MHz, CDCl$_3$) δ ppm: 1.33 (3H, s), 3.57 (1H, dd, J=29.4, 11.0 Hz), 3.66-3.86 (2H, m), 3.95 (1H, dd, J=10.8, 6.1 Hz), 4.99 (1H, dd, J=51.5, 3.2 Hz), 5.16 (2H, s), 7.15-7.52 (5H, m)

MS (ESI) m/z: 304 (M+Na)$^+$.

Reference Example 89

(3R)-1-Benzyloxycarbonyl-3-(tert-butoxycarbonylamino)-4-fluoro-3-methylpyrrolidine (Isomer A)

[Compound 125]

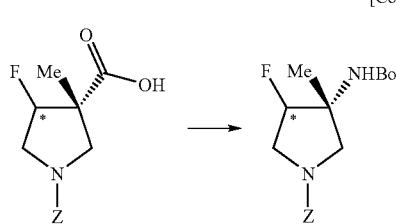

To a solution of (3S)-1-benzyloxycarbonyl-4-fluoro-3-methylpyrrolidine-3-carboxylic acid (isomer A) (1.86 g, 5.33 mmol) in acetonitrile (40 mL), 1,1'-carbonyl bis-1H-imidazole (1.30 g, 8.00 mmol) was added, and the mixture was stirred for 1 hour. Ammonia gas was bubbled into the reaction mixture for 1.5 hours, and the solution was concentrated under reduced pressure. Water (50 mL) was added to the concentrate, and the mixture was extracted with chloroform (100 mL×2). The organic layer was washed with saturated aqueous solution of sodium chloride (100 mL), and dried with anhydrous sodium sulfate. After filtration, the filtrate was concentrated under reduced pressure. The concentrate was azeotropically distilled by adding toluene (20 mL), and dried under reduced pressure to obtain 1.80 g (quantitative) of the crude product (isomer A) in the form of amide as a colorless oily substance.

$^1$H-NMR (400 MHz, CDCl$_3$) δ ppm: 1.41 (3H, s), 3.40 (1H, d, J=12.0 Hz), 3.60-3.97 (3H, m), 5.12-5.31 (3H, m), 5.48-5.89 (2H, m), 7.23-7.35 (5H, m).

To a solution of the crude product in the form of an amide (1.80 g, 5.33 mmol) in tert-butyl alcohol (20 mL), lead tetraacetate (4.73 g, 10.7 mmol) was added, and the mixture was stirred in an oil bath at 80° C. for 15 minutes. After allowing to cool, sodium hydrogencarbonate (5 g) and diethylether (20 mL) were added to the reaction mixture, and the mixture was stirred for 30 minutes in an ice bath. After removing the insoluble content by filtration through celite, the filtrate and the solution used for the washing were combined, and washed with saturated aqueous solution of sodium hydrogencarbonate (50 mL) and saturated aqueous solution of sodium chloride (50 mL). The organic layer was dried with anhydrous magnesium sulfate, and after filtration, the filtrate was concentrated under reduced pressure. The concentrate was purified by silica gel column chromatography (elusion by hexane:ethyl acetate, 20:1→3:2) to obtain 1.00 g (53%) of the title compound (isomer A) as a colorless oily substance.

$^1$H-NMR (400 MHz, CDCl$_3$) δ: 1.42 (9H, s), 1.51 (3H, dd, J=8.8, 2.9 Hz), 3.42 (1H, dd, J=11.8, 2.5 Hz), 3.53 (1H, d, J=11.5 Hz), 3.59-3.72 (1H, m), 3.71-3.87 (1H, m), 4.50 (1H, d, J=28.7 Hz), 5.14 (2H, s), 5.35 (1H, dd, J=52.0, 26.0 Hz), 7.26-7.39 (5H, m).

MS (ESI) m/z: 375 (M+Na)$^+$.

Reference Example 90

(3R)-1-Benzyloxycarbonyl-3-(tert-butoxycarbonylamino)-4-fluoro-3-methylpyrrolidine (Isomer B)

[Compound 126]

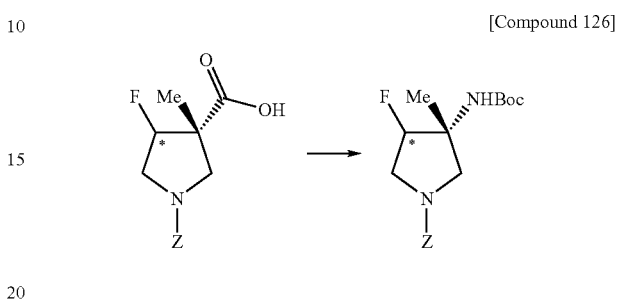

To a solution of (3S)-1-benzyloxycarbonyl-4-fluoro-3-methylpyrrolidine-3-carboxylic acid (isomer B) (1.25 g, 4.00 mmol) in acetonitrile (40 mL), 1,1'-carbonyl bis-1H-imidazole (973 mg, 6.00 mmol) was added, and the mixture was stirred for 1 hour. After bubbling ammonia gas in the reaction mixture for 1.5 hours, the mixture was concentrated under reduced pressure. Water (50 mL) was added to the concentrate, and the solution was extracted with chloroform (100 mL×2). The organic layer was washed with saturated aqueous solution of sodium chloride (100 mL), and dried with anhydrous sodium sulfate. After filtration, the filtrate was concentrated under reduced pressure. The concentrate was azeotropically distilled with toluene (20 mL), and dried under reduced pressure to obtain 1.20 g (quantitative) of the crude product in the form of an amide (isomer B) as a colorless oily substance.

$^1$H-NMR (400 MHz, CDCl$_3$) δ ppm: 1.31 (3H, s), 3.61 (1H, dd, J=25.6, 10.4 Hz), 3.69-3.79 (1H, m), 3.83 (2H, dd, J=16.7, 3.9 Hz), 4.96 (1H, d, J=51.5 Hz), 5.15 (2H, br s), 5.58 (2H, d, J=59.6 Hz), 7.23-7.40 (5H, m).

To a solution of the crude product in the form of an amide (1.20 g, 4.00 mmol) in tert-butyl alcohol (15 mL) was added lead tetraacetate (3.55 g, 8.00 mmol), and the mixture was stirred in an oil bath at 80° C. for 1 hour. After allowing the reaction mixture to cool, sodium hydrogencarbonate (4 g) and diethylether (20 mL) were added to the reaction mixture, and the mixture was stirred in an ice bath for 1 hour. The insoluble content was removed by filtration through celite, and the filtrate and the washing solution of the insoluble content were combined and washed with saturated aqueous solution of sodium hydrogencarbonate (50 mL) and saturated aqueous solution of sodium chloride (50 mL). The organic layer was dried with anhydrous magnesium sulfate, and the solvent was removed by distillation under reduced pressure. The residue was purified by silica gel column chromatography (elusion with hexane:ethyl acetate, 20:1→3:2) to obtain 1.03 g (73%) of the title compound (isomer B) as a colorless oily substance.

$^1$H-NMR (400 MHz, CDCl$_3$) δ ppm: 1.42 (3H, dd, J=4.4, 1.2 Hz), 1.44-1.45 (9H, m), 3.42 (1H, t, J=11.2 Hz), 3.62-3.71 (1H, m), 3.76 (1H, dd, J=10.3, 2.5 Hz), 3.84 (1H, t, J=10.7 Hz), 4.84 (1H, d, J=54.4 Hz), 4.92 (1H, d, J=56.9 Hz), 5.14 (2H, dd, J=15.3, 13.1 Hz), 7.26-7.52 (5H, m).

MS (ESI) m/z: 375 (M+Na)$^+$.

Reference Example 91

(3R)-3-(tert-Butoxycarbonylamino)-4-fluoro-3-methylpyrrolidine (Isomer A)

[Compound 127]

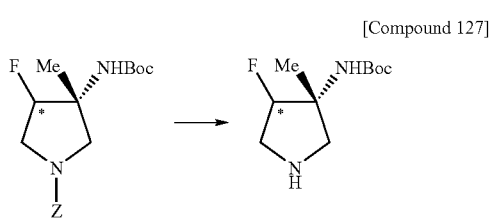

To a solution of (3R)-1-benzyloxycarbonyl-3-(tert-butoxycarbonylamino)-4-fluoro-3-methylpyrrolidine (isomer A) (271 mg, 0.769 mmol) in ethanol (10 mL) was added 10% palladium-carbon catalyst (containing 52.8% water, 27.0 mg), and the suspension was stirred for 2 hours in hydrogen gas atmosphere. After removing the catalyst by filtration, the filtrate was concentrated under reduced pressure to obtain 156 mg (93%) of the crude target compound (isomer A) as a colorless transparent syrup substance.

$^1$H-NMR (400 MHz, CDCl$_3$) δ ppm: 1.43-1.44 (12H, m), 3.06 (1H, dd, J=13.4, 1.7 Hz), 3.13 (1H, d, J=13.4 Hz), 3.34 (1H, dd, J=13.4, 4.6 Hz), 3.42 (1H, dd, J=13.4, 4.6 Hz), 4.58 (1H, s), 5.16 (1H, d, J=53.7 Hz).

MS (ESI) m/z: 219 (M+H)$^+$.

Reference Example 92

(3R)-3-(tert-Butoxycarbonylamino)-4-fluoro-3-methylpyrrolidine (Isomer B)

[Compound 128]

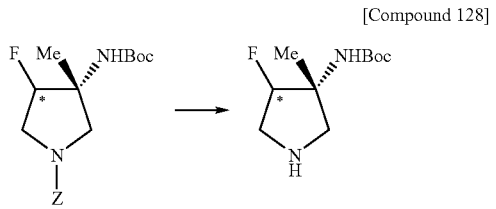

To a solution of (3R)-1-benzyloxycarbonyl-3-(tert-butoxycarbonylamino)-4-fluoro-3-methylpyrrolidine (isomer B) (304 mg, 0.863 mmol) in ethanol (12 mL) was added 10% palladium-carbon catalyst (containing 52.8% water, 30.0 mg), and the suspension was stirred for 2 hours in hydrogen gas atmosphere. After removing the catalyst by filtration, the filtrate was concentrated under reduced pressure to obtain 182 mg (97%) of the crude target compound (isomer B) as a colorless transparent syrup substance.

$^1$H-NMR (400 MHz, CDCl$_3$) δ ppm: 1.40 (3H, d, J=1.7 Hz), 1.45 (9H, s), 3.11-3.17 (2H, m), 3.19-3.25 (1H, m), 3.31 (1H, dd, J=13.7, 4.4 Hz), 4.75 (1H, dd, J=55.3, 3.6 Hz), 4.99 (1H, s).

MS (ESI) m/z: 219 (M+H)$^+$.

Example 25

7-[(3R)-3-Amino-4-fluoro-3-methylpyrrolidin-1-yl]-6-fluoro-1-[(1R,2S)-2-fluoro-1-cyclopropyl]-8-methoxy-1,4-dihydro-4-oxoquinoline-3-carboxylic acid

[Compound 129]

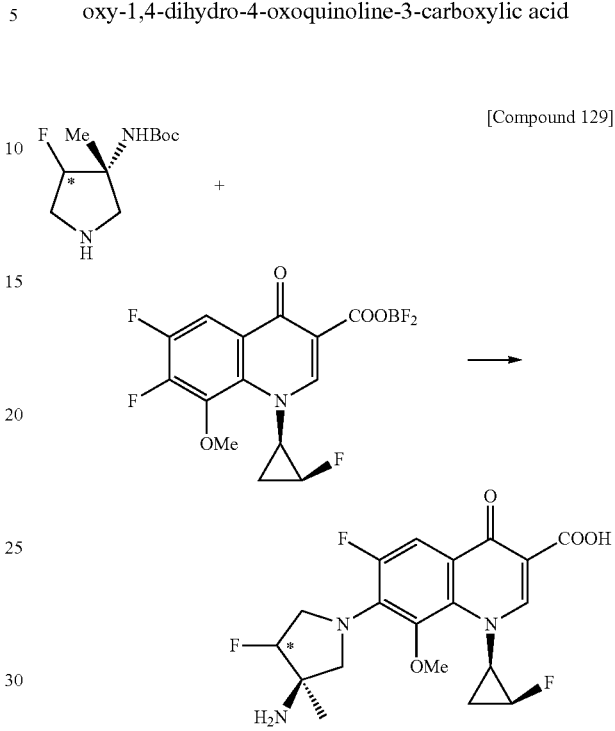

(3R)-3-(tert-butoxycarbonylamino)-4-fluoro-3-methylpyrrolidine isomer A (156 mg, 0.713 mmol), 6,7-difluoro-1-[(1R,2S)-2-fluoro-1-cyclopropyl]-8-methoxy-1,4-dihydro-4-oxoquinoline-3-carboxylic acid—difluoroboron complex (278 mg, 0.769 mmol), and triethylamine (0.129 mL, 0.923 mmol) were added to dimethyl sulfoxide (2 mL) and the mixture was stirred in an oil bath at 35° C. for 19 hours. After concentrating the mixture, a mixed solution of ethanol and water (ethanol:water, 9:1) (60 mL) and triethylamine (2 mL) were added to the concentrate, and the mixture was heated under reflux for 2 hours. The reaction mixture was concentrated under reduced pressure, and the concentrate was dissolved in ethyl acetate (100 mL×2). The solution was washed with 10% aqueous solution of citric acid (100 mL), water (100 mL×3), and saturated aqueous solution of sodium chloride (100 mL). The organic layer was dried with anhydrous sodium sulfate, and after filtration, the filtrate was concentrated under reduced pressure. The concentrate was dissolved in concentrated hydrochloric acid (10 mL) in an ice bath, and the mixture was stirred at room temperature for 30 minutes. The reaction mixture was washed with chloroform (100 mL×4), and to the aqueous layer was added 10 mol/l aqueous solution of sodium hydroxide to pH 12 in an ice bath, and hydrochloric acid was added to adjust the pH to 7.4. The solution was extracted with chloroform (150 mL×3), and the organic layer was dried with anhydrous sodium sulfate. After filtration, the filtrate was concentrated under reduced pressure, and the concentrate was purified by recrystallization from ethanol. The crystals were dried to obtain 165 mg (52%) of the title compound (from isomer A of substituent at position 7) as a pale yellow powder.

mp: 160-163° C.

$^1$H-NMR (400 MHz, 0.1N NaOD) δ ppm: 1.38 (3H, d, J=2.5 Hz), 1.40-1.48 (1H, m), 1.50-1.62 (1H, m), 3.44 (1H, d, J=10.3 Hz), 3.59 (3H, s), 3.68-3.80 (2H, m), 4.00-4.05 (1H, m), 4.29 (1H, dd, J=40.0, 13.5 Hz), 4.82-4.87 (1H, m), 5.03 (1H, dd, J=65.7, 4.7 Hz), 7.69 (1H, d, J=14.2 Hz), 8.41 (1H, d, J=2.9 Hz)

Elementary analysis for $C_{19}H_{20}F_3N_3O_4 \cdot 25H_2O$:
Calculated: C, 54.87; H, 4.97; F, 13.70; N, 10.10.
Found: C, 54.71; H, 4.98; F, 13.54; N, 10.09.
IR (ATR) v: 3386, 2972, 2881, 1722, 1624, 1518, 1452, 1373, 1325, 1279, 1223, 1190, 1149, 1122 cm$^{-1}$.

Example 26

7-[(3R)-3-Amino-4-fluoro-3-methylpyrrolidin-1-yl]-6-fluoro-1-[(1R,2S)-2-fluoro-1-cyclopropyl]-8-methoxy-1,4-dihydro-4-oxoquinoline-3-carboxylic Acid

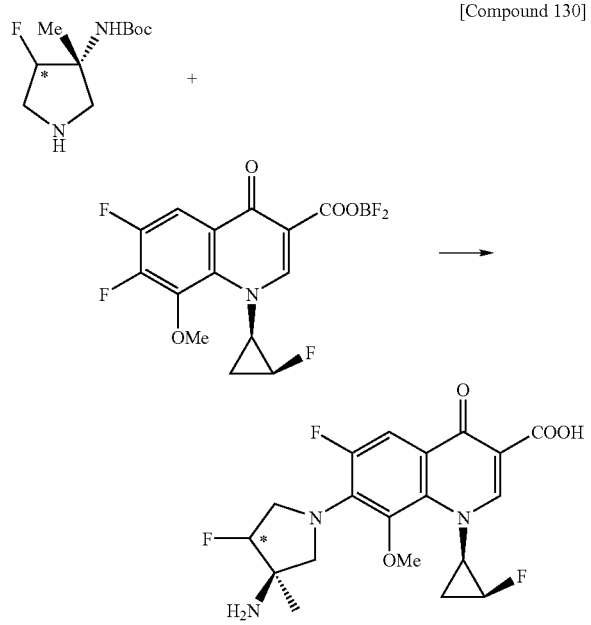

[Compound 130]

(3R)-3-(tert-butoxycarbonylamino)-4-fluoro-3-methylpyrrolidine isomer B (182 mg, 0.833 mmol), 6,7-difluoro-1-[(1R,2S)-2-fluoro-1-cyclopropyl]-8-methoxy-1,4-dihydro-4-oxoquinoline-3-carboxylic acid—difluoroboron complex (311 mg, 0.863 mmol), and triethylamine (0.144 mL, 1.04 mmol) were dissolved in dimethyl sulfoxide (2 mL), and the mixture was stirred in an oil bath at 35° C. for 19 hours. After concentrating the mixture, a mixed solution of ethanol and water (ethanol:water, 9:1) (60 mL) and triethylamine (3 mL) were added, an the mixture was heated under reflux for 2 hours. The reaction mixture was concentrated under reduced pressure, and the concentrate was dissolved in ethyl acetate (100 mL×2), and the solution was washed with 10% aqueous solution of citric acid (100 mL), water (100 m×3), and saturated aqueous solution of sodium chloride (100 mL). The organic layer was dried with anhydrous sodium sulfate, and after filtration, the filtrate was concentrated under reduced pressure. The concentrate was dissolved in concentrated hydrochloric acid (10 mL), and the mixture was stirred at room temperature for 30 minutes. The reaction mixture washed with chloroform (100 mL×4), and to the aqueous layer was added 10 mol/l aqueous solution of sodium hydroxide to pH 12 in an ice bath, and hydrochloric acid was added to the solution to adjust the pH to 7.4. The solution was extracted with chloroform (150 mL×3), and the organic layer was dried with anhydrous sodium sulfate. After filtration, the filtrate was concentrated under reduced pressure. The concentrate was purified by recrystallization from ethanol, and the crystals were dried under reduced pressure to obtain 176 mg (51%) of the title compound (from isomer B of substituent at position 7) as a pale yellow powder.

mp: 206-208° C.
$^1$H-NMR (400 MHz, 0.1N NaOD) δ ppm: 1.29 (3H, br s), 1.57-1.74 (2H, m), 3.37 (1H, d, J=9.8 Hz), 3.56-3.67 (1H, m), 3.60 (3H, s), 3.83 (1H, d, J=10.0 Hz), 4.08 (1H, q, J=6.3 Hz), 4.34 (1H, dd, J=43.3, 13.1 Hz), 4.77-4.84 (1H, m), 4.93 (1H, ddd, J=52.7, 10.0, 3.2 Hz), 7.68 (1H, d, J=14.5 Hz), 8.50 (1H, s). Elementary analysis for $C_{19}H_{20}F_3N_3O_4$:
Calculated: C, 55.47; H, 4.90; F, 13.85; N, 10.21.
Found: C, 55.29; H, 4.86; F, 13.99; N, 10.33.
IR (ATR) v: 3373, 3300, 3074, 2979, 2881, 2837, 1709, 1620, 1510, 1435, 1378, 1338, 1313, 1269, 1225, 1186, 1130 cm$^{-1}$.

Example 27

7-[(3R)-3-Amino-4-fluoro-3-methylpyrrolidine-1-yl]-6-fluoro-1-[(1R,2S)-2-fluoro-1-cyclopropyl]-8-methyl-1,4-dihydro-4-oxoquinoline-3-carboxylic Acid

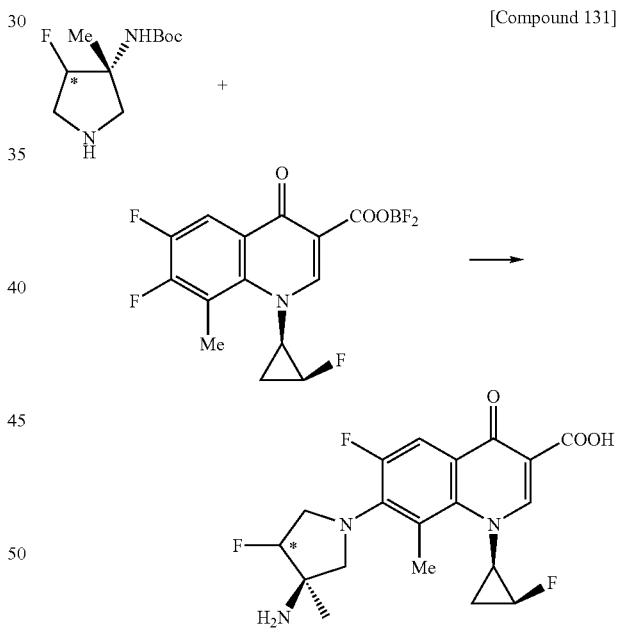

[Compound 131]

(3R)-3-(tert-butoxycarbonylamino)-4-fluoro-3-methylpyrrolidine isomer A (397 mg, 1.82 mmol), 6,7-difluoro-1-[(1R,2S)-2-fluoro-1-cyclopropyl]-8-methyl-1,4-dihydro-4-oxoquinoline-3-carboxylic acid—difluoroboron complex (418 mg, 1.21 mmol), and triethylamine (0.202 mL, 1.45 mmol) were dissolved in sulfolane (2 mL) in an oil bath at 35° C., and the mixture was stirred for 264 hours. After concentrating the mixture, a mixed solution of ethanol and water (ethanol:water, 9:1) (80 mL) and triethylamine (1 mL) were added to the concentrate in an oil bath at 90° C., and the mixture was stirred for 30 minutes. After concentrating the reaction mixture under reduced pressure, the residue was dissolved in ethyl acetate (200 mL×2), and the solution was washed with 10% aqueous solution of citric acid (100 mL), water (100 mL×3), and saturated aqueous solution of sodium chloride (100 mL). The organic layer was dried with anhydrous sodium sulfate, and after filtration, the filtrate was concentrated under reduced pressure, and the residue was purified by short silica gel column chromatography (elusion by chloroform methanol, 49:1→9:1). The residue was dissolved in hydrochloric acid (20 mL), and the solution was stirred at room temperature for 30 minutes, and the washed with chloroform (100 mL×5). To the aqueous layer, 10 mol/l aqueous solution of sodium hydroxide was added to pH 12 in an ice bath, and hydrochloric acid was added to adjust the pH to 7.4. The solution was extracted with chloroform (150 mL×4), and the organic layer was dried with anhydrous sodium sulfate. After the filtration, the filtrate was concentrated under reduced pressure, and the concentrate was purified by recrystallization from ethanol, and the crystals were dried under reduced pressure to obtain 28.3 mg (6%) of the title compound (from isomer A of substituent at position 7) as a pale yellow powder.

mp: 215-217° C.

$^1$H-NMR (400 MHz, 0.1N NaOD) δ ppm: 1.20-1.32 (1H, m), 1.37 (3H, d, J=2.7 Hz), 1.54-1.67 (1H, m), 2.51 (3H, s), 3.17 (1H, d, J=9.8 Hz), 3.47 (1H, dd, J=29.0, 12.6 Hz), 3.86 (1H, d, J=10.0 Hz), 4.05-4.12 (1H, m), 4.30 (1H, ddd, J=40.0, 13.2, 3.2 Hz), 4.80-4.85 (1H, m), 5.01 (1H, ddd, J=67.8, 9.4, 4.6 Hz), 7.70 (1H, d, J=14.0 Hz), 8.45 (1H, d, J=3.4 Hz).

Elementary analysis for $C_{19}H_{20}F_3N_3O_3 \cdot 0.75H_2O$:

Calculated: C, 55.81; H, 5.30; N, 10.28.

Found: C, 55.81; H, 4.89; N, 10.14.

IR (ATR) v: 3394, 3097, 2970, 2941, 2870, 1726, 1618, 1599, 1508, 1456, 1425, 1319, 1267, 1225, 1190, 1146 cm$^{-1}$.

Reference Example 93 tert-Butyl (3S)-3-hydroxymethyl-5-oxo-1-[(1R)-1-phenylethyl]pyrrolidine-3-carboxylate

[Compound 132]

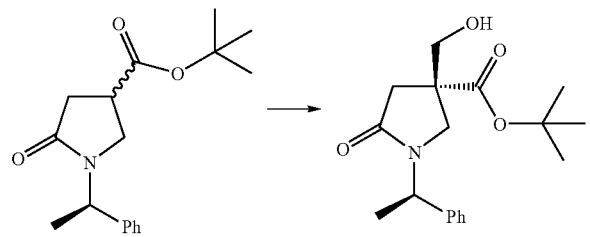

To a solution of tert-butyl 5-oxo-1-[(1R)-1-phenylethyl] pyrrolidine-3-carboxylate (4.00 g, 13.8 mmol) in N,N-dimethylformamide (40 mL), paraformaldehyde (0.830 g, 27.7 mmol) and sodium hydride (0.600 g, 55% in oil, 13.8 mmol) were added at room temperature, and the mixture was stirred at the same temperature for 30 minutes. To the reaction mixture, 10% aqueous solution of citric acid (150 mL) was added in an ice bath, and the solution was extracted with ethyl acetate (300 mL×2). The organic layer was washed with water (100 mL×2) and saturated aqueous solution of sodium chloride (100 mL), and dried with anhydrous sodium sulfate. After the filtration, the filtrate was concentrated under reduced pressure, and the residue was purified by silica gel column chromatography (elusion by hexane:ethyl acetate, 7:3→1:4) to obtain 1.03 g (23%) of the title compound as a white solid.

$^1$H-NMR (400 MHz, CDCl$_3$) δ ppm: 1.35 (9H, s), 1.53 (3H, d, J=7.3 Hz), 2.40 (1H, d, J=17.3 Hz), 2.51 (1H, dd, J=7.8, 5.4 Hz), 2.78 (1H, d, J=17.1 Hz), 3.21 (1H, d, J=10.3 Hz), 3.39 (1H, d, J=10.5 Hz), 3.61 (1H, dd, J=11.2, 7.8 Hz), 3.77 (1H, dd, J=11.2, 5.4 Hz), 5.51 (1H, q, J=7.2 Hz), 7.26-7.37 (5H, m)

MS (ESI) m/z: 320 (M+H)$^+$.

Reference Example 94 tert-Butyl (3S)-3-{[tert-butyl(dimethyl) silyloxy]methyl}-5-oxo-1-[(1R)-1-phenylethyl]pyrrolidine-3-carboxylate

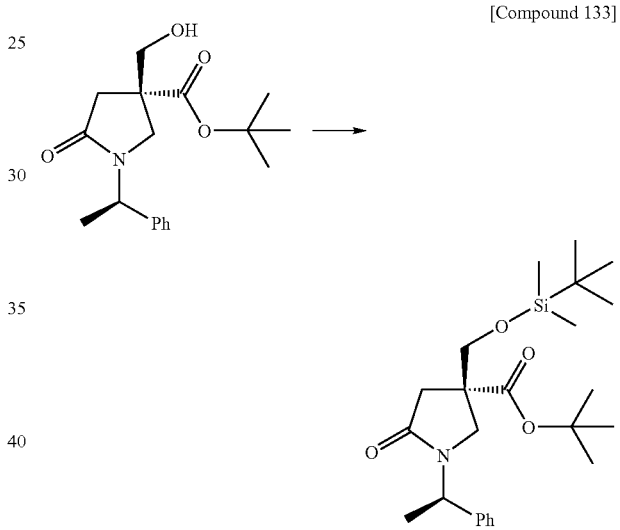

To a solution of tert-butyl (3S)-3-hydroxymethyl-5-oxo-1-[(1R)-1-phenylethyl]pyrrolidine-3-carboxylate (8.23 g, 25.8 mmol) and imidazole (2.63 g, 38.7 mmol) in N,N-dimethylformamide (150 mL), tert-butyl dimethylsilyl chloride (4.66 g, 31.0 mmol) was added in an ice bath, and the mixture was stirred at room temperature for 4 hours. To the reaction mixture, saturated aqueous solution of ammonium chloride (300 mL) was added in an ice bath, and the mixture was extracted with diethylether (300 mL×2). The organic layer was washed with water (300 mL×2) and saturated aqueous solution of sodium chloride (200 mL), and dried with anhydrous magnesium sulfate. After filtration, the filtrate was concentrated under reduced pressure, and the residue was purified by silica gel column chromatography (elusion by hexane:ethyl acetate, 10:1→1:1) to obtain 7.98 g (71%) of the title compound as a colorless oily substance.

$^1$H-NMR (400 MHz, CDCl$_3$) δ ppm: 0.05 (3H, s), 0.06 (3H, s), 0.88 (9H, s), 1.35 (9H, s), 1.51 (3H, d, J=7.1 Hz), 2.47 (1H, d, J=17.1 Hz), 2.77 (1H, d, J=17.3 Hz), 3.28 (2H, dd, J=26.7, 10.1 Hz), 3.68 (2H, dd, J=14.4, 9.5 Hz), 5.49 (1H, q, J=7.1 Hz), 7.25-7.35 (5H, m).

Reference Example 95 tert-Butyl (3S)-3-{[tert-butyl(dimethyl) silyloxy]methyl}-4-methyl-5-oxo-1-[(1R)-1-phenylethyl]pyrrolidine-3-carboxylate

[Compound 134]

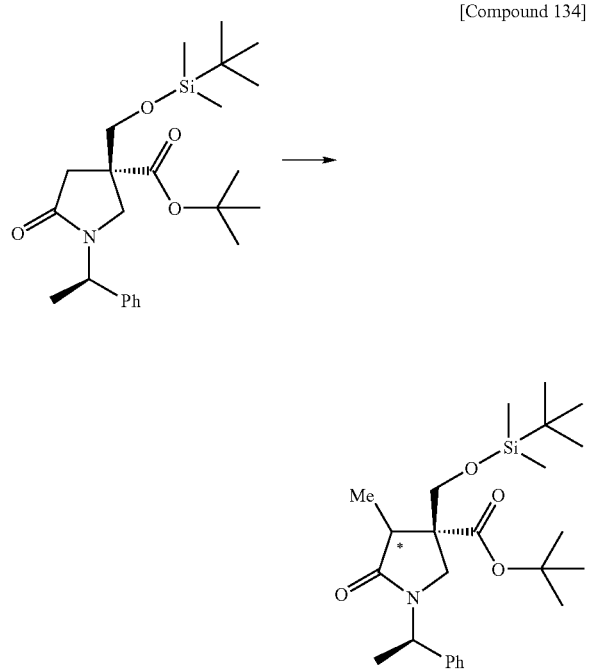

To a solution of tert-butyl (3S)-3-{[tert-butyl(dimethyl) silyloxy]methyl}-5-oxo-1-[(1R)-1-phenylethyl]pyrrolidine-3-carboxylate (8.65 g, 19.9 mmol) and iodomethane (1.37 mL, 21.9 mmol) in tetrahydrofuran (173 mL), lithium bistrimethylsilyl amide (21.9 mL, 21.9 mmol, 1M solution in tetrahydrofuran) was added in an ice bath, and the mixture was stirred at the same temperature for 30 minutes. To the reaction mixture, saturated aqueous solution of ammonium chloride (300 mL, was added, and the mixture was extracted with ethyl acetate (300 mL×2). The organic layer was washed with saturated aqueous solution of sodium chloride (200 mL), and dried with anhydrous sodium sulfate. After the filtration, the filtrate was concentrated under reduced pressure, and the residue was purified by silica gel column chromatography (elusion by hexane:ethyl acetate, 7:1→1:1) to obtain 3.72 g (42%) of the title compound (single component) as a colorless oily substance.

$^1$H-NMR (400 MHz, CDCl$_3$) δ ppm: 0.05 (3H, s), 0.06 (3H, s), 0.88 (9H, s), 1.12 (3H, d, J=7.3 Hz), 1.38 (9H, s), 1.51 (3H, d, J=7.1 Hz), 2.31 (1H, q, J=7.4 Hz), 3.29 (11H, d, J=10.3 Hz), 3.39 (1H, d, J=10.3 Hz), 3.50 (1H, dd, J=9.4, 6.0 Hz), 3.83 (1H, d, J=9.5 Hz), 5.47 (1H, q, J=7.2 Hz), 7.24-7.36 (5H, m)

MS (ESI) m/z: 448 (M+H)$^+$.

Reference Example 96 tert-Butyl (3S)-3-hydroxymethyl-4-methyl-5-oxo-1-[(1R)-1-phenylethyl]pyrrolidine-3-carboxylate

[Compound 135]

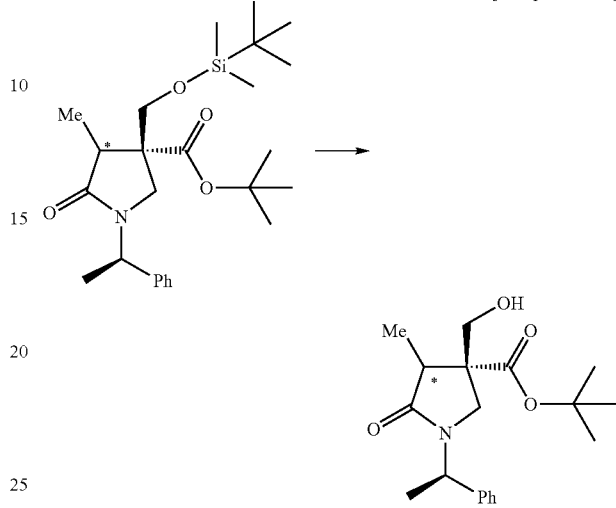

Tert-butyl (3S)-3-{[tert-butyl(dimethyl) silyloxy]methyl}-4-methyl-5-oxo-1-[(1R)-1-phenylethyl]pyrrolidine-3-carboxylate (3.72 g, 8.31 mmol) was dissolved in tetrahydrofuran (70 mL), and tetrabutylammonium fluoride (12.5 mL, 1.0 mol/l solution in tetrahydrofuran, 12.5 mmol) was added dropwise in an ice bath. The mixture was stirred at the same temperature for 1 hour. After concentrating the mixture, saturated aqueous solution of ammonium chloride (200 mL) was added, and the mixture was extracted with ethyl acetate (200 mL×2). The organic layer was washed with saturated aqueous solution of sodium chloride (100 mL), and dried with anhydrous sodium sulfate. After filtration, the filtrate was concentrated under reduced pressure. The concentrate was purified by silica gel column chromatography (elusion by hexane:ethyl acetate=3:1→1:2) to obtain 1.87 g (67%) of the title compound as a white solid.

$^1$H-NMR (400 MHz, CDCl$_3$) δ ppm: 1.18 (3H, d, J=7.6 Hz), 1.32 (9H, s), 1.52 (3H, d, J=7.1 Hz), 2.43-2.49 (2H, m), 3.30 (2H, dd, J=19.0, 10.5 Hz), 3.57 (1H, dd, J=11.1, 6.7 Hz), 3.89 (1H, dd, J=11.0, 5.9 Hz), 5.48 (1H, q, J=7.2 Hz), 7.27-7.36 (5H, m).

MS (ESI) M/Z: 334 (M+H)$^+$.

Reference Example 97 tert-Butyl (3R)-3-fluoromethyl-4-methyl-5-oxo-1-[(1R)-1-phenylethyl]pyrrolidine-3-carboxylate

[Compound 136]

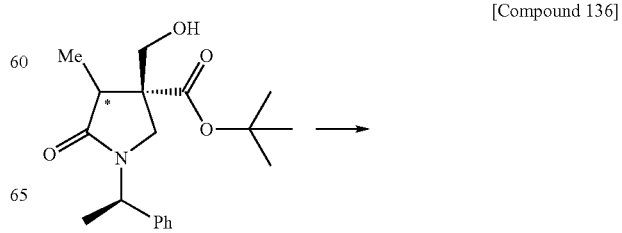

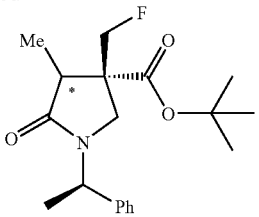

Tert-butyl (3S)-3-hydroxymethyl-4-methyl-5-oxo-1-[(1R)-1-phenylethyl]pyrrolidine-3-carboxylate (1.70 g, 5.10 mmol) was dissolved in dichloromethane (20 mL). To this solution, toluene (20 mL) was added, and diethylaminosulfur trifluoride (1.68 mL, 12.8 mmol) was added dropwise in an ice bath. After stirring at 60° C. for 8 hours, saturated aqueous solution of sodium hydrogencarbonate (50 mL) was added to the reaction mixture, and the mixture was extracted by ethyl acetate (100 mL×2). The organic layer was washed with saturated aqueous solution of sodium chloride (100 mL), and dried with anhydrous sodium sulfate. After filtration, the filtrate was concentrated under reduced pressure. The concentrate was then purified by silica gel column chromatography (solution by hexane:ethyl acetate, 9:1→2:3) to obtain 0.910 mg (53%) of the title compound as a pale yellow oily substance.

$^1$H-NMR (400 MHz, CDCl$_3$) δ ppm: 1.17 (3H, d, J=7.6 Hz), 1.37 (9H, d, J=0.5 Hz), 1.54 (3H, d, J=7.1 Hz), 2.35-2.42 (1H, m), 3.37 (2H, t, J=12.1 Hz), 4.33 (1H, dd, J=46.9, 9.2 Hz), 4.65 (1H, dd, J=46.8, 9.1 Hz), 5.48 (1H, q, J=7.2 Hz), 7.25-7.37 (5H, m) MS (ESI) m/z: 336 (M+H)$^+$.

Reference Example 98

(3R)-3-Fluoromethyl-4-methyl-5-oxo-1-[(1R)-1-phenylethyl]pyrrolidine-3-carboxylic Acid

[Compound 137]

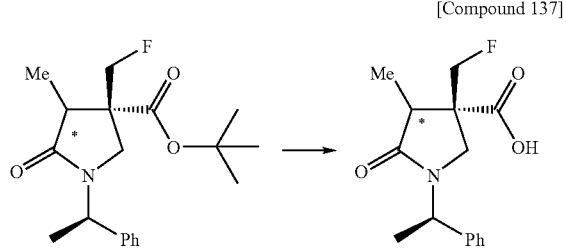

To a solution of tert-butyl (3R)-3-fluoromethyl-4-methyl-5-oxo-1-[(1R)-1-phenylethyl]pyrrolidine-3-carboxylate (910 mg, 2.71 mmol) in dichloromethane (9 mL), trifluoroacetic acid (9 mL) was added dropwise in an ice bath, and the mixture was stirred at room temperature for 3 hours. After concentrating the reaction mixture under reduced pressure, saturated aqueous solution of sodium hydrogencarbonate (20 mL) was added to the concentrate in an ice bath, and the aqueous solution was washed with diethylether (50 mL). To the aqueous layer was added 1 mol/l hydrochloric acid to pH 2 to 3 in an ice bath, and the solution was extracted with chloroform (100 mL×2). The organic layer was washed with saturated aqueous solution of sodium chloride (100 mL), and dried with anhydrous sodium sulfate. After filtration, the filtrate was concentrated under reduced pressure. The concentrate was azeotropically distilled by adding toluene (20 mL), and dried under reduced pressure to obtain 910 mg (quantitative) of the title compound as a white solid.

$^1$H-NMR (400 MHz, CDCl$_3$) δ ppm: 1.18 (3H, d, J=7.4 Hz), 1.55 (3H, d, J=7.1 Hz), 2.49 (1H, q, J=7.4 Hz), 3.35-3.50 (2H, m), 4.38 (1H, dd, J=46.7, 9.2 Hz), 4.71 (1H, dd, J=46.8, 9.3 Hz), 5.50 (1H, q, J=7.1 Hz), 7.26-7.37 (5H, m).

Reference Example 99

(3S)-3-(tert-Butoxycarbonylamino)-3-fluoromethyl-4-methyl-5-oxo-1-[(1R)-1-phenylethyl]pyrrolidine

[Compound 138]

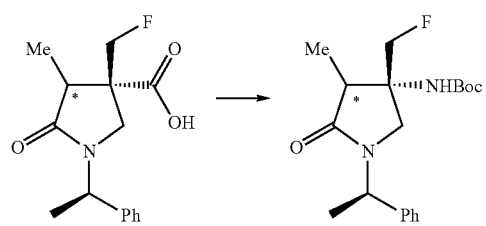

To a solution of (3R)-3-fluoromethyl-4-methyl-5-oxo-1-[(1R)-1-phenylethyl]pyrrolidine-3-carboxylic acid (910 mg, 2.71 mmol) in acetonitrile (20 mL), 1,1'-carbonylbis-1H-imidazole (659 mg, 4.07 mmol) was added, and the mixture was stirred for 20 minutes. Ammonia gas was bubbled into the reaction mixture for 1.5 hours, and the solution was concentrated under reduced pressure. Water (50 mL) was added to the concentrate, and the mixture was extracted with chloroform (100 mL×2). The organic layer was washed with saturated aqueous solution of sodium chloride (100 mL) and dried with anhydrous sodium sulfate. After filtration, the filtrate was concentrated under reduced pressure. The concentrate was azeotropically distilled by adding toluene (20 mL), and dried under reduced pressure to obtain 800 mg (quantitative) of the crude produce in the form of amide as a colorless oily substance.

$^1$H-NMR (400 MHz, CDCl$_3$) δ ppm: 1.18 (3H, d, J=7.4 Hz), 1.56 (3H, d, J=7.4 Hz), 2.72 (1H, q, J=7.3 Hz), 3.26-3.37 (2H, m), 4.52 (1H, dd, J=21.0, 9.7 Hz), 4.64 (1H, dd, J=20.7, 9.7 Hz), 5.15 (2H, d, J=55.4 Hz), 5.57 (1H, q, J=7.0 Hz), 7.26-7.41 (5H, m).

To a solution of the crude product in the form of an amide (800 mg, 2.71 mmol) in tert-butyl alcohol (10 mL), lead tetraacetate (2.40 g, 5.42 mmol) was added, and the mixture was stirred in an oil bath at 80° C. for 30 minutes. After allowing to cool, sodium hydrogencarbonate (2.5 g) and diethylether (20 mL) were added to the reaction mixture, and the mixture was stirred in an ice bath for 30 minutes. The insoluble content was removed by filtration through celite, and filtrate and the solution used for the washing were combined and washed with saturated aqueous solution of sodium hydrogencarbonate (50 mL) and saturated aqueous solution of sodium chloride (50 mL). The organic layer was dried with anhydrous magnesium sulfate, and after filtration, the filtrate was concentrated under reduced pressure. The concentrate was purified by silica gel column chromatography (elusion by hexane:ethyl acetate, 20:1→3:2) to obtain 485 mg (51%) of the title compound as a white solid.

$^1$H-NMR (400 MHz, CDCl$_3$) δ ppm: 1.18 (3H, d, J=7.4 Hz), 1.34 (9H, s), 1.51 (3H, d, J=7.6 Hz), 2.71-2.79 (1H, m), 3.16-3.24 (1H, m), 3.39 (1H, dd, J=10.7, 1.3 Hz), 4.46 (1H, dd, J=47.3, 9.1 Hz), 4.55 (1H, s), 4.71 (1H, dd, J=46.8, 9.1 Hz), 5.50 (1H, q, J=7.1 Hz), 7.23-7.34 (5H, m).

Reference Example 100

(3S)-3-(tert-Butoxycarbonylamino)-3-fluoromethyl-4-methyl-1-[(1R)-1-phenylethyl]pyrrolidine

[Compound 139]

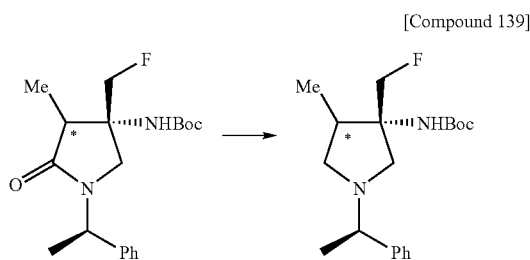

To a solution of (3S)-3-(tert-butoxycarbonylamino)-3-fluoromethyl-4-methyl-5-oxo-1-[(1R)-1-phenylethyl]pyrrolidine (485 mg, 1.38 mmol) in tetrahydrofuran (10 mL), 1.00M solution of borane in tetrahydrofuran (4.57 mL, 4.57 mmol) was added in an ice bath, and the mixture was stirred at room temperature for 15 hours. After concentrating the reaction mixture under reduced pressure, water (1 mL), ethanol (9 mL), and triethylamine (1 mL) were added in an ice bath, and the mixture was heated under reflux for 1.5 hours. After concentrating the reaction mixture under reduced pressure, water (100 mL) was added, and the mixture was extracted with chloroform (100 mL×2). The organic layer was washed with saturated aqueous solution of sodium chloride (100 mL), and dried with anhydrous sodium sulfate. After the filtration, the filtrate was concentrated under reduced pressure, and the residue was purified by silica gel column chromatography (elusion by hexane ethyl acetate, 12:1→1:1) to obtain 350 mg (75%) of the title compound as a colorless oily substance.
$^1$H-NMR (400 MHz, CDCl$_3$) δ ppm: 1.03 (3H, d, J=6.8 Hz), 1.32 (3H, d, J=6.6 Hz), 1.41 (9H, s), 2.11 (1H, t, J=8.5 Hz), 2.19-2.29 (1H, m), 2.38 (1H, dd, J=10.1, 4.5 Hz), 2.84 (1H, d, J=10.3 Hz), 3.16 (1H, t, J=8.1 Hz), 3.25 (1H, q, J=6.5 Hz), 4.54 (2H, d, J=48.3 Hz), 4.65 (1H, s), 7.19-7.31 (5H, m).
MS (ESI) m/z: 337 (M+H)$^+$.

Reference Example 101

(3S)-3-(tert-Butoxycarbonylamino)-3-fluoromethyl-4-methylpyrrolidine

[Compound 140]

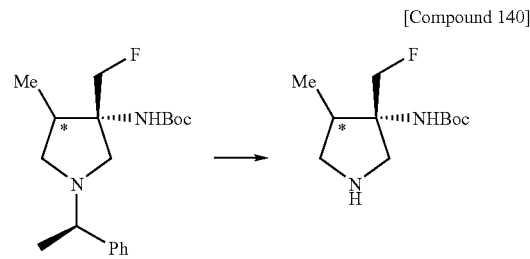

To a solution of (3S)-3-(tert-butoxycarbonylamino)-3-fluoromethyl-4-methyl-1-[(1R)-1-phenylethyl]pyrrolidine (200 mg, 0.594 mmol) in ethanol (12 mL) was added 10% palladium-carbon catalyst (containing 52.8% water, 200 mg), and the suspension was stirred in an oil bath at 40° C. for 2 hours in hydrogen gas atmosphere. After removing the catalyst by filtration, the solvent was removed by distillation under reduced pressure to obtain 150 mg (quantitative) of the crude title compound as a white solid.
$^1$H-NMR (400 MHz, CDCl$_3$) δ ppm: 1.06 (3H, d, J=6.9 Hz), 1.44 (9H, s), 2.28 (1H, q, J=7.4 Hz), 2.80 (1H, t, J=10.0 Hz), 3.24 (1H, d, J=12.3 Hz), 3.32 (2H, dd, J=11.0, 8.1 Hz), 4.54 (2H, d, J=47.3 Hz), 4.74 (1H, s)

Example 28

7-[(3S)-3-Amino-3-fluoromethyl-4-methylpyrrolidin-1-yl]-6-fluoro-1-[(1R,2S)-2-fluoro-1-cyclopropyl]-8-methoxy-1,4-dihydro-4-oxoquinoline-3-carboxylic Acid

[Compound 141]

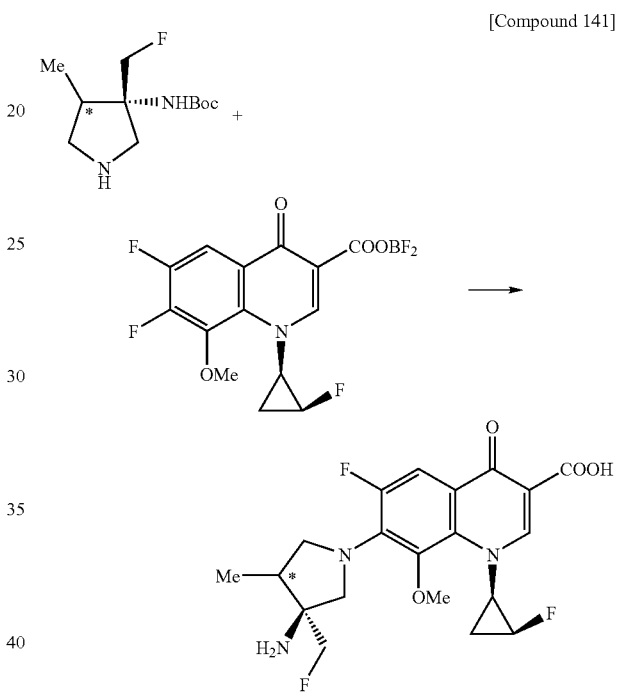

(3S)-3-(tert-butoxycarbonylamino)-3-fluoromethyl-4-methylpyrrolidine (150 mg, 0.594 mmol), 6,7-difluoro-1-[(1R,2S)-2-fluoro-1-cyclopropyl]-8-methoxy-1,4-dihydro-4-oxoquinoline-3-carboxylic acid—difluoroboron complex (214 mg, 0.594 mmol), and triethylamine (0.0994 mL, 0.713 mmol) were dissolved in dimethyl sulfoxide (2 mL), and the mixture was stirred in an oil bath at 35° C. for 15 hours. After concentrating the mixture, a mixed solution of ethanol and water (ethanol:water, 9:1) (11 mL) and triethylamine (0.5 mL) were added to the concentrate, and the mixture was heated under reflux for 2 hours. The reaction mixture was concentrated under reduced pressure, and the concentrate was dissolved in ethyl acetate (100 mL×2), and the solution was washed with 10% aqueous solution of citric acid (100 mL), water mL×3), and saturated aqueous solution of sodium chloride mL). The organic layer was dried with anhydrous sodium sulfate, and after filtration, the filtrate was concentrated under reduced pressure. The concentrate was dissolved in concentrated hydrochloric acid (10 mL), and after stirring the solution at room temperature for 30 minutes, the reaction mixture was washed with chloroform (100 mL×4). To the aqueous layer was added 10 mol/l aqueous solution of sodium hydroxide to pH 12 in an ice bath, and hydrochloric acid was added to adjust the pH to 7.4. The solution was extracted with chloroform (150 mL×3), and the organic layer was dried with anhydrous sodium sulfate. After filtration, the filtrate was concentrated under reduced pressure. The concentrate was purified by recrystallization from ethanol, and the crystals were dried under reduced pressure to obtain 115 mg (45%) of the title compound as a pale yellow powder.

mp: 167-169° C.

$^1$H-NMR (400 MHz, 0.1N NaOD) δ ppm: 1.07 (3H, d, J=6.9 Hz), 1.37-1.50 (1H, m), 1.50-1.62 (1H, m), 2.34 (1H, q, J=7.7 Hz), 3.45 (1H, d, J=11.0 Hz), 3.52-3.58 (1H, m), 3.59 (3H, s), 3.82 (1H, d, J=8.6 Hz), 3.87 (1H, d, J=12.5 Hz), 4.00-4.05 (1H, m), 4.51 (2H, d, J=47.3 Hz), 5.01 (1H, d, J=65.0 Hz), 7.67 (1H, d, J=14.5 Hz), 8.41 (1H, d, J=2.7 Hz).

Elementary analysis for $C_{20}H_{22}F_3N_3O_4 \cdot 0.25H_2O$:
Calculated: C, 55.88; H, 5.28; F, 13.26; N, 9.77.
Found: C, 55.66; H, 5.21; F, 13.26; N, 9.97.
MS (ESI) m/z: 426 (M+H)$^+$.
IR (ATR) ν: 2962, 2939, 2877, 1716, 1622, 1514, 1452, 1441, 1363, 1327, 1273, 1184, 1124 cm$^{-1}$.

Example 29

7-[(7S)-7-Amino-7-methyl-5-azaspiro[2.4]heptan-5-yl]-1-[(1R,2S)-2-fluorocyclopropyl]-8-methyl-1,4-dihydro-4-oxoquinoline-3-carboxylic Acid

[Compound 142]

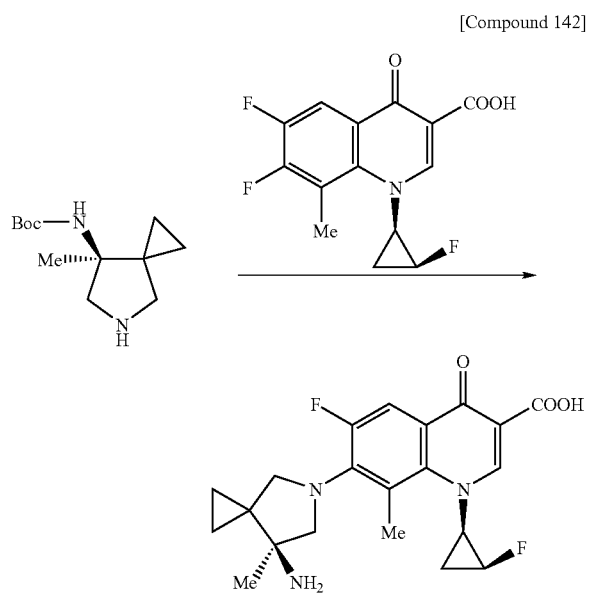

A mixture of (7S)-7-(tert-butoxylcarbonylamino)-7-methyl-5-azaspiro[2.4]heptane (523 mg, 2.31 mmol), 7-fluoro-1-[(1R,2S)-2-fluorocyclopropyl]-8-methyl-1,4-dihydro-4-oxoquinoline-3-carboxylic acid (538 mg, 1.927 mmol), triethylamine (0.537 mL, 3.85 mmol), and dimethyl sulfoxide (6 mL) was stirred in nitrogen atmosphere in an oil bath at 75° C. for 5 days, and in an oil bath at 85° C. for 2 days. To the reaction mixture was added 10% aqueous solution of citric acid (10 mL), and the mixture was extracted with ethyl acetate (50 mL). The organic layer was washed with water (10 mL×2) and saturated aqueous solution of sodium chloride (10 mL), and dried with anhydrous sodium sulfate. After filtration, the filtrate was concentrated under reduced pressure. The residue was purified by silica gel column chromatography (silica gel, 10 g; elusion by chloroform→chloroform:methanol, 98:2) to obtain a pale yellow foam solid. The purified pale yellow foam solid was dissolved in concentrated hydrochloric acid (8 mL) at room temperature, and after transferring the resulting acidic aqueous solution using 6N hydrochloric acid to a separatory funnel, solution was washed with chloroform (50 mL×8). To the aqueous layer was added 10 mol/l aqueous solution of sodium hydroxide to pH 12.0 in an ice bath, and hydrochloric acid was added to adjust the pH to 7.4. The solution was extracted with a mixed solvent of chloroform and methanol (chloroform:methanol, 9:1) (100 mL×3), and lower layer of a mixed solvent chloroform, methanol, and water (chloroform:methanol:water, 7:3:1) (100 mL). The organic layer was dried with anhydrous sodium sulfate, and after filtration, the filtrate was concentrated under reduced pressure. The concentrate was purified by recrystallization from ethanol-isopropanol system, and the crystals were dried under reduced pressure to obtain 332 mg (2 steps, 42%) of the title compound as a pale yellow powder.

mp: 157-159° C.

$[\alpha]_D^{25.0}$=−144.2° (c=0.197, 0.1N NaOE)

$^1$H-NMR (400 MHz, 0.1N NaOD) δ ppm: 0.50-0.54 (1H, m), 0.58-0.62 (1H, m), 0.69-0.80 (2H, m), 1.06 (3H, s), 1.22-1.33 (1H, m), 1.57-1.63 (1H, m), 2.42 (3H, s), 3.14 (1H, d, J=9.8 Hz), 3.35 (1H, d, J=9.6 Hz), 3.65 (1H, d, J=9.6 Hz), 3.89 (1H, d, J=9.8 Hz), 4.04-4.09 (1H, m), 4.93-5.11 (1H, m), 7.06 (1H, d, J=9.1 Hz), 7.99 (1H, d, J=9.1 Hz), 8.45 (1H, d, J=2.9 Hz)

Elementary analysis for $C_{21}H_{24}FN_3O_3 \cdot 1.25H_2O$:
Calculated: C, 61.83; H, 6.55; F, 4.66; N, 10.30.
Found: C, 61.65; H, 6.30; F, 4.77; N, 9.88.
MS (FAB) m/z: 386 (M+H)$^+$.
IR (ATR) ν: 1718, 1608, 1572, 1508, 1460, 1429, 1390, 1358, 1317, 1279, 1259, 1196 cm$^{-1}$.

Example 30

7-[(7S)-7-Amino-7-methyl-5-azaspiro[2.4]heptan-5-yl]-1-cyclopropyl-8-methyl-1,4-dihydro-4-oxoquinoline-3-carboxylic Acid

[Compound 143]

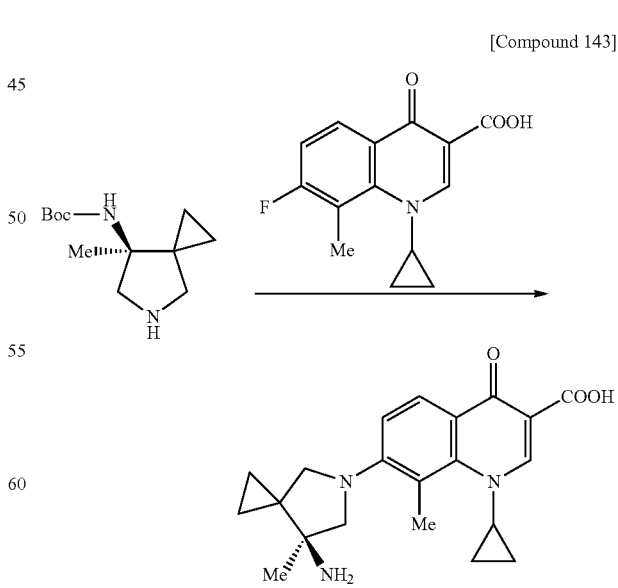

A mixture of (7S)-7-(tert-butoxycarbonylamino)-7-methyl-5-azaspiro[2.4]heptane (524 mg, 2.31 mmol), 1-fluorocyclopropyl-7-fluoro-8-methyl-1,4-dihydro-4-oxoquinoline-3-carboxylic acid (503 mg, 1.925 mmol), triethylamine (0.537 mL, 3.85 mmol), and dimethyl sulfoxide (6 mL) was stirred in nitrogen atmosphere in an oil bath at 75° C. for 5 days, and in an oil bath at 85° C. for 2 days. To the reaction mixture was added 10% aqueous solution of citric acid (10 mL), and the mixture was extracted with ethyl acetate (50 mL). The organic layer was washed with water (10 mL×2) and saturated aqueous solution of sodium chloride (10 mL), and dried with anhydrous sodium sulfate. After filtration, the filtrate was concentrated under reduced pressure. The residue was purified by silica gel column chromatography (silica gel, 10 g; elusion by chloroform→chloroform:methanol, 98:2) to obtain a pale yellow foam solid. The purified pale yellow foam solid was dissolved in concentrated hydrochloric acid (8 mL) at room temperature, and after transferring the resulting acidic aqueous solution to a separatory funnel while washing with 6N hydrochloric acid, the solution was washed with chloroform (50 mL×8). To the aqueous layer was added 10 mol/l aqueous solution of sodium hydroxide to pH 12.0 in an ice bath, and hydrochloric acid was added to adjust the pH to 7.4. The solution was extracted with a mixed solvent of chloroform and methanol (chloroform:methanol, 9:1) (100 mL×3), and the organic layer was dried with anhydrous sodium sulfate. After filtration, the filtrate was concentrated under reduced pressure. The concentrate was purified by recrystallization from ethanol, and dried under reduced pressure to obtain 268 mg (0.641 mmol, 2 steps, 33%) of the title compound as a pale yellow powder.

mp: 227-230° C.

$[\alpha]_D^{25.0}=-38.9°$ (c=0.211, 0.1N NaOH).

$^1$H-NMR (400 MHz, 0.1N NaOD) δ ppm: 0.53 (2H, m), 0.72 (2H, m), 0.79 (2H, m), 1.08 (3H, s), 1.15 (1H, m), 2.41 (3H, s), 3.35 (1H, d, J=10.0 Hz), 3.40 (1H, d, J=9.6 Hz), 3.49 (1H, d, J=9.8 Hz), 3.57 (1H, d, J=9.8 Hz), 4.04-4.07 (1H, m), 7.01 (1H, d, J=9.1 Hz), 7.95 (1H, d, J=9.1 Hz), 8.56 (1E, s)

Elementary analysis for $C_{21}H_{25}N_3O_3 \cdot 1.0EtOH \cdot 0.25H_2O$:

Calculated: C, 66.09; H, 7.60; N, 10.05

Found: C, 66.38; H, 7.48; N, 10.26.

MS (FAB) m/z: 368 (M+H)$^+$.

IR (ATR) ν: 2964, 2916, 2850, 1711, 1610, 1545, 1508, 1466, 1427, 1390, 1352, 1313, 1254, 1194 cm$^{-1}$.

Example 31

7-[(3S)-3-Amino-3-fluoromethyl-4-methylpyrrolidin-1-yl]-6-fluoro-1-[(1R,2S)-2-fluoro-1-cyclopropyl]-8-methyl-1,4-dihydro-4-oxoquinoline-3-carboxylic Acid

[Compound 144]

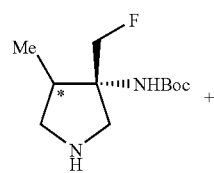

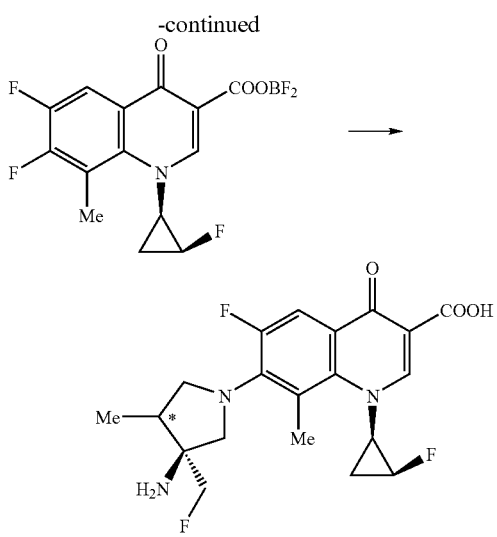

(3S)-3-(tert-butoxycarbonylamino)-3-fluoromethyl-4-methylpyrrolidine (155 mg, 0.663 mmol), 6,7-difluoro-1-[(1R,2S)-2-fluoro-1-cyclopropyl]-8-methyl-1,4-dihydro-4-oxoquinoline-3-carboxylic acid—difluoroboron complex (228 mg, 0.661 mmol), and triethylamine (0.111 ml, 0.795 mmol) were dissolved in sulfolane (0.8 ml), and the mixture was stirred in an oil bath at 35° C. for 480 hours. After concentrating the reaction solution, a mixed solution of ethanol and water (ethanol:water, 9:1) (5 ml) and triethylamine (0.5 ml) were added, and the mixture was stirred in an oil bath at 80° C. for 30 minutes. The reaction system was concentrated under reduced pressure, and the concentrate was dissolved in ethyl acetate (100 ml×2), and washed with 10% aqueous solution of citric acid (100 ml), water (100 ml×2), and saturated aqueous solution of sodium chloride (100 ml). The organic layer was dried with anhydrous sodium sulfate, and the solvent was removed by distillation under reduced pressure. The residue was purified by short silica gel column chromatography (chloroform:methanol, 99:1→4:1). The residue was dissolved in concentrated hydrochloric acid (10 ml) in an ice bath, and the solution was stirred at room temperature for 30 minutes. The reaction solution was washed with chloroform (100 ml×3), and to the aqueous layer was added 10 mol/l aqueous solution of sodium hydroxide to pH 12 in an ice bath, and hydrochloric acid was added to adjust the pH to 7.4. The solution was extracted with chloroform (150 ml×4). The organic layer was dried with anhydrous sodium sulfate, and the solvent was removed by distillation under reduced pressure. The residue was purified by recrystallization from ethanol. The crystals were dried under reduced pressure to obtain 24.0 mg (0.0558 mmol, 8%) of the title compound as a pale yellow powder.

mp: 200-203° C.

$^1$H-NMR (400 MHz, 0.1N NaOD) δ ppm: 1.05 (3H, d, J=6.9 Hz), 1.21-1.33 (1H, m), 1.61 (1H, dt, J=25.2, 7.6 Hz), 2.30-2.40 (1H, m), 2.51 (3H, s), 3.22 (1H, d, J=10.3 Hz), 3.48 (1H, t, J=8.6 Hz), 3.54-3.61 (1H, m), 3.94 (1H, dd, J=10.5, 1.5 Hz), 4.06-4.12 (1H, m), 4.51 (2H, d, J=47.4 Hz), 5.01 (1H, ddd, J=64.2, 9.1, 5.1 Hz), 7.69 (1H, d, J=14.5 Hz), 8.45 (1H, d, J=3.7 Hz).

Elementary analysis for $C_{20}H_{22}F_3N_3O_3 \cdot 0.25EtOH \cdot 0.5H_2O$:

Calculated: C, 57.27; H, 5.74; N, 9.77.

Found: C, 57.17; H, 5.74; N, 9.56.

MS (ESI) m/z: 410 (M+H)$^+$.

IR (ATR) v: 3400, 3367, 3089, 2964, 2883, 1711, 1618, 1508, 1468, 1435, 1356, 1321, 1259, 1227, 1178, 1130 cm$^{-1}$.

Reference Example 102

Tertiary butyl 5-oxo-1-[(1R)-1-phenylethyl]pyrrolidine-3-carboxylate

[Compound 145]

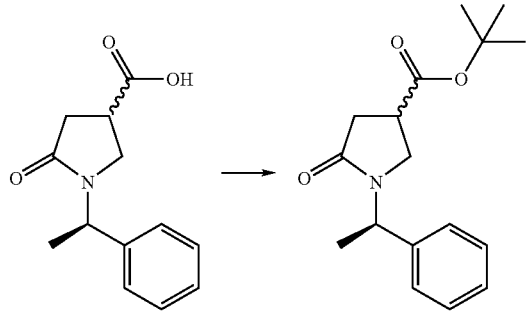

To a suspension of 5-oxo-1-[(1R)-1-phenylethyl]pyrrolidine-3-carboxylic acid produced by the method described in Culbertson T. P., Domagala J. M., Nichols J. F., Priebe S., and Skeean R. W., J. Med. Chem., 1987, 30, 1711-1715 (1165 g, 4.994 mol) in dichloromethane (10 L), O-tertiary butyl-N,N'-diisopropylurea (3020 g, 15.00 mol) was added at room temperature with stirring. When increase in the inner temperature and starting of refluxing were noted, the reaction system was cooled in an ice bath, After cooling the reaction mixture to room temperature, the mixture was stirred for 1 hour after removing the ice bath, and for another 3 hours while heating to 40° C. After stirring the reaction mixture for another 1 hour with cooling in an ice bath, the insoluble content was removed, and the filtrate was dried under reduced pressure. The residue was purified by silica gel column chromatography (silica gel: 4 kg; elusion by hexane:ethyl acetate, 3:1) to obtain 925.2 g (64%) of the title compound (a mixture of isomers at position 3) as a pale yellow syrup. Although separation of the diastereomers of position 3 of the pyrrolidine was easy, the diastereomers were used without separation since the subsequent step involved epimerization. $^1$H-NMR spectrum of the isomers aliquoted for evaluation purpose are shown below.

Low Polarity Isomer:

$^1$H-NMR (400 MHz, CDCl$_3$) δ ppm: 1.45 (9H, s), 1.54 (3H, d, J=7.08 Hz), 2.59-2.74 (2H, m), 2.95-3.03 (1H, m), 3.14 (1H, dd, J=9.77, 8.79 Hz), 3.49 (1H, dd, J=9.77, 6.35 Hz), 7.26-7.36 (5H, m).

High Polarity Isomer:

$^1$H-NMR (400 MHz, CDCl$_3$) δ: 1.36 (9H, s), 1.53 (3H, d, J=7.32 Hz), 2.59-2.75 (2H, m), 3.02-3.11 (1H, m), 3.16 (1H, dd, J=10.01, 5.62 Hz), 3.51 (1H, dd, J=10.01, 8.54 Hz), 7.24-7.36 (5H, m).

Reference Example 103

Tertiary Butyl (3S)-3-methyl-5-oxo-1-[(1R)-1-phenylethyl]pyrrolidine-3-carboxylic Acid

[Compound 146]

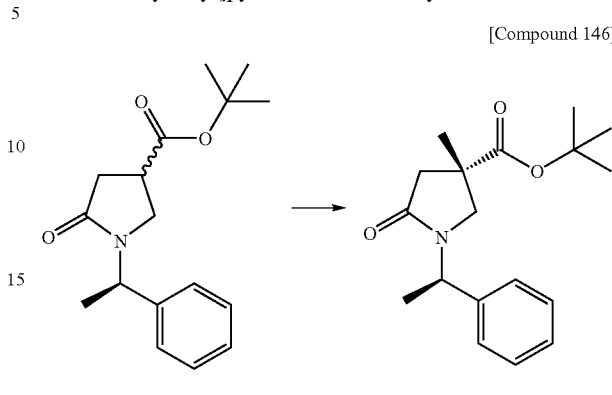

To a solution of 5-oxo-1-[(1R)-1-phenylethyl]pyrrolidine-3-carboxylic acid tertiary butyl (30.05 g, 0.104 mol) in N,N'-dimethylformamide (210 mL), iodomethane 26.0 mL (59.28 g, 0.418 mol), and then, sodium hydride (55% in oil, 11.35 g, 0.260 mol) was added with stirring at room temperature in nitrogen atmosphere. When the inner temperature increased to about 50° C., the reaction mixture was cooled to 30° C. by using an ice bath, and then, the mixture was stirred for 23 hours by replacing the ice bath with a water bath at an exterior temperature of 17° C. The reaction mixture was poured to cool aqueous solution of citric acid (a mixture of 1 L of 10% citric acid and 500 g of ice), and the mixture was stirred for 30 minutes, and extracted with ethyl acetate (800 mL, 500 mL). The organic layers were combined, and washed with saturated aqueous solution of sodium chloride and dried with anhydrous sodium sulfate. After filtration, the filtrate was dried under reduced pressure. The residue was flash purified by silica gel column chromatography (elusion by hexane ethyl acetate, 5:1→4:1) to obtain 10.63 g (33.7%) of high polarity isomer of the title compound as a white solid. 14.91 g (47.3%) of low polarity isomer of tertiary butyl (3R)-3-methyl-5-oxo-1-[(1R)-1-phenylethyl]pyrrolidine-3-carboxylate was also obtained.

$^1$H-NMR (400 MHz, CDCl$_3$) δ ppm: 1.34 (12H, s), 1.52 (3H, d, J=7.10 Hz), 2.27 (1H, d, J=17.0 Hz), 2.93 (1H, d, J=17.0 Hz), 3.05 (1H, d, J=10.1 Hz), 3.32 (1H, d, J=10.1 Hz), 5.50 (1H, q, J=7.1 Hz), 7.23-7.38 (5H, m).

Reference Example 104

Tertiary butyl (3S)-4-[2-(tertiary butyl dimethylsilyl)hydroxyethyl]-3-methyl-5-oxo-1-[(1R)-phenylethyl]pyrrolidine-3-carboxylate

[Compound 147]

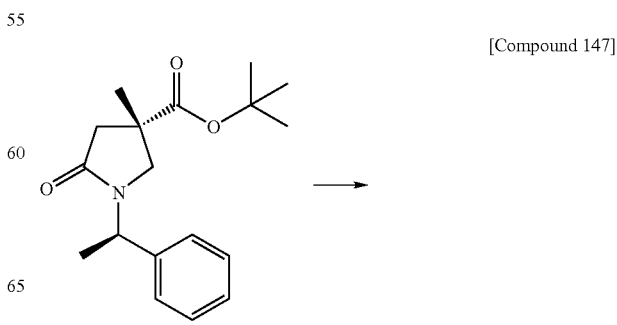

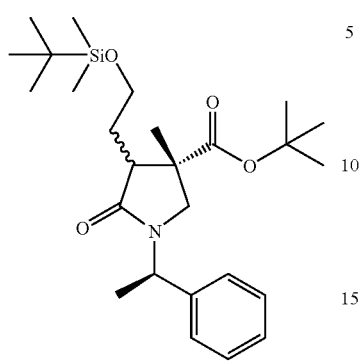

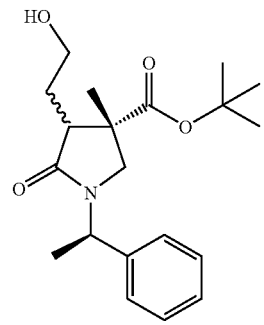

To a solution of (3S)-3-methyl-5-oxo-1-[(1R)-phenylethyl]pyrrolidine-3-carboxylic acid tertiary butyl (30.0 g, 98.9 mmol) and tertiary butyl(2-iodoethoxy)dimethylsilane (36.8 g, 129 mmol) in anhydrous tetrahydrofuran (288 mL), lithium bis(trimethylsilyl)amide (1.0M solution in tetrahydrofuran, 129 mL, 129 mmol) was added dropwise at −4° C., and the mixture was stirred at 2° C. for 3.5 hours. Saturated aqueous solution of ammonium chloride (300 mL) was added to the reaction mixture, and the mixture was extracted with ethyl acetate (300 mL, 200 mL). The organic layer was washed with saturated aqueous solution of sodium chloride (200 mL), and dried with anhydrous sodium sulfate. After filtration, the filtrate was dried under reduced pressure to obtain 54.1 g of the title compound. The product was used in the subsequent step with no further purification.

MS (ESI) m/z: 363 (M-Boc+H)$^+$.

Reference Example 105

Tertiary butyl (3S)-4-(2-hydroxyethyl)-3-methyl-5-oxo-1-[(1R)-phenylethyl]pyrrolidine-3-carboxylate The crude product in the form of a silyl compound (54.1 g, 98.9 mmol) was dissolved in tetrahydrofuran (450 mL), and 1.0 mol/l solution of tetrabutylammonium fluoride in tetrahydrofuran (148 mL, 148 mmol) was added dropwise to the solution in an ice bath. The mixture was stirred at room temperature for 2 hours, and after concentrating the mixture, the concentrate was extracted with ethyl acetate (200 mL, 100 mL). The organic layer was washed with 10% aqueous solution of sodium hydrogencarbonate (200 mL), aqueous solution of citric acid (300 mL), and saturated aqueous solution of sodium chloride (100 mL), and dried with anhydrous sodium sulfate. After filtration, the filtrate was dried under reduced pressure. The residue was purified by silica gel column chromatography (elusion by hexane:ethyl acetate, 6:1→4:1→1:1) to obtain 29.1 g (83.9 mmol, 85%) of the title compound as a colorless transparent syrup substance.

$^1$H-NMR (400 MHz, CDCl$_3$) δ ppm: 1.28 (3H, s), 1.40 (9H, s), 1.51-1.53 (1H, m), 1.53 (3H, d, J=7.1 Hz), 1.78-1.94 (2H, m), 2.90-3.08 (2H, m), 3.67-3.75 (1H, m), 3.80-3.91 (1H, m), 4.85-4.89 (1H, m), 5.43-5.53 (1H, m), 7.27-7.37 (5H, m).

MS (ESI) m/z: 348 (M+H)$^+$.

Reference Example 106

Tertiary butyl (3S)-4-[2-(benzenesulfonyl)oxyethyl]-3-methyl-5-oxo-1-[(1R)-phenylethyl]pyrrolidine-3-carboxylate

[Compound 148]

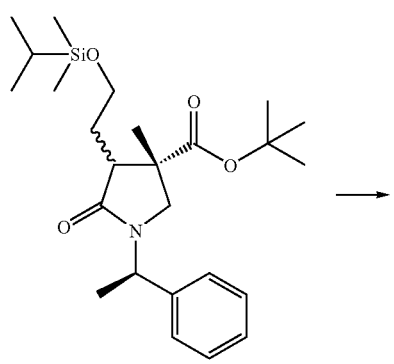

[Compound 149]

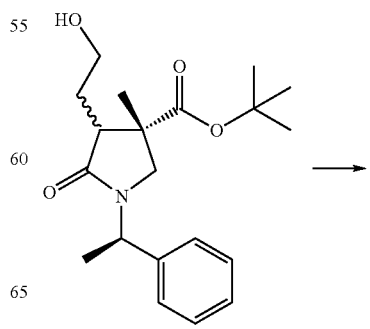

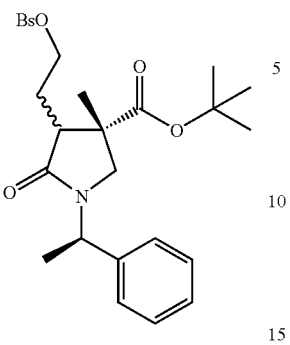

To a solution of (3S)-4-(2-hydroxyethyl)-3-methyl-5-oxo-1-[(1R)-phenylethyl]pyrrolidine-3-carboxylic acid tertiary butyl (29.1 g, 83.9 mmol) in dichloromethane (280 mL), triethylamine (15.2 mL, 109 mmol), benzenesulfonyl chloride (11.8 mL, 92.3 mmol), and 4-dimethyl aminopyridine (1.02 g, 8.39 mmol) were added in an ice bath, and the mixture was stirred at room temperature for 19 hours. Saturated aqueous solution of ammonium chloride (280 mL) was added to the reaction mixture, and after separating the organic layer and removing the solvent under reduced pressure, the residue was dissolved in ethyl acetate (280 mL, 180 mL). The solution was washed again with the saturated aqueous solution of ammonium chloride. The organic layer was washed with 1 mol/l hydrochloric acid aqueous solution (250 mL), saturated sodium bicarbonate water (250 mL), and saturated aqueous solution of sodium chloride (200 mL), and dried with anhydrous sodium sulfate. After the filtration, the filtrate was dried under reduced pressure to obtain the crude product in the form of a benzenesulfonyl compound (43.7 g). The product was used in the subsequent step with no further purification.

MS (ESI) m/z: 510 (M+Na)$^+$.

Reference Example 107

Tertiary butyl (7S)-7-methyl-4-oxo-5-[(1R)-phenylethyl]-5-azaspiro[2.4]heptane-7-carboxylate

[Compound 150]

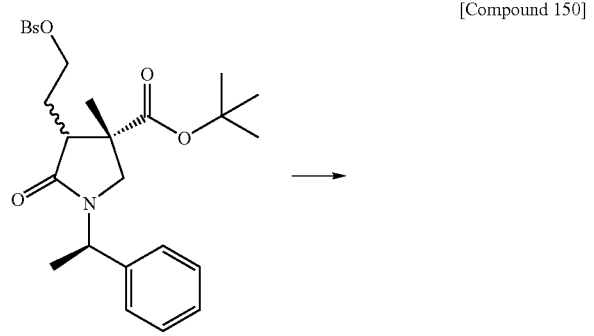

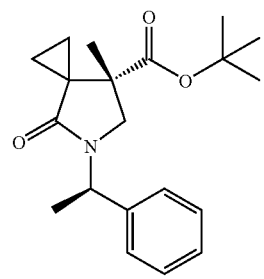

To a solution of the crude product in the form of a benzenesulfonyl compound (43.7 g, 83.9 mmol) in anhydrous tetrahydrofuran (470 mL) was added 1.0 mol/l solution of sodium bis(trimethylsilyl)amide in tetrahydrofuran (109 mL, 109 mmol) in an ice bath, and the mixture was stirred at room temperature for 1 hour. To the reaction mixture was added saturated aqueous solution of ammonium chloride (300 mL), and the mixture was extracted with ethyl acetate (300 mL, 200 mL), and the organic layer was washed with saturated aqueous solution of sodium chloride (200 mL). After drying the organic layer with anhydrous sodium sulfate, the residue was filtered and the filtrate was dried under pressure. The residue was purified by silica gel column chromatography (eluted with hexane:ethyl acetate, 3:1→2:1) to obtain 24.6 g (89%, 2 steps) of the title compound as a white solid.

mp: 55-57° C.

$[\alpha]_D^{25.1}$=122.1° (c=0.517, CHCl$_3$).

$^1$H-NMR (400 MHz, CDCl$_3$) δ ppm: 0.72-0.77 (1H, m), 0.85-0.90 (1H, m), 1.04-1.13 (2H, m), 1.18 (3H, s), 1.32 (9H, s), 1.54 (3H, d, J=7.1 Hz), 3.08 (1H, d, J=9.8 Hz), 3.53 (1H, d, J=9.8 Hz), 5.52 (1H, q, J=7.1 Hz), 7.26-7.34 (5H, m).

Elementary analysis for C$_{20}$H$_{27}$NO$_3$:

Calculated: C, 72.92; H, 8.26; N, 4.25.

Found: C, 72.64; H, 8.27; N, 4.06.

MS (FAB) m/z: 330 (M+H)$^+$.

HRMS (FAB) m/z: 330.2069 (Calcd for C$_{20}$H$_{28}$NO$_3$ 330.2069).

IR (ATR) ν: 3066, 2976, 2933, 2879, 1720, 1676, 1481, 1454, 1433, 1365, 1329, 1286, 1238, 1203 cm$^{-1}$.

Figure 3:
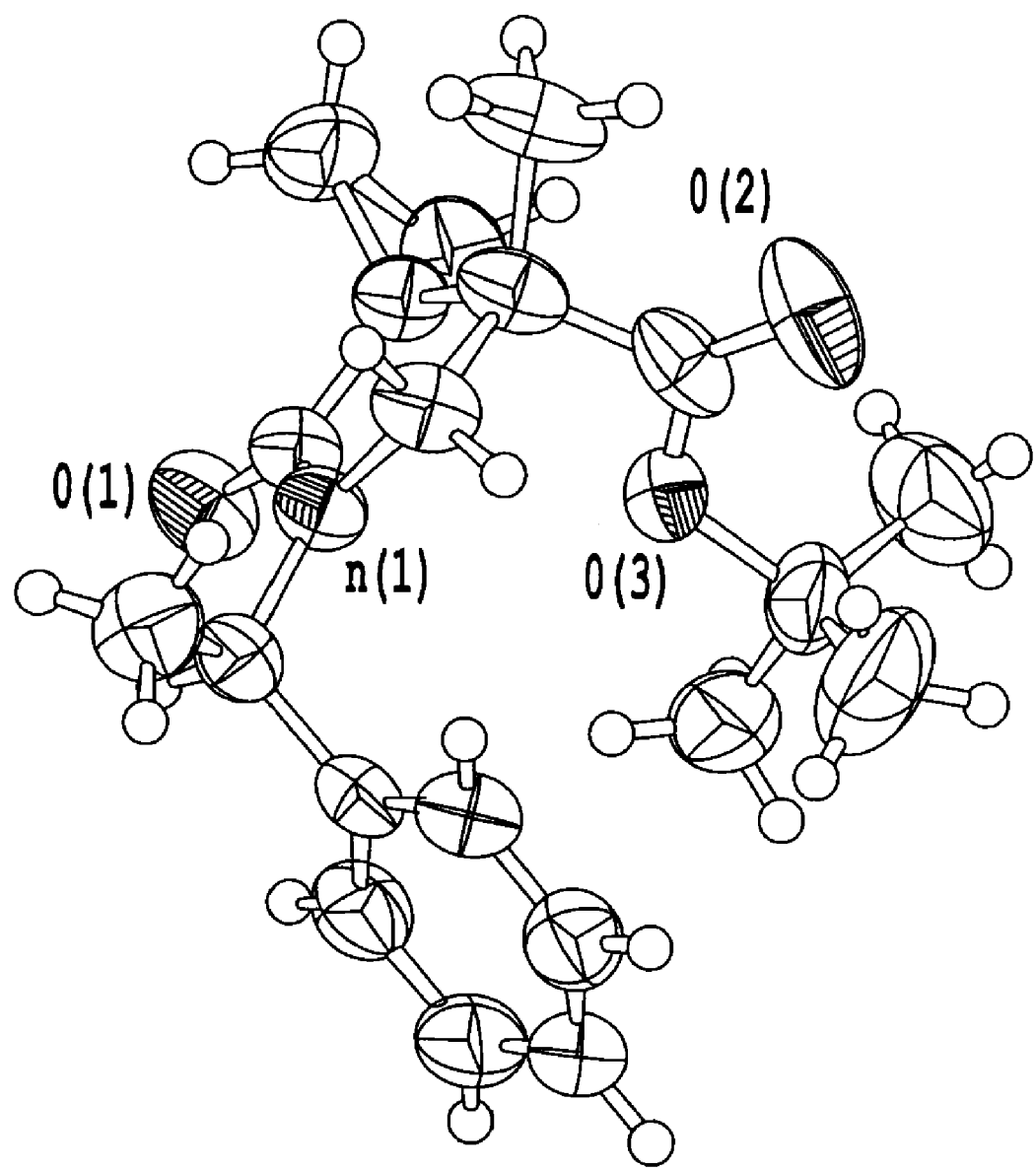
FIG. 3 is a view showing the results of X ray structural analysis for the compound produced in Reference Example 107.

X ray structural analysis was conducted to determine the configuration of position 7 of this compound. The results were as shown in FIG. 3.

After collecting the data, initial phase was resolved by direct method, and refined by full matrix least square method. In the refinement, anisotropic thermal parameters were used for the non-hydrogen atoms, and hydrogen atoms were placed in calculated positions in the coordinates. This compound has two asymmetric carbon atoms, and absolute configuration of one asymmetric carbon atom was known. The absolute configuration of the other asymmetric carbon atom, therefore, was determined based on the absolute configuration of the known asymmetric carbon atom. The results are shown in FIG. 1. The configuration of the position 7 of the title compound was thus determined to be (S). The configuration of a series of compounds produced by using this compound as an intermediate was also determined.

Reference Example 108

(7S)-7-Methyl-4-oxo-5-[(1R)-phenylethyl]-5-azaspiro[2.4]heptane-7-carboxylic Acid

[Compound 151]

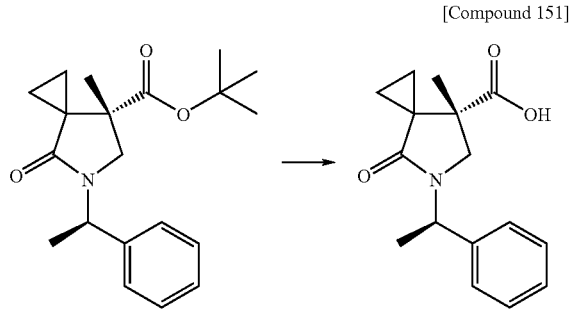

To a solution of tertiary butyl (7S)-7-methyl-4-oxo-5-[(1R)-phenylethyl]-5-azaspiro[2.4]heptane-7-carboxylate (24.5 g, 74.4 mmol) in dichloromethane (120 mL), trifluoroacetic acid (120 mL) was added dropwise in an ice bath, and the mixture was stirred for 2 hours. The reaction mixture was dried under reduced pressure, and after adding toluene (20 mL) to the residue, the mixture was dried under reduced pressure. The residue was dissolved in 1 mol/l aqueous solution of sodium hydroxide (300 mL), and the aqueous solution was washed with ethyl acetate (350 mL). To the aqueous layer was added concentrated hydrochloric acid (25 mL) to pH 2 to 3 in an ice bath, and the mixture was extracted with chloroform (300 mL×2). The organic layer was washed with water (200 mL) and saturated aqueous solution of sodium chloride (100 mL), and dried with anhydrous sodium sulfate, and the solvent was removed by distillation under reduced pressure. Toluene (20 mL) was added to the residue, and the mixture was dried under reduced pressure. The residue was suspended in chloroform (20 mL), and hexane (200 mL) was added for recrystallization. The precipitated solid was washed with hexane (100 mL), and dried under reduced pressure to obtain 20.48 g (quantitative) of the title compound as a white solid. The product was used in the subsequent step with no further purification.

$^1$H-NMR (400 MHz, CDCl$_3$) δ ppm: 0.78-0.83 (1H, m), 0.90-0.95 (1H, m), 1.08-1.18 (2H, m), 1.24 (3H, s), 1.55 (3H, d, J=7.3 Hz), 3.11 (1H, d, J=10.0 Hz), 3.55 (1H, d, J=10.0 Hz), 5.52 (1H, q, J=7.1 Hz), 7.28-7.32 (5H, m).
MS (ESI) m/z: 274 (M+H)$^+$.

Reference Example 109

(7S)-7-Amino-7-methyl-4-oxo-5-[(1R)-phenylethyl]-5-azaspiro[2.4]heptane

[Compound 152]

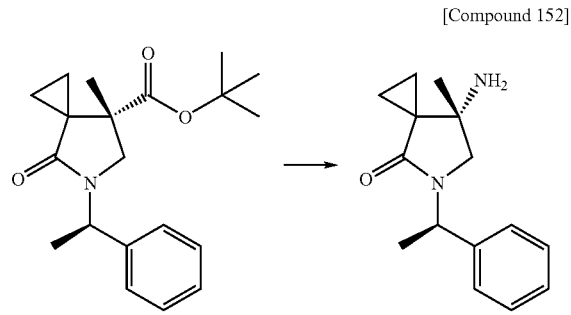

To a solution of (7S)-7-methyl-4-oxo-5-[(1R)-phenylethyl]-5-azaspiro[2.4]heptane-7-carboxylic acid (20.4 g, 74.4 mmol) and diphenylphosphoric acid azide (17.6 mL, 81.8 mmol) in toluene (200 mL), triethylamine (20.7 mL, 149 mmol) was added, and the mixture was stirred in an oil bath at 125° C. for 1 hour. The reaction mixture was concentrated under reduced pressure to obtain the crude product in the form of an isocyanate.

After dissolving the crude product in the form of an isocyanate in 1,4-dioxane (180 mL), water (90 mL) and concentrated hydrochloric acid (90 mL) were added to the mixture. The mixture was stirred in an oil bath at 50° C. for 1 hour, and water (200 mL) was added to the reaction mixture. After washing with ethyl acetate (200 mL), 10 mol/l aqueous solution of sodium hydroxide (170 mL) was added to the aqueous layer to pH 9 to 10, and the solution was extracted with toluene (200 mL×2). The organic layer was washed with saturated aqueous solution of sodium chloride (100 mL), and dried with anhydrous sodium sulfate. After filtration, the filtrate was concentrated under reduced pressure to obtain 15.8 g (64.7 mmol) of the title compound as a pale yellow oily product. The product was used in the subsequent step with no further purification.

$^1$H-NMR (400 MHz, CDCl$_3$) δ ppm: 0.72-0.78 (2H, m), 0.99-1.10 (2H, m), 1.08 (3H, s), 1.53 (3H, d, J=7.4 Hz) 2.82 (1H, d, J=9.6 Hz), 3.27 (1H, d, J=9.6 Hz), 5.56 (1H, q J=7.1 Hz), 7.14-7.37 (5H, m).

Reference Example 110

(7S)-7-(Tertiary butoxycarbonylamino)-7-methyl-5-[(1R)-phenylethyl]-5-azaspiro[2.4]heptane

[Compound 153]

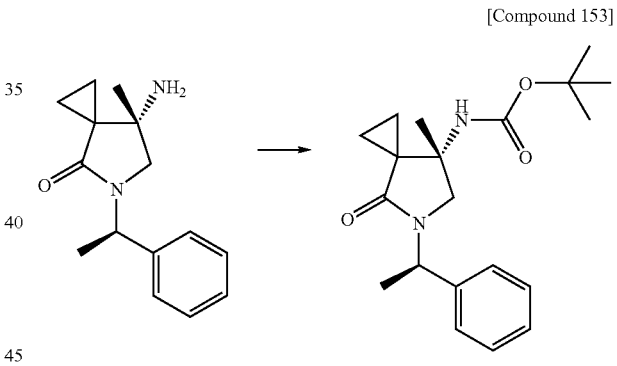

The (7S)-7-amino-7-methyl-4-oxo-5-[(1R)-phenylethyl]-5-azaspiro[2.4]heptane (15.8 g, 64.7 mmol) was dissolved in toluene (82 mL), and a solution of 65% (by weight) solution of sodium bis(2-methoxyethoxy)aluminum hydride in toluene solution (77.6 mL, 259 mmol) in toluene (6 mL) was added dropwise in 15 minutes in an ice bath so that the inner temperature did not exceed 70° C., and the mixture was stirred at room temperature for 10 minutes. The reaction mixture was cooled in an ice bath, and 25% (by weight) aqueous solution of sodium hydroxide (100 mL) was added dropwise. After quenching the solution, the solution was extracted with toluene (135 mL). The organic layer was washed with saturated aqueous solution of sodium chloride (100 mL), and di-tert-butyl dicarbonate (15.6 g, 71.2 mmol) was added. The reaction mixture was stirred at room temperature for 3 hours, and the solvent was removed by distillation under reduced pressure. The residue was purified by silica gel column chromatography (elusion by hexane ethyl acetate, 8:1→4:1→1:1) to obtain 18.0 g (73%) of the title compound as a colorless transparent syrup substance.

$^1$H-NMR (400 MHz, CDCl$_3$) δ ppm: 0.37-0.49 (2H, m), 0.62-0.68 (1H, m), 0.77-0.82 (1H, m), 1.20 (3H, s), 1.32 (3H, d, J=6.6 Hz), 1.44 (9H, s), 2.46 (2H, dd, J=33.2, 9.3 Hz), 2.68 (1H, d, J=8.8 Hz), 3.27 (1H, q, J=6.6 Hz), 3.31-3.34 (1H, m), 4.71 (1H, s), 7.19-7.34 (5H, m).

MS (ESI) m/z: 331 (M+H)+.

Reference Example 111

(7S)-7-(Tertiary butoxycarbonylamino)-7-methyl-5-azaspiro[2.4]heptane

[Compound 154]

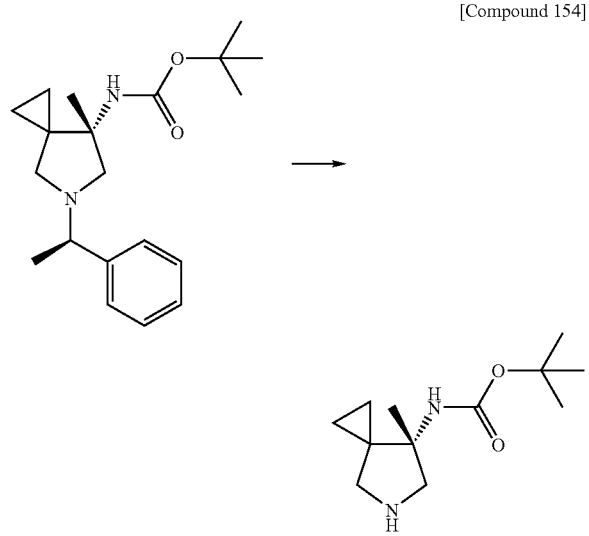

To a solution of (7S)-7-(tertiary butoxycarbonylamino)-7-methyl-5-[(1R)-phenylethyl]-5-azaspiro[2.4]heptane (18.0 g, 54.5 mmol) in methanol (180 mL) was added 10% palladium-carbon catalyst (water content, 52.8%; 9.00 g), and the mixture was stirred at room temperature for 18 hours in hydrogen gas atmosphere, and in an oil bath at 40° C. for 5.5 hours. After removing the catalyst, the solvent was dried under reduced pressure to obtain 13.4 g (quantitative) of the crude target compound as a white solid.

$^1$H-NMR (400 MHz, CDCl$_3$) δ ppm: 0.38-0.43 (1H, m), 0.54-0.61 (2H, m), 0.74-0.80 (1H, m), 1.08 (3H, s), 1.44 (9H, s), 2.75 (1H, d, J=7.6 Hz), 2.78 (1H, d, J=7.1 Hz), 3.13 (1H, d, J=11.5 Hz), 3.73-3.77 (1H, m), 4.45 (1H, s).

MS (ESI) m/z: 227 (M+H)+.

Reference Example 112

7-[(7S)-7-Amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic Acid

[Compound 155]

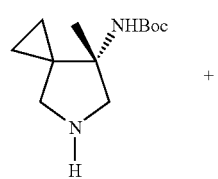

+

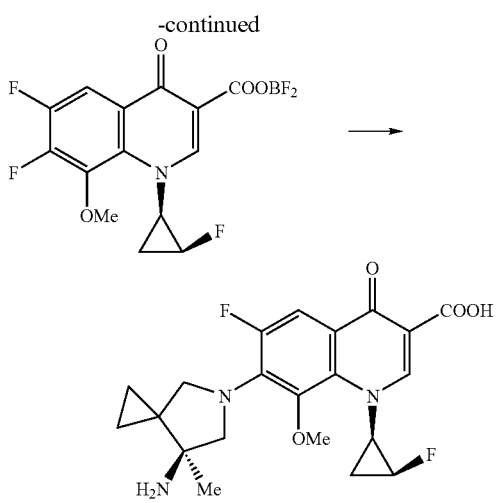

(7S)-7-(tertiary butoxycarbonylamino)-7-methyl-5-azaspiro[2.4]heptane (13.4 g, 54.5 mmol), 6,7-difluoro-1-[(1R,2S)-2-fluorocyclopropyl]-8-methoxy-1,4-dihydro-4-oxo-quinoline-3-carboxylic acid—difluoroborane complex (17.9 g, 49.5 mmol), and triethylamine (8.97 mL, 64.4 mmol) were dissolved in dimethyl sulfoxide (52 mL), and the mixture was stirred in an oil bath at 40° C. for 17 hours. The reaction mixture was poured into cold water (1000 mL), and the precipitated solid was collected by filtration. To this solid were added a mixed solution of ethanol and water (ethanol:water, 5:1) (180 mL) and triethylamine (15 mL), and the mixture was heated under reflux for 1.5 hours. The reaction mixture was dried under reduced pressure, and the residue was dissolved in ethyl acetate (150 mL×2) and washed with 10% aqueous solution of citric acid (200 mL), water (200 mL), and saturated aqueous solution of sodium chloride (100 mL). The organic layer was dried with anhydrous sodium sulfate, and the solvent was removed by distillation under reduced pressure. The residue was dissolved in a mixed solution of chloroform and methanol (chloroform:methanol, 9:1) (100 mL), and after adding silica gel (10 g), the mixture was stirred for 1 hour. After removing silica gel by filtration, the mixture was washed with a mixed solution of chloroform and methanol (chloroform:methanol, 9:1) (50 mL×2), and the filtrates were combined and concentrated to dryness. The residue was dissolved in concentrated hydrochloric acid (200 mL) in an ice bath, and stirred at room temperature for 30 minutes. The reaction mixture was washed with chloroform (400 mL×5). In an ice bath, 10 mol/l aqueous solution of sodium hydroxide was added to the aqueous layer to adjust the pH to 11.8, and the pH was further adjusted to 7.4 by adding hydrochloric acid. The solution was extracted by adding chloroform (1000 mL×3). The organic layer was dried with anhydrous sodium sulfate, and the solvent was removed by distillation under reduced pressure. The residue was purified by recrystallization from ethanol, and the crystals were dried under reduced pressure to obtain 18.5 g (79%) of the title compound as a pale pink powder.

$^1$H-NMR and other data from instrumental analysis of this product were fully consistent with the data of the compound produced in Example 9. In other words, of the quinolone derivatives having 7-amino-7-methyl-5-azaspiro[2.4]heptane-5-yl group, the quinolone derivative described in Example 9 which is a compound with high activity has a 5-azaspiro[2.4]heptane-5-yl group in which the stereochemical configuration at position 7 is (7S).

Test Example 1

The compounds of the present invention were evaluated for their antibacterial activity according to the standard method defined by Japanese Society of Chemotherapy, and the results are shown in MIC (μg/ml) in the table, below. In the table, MIC value is also shown for moxifloxacin (MFLX), Comparative compound 1 which is the compound described in Japanese Patent Application Laid-Open No. 2-231475 (Patent Document 2), levofloxacin (LVFX), gatifloxacin (GTFX), and ciprofloxacin (CPFX), in addition to the compound of the present invention. (The structure below shows only the core structure). *S. aureus*, 87037 is LVFX-resistant MRSA and *S. pneumoniae*, J24 is penicillin-intermediate resistant bacteria.

[Compound 156]

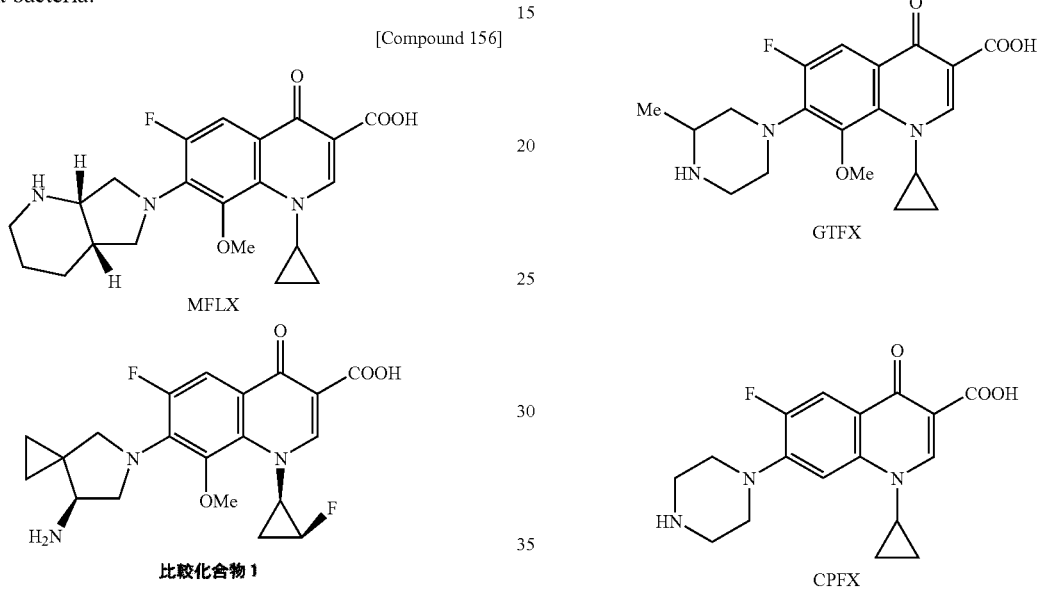

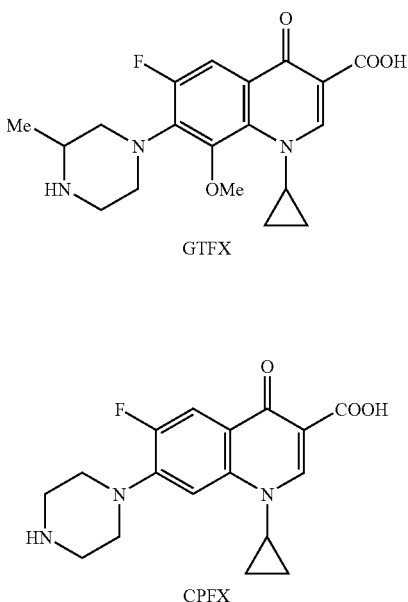

TABLE 1

|  | Example 1 | Example 2 | Example 3 | Example 8 | Example 9 | Example 10 | Example 15 | Example 16 |
|---|---|---|---|---|---|---|---|---|
| *E. coli* NIHJ | 0.025 | 0.012 | 0.012 | 0.012 | 0.025 | 0.025 | 0.012 | 0.012 |
| *P. vulgaris*, 08601 | 0.05 | 0.025 | 0.05 | 0.025 | 0.025 | 0.05 | 0.025 | 0.006 |
| *S. marscecens*, 10100 | 0.2 | 0.1 | 0.2 | 0.2 | 0.1 | 0.2 | 0.2 | 0.1 |
| *P. aeruginosa*, 32104 | 0.39 | 0.2 | 0.39 | 0.78 | 0.39 | 0.39 | 0.39 | 0.1 |
| *P. aeruginosa*, 32121 | 0.2 | 0.1 | 0.2 | 0.2 | 0.2 | 0.2 | 0.2 | 0.05 |
| *S. aureus*, 209P | 0.025 | 0.025 | 0.025 | 0.025 | 0.025 | 0.05 | 0.05 | 0.025 |
| *S. epidermidis*, 56500 | 0.1 | 0.05 | 0.1 | 0.1 | 0.1 | 0.2 | 0.1 | 0.1 |
| *E. faecalis*, ATCC 19433 | 0.2 | 0.2 | 0.2 | 0.2 | 0.2 | 0.78 | 0.2 | 0.39 |
| *S. aureus*, 87037 | 0.78 | 0.78 | 0.78 | 0.78 | 0.78 | 1.56 | 0.78 | 3.13 |
| *S. pneumoniae*, J24 | 0.1 | 0.1 | 0.1 | 0.1 | 0.1 | 0.39 | 0.1 | 0.2 |

|  | Example 17 | Example 21 | Example 22 | Example 23 | Example 27 | Example 28 | Example 29 | Example 30 |
|---|---|---|---|---|---|---|---|---|
| *E. coli* NIHJ | 0.006 | 0.012 | 0.012 | ≦0.003 | 0.006 | 0.025 | 0.05 | 0.006 |
| *P. vulgaris*, 08601 | 0.012 | 0.05 | 0.012 | 0.006 | 0.006 | 0.05 | 0.025 | 0.025 |
| *S. marscecens*, 10100 | 0.1 | 0.2 | 0.1 | 0.05 | 0.1 | 0.39 | 0.2 | 0.1 |
| *P. aeruginosa*, 32104 | 0.39 | 0.78 | 0.39 | — | 0.39 | — | 0.2 | 0.2 |
| *P. aeruginosa*, 32121 | 0.1 | 0.2 | 0.1 | 0.05 | 0.1 | 0.39 | 0.1 | 0.05 |
| *S. aureus*, 209P | 0.025 | 0.025 | 0.025 | 0.025 | 0.012 | 0.025 | 0.05 | 0.05 |
| *S. epidermidis*, 56500 | 0.1 | 0.1 | 0.05 | 0.05 | 0.05 | 0.05 | 0.2 | 0.2 |
| *E. faecalis*, ATCC 19433 | 0.2 | 0.2 | 0.2 | 0.1 | 0.2 | 0.2 | 0.78 | 0.39 |
| *S. aureus*, 87037 | 0.39 | 0.78 | 0.78 | 0.39 | 0.39 | 0.2 | 3.13 | 1.56 |
| *S. pneumoniae*, J24 | 0.1 | 0.1 | 0.1 | 0.05 | 0.1 | 0.1 | 0.39 | 0.2 |

|  | Example 31 | MFLX | Cop. Ex. 1 | LVFX | GTFX | CPFX |
|---|---|---|---|---|---|---|
| *E. coli* NIHJ | 0.006 | 0.012 | ≦0.003 | 0.012 | 0.006 | ≦0.003 |
| *P. vulgaris*, 08601 | 0.012 | 0.025 | 0.012 | 0.012 | 0.006 | ≦0.003 |
| *S. marscecens*, 10100 | 0.1 | 0.1 | 0.05 | 0.1 | 0.1 | 0.025 |

TABLE 1-continued

| | | | | | | |
|---|---|---|---|---|---|---|
| P. aeruginosa, 32104 | — | 0.39 | 0.1 | 0.2 | 0.2 | 0.05 |
| P. aeruginosa, 32121 | 0.05 | 0.2 | 0.05 | 0.1 | 0.1 | 0.025 |
| S. aureus, 209P | 0.012 | 0.05 | 0.006 | 0.2 | 0.05 | 0.1 |
| S. epidermidis, 56500 | 0.025 | 0.2 | 0.05 | 0.39 | 0.2 | 0.2 |
| E. faecalis, ATCC 19433 | 0.1 | 0.2 | 0.1 | 0.78 | 0.39 | 0.78 |
| S. aureus, 87037 | 0.1 | 1.56 | 0.39 | >6.25 | 1.56 | >6.25 |
| S. pneumoniae, J24 | 0.05 | 0.1 | 0.025 | 0.78 | 0.2 | 0.39 |

Test Example 2

The compounds produced in Examples 2, 3, and 9 of the present invention were evaluated by mouse bone marrow micronucleus test by using 5 animals per group of 6-week-old Slc:ddY male mice, and the compounds diluted with 0.1 mol/l NaOH/physiological saline. The control was 0.1 mol/l NaOH/physiological saline solvent, and the positive control was cyclophosphamide (cyclophoshamide, CP) dissolved and diluted in physiological saline. All samples were sterilized by filtering through Milex GS filter (0.22 μm). Each solution was intravenously administered at a dose of 10 mL/kg in single dose at an administration rate of 0.2 mL/min.

Bone marrow cells were collected from thigh bone at 24 hours after the administration, and smear preparation was prepared. After staining with acridine orange, 1000 polychromatic erythrocytes per animal were observed under fluorescence microscope to count frequency of micronucleated polychromatic erythrocyte and ratio of the orthochromatic erythrocytes to the polychromatic erythrocyte in 1000 erythrocytes.

No significant difference in the micronucleus induction rate with the control was found in all of the administration groups of the compound of Example 2 at a dose of 50 and 100 mg/kg, the administration groups of the compound of Example 3: at a dose of 100 and 150 mg/kg, and the administration group of the compound of Example 9 at a dose of 50, 100, and 150 mg/kg, and the evaluation result was negative. In other words, the compounds of the present invention has very weak micronucleus induction in the in vivo mouse bone marrow micronucleus test used in evaluating genotoxicity, and therefore, highly safe.

Test Example 3

The compounds described in Examples 2, 3, and 9 of the present invention were evaluated for concentration in blood and other organs after the administration by the procedure as described below. The Comparative compound was also evaluated by the same procedure.

The test substance was orally administered to fasted rats (7 week old male Crj:CD IGS rats purchased from Charles River Laboratories Japan, Inc.) at a dose of 5 mg/kg.

Animals of absorption test group (3 animals per group) were sacrificed by bleeding under etherization at 0.25, 0.5, 1, 2, 4, and 8 hours after the drug administration, and blood, lever, kidney, and lung were collected. The blood was centrifuged (3000 rpm×15 minutes, 4° C.) after coagulation to collect serum. Tissue was homogenized after adding 3 to 5 mL of 0.1 mol/l phosphate buffer (pH 7.0), and the supernatant was collected from the homogenate (3000 rpm×15 minutes, 4° C.).

Animals of excretion test group (3 animals per group) were placed in a metabolic cage, and the urine of 0 to 4 hours and 4 to 24 hours after the administration was collected in a water-cooled container. Simultaneously with the collection of the urine, the cage was also washed with about 15 mL of 0.1 mol/l phosphate buffer (pH 7.0) to collect the urine attached to the cage. For evaluation of conjugates such as glucuronide, the collected sample was also aliquoted and hydrolyzed with an equal amount of 1 mol/l aqueous solution of sodium hydroxide, and the hydrolysate was neutralized with 0.5 mol/l hydrochloric acid and measured for its concentration. The concentration was measured by LC-MS/MS method.

Pharmacokinetic parameters of the each drug in rat were calculated by from the time course of the average concentration by using pharmacokinetic analysis software PSAG-CP (AS Medica Inc.) in a manner not dependent on the model animal.

TABLE 2

Pharmacokinetics in rat

| | | | Compound | | | | |
|---|---|---|---|---|---|---|---|
| | | Hydrating molecule | Example 2 0.75$H_2O$ | Example 3 2$H_2O$ | Example 9 EtOH•0.5$H_2O$ | Comparative compound 1 HCl•$H_2O$ | MFLX HCl•0.5$H_2O$ |
| Serum | Cmax (μg/mL) (0.25 h) | | 0.67 | 1.03 | 1.22 | 0.82 | 1.49 |
| | AUC0-8 h (μg · h/mL) | | 1.31 | 1.85 | 3.08 | 1.59 | 4.46 |
| Tissue | Cmax (μg/g) | Liver | 10.2 | 9.02 | 13.7 | 9.3 | 9.49 |
| | | Kidney | 7.78 | 8.83 | 9.88 | 8.63 | 10.1 |
| | | Lung | 2.46 | 3.47 | 3.86 | 2.59 | 4.69 |
| | AUC0-8 h (μg · h/mL) | Liver | 17.4 | 15.4 | 32.1 | 15.0 | — |
| | | Kidney | 14.7 | 17.1 | 27.8 | 19.3 | — |
| | | Lung | 8.07 | 7.38 | 13.7 | 6.77 | — |

TABLE 2-continued

| | Pharmacokinetics in rat | | | | | |
|---|---|---|---|---|---|---|
| | | Compound | | | | |
| Hydrating molecule | | Example 2 0.75H$_2$O | Example 3 2H$_2$O | Example 9 EtOH•0.5H$_2$O | Comparative compound 1 HCl•H$_2$O | MFLX HCl•0.5H$_2$O |
| Recovery (%) in urine in relation to the amount administered | 0-24 h | 25.4 | 24.5 | 27.7 | 21.8 | 26.6 |
| | Recovery (%) including conjugate | 26.6 | 24.7 | 32.0 | 23.1 | 30.8 |

By repeating the procedure used for the rats, the compound of Example 9, comparative compound 1, and MFLX were evaluated for cynomolgus monkey by using fasted female cynomolgus monkey (3 animals per group) which had been administered with a dose of 5 mg/kg in single dose, and measuring intact compounds in serum and excreted urine. The measurement was conducted by LC-MS/MS method.

TABLE 3

| | Pharmacokinetics in cynomolgus monkey | | | |
|---|---|---|---|---|
| | | Compound | | |
| Hydrating molecule | | Example 9 EtOH•0.5H$_2$O | Comparative compound 1 HCl•H$_2$O | MFLX HCl•0.5H$_2$O |
| Serum | Cmax (μg/mL) | 2.18 | 0.84 | 1.03 |
| | t½ (h) | 4.8 | 5.0 | 5.3 |
| | AUC0-24 h (μg · h/mL) | 16.9 | 5.11 | 6.64 |
| Recovery (%) in urine in relation to the amount administered | 0-24 h | 61.3 | 25.8 | 8.1 |
| | Recovery (%) including conjugate | 59.5 | 32.9 | 12.2 |

As apparent from the data of the serum concentration, the tissue concentration, and AUC, the compound of the present invention, and in particular, the compound of Example 9 exhibited a serum concentration and a tissue concentration by oral administration which is about 2 times higher, and an AUC value which is 1.5 to 2 times higher than those of the Comparative compound 1 indicating the excellent oral absorptivity and tissue penetration of the present compound. Excretion rate in urine was about 1.5 times higher than that of the Comparative compound 1 indicating the excellent urine excretion. The data was even superior in cynomolgus monkey, and the blood penetration was about 2.5 times higher, and the urine excretion rate was more than 2 times higher than those of the Comparative compound 1.

The compound of Example 9 and MFLX exhibited similar pharmacokinetics in rat and cynomolgus monkey. However, the compound of Example 9 exhibited significantly superior blood penetration and urine excretion in cynomolgus monkey, clearly indicating that the compound of Example 9 exhibits excellent pharmacokinetic properties not only in single species but in more than one animal species.

Test Example 4

The potential convulsant activity upon intracisternal administration to mouse was evaluated according to the method of Ueda et al. (Eur. J. Pharmacol., 1979, 56, 265-268). The test substance was intracisternally administered to male Slc:ddy mice animals per group), and the convulsion and death were monitored for each cage until 30 minutes after the administration. The test substance was dissolved in 5 μl of 1% aqueous solution of lactic acid, and the dose was 5, 15, or 50 μg per animal.

TABLE 4

| | Number of mice which showed convulsion | | | | | |
|---|---|---|---|---|---|---|
| | Example 2 | Example 3 | Example 9 | Comparative compound 1 | MFLX | CPFX |
| 5 μg/mouse | 1/6 | 0/6 | 0/6 | 0/6 | 0/6 | 1/6 |
| 15 μg/mouse | 4/6 | 2/6 | 2/6 | 0/6 | 0/6 | 3/6 |
| 50 μg/mouse | 6/6 | 6/6 | 6/6 | 0/6 | 0/6 | 6/6 |

The potential convulsant activity upon intracisternal administration to mouse was also evaluated for the concomitant and administration with 4-biphenyl acetic acid (BPAA: an active metabolite of fenbufen) and in the absence of such concomitant administration. The evaluation was conducted by using 4 week old male Slc:ddY mice (6 animals per group) and intracisternally administering the test substance at a dose of 5 μg/5 μl/mouse (solvent, 0.5% lactic acid). Monitoring of the animals for the convulsion and death was started immediately after the administration and continued to 30 minutes after the administration. When used concomitantly with the BPAA, BPAA was suspended in 5% CMC, and 400 mg/kg was orally administered at a solution amount of 10 mL/kg, and the test substance was intracisternally administered 30 minutes after the BPAA.

TABLE 5

Effect of biphenyl acetate

| | Dose µg/5 µL/mouse, i. cist | Number of animals which showed convulsion (number of dead animals) | |
|---|---|---|---|
| | | BPAAなし | BPAA 併用 |
| 0.5% lactate | 0 | 0/6 (0/6) | 0/6 (0/6) |
| Compound of Example 9 | 5 | 0/6 (0/6) | 0/6 (0/6) |
| CPFX | 5 | 0/6 (0/6) | 6/6**## (6/6**##) |

*p < 0.05,
**p < 0.01: Sinificantly different from 0.5% Lactate group (Fisher's probability test)
p < 0.05,
p < 0.01: Sinificantly different from the without BPAA group (Fisher's probability test)

The compound of the present invention exhibited a convulsion inducing frequency at a high dose which is higher that of the comparative compound 1 but lower than ciprofloxacin (CPFX) which are widely used in clinical practice indicating weaker convulsion inducing activity, hence, higher safety compared to CPFX. The test of concomitant administration with the biphenyl acetic acid which is the model of the concomitant administration with the fenbufen also indicated the excellent safety of the present compound since no case of convulsion or death was found for the compound of Example 9 whereas convulsion and death were noted in the administration of ciprofloxacin.

Test Example 5

Guinea pig maximization test (GPMT) which is a widely accepted model for delayed antigenicity was conducted according to the method of Mugnusson et al. (J. invest. Dermatol., 52, 1969) by using a cutaneous sensitization concentration of 1% and a patch sensitization and induction concentration of 10%. At day 1, the animal was sensitized by cutaneously administering the test substance (the quinolone compounds and the control: vehicle, vaseline) (1% solution in physiological saline + FCA emulsion) at the back of the head of the shaved guinea pigs (7 week old male Slc:Hertley). At day 7, lauryl sodium sulfate (SLC) was applied for stimulus (adjuvant treatment), and on the next day, the test substance coated on a wax paper was patched onto the shaved skin to for sealed sensitization, and after 48 hours (at day 10), the waxed paper was removed. The skin reaction was observed upon the removal. On day 22, the test substance (10%) was patched onto the anterior side of the body for induction, and the induction patching was removed after 24 hours. On the next day (at day 24) and the next day (at day 25), the skin reaction was evaluated according to the description of the document as mentioned above. Erythema and edema were scored, and the case with the total score of 2 or higher was evaluated to be positive with the maximum of the score being 7.

TABLE 6

Average score and the results of evaluation in GPMT

| | Example 9 | Comparative compound 1 | MFLX | Gemifloxacin |
|---|---|---|---|---|
| Averate score | 0 | 6.8 | 0 | 6.8 |
| Evaluation | Positive | Positive | Negative | Positive |

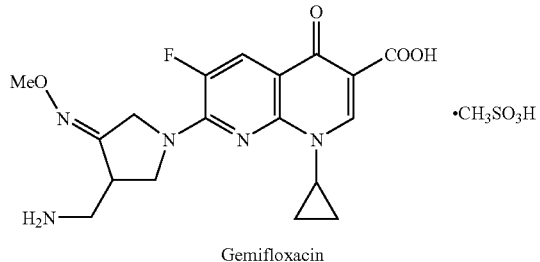

Gemifloxacin

The compound of Example 9 was confirmed to be GPMT negative (score, 0). On the other hand, Comparative compound 1 exhibited a score of 6.8, which is almost the highest score. In the meanwhile, gemifloxacin (gemifloxacin mesylate; product name, FACTIVE™) which recently became commercially available in the U.S. has been reported in the phase 3 clinical trial which was conducted for community-acquired pneumonia and acute exacerbation of chromic bronchitis that it frequently develops the side effect of rash and the rash development is frequently found after day 7 of the repeated administration. This gemifloxacin was also confirmed to be GPMT positive with the score of 6.8 which is almost the highest score as was the case Comparative compound 1. Since the gemifloxacin that had been reported to induce rash development was GPMT positive, the GPMT negative compound of the present invention was indicated to have a reduced risk of rash development.

Test Example 6

Measurement of hERG-K$^+$ channel blocking effect which is an in vitro standard evaluation system for cardiotoxicity (an abnormality inducing lethal arrhythmia which is found by an electrocardiogram and which is observed as prolonged QT or QTc interval) which has recently been reported as a side effect of quinolone antibacterial agent was conducted by the method described in Biophysical Journal, vol. 74, page 230, 1998.

TABLE 7 hERG-K$^+$ channel blocking effect (1)

| Inhibition (%) | Example 2 | Example 3 | Example 9 | Comparative compound 1 | MFLX | GTFX |
|---|---|---|---|---|---|---|
| 30 μM | 3.8 ± 2.1 | 5.3 ± 4.1 | 7.4 ± 4.5 | 6.7 ± 8.3 | 33.9 ± 8.3 | 8.1 ± 6.0 |
| 100 μM | 8.5 ± 1.2 | 12.0 ± 4.0 | 10.2 ± 5.4 | 13.5 ± 3.1 | 44.6 ± 10.2 | 17.6 ± 11.5 |
| 300 μM | 18.2 ± 4.2 | 22.3 ± 0.7 | 20.1 ± 7.4 | 24.8 ± 16.5 | 69.9 ± 8.3 | 39.0 ± 10.8 | n = 3

TABLE 8 hERG-K$^+$ channel blocking effect (2)

| Inhibition (%) | Example 8 | Example 22 | Example 20 | Example 25 | Example 23 | Example 27 |
|---|---|---|---|---|---|---|
| 30 μM | 1.5 ± 1.8 | −1.3 ± 10.1 | 1.4 ± 4.5 | 2.0 ± 7.2 | 3.0 ± 4.1 | −1.8 ± 6.8 |
| 100 μM | 2.1 ± 2.3 | −0.6 ± 7.9 | 8.5 ± 6.1 | 4.2 ± 7.9 | 4.6 ± 4.7 | 0.6 ± 8.0 |
| 300 μM | 2.3 ± 7.3 | 21.5 ± 6.9 | 14.5 ± 6.0 | 17.1 ± 14.4 | 16.7 ± 8.4 | 8.9 ± 11.0 | n = 3

The hERG-K$^+$ channel blocking effect was confirmed to be markedly weak in the compound of the present invention compared to MFLX and GTFX with clinical reports for the action of elongating the QT or QTc interval, and Comparative compound 1.

Test Example 7

Mechanism-based inhibition (MBI) of CYP3A4 was evaluated by using inhibition of hydroxylation at position 1 of midazolam. While Comparative compound 1 exhibited significant inhibition in a manner dependent on the preincubation time and the drug concentration, the compound of Example 9 exhibited weak inhibition even when used at a high concentration.

Several mechanisms are involved in the drug interaction by the CYP inhibition, and among such inhibition, the inhibition by generation of a stable complex of the metabolite of the concomitant drug with the CYP, and the inhibition by the inactivation of the CYP by the binding of the metabolite of the concomitant drug with the hem- or apo-protein moiety are irreversible, and such irreversible inhibition may last for a substantial period after stopping the administration of the concomitant drug and may induce a serious side effect. Such irreversible inhibition is called a "metabolism-based inhibition". Of the CYP molecular species involved in the drug metabolism in human, CYP3A4 is involved in the metabolism of 50% or higher of the drug in clinical use. (Non-patent document: Drug Metabolism, 2nd ed., Tokyo Kagaku Dojin, 2000). Accordingly, a reagent which exhibits MBI action for CYP3A4 can be regarded as a substance having a high risk of being involved in a drug interaction.

For example, clarithromycin which is frequently used as a therapeutic drug for bacterial respiratory infection is known to exhibit MBI action for CYP3A4 (see the document as mentioned above), and use of clarithromycin concomitantly with terfenadine (an antihistamine) is contraindicated since such concomitant administration results in the increased blood concentration of the terfenadine due to the inhibition of the terfenadine metabolism by CYP3A4 caused by the clarithromycin, and prolonged QT interval in the electrocardiogram, ventricular arrhythmia, and occasionally, cardiac arrest are found. However, the compound of Example 9 was revealed to have a clearly weaker MBI even when tested at a high concentration (with a significant safe margin compared to the postulated concentration in clinical use). Therefore, the compound of the present invention is estimated to be associated with a greatly reduced risk of developing clinical side effects by the drug interaction based on the MBI action for CYP3A4.

Test Example 8

Mouse local lung infection model by penicillin resistant *Streptococcus pneumoniae* (PRSP) was used to compare the therapeutic effect of the compound of Example 9 and Comparative compound 1.

PRSP strain 033806 that had been anaerobically cultivated in Todd Hewitt Broth was nasally administered to Male CBA/JNCrlj mice (3 to 4 week old; Charles River Laboratories Japan, Inc.; 4 animals per group) under anesthesia with ketamine-xylazine mixture. Compound of Example 9 and comparative compound 1 were orally administered to this injection model, respectively, at a dose shown in FIG. 2 (25, 50, and 100 mg/kg/day) at 2 and 8 hours after the infection (treated for only 1 day at a daily dose of 50, 100, or 200 mg/kg/day). Untreated control group was administered with distilled water for injection.

Number of the bacteria in the lung was measured immediately before the drug administration for the untreated group (2 hours after the infection, indicated in the drawing as "Pre-control"), and on the next day of the drug administration for the untreated group (the next day of the infection, indicated as "Post-control") and treated groups for use as an index of therapeutic effect.

Figure 2:
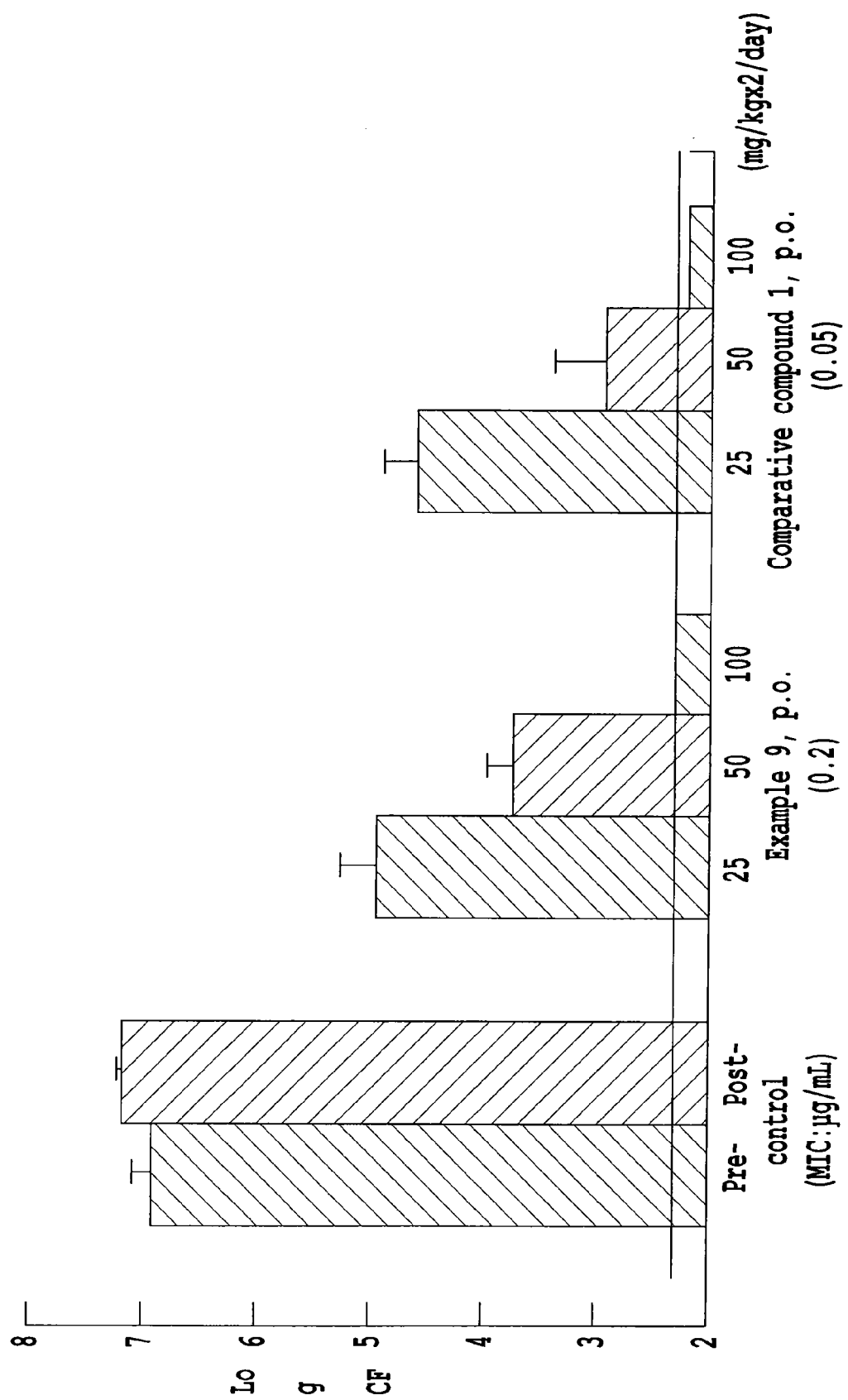
FIG. 2 is a graph showing therapeutic effects of Comparative compound 1 and the compound of Example 9 in mouse local lung infection model by PRSP.

As evident from FIG. 2, while the in vivo antibacterial activity of the compound of Example 9 for the test bacteria was about ¼ of the comparative compound 1, no significant difference was found between the therapeutic effect of the compound of Example 9 and that of the comparative: compound 1 in the oral administration to the mouse local lung infection model by PRSP for all groups administered with the same dose.

Test Example 9

Therapeutic Effect in Rat Simple Cystitis Model (*E. Coli*)

Infection model: Rats (7 week old male Crl:CD(SD) (IGS) rats, Charles River Laboratories Japan, Inc., 4 animals per group) that had been deprived of water from the previous day were anesthetized with ketamine-xylazine mixture, and *E. coli* strain E77156 was transurethrally inoculated ($1.2 \times 10^7$ CFU/rat) in the bladder. After the administration, urethral orifice was closed for 2 hours to thereby prevent discharge of the bacterial solution, and feeding of the water was started simultaneously with the termination of closure.

Drug administration: Compound of Example 9 and Comparative Compound 1 were orally administered respectively at a dose of 5, 20, or 80 mg/kg on the next day of the infection in a single dose.

Evaluation of the effectiveness: Number of the bacteria in the bladder was measured immediately before the drug administration and on the next day of the drug administration (2 days after the infection) for the untreated group, and on the next day of the drug administration for the treated groups for use as an index of therapeutic effect.

Figure 4:
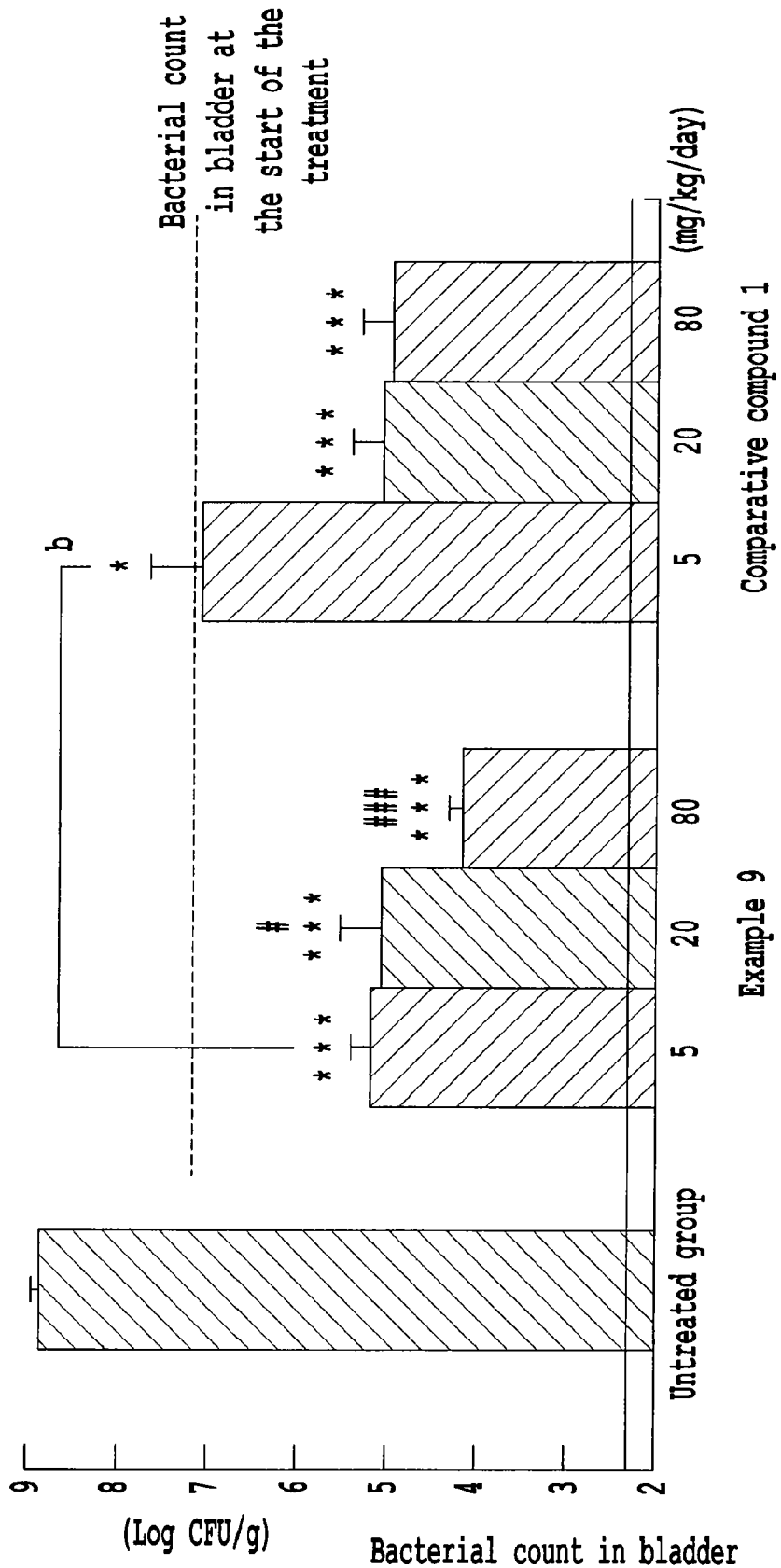
FIG. 4 is a graph showing therapeutic effects of Comparative compound 1 and the compound of Example 9 in rat simple cystitis model by *E. coli*.

Results: A significant decrease in the number of bacteria was found only for the compound of Example 9 when the dose was 20 or 80 mg/kg/day. The therapeutic effect of this compound for the group with the dose of 5 mg/kg/day was significantly stronger than the Comparative Compound 1. Accordingly, the compound of Example 9 was demonstrated to be a compound which is capable of realizing therapeutic effects superior to those of the Comparative Compound 1 (FIG. 4).

Test Example 10

The compounds of the present invention were evaluated for their anti-*Mycobacterium tuberculosis* activity according to the standard method defined by Japanese Society of Chemotherapy (Journal of Japanese Society of Chemotherapy, vol. 29, pages 76 to 79, 1981), and the results are shown in MIC (μg/ml) in the Tables 9 and 10, below. The compounds of the present invention exhibited superior antibacterial activity for *Mycobacterium tuberculosis*.

TABLE 9

Anti-*Mycobacterium tuberculosis* (sensitive bacteria) activity (MIC: μg/ml)

| Strain/compound | Example 9 | RFP | Comparative compound 1 |
| --- | --- | --- | --- |
| TB-s 2 | 0.06 | 0.03 | 0.125 |
| TB-s 3 | 0.06 | 0.125 | 0.125 |
| TB-s 4 | 0.06 | 0.06 | 0.125 |
| TB-s 5 | 0.06 | 0.06 | 0.06 |
| TB-s 6 | 0.06 | 0.125 | 0.125 |
| TB-s 7 | 0.06 | 0.06 | 0.25 |
| TB-s 8 | 0.03 | 0.015 | 0.06 |
| TB-s 9 | 0.06 | 0.06 | 0.125 |
| TB-s 10 | 0.03 | 0.06 | 0.06 |
| TB-s 11 | 0.06 | 0.06 | 0.125 |
| TB-s 12 | 0.125 | 0.125 | 0.25 |
| TB-s 13 | 0.06 | 0.06 | 0.125 |
| TB-s 14 | 0.06 | 0.03 | 0.125 |
| TB-s 15 | 0.06 | 0.06 | 0.125 |
| TB-s 16 | 0.06 | 0.06 | 0.125 |
| TB-s 17 | 0.06 | 0.06 | 0.125 |
| TB-s 18 | 0.06 | 0.03 | 0.125 |
| TB-s 19 | 0.06 | 0.125 | 0.125 |
| TB-s 20 | 0.06 | 0.25 | 0.25 |
| TB-s 21 | 0.06 | 0.03 | 0.125 |
| TB-s 22 | 0.03 | 0.015 | 0.06 |
| Kurono | 0.03 | 0.06 | 0.06 |
| H37Rv | 0.03 | 0.125 | 0.06 |
| Ravenel | 0.03 | 0.125 | 0.06 |

RFP: Rifampicin

TABLE 10

Anti-*Mycobacterium tuberculosis* (quinolone sensitive) activity (MIC: μg/ml)

| Strain/compound | Example 9 | RFP | Comparative compound 1 |
| --- | --- | --- | --- |
| S 1 | 1 | 16 | 2 |
| MDR 1 | 0.125 | 16 | 0.5 |
| MDR 3 | 0.125 | 128 | 0.5 |
| MDR 4 | 0.25 | 64 | 0.5 |
| MDR 5 | 0.5 | 32 | 1 |
| MDR 7 | 0.125 | >128 | 0.5 |
| MDR 9 | 0.125 | 128 | 0.5 |
| MDR 12 | 0.125 | 128 | 0.5 |
| 1 (QR-3) | 0.125 | >128 | 1 |
| 2 (QR-6) | 0.5 | >128 | 128 |
| 3 (QR-1) | 0.25 | 128 | 2 |
| 4 (QR-9) | 0.25 | >128 | 32 |

The invention claimed is:

1. A compound of formula (I):

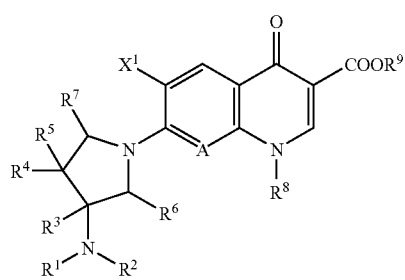

or a salt thereof, wherein
$R^1$ and $R^2$ each represents hydrogen atom;
$R^3$ represents an alkyl group containing 1 to 6 carbon atoms, which being optionally substituted with halogen atom;

R⁴ and R⁵ together represent a 3-membered cyclic structure including the carbon atom shared by R⁴ and R⁵ to form a spirocyclic structure with the pyrrolidine ring;

R⁶ and R⁷, each represents hydrogen atom;

R⁸ represents a halogen-substituted cycloalkyl group containing 3 to 6 carbon atoms;

R⁹ represents hydrogen atom or an alkyl group containing 1 to 6 carbon atoms;

X¹ represents hydrogen atom or a halogen atom; and

A represents a moiety represented by formula (II):

wherein X² represents an alkyl group containing 1 to 6 carbon atoms or an alkoxy group containing 1 to 6 carbon atoms.

2. The compound, or a salt thereof, according to claim 1, wherein the compound represented by the formula (I) is a compound represented by the following formula:

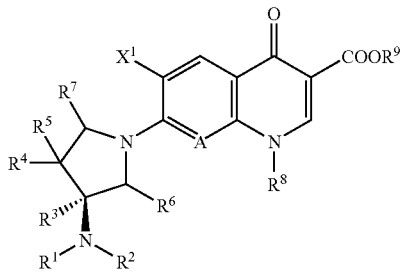

wherein R¹, R², R³, R⁴, R⁵, R⁶, R⁷, R⁸, R⁹, X¹, and A are as defined above.

3. The compound, or a salt thereof, according to claim 1, wherein R³ in formula (I) is methyl group.

4. The compound, or a salt thereof, according to claim 1, wherein X¹ in formula (I) is fluorine atom.

5. The compound, or a salt thereof, according to claim 1, wherein X² in formula (II) is methyl group or methoxy group.

6. The compound, or a salt thereof, according to claim 1, wherein R⁸ in formula (I) is a 1,2-cis-2-halogenocyclopropyl group.

7. The compound, or a salt thereof, according to claim 1, wherein R⁸ in formula (I) is a stereochemically pure 1,2-cis-2-halogenocyclopropyl group.

8. The compound, or a salt thereof, according to claim 7, wherein the 1,2-cis-2-halogenocyclopropyl group which is R⁸ in formula (I) is (1R,2S)-2-halogenocyclopropyl group.

9. The compound, or a salt thereof, according to claim 8, wherein the (1R,2S)-2-halogenocyclopropyl group which is R⁸ in formula (I) is (1R,2S)-2-fluorocyclopropyl group.

10. The compound, or a salt thereof, according to claim 1, wherein R⁹ in formula (I) is hydrogen atom.

11. The compound, or a salt thereof, according to claim 1, wherein the compound of formula (I) is a stereochemically pure compound.

12. A pharmaceutical composition comprising the compound according to claim 1, or a salt thereof, and a pharmaceutically acceptable carrier.

13. A method for treating a bacterial or microbial infection, comprising administering an effective amount of the compound according to claim 1, or a salt thereof, to a subject in need thereof, wherein said bacterial or microbial infection is caused by a microorganism selected from the group consisting of *Staphylococcus, Streptococcus pyogenes*, hemolytic *streptococcus, enterococcus, pneumococcus, Peptostreptococcus, Neisseria gonorrhoeae, Escherichia coli, Citrobacter, Shigella, Klebsiella pneumoniae, Enterobacter, Serratia, Proteus, Pseudomonas aeruginosa, Haemophilus influenzae, Acinetobacter, Campylobacter, Chlamydia trachomatis, Mycobacterium tuberculosis, Mycobacterium bovis, Mycobacterium africans, Mycobacterium kansasii, Mycobacterium marianum, Mycobacterium scrofulaceum, Mycobacterium avium, Mycobacterium intracellulare, Mycobacterium xenopi, Mycobacterium fortuitum,* and *Mycobacterium chelonae.*

14. A compound selected from the group consisting of:
7-[(7S)-7-amino-7-methyl-5-azaspiro[2.4]heptane-5-yl]-6-fluoro-1-[(1R,2S)-2-fluorocyclopropyl]-8-methyl-1,4-dihydro-4-oxoquinoline-3-carboxylic acid, or a salt thereof; and
7-[(7S)-7-amino-7-methyl-5-azaspiro[2.4]heptane-5-yl]-6-fluoro-1-[(1R,2S)-2-fluorocyclopropyl] -8-methoxy-1,4-dihydro-4-oxoquinoline-3-carboxylic acid, or a salt thereof.

15. A pharmaceutical composition comprising the compound according to claim 14, or a salt thereof, and a pharmaceutically acceptable carrier.

16. A method for treating a bacterial or microbial infection, comprising administering an effective amount of the compound according to claim 14, or a salt thereof, to a subject in need thereof, wherein said bacterial or microbial infection is caused by a microorganism selected from the group consisting of *Staphylococcus, Streptococcus pyogenes*, hemolytic *streptococcus, enterococcus, pneumococcus, Peptostreptococcus, Neisseria gonorrhoeae, Escherichia coli, Citrobacter, Shigella, Klebsiella pneumoniae, Enterobacter, Serratia, Proteus, Pseudomonas aeruginosa, Haemophilus influenzae, Acinetobacter, Campylobacter, Chlamydia trachomatis, Mycobacterium tuberculosis, Mycobacterium bovis, Mycobacterium africans, Mycobacterium kansasii, Mycobacterium marianum, Mycobacterium scrofulaceum, Mycobacterium avium, Mycobacterium intracellulare, Mycobacterium xenopi, Mycobacterium fortuitum,* and *Mycobacterium chelonae.*

17. 7-[(7S)-7-amino-7-methyl-5-azaspiro[2.4]heptane-5-yl]-6-fluoro-1-[(1R,2S)-2-fluorocyclopropyl]-8-methyl-1,4-dihydro-4-oxoquinoline-3-carboxylic acid, or a salt thereof.

18. A pharmaceutical composition comprising 7-[(7S)-7-amino-7-methyl-5-azaspiro[2.4]heptane-5-yl]-6-fluoro-1-[(1R,2S)-2-fluorocyclopropyl]-8methyl-1,4-dihydro-4-oxoquinoline-3-carboxylic acid, or a salt thereof, according to claim 17, and a pharmaceutically acceptable carrier.

19. A method for treating a bacterial or microbial infection, comprising administering an effective amount of 7-[(7S)-7-amino-7-methyl-5-azaspiro[2.4]heptane-5-yl]-6-fluoro-1-[(1R,2S)-2-fluorocyclopropyl]-8-methyl-1,4-dihydro-4-oxoquinoline-3-carboxylic acid, or a salt thereof, according to claim 17, to a subject in need thereof, wherein said bacterial or microbial infection is caused by a microorganism selected from the group consisting of *Staphylococcus, Streptococcus pyogenes*, hemolytic *streptococcus, enterococcus, pneumococcus, Peptostreptococcus, Neisseria gonorrhoeae, Escherichia coli, Citrobacter, Shigella, Klebsiella pneumoniae, Enterobacter, Serratia, Proteus, Pseudomonas aeruginosa, Haemophilus influenzae, Acinetobacter, Campylobacter, Chlamydia trachomatis, Mycobacterium tuberculosis, Mycobacterium bovis, Mycobacterium afri-* cans, *Mycobacterium kansasii, Mycobacterium marianum, Mycobacterium scrofulaceum, Mycobacterium avium, Mycobacterium intracellulare, Mycobacterium xenopi, Mycobacterium fortuitum*, and *Mycobacterium chelonae*.

20. 7-[(7S)-7-amino-7-methyl-5-azaspiro[2.4]heptane-5-yl]-6-fluoro-1-[(1R,2S)-2-fluorocyclopropyl]-8-methoxy-1,4-dihydro-4-oxoquinoline-3-carboxylic acid, or a salt thereof.

21. A pharmaceutical composition comprising 7-[(7S)-7-amino-7-methyl-5-azaspiro[2.4]heptane-5-yl]-6-fluoro-1-[(1R,2S)-2-fluorocyclopropyl]-8-methoxy-1,4-dihydro-4-oxoquinoline-3-carboxylic acid, or a salt thereof, according to claim 20, and a pharmaceutically acceptable carrier.

22. A method for treating a bacterial or microbial infection, comprising administering an effective amount of 7-[(7S)-7-amino-7-methyl-5-azaspiro[2.4]heptane-5-yl]-6-fluoro-1-[(1R,2S)-2-fluorocyclopropyl]-8-methoxy-1,4-dihydro-4-oxoquinoline-3-carboxylic acid, or a salt thereof, according to claim 20, to a subject in need thereof, wherein said bacterial or microbial infection is caused by a microorganism selected from the group consisting of *Staphylococcus, Streptococcus pyogenes*, hemolytic *streptococcus, enterococcus, pneumococcus, Peptostreptococcus, Neisseria gonorrhoeae, Escherichia coli, Citrobacter, Shigella, Klebsiella pneumoniae, Enterobacter, Serratia, Proteus, Pseudomonas aeruginosa, Haemophilus influenzae, Acinetobacter, Campylobacter, Chlamydia trachomatis, Mycobacterium tuberculosis, Mycobacterium bovis, Mycobacterium africans, Mycobacterium kansasii, Mycobacterium marianum, Mycobacterium scrofulaceum, Mycobacterium avium, Mycobacterium intracellulare, Mycobacterium xenopi, Mycobacterium fortuitum*, and *Mycobacterium chelonae*.

* * * * *